United States Patent
Le Huerou et al.

(10) Patent No.: US 8,981,085 B2
(45) Date of Patent: Mar. 17, 2015

(54) PYRROLOPYRIDINES AS KINASE INHIBITORS

(71) Applicant: Array BioPharma Inc., Boulder, CO (US)

(72) Inventors: Yvan Le Huerou, Boulder, CO (US); James F. Blake, Boulder, CO (US); Indrani W. Gunawardana, Boulder, CO (US); Peter J. Mohr, Boulder, CO (US); Eli M. Wallace, Boulder, CO (US); Bin Wang, Boulder, CO (US); Mark Joseph Chicarelli, Boulder, CO (US); Michael Lyon, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 14/271,129

(22) Filed: May 6, 2014

(65) Prior Publication Data

US 2014/0243520 A1    Aug. 28, 2014

Related U.S. Application Data

(60) Continuation of application No. 13/974,895, filed on Aug. 23, 2013, now Pat. No. 8,758,830, which is a continuation of application No. 13/425,186, filed on Mar. 20, 2012, now Pat. No. 8,545,897, which is a division of application No. 12/992,468, filed as application No. PCT/US2009/043691 on May 13, 2009, now Pat. No. 8,178,131.

(60) Provisional application No. 61/052,926, filed on May 13, 2008.

(51) Int. Cl.
C07D 471/04    (2006.01)

(52) U.S. Cl.
CPC ................ *C07D 471/04* (2013.01)
USPC ........... 540/597; 544/127; 544/238; 544/355; 544/405; 546/113; 546/15

(58) Field of Classification Search
None
See application file for complete search history.

(56) References Cited

U.S. PATENT DOCUMENTS

| | | | |
|---|---|---|---|
| 8,178,131 B2 * | 5/2012 | Le Huerou et al. ........... | 424/649 |
| 8,372,842 B2 | 2/2013 | Blake et al. | |
| 8,545,897 B2 | 10/2013 | Le Huerou | |
| 8,758,830 B2 | 6/2014 | Le Huerou | |
| 2003/0162785 A1 | 8/2003 | Lin et al. | |
| 2005/0256157 A1 | 11/2005 | Gesner et al. | |
| 2007/0082900 A1 | 4/2007 | Guzi et al. | |
| 2010/0260868 A1 | 10/2010 | Humphries et al. | |
| 2010/0280043 A1 | 11/2010 | Blake et al. | |
| 2010/0324041 A1 | 12/2010 | Blake et al. | |
| 2014/0100369 A1 * | 4/2014 | Le Huerou et al. ........... | 546/113 |

FOREIGN PATENT DOCUMENTS

| | | |
|---|---|---|
| WO | WO 01/58869 | 8/2001 |
| WO | WO 01/79198 | 10/2001 |
| WO | WO 03/022214 | 3/2003 |
| WO | WO 03/028724 | 4/2003 |
| WO | WO 2004/014910 | 2/2004 |
| WO | WO 2004/081008 | 9/2004 |
| WO | WO 2005/063746 | 7/2005 |
| WO | WO 2006/046023 | 5/2006 |
| WO | WO 2006/106326 | 10/2006 |
| WO | WO 2007/041712 | 4/2007 |
| WO | WO 2007/125321 | 11/2007 |
| WO | WO 2008/012635 | 1/2008 |
| WO | WO 2008/075007 | 6/2008 |
| WO | WO 2008/130569 | 10/2008 |
| WO | WO 2009/004329 | 1/2009 |
| WO | WO 2009/061781 | 5/2009 |
| WO | WO 2012/074754 | 6/2012 |

OTHER PUBLICATIONS

CancerPrevention, http://www.educationupdate.com/archives/2003/apr03/issue/med-can-cancer.html (2012).
CancerCure, http://www.webmd.com/cancer/news/20121024/incurable-cancer-patients-think-cure (2012).
CancerCure2, http://www.healthoma.com/can-cancer-be-cured-is-cancer-curable (2012).
Carlowitz et al., "Characterization of a Novel, Oral Chk1 Inhibitor", presented at AACR, Abstract # 1803, 1 page, Apr. 21, 2009.
Davies et al., "Single-Agent Inhibition of Chk1 is Antiproliferative in Human Cancer Cell Lines in Vitro and Inhibits Tumor Xenograft Growth in Vivo", *Oncology Research*, vol. 19, 349-363 (2011).
Davies et al., "Chk1 inhibition and Wee1 inhibition combine synergistically to inhibit cellular proliferation", presented at American Association of Cancer Research (AACR) 102nd Annual Meeting, Abstract # 2939, 1 page, Apr. 5, 2011.

(Continued)

*Primary Examiner* — Sun Jae Yoo
(74) *Attorney, Agent, or Firm* — Viksnins Harris & Padys PLLP

(57) ABSTRACT

Compounds of Formula I are useful for inhibition of CHK1 and/or CHK2. Methods of using compounds of Formula I and stereoisomers and pharmaceutically acceptable salts thereof, for in vitro, in situ, and in vivo diagnosis, prevention or treatment of such disorders in mammalian cells, or associated pathological conditions are disclosed.

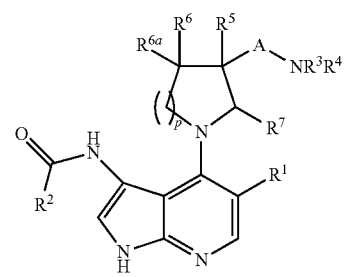

20 Claims, No Drawings

(56) References Cited

OTHER PUBLICATIONS

Davies et al., "Single-agent Chk1 inhibition is anti-proliferative in leukemia cells in vitro and in vivo", presented at American Association of Cancer Research (AACR) 101st Annual Meeting, Abstract #3874, 1 page, Apr. 20, 2010.

European Examination Report for European Pat. App. No. 09747404.3, 4 pages, dated Dec. 2, 2011.

Foloppe, Nicholas, et al. "Identification of buried pocket for potent and selective inhibition of Chk1: Prediction and Verification", *Bioorg. Med. Chem. 14*, 1792-1804 (2006).

Foloppe, Nicholas, et al. "Structure-Based Design of Novel Chk1 Inhibitors: Insights into Hydrogen Bonding and Protein-Ligand Affinity", *J. Med. Chem.* vol. 48, No. 13, 4332-4345 (2005).

Humphries, "Targeting Checkpoint Kinase 1: A study in the application of preclinical data to inform clinical strategy", presented at 2nd Annual Cancer Targets And Therapeutics Conference, 21 pages Oct. 21, 2010.

Humphries et al., "Extended target-coverage by selective Chk1 inhibitors enhances pharmacodynamics inhibition of Chk1 signaling and anti-tumor activity in vivo", presented at 2009 Molecular Targets and Cancer Therapeutics, Abstract # B254, 1 page Nov. 17, 2009.

Humphries et al., "Schedule-dependence and extended target-coverage of selective Chk1 inhibitors enhances the anti-tumor activity of chemotherapy in vivo", presented at American Association of Cancer Research (AACR) 100th Annual Meeting, Abstract # 4599 1 page Apr. 21, 2009.

Humphries, "Preclinical characterization of ARRY-575: A potent, selective, and orally bioavailable small molecule inhibitor of Chk1", presented at International Symposium on Targeted Anticancer Therapies 2011, 11 pages Mar. 11, 2011.

International Search Report for corresponding PCT Application No. PCT/US2009/043691.

Li, Qun et al., "Targeting Serine/Threonine Protein Kinase B/Akt and Cell-cycle Checkpoint Kinases for Treating Cancer"*Current Topics in Medicinal Chemistry* vol. 2, No. 9, (2002).

Maugeri-Sacca et al., Cancer Treatment Reviews, article in press, 2012.

Reader, John, et al. "Identification and Structure-guided Optimisation of Novel Inhibitors of Checkpoint Kinase 1 (Chk1) through Combined Biochemical and Crystallographic Screening"AACR Poster, Abstarct 757 (2008).

Tao, Zhi-Fu et al., "Chk1 Inhibitors for Novel Cancer Treatment", *Anti-Cancer Agents in Medicinal Chemistry*. vol. 6, No. 4, 377-388 (2006).

Tse et al., *Clinical Cancer Research*, 13 1955-1960 (2007).

Written Opinion for corresponding PCT Application No. PCT/US2009/043691.

\* cited by examiner

PYRROLOPYRIDINES AS KINASE INHIBITORS

PRIORITY OF INVENTION

This application is a continuation of U.S. patent application Ser. No. 13/974,895, filed Aug. 23, 2013 (now U.S. Pat. No. 8,758,830), which is a continuation of U.S. patent application Ser. No. 13/425,186, filed Mar. 20, 2012, which has issued as U.S. Pat. No. 8,545,897, which is a divisional of U.S. patent application Ser. No. 12/992,468, filed Nov. 12, 2010, which has issued as U.S. Pat. No. 8,178,131, which is a 35 U.S.C. 371 national stage application of International Patent Application No. PCT/US2009/043691, filed May 13, 2009, and claims priority to U.S. Provisional Application No. 61/052,926 that was filed on May 13, 2008, which are incorporated herein by reference in their entirety.

FIELD OF THE INVENTION

The present invention relates to novel compounds, to pharmaceutical compositions comprising the compounds, to a process for making the compounds and to the use of the compounds in therapy. More particularly it relates to certain substituted pyrrolo[2,3-b]pyridines useful in the treatment and prevention of hyperproliferative diseases.

DESCRIPTION OF THE STATE OF THE ART

Protein kinases are kinase enzymes that phosphorylate other proteins. The phosphorylation of these proteins usually produces a functional change in the protein. Most kinases act on serine and threonine or tyrosine, and some kinases act on all three. Through these functional changes, kinases can regulate many cellular pathways. Protein kinase inhibitors are compounds that inhibit these protein kinases, and thus can be used to affect cellular pathways.

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al., "Targeting Checkpoint Kinase 1 in Cancer Therapeutics." *Clin. Cancer Res.* 13(7) (2007) 1955-1960). It has been observed that many tumors are deficient in the $G_1$ DNA damage checkpoint pathway, resulting in the reliance on S and $G_2$ checkpoints to repair DNA damage and survive. (Janetka, James W., et al., "Inhibitors of checkpoint kinases: From discovery to the clinic." *Drug Discovery & Development* Vol. 10, No. 4 (2007) 473-486). The S and $G_2$ checkpoints are regulated by CHK1. Inhibition of CHK1 has been shown to cancel the S and $G_2$ checkpoints, thereby impairing DNA repair and resulting in increased tumor cell death. However, non-cancerous cells have a functioning G checkpoint, allowing for DNA repair and survival.

Checkpoint kinase 2 ("CHK2") is also a serine/threonine kinase. CHK2's functions are central to the induction of cell cycle arrest and apoptosis by DNA damage. (Ahn, Jinwoo, et al., "The Chk2 protein kinase." *DNA Repair* 3 (2004) 1039-1047). CHK2 is activated in response to genotoxic insults and propagates the checkpoint signal along several pathways, which eventually causes cell-cycle arrest in the $G_1$, S and $G_2/M$ phases, activation of DNA repair, and apoptotic cell death. (Bartek, Jiri, et al., "CHK2—Kinase A Busy Messenger." *Nature Reviews Molecular Cell Biology*. Vol. 2(12) (2001) 877-886). Cancer cells often lack one or more genome-integrity checkpoints, so inhibition of CHK2 could make tumor cells selectively more sensitive to anti-cancer therapies, such as γ-radiation or DNA-damaging drugs. Normal cells would still activate other checkpoints and recover, while cancer cells deprived of checkpoints would be more likely to die. It has been demonstrated that a peptide-based inhibitor of CHK2 abrogated the $G_2$ checkpoint and sensitized p53-defective cancer cells to DNA damaging agents. (Pommier, Yves, et al., "Targeting Chk2 Kinase: Molecular Interaction Maps and Therapeutic Rationale." *Current Pharmaceutical Design*. Vol. 11, No. 22 (2005) 2855-2872).

CHK1 and/or CHK2 inhibitors are known, see for example, International Publication WO 2009/004329, International Publication WO 2008/075007, International Publication WO 2007/090493, International Publication WO 2007/090494, International Publication WO 2006/106326, International Publication WO 2006/120573, International Publication WO 2005/103036 and International Publication WO 03/028724.

Kinase inhibitors are known, see for example, International Publication WO 2008/106692, International Publication WO 2008/012635, International Publication WO 2006/046023, International Publication WO 2006/127587, International Publication WO 2007/070514, International Publication WO 2007/084667, International Publication WO 2007/125310, International Publication WO 2007/125315 and International Publication WO 2007/125321.

SUMMARY OF THE INVENTION

In one aspect, the present invention relates to compounds that are inhibitors of CHK1 and/or CHK2. Accordingly, the compounds of the present invention are useful in the treatment of diseases and conditions that can be treated by the inhibition of CHK1 and/or CHK2 protein kinases.

More specifically, one aspect of the present invention provides compounds of Formula I:

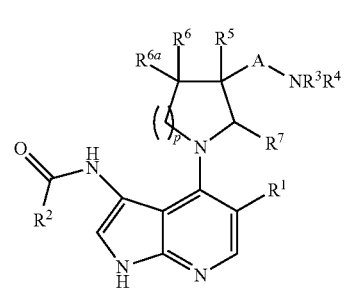

and stereoisomers, tautomers and pharmaceutically acceptable salts thereof, wherein $R^1$, $R^2$, $R^3$, $R^4$, $R^5$, $R^6$, $R^{6a}$, $R^7$, A and p are as defined herein.

Another aspect of the present invention provides methods of preventing or treating a disease or disorder modulated by CHK1 and/or CHK2, comprising administering to a mammal in need of such treatment an effective amount of a compound of this invention or a stereoisomer or pharmaceutically acceptable salt thereof. Examples of such diseases and disorders include, but are not limited to, hyperproliferative disorders (such as cancer), neurodegeneration, cardiac hypertrophy, pain, migraine, and neurotraumatic disease.

Another aspect of the present invention provides methods of preventing or treating cancer, comprising administering to a mammal in need of such treatment an effective amount of a compound of this invention, or a stereoisomer or pharmaceutically acceptable salt thereof, alone or in combination with one or more additional compounds having anti-cancer properties.

Another aspect of the present invention provides a method of treating a hyperproliferative disease in a mammal comprising administering a therapeutically effective amount of a compound of this invention to the mammal.

Another aspect of the present invention provides the compounds of this invention for use in therapy.

Another aspect of the present invention provides the compounds of this invention for the use in the treatment of a hyperproliferative disease.

Another aspect of the present invention provides the use of a compound of this invention in the manufacture of a medicament for the treatment of a hyperproliferative disease. In a further embodiment, the hyperproliferative disease is cancer.

Another aspect of the present invention provides the use of a compound of the present invention in the manufacture of a medicament, for use as a CHK1 and/or CHK2 inhibitor in the treatment of a patient undergoing cancer therapy.

Another aspect of the present invention provides the use of a compound of the present invention in the treatment of a hyperproliferative disease. In a further aspect, the hyperproliferative disease is cancer.

Another aspect of the present invention provides a pharmaceutical composition comprising a compound of the present invention for use in the treatment of a hyperproliferative disease.

Another aspect of the present invention provides a pharmaceutical composition comprising a compound of the present invention for use in the treatment of cancer.

Another aspect of the present invention provides a pharmaceutical composition comprising a compound of this invention or a pharmaceutically acceptable salt thereof, and a pharmaceutically acceptable carrier or excipient.

Another aspect of the present invention provides intermediates for preparing compounds of Formula I. Certain compounds of Formula I may be used as intermediates for other compounds of Formula I.

Another aspect of the present invention includes methods of preparing, methods of separation, and methods of purification of the compounds of this invention.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

Additional abbreviations that may be used throughout the application include, for example, benzyl ("Bn"), phenyl ("Ph") and acetate ("Ac").

The terms "heterocycle" and "heterocyclic" include four to seven membered rings containing one, two or three heteroatoms selected from the group consisting of oxygen, nitrogen and sulfur. In certain instances, these terms may be specifically further limited, such as, "five to six membered heterocyclic" only including five and six membered rings. Exemplary heterocyclic groups include, but are not limited to, oxiranyl, thiaranyl, aziridinyl, oxetanyl, thiatanyl, azetidinyl, 1,2-dithietanyl, 1,3-dithietanyl, tetrahydrofuranyl, tetrahydrothiophenyl, dithiolanyl, pyrrolidinyl, pyrazolidinyl, imidazolidinyl, 1,3-dioxolanyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, thioxanyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, and 1,4-diazepanyl.

Exemplary partially unsaturated heterocyclic groups include, but are not limited to, tetrahydropyridinyl, dihydropyridinyl, dihydropyranyl, dihydrofuranyl, 1-pyrrolinyl, 2-pyrrolinyl, 3-pyrrolinyl, 2H-pyranyl, 4H-pyranyl, and pyrazolinyl.

The term "heteroaryl" includes five to six membered aromatic rings containing one, two or three heteroatoms selected from the group consisting of oxygen, nitrogen and sulfur. In certain instances, these terms may be specifically further limited, such as, five to six membered heteroaryl, wherein the heteroaryl contains one or two nitrogen heteroatoms. Exemplary heteroaryl groups include, but are not limited to, pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, furazanyl, and triazinyl.

The term "$C_2$-$C_6$ alkanoylalkyl" as used herein, represents an alkanoyl group attached through an alkyl group (i.e., (alkanoyl)-(alkyl)-compound), wherein the alkanoyl and alkyl groups have a combined two to six carbon atoms. Exemplary $C_2$-$C_6$ alkanoylalkyl groups include ethanoylmethyl, ethanoylethyl, ethanoylpropyl, ethanoylbutyl, propanoylmethyl, propanoylethyl, propanoylpropyl, butanoylmethyl, butanoylethyl, and pentanoylmethyl.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound of the present invention that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer (including small-cell lung cancer, non-small cell lung cancer ("NSCLC"), adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

CHK1/2 Inhibitors

The present invention provides certain substituted pyrrolo[2,3-b]pyridines, and pharmaceutical formulations thereof, that inhibit CHK1 and/or CHK2. These compounds are potentially useful in the treatment of diseases, conditions and/or disorders modulated by CHK1 and/or CHK2.

One embodiment of this invention provides compounds of Formula I:

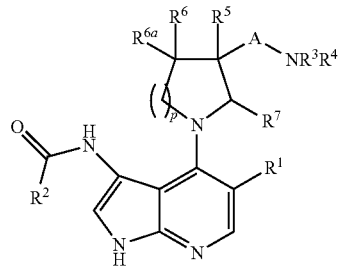

and stereoisomers, tautomers and pharmaceutically acceptable salts thereof, wherein:

A is selected from a direct bond or $CR^aR^b$;

$R^1$ is selected from hydrogen, halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, a 4 to 6 membered heterocyclic, phenyl, and a 5 or 6 membered heteroaryl, wherein the alkyls, alkenyl, cycloalkyl, heterocyclic, phenyl or heteroaryl are optionally substituted with one or more groups selected from halogen, CN, $CF_3$, $C_1$-$C_3$ alkyl, —O($C_1$-$C_3$ alkyl) and $NR^cR^d$;

$R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$;

$R^3$ and $R^4$ are independently selected from hydrogen or $C_1$-$C_4$ alkyl optionally substituted with OH, F, —O($C_1$-$C_3$ alkyl) or $C_3$-$C_6$ cycloalkyl, or $R^3$ and $R^4$ together with the atoms to which they are attached form a 5 or 6 membered ring;

$R^5$ is selected from hydrogen and $CH_3$, or

A is $CR^aR^b$, $R^a$ and $R^b$ are hydrogen, and $R^3$ and $R^5$ together with the atoms to which they are attached form a 5 or 6 membered ring;

$R^6$ is selected from hydrogen, F, OH, —$OCH_3$, $C_1$-$C_3$ alkyl and cyclopropyl, or A is a direct bond, $R^{6a}$ is hydrogen and $R^3$ and $R^6$ together with the atoms to which they are attached form a 5 or 6 membered ring;

$R^{6a}$ is selected from hydrogen, F, OH and $CH_3$;

$R^7$ is hydrogen, or

A is $CR^aR^b$ and $R^3$ and $R^7$ together with the atoms to which they are attached form a 5 or 6 membered ring;

$R^a$ is hydrogen, or $R^4$ and $R^b$ are absent and $R^3$ and $R^a$ together with the atoms to which they are attached form an aromatic 5 or 6 membered ring;

$R^b$ is hydrogen or absent;

$R^c$ and $R^d$ are independently selected from hydrogen and $C_1$-$C_3$ alkyl, or $R^c$ and $R^d$ together with the atom to which they are attached form a 5 or 6 membered ring;

$R^e$ and $R^f$ are independently selected from hydrogen and $C_1$-$C_3$ alkyl;

$R^g$ and $R^h$ are independently selected from hydrogen and $C_1$-$C_3$ alkyl;

$R^i$ is $C_1$-$C_3$ alkyl; and p is 0, 1, 2 or 3.

Compounds of Formula I include compounds wherein:

A is selected from a direct bond or $CR^aR^b$;

$R^1$ is selected from halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, a 4 to 6 membered heterocyclic, phenyl, and a 5 or 6 membered heteroaryl, wherein the alkyls, alkenyl, cycloalkyl, heterocyclic, phenyl or heteroaryl are optionally substituted with one or more groups selected from halogen, CN, $CF_3$, $C_1$-$C_3$ alkyl, —O($C_1$-$C_3$ alkyl) and $NR^cR^d$;

$R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), $CF_3$, cyclopropyl, cyclopropylmethyl, $—SO_2R^i$, $C_1$-$C_6$ alkyl, $—O(C_1$-$C_6$ alkyl), $—S(C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, $—O(C_1$-$C_3$ alkyl), and $NR^gR^h$;

$R^3$ and $R^4$ are independently selected from hydrogen or $C_1$-$C_4$ alkyl optionally substituted with OH, F, $—O(C_1$-$C_3$ alkyl) or $C_3$-$C_6$ cycloalkyl, or $R^3$ and $R^4$ together with the atoms to which they are attached form a 5 or 6 membered ring;

$R^5$ is selected from hydrogen and $CH_3$, or

A is $CR^aR^b$, $R^a$ and $R^b$ are hydrogen, and $R^3$ and $R^5$ together with the atoms to which they are attached form a 5 or 6 membered ring;

$R^6$ is selected from hydrogen, F, OH, $—OCH_3$, $C_1$-$C_3$ alkyl and cyclopropyl, or A is a direct bond, $R^{6a}$ is hydrogen and $R^3$ and $R^6$ together with the atoms to which they are attached form a 5 or 6 membered ring;

$R^{6a}$ is selected from hydrogen, F, OH and $CH_3$;

$R^7$ is hydrogen, or

A is $CR^aR^b$ and $R^3$ and $R^7$ together with the atoms to which they are attached form a 5 or 6 membered ring;

$R^a$ is hydrogen, or $R^4$ and $R^b$ are absent and $R^3$ and $R^a$ together with the atoms to which they are attached form an aromatic 5 or 6 membered ring;

$R^b$ is hydrogen or absent;

$R^c$ and $R^d$ are independently selected from hydrogen and $C_1$-$C_3$ alkyl, or $R^c$ and $R^d$ together with the atom to which they are attached form a 5 or 6 membered ring;

$R^e$ and $R^f$ are independently selected from hydrogen and $C_1$-$C_3$ alkyl;

$R^g$ and $R^h$ are independently selected from hydrogen and $C_1$-$C_3$ alkyl;

$R^i$ is $C_1$-$C_3$ alkyl; and p is 0, 1, 2 or 3.

Compounds of Formula I include compounds wherein:

A is selected from a direct bond or $CR^aR^b$;

$R^1$ is selected from hydrogen, halogen, CN, $C_1$-$C_6$ alkyl, $C_1$-$C_6$ alkenyl, $—O(C_1$-$C_6$ alkyl), $—S(C_1$-$C_6$ alkyl), $C_3$-$C_6$ cycloalkyl, phenyl, and a 5 or 6 membered heteroaryl, wherein the alkyls, alkenyl, cycloalkyl, phenyl or heteroaryl are optionally substituted with one or more groups selected from halogen, $C_1$-$C_3$ alkyl and $—O(C_1$-$C_3$ alkyl);

$R^2$ is selected from $C_1$-$C_6$ alkyl, $—O(C_1$-$C_6$ alkyl), $—NH(C_1$-$C_6$ alkyl), a saturated $C_3$-$C_6$ cycloalkyl, phenyl, a saturated or partially unsaturated 4 to 6 membered heterocycle, a 5 or 6 membered heteroaryl, and an 8 to 10 membered bicyclic heteroaryl, wherein the alkyls, cycloalkyl, phenyl, heterocycle, and heteroaryls are optionally substituted with one or more groups selected from OH, CN, halogen, oxo (except not on phenyl or heteroaryl), $CF_3$, cyclopropyl, cyclopropylmethyl, $—SO_2R^i$, $C_1$-$C_6$ alkyl, $—O(C_1$-$C_6$ alkyl), and phenyl;

$R^3$ and $R^4$ are independently selected from hydrogen or $C_1$-$C_4$ alkyl optionally substituted with OH, F, $—O(C_1$-$C_3$ alkyl) or $C_3$-$C_6$ cycloalkyl;

$R^5$ is selected from hydrogen and $CH_3$, or

A is $CR^aR^b$, $R^a$ and $R^b$ are hydrogen, and $R^3$ and $R^5$ together with the atoms to which they are attached form a 5 or 6 membered ring;

$R^6$ is selected from hydrogen, F, $—OCH_3$, $C_1$-$C_3$ alkyl, and cyclopropyl, or A is a direct bond, $R^{6a}$ is hydrogen and $R^3$ and $R^6$ together with the atoms to which they are attached form a 5 or 6 membered ring;

$R^{6a}$ is hydrogen;

$R^7$ is hydrogen, or

A is $CR^aR^b$ and $R^3$ and $R^7$ together with the atoms to which they are attached form a 5 or 6 membered ring;

$R^a$ is hydrogen, or $R^4$ and $R^b$ are absent and $R^3$ and $R^a$ together with the atoms to which they are attached form an aromatic 5 or 6 membered ring;

$R^b$ is hydrogen or absent;

$R^i$ is $C_1$-$C_3$ alkyl; and p is 0, 1, 2 or 3.

Compounds of Formula I include compounds wherein:

A is selected from a direct bond or $CR^aR^b$;

$R^1$ is selected from halogen, CN, $C_1$-$C_6$ alkyl, $C_1$-$C_6$ alkenyl, $—O(C_1$-$C_6$ alkyl), $—S(C_1$-$C_6$ alkyl), $C_3$-$C_6$ cycloalkyl, phenyl, and a 5 or 6 membered heteroaryl, wherein the alkyls, alkenyl, cycloalkyl, phenyl or heteroaryl are optionally substituted with one or more groups selected from halogen and $C_1$-$C_3$ alkyl;

$R^2$ is selected from $C_1$-$C_6$ alkyl, $—O(C_1$-$C_6$ alkyl), $—NH(C_1$-$C_6$ alkyl), a saturated $C_3$-$C_6$ cycloalkyl, phenyl, a saturated or partially unsaturated 4 to 6 membered heterocycle, a 5 or 6 membered heteroaryl, and an 8 to 10 membered bicyclic heteroaryl, wherein the alkyls, cycloalkyl, phenyl, heterocycle, and heteroaryls are optionally substituted with one or more groups selected from OH, CN, halogen, oxo (except not on phenyl or heteroaryl), $CF_3$, cyclopropyl, cyclopropylmethyl, $—SO_2R^i$, $C_1$-$C_6$ alkyl, $—O(C_1$-$C_6$ alkyl), and phenyl;

$R^3$ and $R^4$ are independently selected from hydrogen or $C_1$-$C_4$ alkyl optionally substituted with OH, F, $—O(C_1$-$C_3$ alkyl) or $C_3$-$C_6$ cycloalkyl;

$R^5$ is selected from hydrogen and $CH_3$, or

A is $CR^aR^b$, $R^a$ and $R^b$ are hydrogen, and $R^3$ and $R^5$ together with the atoms to which they are attached form a 5 or 6 membered ring;

$R^6$ is selected from hydrogen, F, $—OCH_3$, $C_1$-$C_3$ alkyl, and cyclopropyl, or A is a direct bond, $R^{6a}$ is hydrogen and $R^3$ and $R^6$ together with the atoms to which they are attached form a 5 or 6 membered ring;

$R^{6a}$ is hydrogen;

$R^7$ is hydrogen, or

A is $CR^aR^b$ and $R^3$ and $R^7$ together with the atoms to which they are attached form a 5 or 6 membered ring;

$R^a$ is hydrogen, or $R^4$ and $R^b$ are absent and $R^3$ and $R^a$ together with the atoms to which they are attached form an aromatic 5 or 6 membered ring;

$R^b$ is hydrogen or absent;

$R^i$ is $C_1$-$C_3$ alkyl; and p is 0, 1, 2 or 3.

Compounds of Formula I include compounds wherein:

A is selected from a direct bond or $CR^aR^b$;

$R^1$ is selected from hydrogen, halogen, $C_1$-$C_6$ alkyl, $—S(C_1$-$C_6$ alkyl), $C_3$-$C_6$ cycloalkyl, a 5 or 6 membered heterocyclic, phenyl, and a 5 or 6 membered heteroaryl, wherein the alkyls, cycloalkyl, heterocyclic, phenyl or heteroaryl are optionally substituted with one or more groups selected from halogen, CN, CF$_3$, C$_1$-C$_3$ alkyl, —O(C$_1$-C$_3$ alkyl), and NR$^c$R$^d$;

R$^2$ is selected from C$_1$-C$_6$ alkyl, a saturated or partially unsaturated C$_3$-C$_6$ cycloalkyl, phenyl, a saturated or partially unsaturated 5 or 6 membered heterocycle, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclics, heteroaryls and aryl are optionally substituted with one or more groups selected from OH, CN, halogen, oxo (except not on phenyl, aryl or heteroaryl), CF$_3$, C$_1$-C$_6$ alkyl, —O(C$_1$-C$_6$ alkyl), —S(C$_1$-C$_6$ alkyl), and NR$^e$R$^f$;

R$^3$ and R$^4$ are independently selected from hydrogen or C$_1$-C$_4$ alkyl optionally substituted with OH, F or C$_3$-C$_6$ cycloalkyl, or R$^3$ and R$^4$ together with the atoms to which they are attached form a 5 or 6 membered ring;

R$^5$ is selected from hydrogen and CH$_3$, or

A is CR$^a$R$^b$, R$^a$ and R$^b$ are hydrogen, and R$^3$ and R$^5$ together with the atoms to which they are attached form a 5 or 6 membered ring;

R$^6$ is selected from hydrogen, F, OH, —OCH$_3$, and C$_1$-C$_3$ alkyl, or

A is a direct bond, R$^{6a}$ is hydrogen and R$^3$ and R$^6$ together with the atoms to which they are attached form a 5 or 6 membered ring;

R$^{6a}$ is selected from hydrogen, F, OH and —OCH$_3$;

R$^7$ is hydrogen, or

A is CR$^a$R$^b$ and R$^3$ and R$^7$ together with the atoms to which they are attached form a 5 or 6 membered ring;

R$^a$ is hydrogen, or

R$^4$ and R$^b$ are absent and R$^3$ and R$^a$ together with the atoms to which they are attached form an aromatic 5 or 6 membered ring;

R$^b$ is hydrogen or absent;

R$^c$ and R$^d$ are independently selected from hydrogen and C$_1$-C$_3$ alkyl, or R$^c$ and R$^d$ together with the atom to which they are attached form a 5 or 6 membered ring;

R$^e$ and R$^f$ are independently selected from hydrogen and C$_1$-C$_3$ alkyl; and p is 0, 1, 2 or 3.

Compounds of Formula I include compounds wherein:

A is selected from a direct bond or CR$^a$R$^b$;

R$^1$ is selected from halogen, C$_3$-C$_6$ cycloalkyl and C$_1$-C$_6$ alkyl, wherein the alkyl is optionally substituted with one or more halogen groups;

R$^2$ is selected from C$_1$-C$_6$ alkyl, saturated C$_3$-C$_6$ cycloalkyl, phenyl, saturated or partially unsaturated 5 or 6 membered heterocyclic, a 5 or 6 membered heteroaryl, and an 8 to 10 membered bicyclic heteroaryl, wherein the alkyl, cycloalkyl, phenyl, heterocyclic and heteroaryls are optionally substituted with halogen, oxo (except not on phenyl or heteroaryl), CF$_3$, C$_1$-C$_6$ alkyl, —O(C$_1$-C$_6$ alkyl) or C$_3$-C$_6$ cycloalkyl;

R$^3$ is selected from hydrogen or C$_1$-C$_4$ alkyl optionally substituted with OH or C$_3$-C$_6$ cycloalkyl;

R$^4$ is selected from hydrogen and C$_1$-C$_4$ alkyl;

R$^5$ is selected from hydrogen and CH$_3$, or

A is CR$^a$R$^b$, R$^a$ and R$^b$ are hydrogen, and R$^3$ and R$^5$ together with the atoms to which they are attached form a 5 or 6 membered ring;

R$^6$ is hydrogen, or

A is a direct bond and R$^3$ and R$^6$ together with the atoms to which they are attached form a 5 or 6 membered ring;

R$^{6a}$ is hydrogen;

R$^7$ is selected from hydrogen, or

A is CR$^a$R$^b$ and R$^3$ and R$^7$ together with the atoms to which they are attached form a 5 or 6 membered ring;

R$^a$ and R$^b$ are hydrogen, or

R$^4$ and R$^b$ are absent and R$^3$ and R$^a$ together with the atoms to which they are attached form an aromatic 5 or 6 membered ring; and p is 1 or 2.

Compounds of Formula I include compounds wherein:

A is selected from a direct bond or CR$^a$R$^b$;

R$^1$ is selected from halogen, C$_3$-C$_6$ cycloalkyl and C$_1$-C$_6$ alkyl, wherein the alkyl is optionally substituted with one or more halogen groups;

R$^2$ is selected from C$_1$-C$_6$ alkyl, saturated C$_3$-C$_6$ cycloalkyl, phenyl, saturated or partially unsaturated 5 or 6 membered heterocyclic, a 5 or 6 membered heteroaryl, and an 8 to 10 membered bicyclic heteroaryl, wherein the alkyl, cycloalkyl, phenyl, heterocyclic and heteroaryls are optionally substituted with halogen, oxo (except not on phenyl or heteroaryl), CF$_3$, C$_1$-C$_6$ alkyl, —O(C$_1$-C$_6$ alkyl) or C$_3$-C$_6$ cycloalkyl;

R$^3$ is selected from hydrogen or C$_1$-C$_4$ alkyl optionally substituted with OH or C$_3$-C$_6$ cycloalkyl;

R$^4$ is selected from hydrogen and C$_1$-C$_4$ alkyl;

R$^5$ is selected from hydrogen and CH$_3$, or

A is CR$^a$R$^b$, R$^a$ and R$^b$ are hydrogen, and R$^3$ and R$^5$ together with the atoms to which they are attached form a 5 or 6 membered ring;

R$^6$ is hydrogen, or

A is a direct bond and R$^3$ and R$^6$ together with the atoms to which they are attached form a 5 or 6 membered ring;

R$^{6a}$ is hydrogen;

R$^7$ is selected from hydrogen, or

A is CR$^a$R$^b$ and R$^3$ and R$^7$ together with the atoms to which they are attached form a 5 or 6 membered ring;

R$^a$ and R$^b$ are hydrogen, or

R$^4$ and R$^b$ are absent and R$^3$ and R$^a$ together with the atoms to which they are attached form an aromatic 5 or 6 membered ring; and p is 1 or 2.

In certain embodiments, p is 0, 1, 2 or 3.

In certain embodiments, p is 0, 1, or 2.

In certain embodiments, p is 1 or 2.

In certain embodiments, p is 0, as shown in Formula IIa:

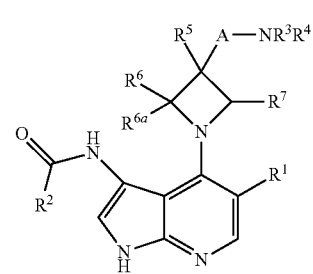

wherein R$^1$, R$^2$, R$^3$, R$^4$, R$^5$, R$^6$, R$^{6a}$, R$^7$ and A are as defined herein.

In certain embodiments, p is 1, as shown in Formula IIb:

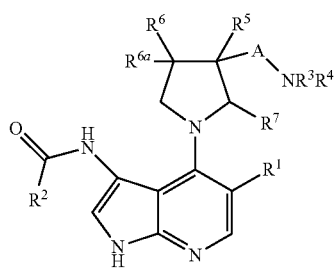

IIb wherein $R^1$, $R^2$, $R^3$, $R^4$, $R^5$, $R^6$, $R^{6a}$, $R^7$ and A are as defined herein.

In certain embodiments, p is 2, as shown in Formula IIc:

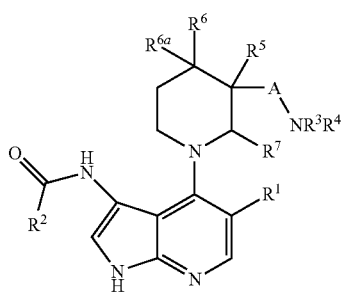

IIc wherein $R^1$, $R^2$, $R^3$, $R^4$, $R^5$, $R^6$, $R^{6a}$, $R^7$ and A are as defined herein.

In certain embodiments, p is 3, as shown in Formula IId:

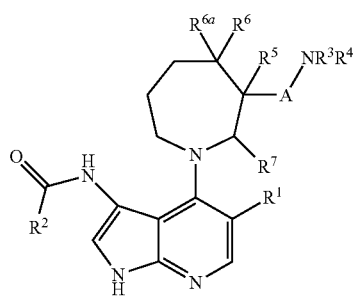

IId wherein $R^1$, $R^2$, $R^3$, $R^4$, $R^5$, $R^6$, $R^{6a}$, $R^7$ and A are as defined herein.

In certain embodiments, $R^1$ is selected from hydrogen, halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, a 4 to 6 membered heterocyclic, phenyl, and a 5 or 6 membered heteroaryl, wherein the alkyls, alkenyl, cycloalkyl, heterocyclic, phenyl or heteroaryl are optionally substituted with one or more groups selected from halogen, CN, $CF_3$, $C_1$-$C_3$ alkyl, —O($C_1$-$C_3$ alkyl) and $NR^cR^d$.

In certain embodiments, $R^1$ is selected from halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, a 4 to 6 membered heterocyclic, phenyl, and a 5 or 6 membered heteroaryl, wherein the alkyls, alkenyl, cycloalkyl, heterocyclic, phenyl or heteroaryl are optionally substituted with one or more groups selected from halogen, CN, $CF_3$, $C_1$-$C_3$ alkyl, —O($C_1$-$C_3$ alkyl) and $NR^cR^d$.

In certain embodiments, $R^1$ is selected from hydrogen, halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, phenyl, and a 5 or 6 membered heteroaryl, wherein the alkyls, alkenyl, cycloalkyl, phenyl or heteroaryl are optionally substituted with one or more groups selected from halogen, $C_1$-$C_3$ alkyl and —O($C_1$-$C_3$ alkyl).

In certain embodiments, $R^1$ is selected from halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, phenyl, and a 5 or 6 membered heteroaryl, wherein the alkyls, alkenyl, cycloalkyl, phenyl or heteroaryl are optionally substituted with one or more groups selected from halogen, $C_1$-$C_3$ alkyl and —O($C_1$-$C_3$ alkyl).

In certain embodiments, $R^1$ is selected from hydrogen, halogen, $C_1$-$C_6$ alkyl, —S($C_1$-$C_6$ alkyl), $C_3$-$C_6$ cycloalkyl, a 5 or 6 membered heterocyclic, phenyl, and a 5 or 6 membered heteroaryl, wherein the alkyls, cycloalkyl, heterocyclic, phenyl or heteroaryl are optionally substituted with one or more groups selected from halogen, CN, $CF_3$, $C_1$-$C_3$ alkyl, —O($C_1$-$C_3$ alkyl) and $NR^cR^d$.

In certain embodiments, $R^1$ is selected from halogen, $C_3$-$C_6$ cycloalkyl and $C_1$-$C_6$ alkyl, wherein the alkyl is optionally substituted with one or more halogen groups. In certain embodiments, $R^1$ is selected from halogen, $C_3$-$C_6$ cycloalkyl and $C_1$-$C_6$ alkyl, wherein the alkyl is optionally substituted with one or more F groups.

In certain embodiments, $R^1$ is selected from hydrogen, Br, Cl, F, CN, $CF_3$, methyl, ethyl, isopropyl, prop-1-en-2-yl, —$OCH_2CH_3$, —$OCH_2CH_2OCH_3$, —$SCH_3$, —$SCH_2CH_3$, —$SCH(CH_3)_2$, cyclopropyl, phenyl and 6-methylpyridin-3-yl.

In certain embodiments, $R^1$ is selected from Br, Cl, F, CN, $CF_3$, methyl, ethyl, isopropyl, prop-1-en-2-yl, —$OCH_2CH_3$, —$OCH_2CH_2OCH_3$, —$SCH_3$, —$SCH_2CH_3$, —$SCH(CH_3)_2$, cyclopropyl, phenyl and 6-methylpyridin-3-yl.

In certain embodiments, $R^1$ is selected from Br, Cl, F, cyclopropyl and $CF_3$.

In certain embodiments, $R^1$ is hydrogen.

In certain embodiments, $R^1$ is halogen. In certain embodiments, $R^1$ is selected from Br, Cl and F.

In certain embodiments, $R^1$ is CN.

In certain embodiments, $R^1$ is $C_1$-$C_6$ alkyl, wherein the alkyl is optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is $C_1$-$C_6$ alkyl. In certain embodiments, $R^1$ is methyl, ethyl or isopropyl.

In certain embodiments, $R^1$ is $C_1$-$C_6$ alkenyl, wherein the alkenyl is optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is $C_1$-$C_6$ alkenyl. In certain embodiments, $R^1$ is prop-1-en-2-yl.

In certain embodiments, $R^1$ is —O($C_1$-$C_6$ alkyl), wherein the alkyl is optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is —O($C_1$-$C_6$ alkyl) optionally substituted with —O($C_1$-$C_3$ alkyl). In certain embodiments, $R^1$ is —$OCH_2CH_3$ and —$OCH_2CH_2OCH_3$.

In certain embodiments, $R^1$ is —S($C_1$-$C_6$ alkyl), wherein the alkyl is optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is —S($C_1$-$C_6$ alkyl). In certain embodiments, $R^1$ is —$SCH_3$, —$SCH_2CH_3$ or —$SCH(CH_3)_2$.

In certain embodiments, $R^1$ is $C_3$-$C_6$ cycloalkyl optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is $C_3$-$C_6$ cycloalkyl. In certain embodiments, $R^1$ is cyclopropyl.

In certain embodiments, $R^1$ is $C_3$-$C_6$ cycloalkyl. In certain embodiments, $R^1$ is cyclopropyl.

In certain embodiments, $R^1$ is $C_1$-$C_6$ alkyl, wherein the alkyl is optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is $C_1$-$C_6$ alkyl, wherein the alkyl is optionally substituted with one or more halogen groups. In certain embodiments, $R^1$ is $C_1$-$C_6$ alkyl, wherein the alkyl is optionally substituted with three F groups. In certain embodiments, $R^1$ is $CF_3$.

In certain embodiments, $R^1$ is $C_1$-$C_6$ alkyl, wherein the alkyl is optionally substituted with one or more halogen groups. In certain embodiments, $R^1$ is $C_1$-$C_6$ alkyl, wherein the alkyl is optionally substituted with three F groups. In certain embodiments, $R^1$ is $CF_3$.

In certain embodiments, $R^1$ is phenyl optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is phenyl.

In certain embodiments, $R^1$ is a 5 or 6 membered heteroaryl optionally substituted with one or more groups selected from halogen, CN, $CF_3$, $C_1$-$C_3$ alkyl, —O($C_1$-$C_3$ alkyl) and $NR^cR^d$. In certain embodiments, $R^1$ is a 5 or 6 membered heteroaryl optionally substituted with $C_1$-$C_3$ alkyl. In certain embodiments, $R^1$ is a 5 or 6 membered heteroaryl optionally substituted with $C_1$-$C_3$ alkyl, wherein the heteroaryl contains one or two heteroatoms selected from nitrogen, oxygen and sulfur. In certain embodiments, $R^1$ is a 5 or 6 membered heteroaryl optionally substituted with $C_1$-$C_3$ alkyl, wherein the heteroaryl contains one or two nitrogen heteroatoms. In certain embodiments, $R^1$ is a 5 or 6 membered heteroaryl optionally substituted with $C_1$-$C_3$ alkyl, wherein the heteroaryl is pyridinyl. In certain embodiments, $R^1$ is 6-methylpyridin-3-yl.

In certain embodiments, $R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$.

In certain embodiments, $R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl.

In certain embodiments, $R^2$ is selected from $C_1$-$C_6$ alkyl, —O($C_1$-$C_6$ alkyl), —NH($C_1$-$C_6$ alkyl), a saturated $C_3$-$C_6$ cycloalkyl, phenyl, a saturated or partially unsaturated 4 to 6 membered heterocyclic, a 5 or 6 membered heteroaryl, and an 8 to 10 membered bicyclic heteroaryl, wherein the alkyls, cycloalkyl, phenyl, heterocyclic, and heteroaryls are optionally substituted with one or more groups selected from OH, CN, halogen, oxo (except not on phenyl, aryl or heteroaryl), $CF_3$, cyclopropyl, cyclopropylmethyl, —$SO_2R^i$, $C_1$-$C_6$ alkyl, —O($C_1$-$C_6$ alkyl), and phenyl.

In certain embodiments, $R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein: (1) the alkyls, cycloalkyl, and heterocyclics are optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$; and (2) the phenyl, heteroaryls and aryl are optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$.

In certain embodiments, $R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein: (1) the alkyls, cycloalkyl, and heterocyclics are optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl; and (2) the phenyl, heteroaryls and aryl are optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl.

In certain embodiments, $R^2$ is selected from $C_1$-$C_6$ alkyl, —O($C_1$-$C_6$ alkyl), —NH($C_1$-$C_6$ alkyl), a saturated $C_3$-$C_6$ cycloalkyl, phenyl, a saturated or partially unsaturated 4 to 6 membered heterocyclic, a 5 or 6 membered heteroaryl, and an 8 to 10 membered bicyclic heteroaryl, wherein: (1) the alkyls, cycloalkyl, and heterocyclic are optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), and phenyl; and (2) the phenyl and heteroaryls are optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), and phenyl.

In certain embodiments, $R^2$ is selected from $C_1$-$C_6$ alkyl, a saturated or partially unsaturated $C_3$-$C_6$ cycloalkyl, phenyl, a saturated or partially unsaturated 5 or 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclics, heteroaryls and aryl are optionally substituted with one or more groups selected from OH, CN, halogen, oxo (except not on phenyl, aryl or heteroaryl), $CF_3$, $C_1$-$C_6$ alkyl, —O($C_1$-$C_6$ alkyl), —S($C_1$-$C_6$ alkyl), and $NR^eR^f$.

In certain embodiments, $R^2$ is selected from $C_1$-$C_6$ alkyl, a saturated or partially unsaturated $C_3$-$C_6$ cycloalkyl, phenyl, a saturated or partially unsaturated 5 or 6 membered heterocyclic, a 5 or 6 membered heteroaryl, and an 8 to 10 membered bicyclic heteroaryl, wherein the alkyl, cycloalkyl, phenyl, heterocyclic and heteroaryls are optionally substituted with halogen, oxo (except not on phenyl or heteroaryl), $CF_3$, $C_1$-$C_6$ alkyl, —O($C_1$-$C_6$ alkyl), or $C_3$-$C_6$ cycloalkyl. In certain embodiments, $R^2$ is selected from $C_1$-$C_6$ alkyl, a saturated $C_3$-$C_6$ cycloalkyl, phenyl, a saturated or partially unsaturated 5 or 6 membered heterocyclic, a 5 or 6 membered heteroaryl, and an 8 to 10 membered bicyclic heteroaryl, wherein the alkyl, cycloalkyl, heterocyclic are optionally substituted with halogen, oxo, $CF_3$, $C_1$-$C_6$ alkyl, —O($C_1$-$C_6$ alkyl), or $C_3$-$C_6$ cycloalkyl, and wherein the phenyl and heteroaryls are optionally substituted with halogen, $CF_3$, $C_1$-$C_6$ alkyl, —O($C_1$-$C_3$ alkyl), or $C_3$-$C_6$ cycloalkyl.

In certain embodiments, $R^2$ is selected from methyl, ethyl, propyl, isopropyl, tert-butyl, isobutyl, cyclopropylmethyl, —$CH_2CF_3$, —$CH(CH_2CH_3)_2$, —$CH_2OH$, —$CH_2OCH_3$, —$CH_2OCH_2CH_3$, —$CH(CH_3)OCH_3$, —$CH_2CH_2OCH_3$, —$CH(CH_3)OH$, —$C(CH_3)_2OH$, —$CH_2CN$, —$CH_2CH_2F$, —$C(CH_3)_2F$, —$CH(CH_3)CH_2CH_3$, —$CH_2OCH(CH_3)_2$, —$CH(CH_3)OCH(CH_3)_2$, —$CH_2SO_2CH_3$, —$CH(CH_3)$phenyl, —$CH_2$(phenyl), —$OCH_2CH_3$, —$NH(CH_2CH_3)$, cyclopropyl, cyclobutyl, cyclopentyl, 1-(trifluoromethyl)cyclopropyl, 1-(methoxy)cyclopropyl, 2,2-difluorocyclopropyl, 1-methylcyclopropyl, 2-phenylcyclopropyl, 2,2-dimethylcyclopropyl, phenyl, 3-methylphenyl, 4-fluorophenyl, 3-methoxyphenyl, 3-fluorophenyl, 3-chloro-4-fluorophenyl, 3-fluoro-4-methoxyphenyl, 3-trifluoromethylphenyl, 2-fluoro-5-methylphenyl, 3-methyloxetan-3-yl, azetidin-1-yl, tetrahydrofuran-2-yl, tetrahydrofuran-3-yl, 1-methyl-6-oxo-1,6-dihydropyridin-3-yl, 1-methyl-6-oxo-1,6-dihydropyridazin-3-yl, 1-isopropyl-6-oxo-1,6-dihydropyridazin-3-yl, 1-(cyclopropylmethyl)-6-oxo-1,6-dihydropyridazin-3-yl, morpholin-2-yl, pyrrolidin-1-yl, 5-oxopyrrolidin-2-yl, pyrazol-4-yl, 1-methyl-1H-pyrazol-3-yl, 1-methyl-1H-pyrazol-4-yl, 2-methyloxazol-4-yl, 5-methylisoxazol-3-yl, 2-methylthiazol-4-yl, pyridin-2-yl, pyridin-3-yl, 6-methoxypyridin-2-yl, 3-methylpyridin-2-yl, 5-chloro-pyridin-2-yl, 5-trifluoromethylpyridin-2-yl, 2-methylpyridin-3-yl, 5-methylpyridin-3-yl, 5-chloropyridin-3-yl, 6-methylpyridin-3-yl, pyrimidin-2-yl, 5-ethylpyrimidin-2-yl, pyrazin-2-yl, 5-methylpyrazin-2-yl, and quinoxalin-2-yl.

In certain embodiments, $R^2$ is selected from isopropyl, tert-butyl, isobutyl, cyclopropylmethyl, —$CH(CH_2CH_3)_2$, —$CH_2OCH_3$, —$CH(CH_3)OCH_3$, —$CH_2CH_2OCH_3$, —$CH$(cyclopropyl)$CF_3$, cyclopropyl, cyclobutyl, cyclopentyl, phenyl, 3-methylphenyl, 4-fluorophenyl, 3-methoxyphenyl, 3-fluorophenyl, 3-chloro-4-fluorophenyl, 3-fluoro-4-methoxyphenyl, 3-trifluoromethylphenyl, 2-fluoro-5-methylphenyl, tetrahydrofuran-2-yl, tetrahydrofuran-3-yl, 1-methyl-6-oxo-1,6-dihydropyridin-3-yl, 1-methyl-6-oxo-1,6-dihydropyridazin-3-yl, morpholin-2-yl, pyrazol-4-yl, 1-methyl-1H-pyrazol-3-yl, 2-methyloxazol-4-yl, 5-methylisoxazol-3-yl, 2-methylthiazol-4-yl, pyridin-2-yl, pyridin-3-yl, 6-methoxy-pyridin-2-yl, 3-methylpyridin-2-yl, 5-chloro-pyridin-2-yl, 5-methylpyridin-2-yl, 2-methylpyridin-3-yl, 5-methylpyridin-3-yl, 5-chloropyridin-3-yl, 6-methylpyridin-3-yl, pyrimidin-2-yl, pyrazin-2-yl, 5-methylpyrazin-2-yl and quinoxalin-2-yl.

In the present invention, $R^2$ may be $C_1$-$C_6$ alkyl optionally substituted with oxo. As the $R^2$ substituent is immediately adjacent to the carbonyl group of the amide at the 3 position of the 1H-pyrrolo[2,3-b]pyridine of Formula I, when $R^2$ is $C_1$-$C_6$ alkyl optionally substituted with oxo then the first carbon (immediately adjacent to the carbonyl group of the amide) may not be substituted with an oxo group.

In certain embodiments, $R^2$ is selected from $C_1$-$C_6$ alkyl, —O($C_1$-$C_6$ alkyl), —NH($C_1$-$C_6$ alkyl), $C_2$-$C_6$ alkanoylalkyl, a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, alkanoyl, cycloalkyl, phenyl, heterocyclics, heteroaryls and aryl are optionally substituted with one or more groups selected from OH, CN, halogen, oxo (except not on alkyl, phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$.

In certain embodiments, $R^2$ is selected from $C_1$-$C_6$ alkyl, —O($C_1$-$C_6$ alkyl), —NH($C_1$-$C_6$ alkyl), $C_2$-$C_6$ alkanoylalkyl, a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, alkanoyl, cycloalkyl, phenyl, heterocyclics, heteroaryls and aryl are optionally substituted with one or more groups selected from OH, CN, halogen, oxo (except not on alkyl, phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl.

In certain embodiments, $R^2$ is selected from $C_1$-$C_6$ alkyl, —O($C_1$-$C_6$ alkyl), —NH($C_1$-$C_6$ alkyl), $C_2$-$C_6$ alkanoylalkyl, a saturated $C_3$-$C_6$ cycloalkyl, phenyl, a saturated or partially unsaturated 4 to 6 membered heterocyclic, a 5 or 6 membered heteroaryl, and an 8 to 10 membered bicyclic heteroaryl, wherein the alkyls, alkanoyl, cycloalkyl, phenyl, heterocyclic, and heteroaryls are optionally substituted with one or more groups selected from OH, CN, halogen, oxo (except not on alkyl, phenyl, aryl or heteroaryl), $CF_3$, cyclopropyl, cyclopropylmethyl, —$SO_2R^i$, $C_1$-$C_6$ alkyl, —O($C_1$-$C_6$ alkyl), and phenyl.

In certain embodiments, $R^2$ is selected from $C_1$-$C_6$ alkyl, —O($C_1$-$C_6$ alkyl), —NH($C_1$-$C_6$ alkyl), $C_2$-$C_6$ alkanoylalkyl, a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein: (1) the O(alkyl), —NH(alkyl), cycloalkyl, and heterocyclics are optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$; and (2) the alkyl, phenyl, heteroaryls and aryl are optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$.

In certain embodiments, $R^2$ is selected from $C_1$-$C_6$ alkyl, —O($C_1$-$C_6$ alkyl), —NH($C_1$-$C_6$ alkyl), $C_2$-$C_6$ alkanoylalkyl, a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein: (1) the O(alkyl), —NH(alkyl), cycloalkyl, and heterocyclics are optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl; and (2) the alkyl, phenyl, heteroaryls and aryl are optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl.

In certain embodiments, $R^2$ is selected from $C_1$-$C_6$ alkyl, —O($C_1$-$C_6$ alkyl), —NH($C_1$-$C_6$ alkyl), $C_2$-$C_6$ alkanoylalkyl, a saturated $C_3$-$C_6$ cycloalkyl, phenyl, a saturated or partially unsaturated 4 to 6 membered heterocyclic, a 5 or 6 membered heteroaryl, and an 8 to 10 membered bicyclic heteroaryl, wherein: (1) the O(alkyl), —NH(alkyl), cycloalkyl, and heterocyclics are optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), and phenyl; and (2) the alkyl, phenyl, heteroaryls and aryl are optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), and phenyl.

In the present invention, $R^2$ may be optionally substituted $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, or an 8 to 10 membered bicyclic heteroaryl. These optional substitutions include an oxo substituent. This oxo substituent may not be a substituent if $R^2$ is phenyl, aryl or heteroaryl. Thus, "oxo (except not on phenyl, aryl or heteroaryl)" means that the oxo substituent is not an optional substituent for phenyl, aryl or heteroaryl.

In certain embodiments, $R^2$ is $C_1$-$C_6$ alkyl optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is $C_1$-$C_6$ alkyl optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is $C_1$-$C_6$ alkyl optionally substituted with one or more groups selected from OH, CN, halogen, oxo, $CF_3$, —$SO_2R^i$, $C_1$-$C_6$ alkyl, —O($C_1$-$C_6$ alkyl), —S($C_1$-$C_6$ alkyl), and $NR^eR^f$, and phenyl. In certain embodiments, $R^2$ is $C_1$-$C_6$ alkyl optionally substituted with one or more groups selected from OH, CN, halogen, $CF_3$, cyclopropyl, —$SO_2R^i$, —O($C_1$-$C_6$ alkyl), and phenyl. In certain embodiments, $R^2$ is $C_1$-$C_6$ alkyl optionally substituted with —O($C_1$-$C_6$ alkyl), wherein the —O($C_1$-$C_6$ alkyl) is methoxy (—$OCH_3$), ethoxy (—$OCH_2CH_3$), or isopropoxy (—$OCH(CH_3)_2$). In certain embodiments, $R^2$ is $C_1$-$C_6$ alkyl optionally substituted with cyclopropyl. In certain embodiments, $R^2$ is $C_1$-$C_6$ alkyl optionally substituted with —$SO_2R^i$, wherein $R^i$ is $C_1$-$C_3$ alkyl. In certain embodiments, $R^2$ is selected from methyl, ethyl, propyl, isopropyl, tert-butyl, isobutyl (—$CH_2CH(CH_3)_2$), cyclopropylmethyl, —$CH_2CF_3$, $CH(CH_2CH_3)_2$, —$CH_2OH$, —$CH_2OCH_3$, —$CH_2OCH_2CH_3$, —$CH(CH_3)OCH_3$, —$CH_2CH_2OCH_3$, —$CH(CH_3)OH$, —$C(CH_3)_2OH$, —$CH_2CN$, —$CH_2CH_2F$, —$C(CH_3)_2F$, —$CH(CH_3)CH_2CH_3$, —$CH_2OCH(CH_3)_2$, —$CH(CH_3)OCH(CH_3)_2$, —$CH_2SO_2CH_3$, $CH(CH_3)$phenyl, and $CH_2$(phenyl).

In certain embodiments, $R^2$ is $C_1$-$C_6$ alkyl optionally substituted with one or more groups selected from OH, CN, halogen, oxo, $CF_3$, $C_1$-$C_6$ alkyl, —O($C_1$-$C_6$ alkyl), —S($C_1$-$C_6$ alkyl), and $NR^eR^f$. In certain embodiments, $R^2$ is $C_1$-$C_6$ alkyl optionally substituted with one or more groups selected from oxo, $CF_3$, —O($C_1$-$C_6$ alkyl), or $C_3$-$C_6$ cycloalkyl. In certain embodiments, $R^2$ is $C_1$-$C_6$ alkyl optionally substituted with oxo. In certain embodiments, $R^2$ is $C_1$-$C_6$ alkyl optionally substituted with —O($C_1$-$C_6$ alkyl), wherein the —O($C_1$-$C_6$ alkyl) is methoxy (—$OCH_3$). In certain embodiments, $R^2$ is $C_1$-$C_6$ alkyl optionally substituted with $C_3$-$C_6$ cycloalkyl, wherein the $C_3$-$C_6$ cycloalkyl is cyclopropyl. In certain embodiments, $R^2$ is selected from isopropyl, tert-butyl, isobutyl (—$CH_2CH(CH_3)_2$), cyclopropylmethyl, $CH(CH_2CH_3)_2$, —$CH_2OCH_3$, —$CH(CH_3)OCH_3$, —$CH_2CH_2OCH_3$, and $C$(cyclopropyl)$CF_3$.

In certain embodiments, $R^2$ is $C_1$-$C_6$ alkyl. In certain embodiments, $R^2$ is selected from methyl, ethyl, propyl, isopropyl, tert-butyl, isobutyl, $CH(CH_2CH_3)_2$ and —$CH(CH_3)CH_2CH_3$.

In certain embodiments, $R^2$ is $C_1$-$C_6$ alkyl. In certain embodiments, $R^2$ is selected from isopropyl, tert-butyl, isobutyl, and $CH(CH_2CH_3)_2$.

In certain embodiments, $R^2$ is $C_1$-$C_6$ alkyl substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is $C_1$-$C_6$ alkyl substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is $C_1$-$C_6$ alkyl substituted with one or more groups selected from OH, CN, halogen, $CF_3$, cyclopropyl, —$SO_2R^i$, —O($C_1$-$C_6$ alkyl), and phenyl. In certain embodiments, $R^2$ is $C_1$-$C_6$ alkyl optionally substituted with —O($C_1$-$C_6$ alkyl), wherein the —O($C_1$-$C_6$ alkyl) is methoxy, ethoxy or isopropoxy. In certain embodiments, $R^2$ is $C_1$-$C_6$ alkyl substituted with cyclopropyl. In certain embodiments, $R^2$ is $C_1$-$C_6$ alkyl optionally substituted with —$SO_2R^i$, wherein $R^i$ is $C_1$-$C_3$ alkyl. In certain embodiments, $R^2$ is $C_1$-$C_6$ alkyl optionally substituted with phenyl. In certain embodiments, $R^2$ is cyclopropylmethyl, —$CH_2CF_3$, —$CH_2OH$, —$CH_2OCH_3$, —$CH_2OCH_2CH_3$, —$CH(CH_3)OCH_3$, —$CH_2CH_2OCH_3$, —$CH(CH_3)OH$, —$C(CH_3)_2OH$, —$CH_2CN$, —$CH_2CH_2F$, —$C(CH_3)_2F$, —$CH(CH_3)CH_2CH_3$, —$CH_2OCH(CH_3)_2$, —$CH(CH_3)OCH(CH_3)_2$, —$CH_2SO_2CH_3$, $CH(CH_3)$phenyl, and $CH_2$(phenyl).

In certain embodiments, $R^2$ is $C_1$-$C_6$ alkyl substituted with one or more groups selected from OH, CN, halogen, oxo, $CF_3$, $C_1$-$C_6$ alkyl, —O($C_1$-$C_6$ alkyl), —S($C_1$-$C_6$ alkyl), and $NR^eR^f$. In certain embodiments, $R^2$ is $C_1$-$C_6$ alkyl substituted with one or more groups selected from oxo, $CF_3$, —O($C_1$-$C_6$ alkyl), or $C_3$-$C_6$ cycloalkyl. In certain embodiments, $R^2$ is $C_1$-$C_6$ alkyl optionally substituted with oxo. In certain embodiments, $R^2$ is $C_1$-$C_6$ alkyl optionally substituted with —O($C_1$-$C_6$ alkyl), wherein the —O($C_1$-$C_6$ alkyl) is methoxy. In certain embodiments, $R^2$ is $C_1$-$C_6$ alkyl substituted with $C_3$-$C_6$ cycloalkyl, wherein the $C_3$-$C_6$ cycloalkyl is cyclopropyl. In certain embodiments, $R^2$ is $C_1$-$C_6$ alkyl substituted with oxo and —O($C_1$-$C_6$ alkyl). In certain embodiments, $R^2$ is $C_1$-$C_6$ alkyl substituted with oxo and —O($C_1$-$C_6$ alkyl), wherein the —O($C_1$-$C_6$ alkyl) is methoxy. In certain embodiments, $R^2$ is $C_1$-$C_6$ alkyl substituted with oxo, $CF_3$, and $C_3$-$C_6$ cycloalkyl. In certain embodiments, $R^2$ is $C_1$-$C_6$ alkyl substituted with oxo, $CF_3$, and $C_3$-$C_6$ cycloalkyl, wherein the $C_3$-$C_6$ cycloalkyl is cyclopropyl. In certain embodiments, $R^2$ is cyclopropylmethyl, —$CH_2OCH_3$, —$CH(CH_3)OCH_3$, —$CH_2CH_2OCH_3$, and C(cyclopropyl)$CF_3$.

In certain embodiments, $R^2$ is —O($C_1$-$C_6$ alkyl), wherein the alkyl is optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is —O($C_1$-$C_6$ alkyl). In certain embodiments, $R^2$ is —$OCH_2CH_3$.

In certain embodiments, $R^2$ is —NH($C_1$-$C_6$ alkyl), wherein the alkyl is optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is —NH($C_1$-$C_6$ alkyl). In certain embodiments, $R^2$ is —NH($CH_2CH_3$).

In certain embodiments, $R^2$ is a $C_2$-$C_6$ alkanoylalkyl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is a $C_2$-$C_6$ alkanoylalkyl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is a $C_2$-$C_6$ alkanoylalkyl.

In certain embodiments, $R^2$ is a saturated or partially unsaturated $C_3$-$C_6$ cycloalkyl optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is a saturated or partially unsaturated $C_3$-$C_6$ cycloalkyl optionally substituted with one or more groups selected from OH, CN, halogen, oxo, $CF_3$, cyclopropyl, cyclopropylmethyl, $C_1$-$C_6$ alkyl, —O($C_1$-$C_6$ alkyl), —S($C_1$-$C_6$ alkyl), $NR^eR^f$, and phenyl. In certain embodiments, $R^2$ is a saturated or partially unsaturated $C_3$-$C_6$ cycloalkyl optionally substituted with one or more groups selected from halogen, $CF_3$, $C_1$-$C_6$ alkyl, —O($C_1$-$C_6$ alkyl), and phenyl. In certain embodiments, $R^2$ is a saturated $C_3$-$C_6$ cycloalkyl optionally substituted with one or more groups selected from halogen, $CF_3$, $C_1$-$C_6$ alkyl, —O($C_1$-$C_6$ alkyl), and phenyl. In certain embodiments, $R^2$ is selected from cyclopropyl, cyclobutyl, cyclopentyl, 1-(trifluoromethyl)cyclopropyl, 1-(methoxy)cyclopropyl, 2,2-difluorocyclopropyl, 1-methylcyclopropyl, 2-phenylcyclopropyl, and 2,2-dimethylcyclopropyl.

In certain embodiments, $R^2$ is a saturated or partially unsaturated $C_3$-$C_6$ cycloalkyl optionally substituted with one or more groups selected from OH, CN, halogen, oxo, $CF_3$, $C_1$-$C_6$ alkyl, —O($C_1$-$C_6$ alkyl), —S($C_1$-$C_6$ alkyl), and $NR^eR^f$.

In certain embodiments, $R^2$ is a saturated or partially unsaturated $C_3$-$C_6$ cycloalkyl. In certain embodiments, $R^2$ is a saturated $C_3$-$C_6$ cycloalkyl. In certain embodiments, $R^2$ is selected from cyclopropyl, cyclobutyl and cyclopentyl.

In certain embodiments, $R^2$ is phenyl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is phenyl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is phenyl optionally substituted with one or more groups selected from halogen, $CF_3$, $C_1$-$C_6$ alkyl or —O($C_1$-$C_6$ alkyl). In certain embodiments, $R^2$ is phenyl substituted with halogen, wherein the halogen is F or Cl. In certain embodiments, $R^2$ is phenyl substituted with —O($C_1$-$C_6$ alkyl), wherein the —O($C_1$-$C_6$ alkyl) is methoxy. In certain embodiments, $R^2$ is selected from phenyl, 3-methylphenyl, 4-fluorophenyl, 3-methoxyphenyl, 3-fluorophenyl, 3-chloro-4-fluorophenyl, 3-fluoro-4-methoxyphenyl, 3-trifluoromethylphenyl, and 2-fluoro-5-methylphenyl.

In certain embodiments, $R^2$ is phenyl optionally substituted with one or more groups selected from OH, CN, halogen, $CF_3$, $C_1$-$C_6$ alkyl, —O($C_1$-$C_6$ alkyl), —S($C_1$-$C_6$ alkyl), and $NR^eR^f$. In certain embodiments, $R^2$ is phenyl optionally substituted with one or more groups selected from halogen, $CF_3$, $C_1$-$C_6$ alkyl or —O($C_1$-$C_6$ alkyl). In certain embodiments, $R^2$ is phenyl substituted with halogen, wherein the halogen is F or Cl. In certain embodiments, $R^2$ is phenyl substituted with $CF_3$. In certain embodiments, $R^2$ is phenyl substituted with $C_1$-$C_6$ alkyl, wherein the $C_1$-$C_6$ alkyl is methyl. In certain embodiments, $R^2$ is phenyl substituted with —O($C_1$-$C_6$ alkyl), wherein the —O($C_1$-$C_6$ alkyl) is methoxy. In certain embodiments, $R^2$ is selected from phenyl, 3-methylphenyl, 4-fluorophenyl, 3-methoxyphenyl, 3-fluorophenyl, 3-chloro-4-fluorophenyl, 3-fluoro-4-methoxyphenyl, 3-trifluoromethylphenyl, and 2-fluoro-5-methylphenyl.

In certain embodiments, $R^2$ is phenyl optionally substituted with two groups selected from halogen, $C_1$-$C_6$ alkyl or —O($C_1$-$C_6$ alkyl). In certain embodiments, $R^2$ is phenyl substituted with halogen, wherein the halogen is F or Cl. In certain embodiments, $R^2$ is phenyl substituted with $C_1$-$C_6$ alkyl, wherein the $C_1$-$C_6$ alkyl is methyl. In certain embodiments, $R^2$ is phenyl substituted with —O($C_1$-$C_6$ alkyl), wherein the —O($C_1$-$C_6$ alkyl) is methoxy. In certain embodiments, $R^2$ is selected from 3-chloro-4-fluorophenyl, 3-fluoro-4-methoxyphenyl, and 2-fluoro-5-methylphenyl.

In certain embodiments, $R^2$ is a saturated or partially unsaturated 4 to 6 membered heterocyclic optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is a saturated or partially unsaturated 4 to 6 membered heterocyclic optionally substituted with one or more groups selected from OH, CN, halogen, oxo, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is a saturated or partially unsaturated 4 to 6 membered heterocyclic optionally substituted with one or more groups selected from OH, oxo, cyclopropylmethyl, and $C_1$-$C_6$ alkyl. In certain embodiments, $R^2$ is a saturated 4 to 6 membered heterocyclic containing one or two heteroatoms selected from nitrogen and oxygen, wherein the heterocyclic is optionally substituted with oxo. In certain embodiments, $R^2$ is a saturated 4 to 6 membered heterocyclic optionally substituted with oxo, wherein the heterocyclic is selected from oxetanyl, tetrahydrofuranyl, morpholinyl and pyrrolidinyl. In certain embodiments, $R^2$ is a partially unsaturated 4 to 6 membered heterocyclic optionally substituted with oxo or $C_1$-$C_6$ alkyl. In certain embodiments, $R^2$ is a partially unsaturated 4 to 6 membered heterocyclic containing one or two nitrogen heteroatoms, wherein the heterocyclic is optionally substituted with oxo or $C_1$-$C_6$ alkyl. In certain embodiments, $R^2$ is a partially unsaturated 6 membered heterocyclic optionally substituted with halogen, oxo or $C_1$-$C_6$ alkyl, wherein the heterocyclic is selected from 1,2-dihydropyridine and 1,6-dihydropyridazine. In certain embodiments, $R^2$ is 1,2-dihydropyridine or 1,6-dihydropyridazine optionally substituted with halogen, oxo, or $C_1$-$C_3$ alkyl. In certain embodiments, $R^2$ is selected from 3-methyloxetan-3-yl, azetidin-1-yl, tetrahydrofuran-2-yl, tetrahydrofuran-3-yl, 1-methyl-6-oxo-1,6-dihydropyridin-3-yl, 1-methyl-6-oxo-1,6-dihydropyridazin-3-yl, 1-isopropyl-6-oxo-1,6-dihydropyridazin-3-yl, 1-(cyclopropylmethyl)-6-oxo-1,6-dihydropyridazin-3-yl, morpholin-2-yl, pyrrolidin-1-yl and 5-oxopyrrolidin-2-yl.

In certain embodiments, $R^2$ is a saturated or partially unsaturated 5 or 6 membered heterocyclic optionally substituted with one or more groups selected from OH, CN, halogen, oxo, $CF_3$, $C_1$-$C_6$ alkyl, —O($C_1$-$C_6$ alkyl), —S($C_1$-$C_6$ alkyl), and $NR^eR^f$. In certain embodiments, $R^2$ is a saturated or partially unsaturated 5 or 6 membered heterocyclic optionally substituted with oxo or $C_1$-$C_6$ alkyl. In certain embodiments, $R^2$ is a saturated 5 or 6 membered heterocyclic. In certain embodiments, $R^2$ is a saturated 5 or 6 membered heterocyclic containing one or two heteroatoms selected from nitrogen and oxygen. In certain embodiments, $R^2$ is a saturated 5 or 6 membered heterocyclic, wherein the heterocyclic is selected from tetrahydrofuranyl and morpholinyl. In certain embodiments, $R^2$ is a saturated 5 membered heterocyclic containing an oxygen heteroatom. In certain embodiments, $R^2$ is a saturated 5 membered heterocyclic, wherein the heterocyclic is tetrahydrofuran. In certain embodiments, $R^2$ is a saturated 6 membered heterocyclic containing one or two heteroatoms selected from oxygen and nitrogen. In certain embodiments, $R^2$ is a saturated 6 membered heterocyclic, wherein the heterocyclic is morpholinyl. In certain embodiments, $R^2$ is a partially unsaturated 5 or 6 membered heterocyclic optionally substituted with oxo or $C_1$-$C_6$ alkyl. In certain embodiments, $R^2$ is a partially unsaturated 5 or 6 membered heterocyclic containing one or two nitrogen heteroatoms, wherein the heterocyclic is optionally substituted with oxo or $C_1$-$C_6$ alkyl. In certain embodiments, $R^2$ is a partially unsaturated 6 membered heterocyclic containing one or two nitrogen heteroatoms, wherein the heterocyclic is optionally substituted with oxo or $C_1$-$C_6$ alkyl. In certain embodiments, $R^2$ is a partially unsaturated 6 membered heterocyclic optionally substituted with halogen, oxo or $C_1$-$C_6$ alkyl, wherein the heterocyclic is selected from 1,2-dihydropyridine and 1,-6-dihydropyridazine. In certain embodiments, $R^2$ is a partially unsaturated 6 membered heterocyclic optionally substituted with oxo and $C_1$-$C_6$ alkyl, wherein the heterocyclic is selected from 1,2-dihydropyridine and 1,6-dihydropyridazine. In certain embodiments, $R^2$ is 1,2-dihydropyridine or 1,6-dihydropyridazine optionally substituted with halogen, oxo, or $C_1$-$C_3$ alkyl. In certain embodiments, $R^2$ is 1,2-dihydropyridine or 1,6-dihydropyridazine substituted with oxo and $C_1$-$C_3$ alkyl. In certain embodiments, $R^2$ is selected from tetrahydrofuran-2-yl, tetrahydrofuran-3-yl, 1-methyl-6-oxo-1,6-dihydropyridin-3-yl, 1-methyl-6-oxo-1,6-dihydropyridazin-3-yl and morpholin-2-yl.

In certain embodiments, $R^2$ is a saturated 5 or 6 membered heterocyclic optionally substituted with one or more groups selected from OH, CN, halogen, oxo, $CF_3$, $C_1$-$C_6$ alkyl, —O($C_1$-$C_6$ alkyl), —S($C_1$-$C_6$ alkyl), and $NR^eR^f$. In certain embodiments, $R^2$ is a saturated 5 or 6 membered heterocyclic optionally substituted with oxo or $C_1$-$C_6$ alkyl. In certain embodiments, $R^2$ is a saturated 5 or 6 membered heterocyclic. In certain embodiments, $R^2$ is a saturated 5 or 6 membered heterocyclic containing one or two heteroatoms selected from nitrogen and oxygen. In certain embodiments, $R^2$ is a saturated 5 membered heterocyclic. In certain embodiments, $R^2$ is a saturated 5 membered heterocyclic containing an oxygen heteroatom. In certain embodiments, $R^2$ is a saturated 5 membered heterocyclic, wherein the heterocyclic is tetrahydrofuran. In certain embodiments, $R^2$ is a saturated 6 membered heterocyclic. In certain embodiments, $R^2$ is a saturated 6 membered heterocyclic containing one or two heteroatoms selected from nitrogen and oxygen. In certain embodiments, $R^2$ is a saturated 6 membered heterocyclic containing two heteroatoms selected from nitrogen and oxygen. In certain embodiments, $R^2$ is a saturated 6 membered heterocyclic, wherein the heterocyclic is morpholinyl. In certain embodiments, $R^2$ is tetrahydrofuran-2-yl, tetrahydrofuran-3-yl or morpholin-2-yl.

In certain embodiments, $R^2$ is a partially unsaturated 5 or 6 membered heterocyclic optionally substituted with one or more groups selected from OH, CN, halogen, oxo, $CF_3$, $C_1$-$C_6$ alkyl, —O($C_1$-$C_6$ alkyl), —S($C_1$-$C_6$ alkyl), and $NR^eR^f$. In certain embodiments, $R^2$ is a partially unsaturated 5 or 6 membered heterocyclic optionally substituted with oxo or $C_1$-$C_6$ alkyl. In certain embodiments, $R^2$ is a partially unsaturated 5 or 6 membered heterocyclic containing one or two nitrogen heteroatoms, wherein the heterocyclic is optionally substituted with oxo or $C_1$-$C_6$ alkyl. In certain embodiments, $R^2$ is a partially unsaturated 6 membered heterocyclic containing one or two nitrogen heteroatoms, wherein the heterocyclic is optionally substituted with oxo or $C_1$-$C_6$ alkyl. In certain embodiments, $R^2$ is a partially unsaturated 6 membered heterocyclic optionally substituted with oxo or $C_1$-$C_6$ alkyl, wherein the heterocyclic is selected from 1,2-dihydropyridine and 1,-6-dihydropyridazine. In certain embodiments, $R^2$ is 1,2-dihydropyridine or 1,6-dihydropyridazine optionally substituted with halogen, oxo, or $C_1$-$C_3$ alkyl. In certain embodiments, $R^2$ is 1,2-dihydropyridine or 1,6-dihydropyridazine substituted with oxo and $C_1$-$C_3$ alkyl. In certain embodiments, $R^2$ is selected from 1-methyl-6-oxo-1,6-dihydropyridin-3-yl and 1-methyl-6-oxo-1,6-dihydropyridazin-3-yl.

In certain embodiments, $R^2$ is a 5 or 6 membered heteroaryl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is a 5 or 6 membered heteroaryl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is a 5 or 6 membered heteroaryl optionally substituted with halogen, $CF_3$, $C_1$-$C_6$ alkyl or —O($C_1$-$C_6$ alkyl). In certain embodiments, $R^2$ is a 5 or 6 membered heteroaryl optionally substituted with halogen, $CF_3$, $C_1$-$C_6$ alkyl or —O($C_1$-$C_6$ alkyl), wherein the heteroaryl contains 1 or 2 heteroatoms selected from nitrogen, oxygen and sulfur. In certain embodiments, $R^2$ is a 5 or 6 membered heteroaryl optionally substituted with halogen, $CF_3$, $C_1$-$C_6$ alkyl or —O($C_1$-$C_6$ alkyl), wherein the heteroaryl is selected from pyrazole, oxazole, isoxazole, thiazole, pyridine, pyrimidine and pyrazine. In certain embodiments, $R^2$ is a 5 or 6 membered heteroaryl optionally substituted with halogen, wherein the halogen is Cl or F. In certain embodiments, $R^2$ is a 5 or 6 membered heteroaryl optionally substituted with $C_1$-$C_6$ alkyl, wherein the $C_1$-$C_6$ alkyl is methyl or ethyl. In certain embodiments, $R^2$ is a 5 or 6 membered heteroaryl optionally substituted with —O($C_1$-$C_6$ alkyl), wherein the $C_1$-$C_6$ alkyl is methoxy. In certain embodiments, $R^2$ is selected from pyrazol-4-yl, 1-methyl-1H-pyrazol-3-yl, 1-methyl-1H-pyrazol-4-yl, 2-methyloxazol-4-yl, 5-methylisoxazol-3-yl, 2-methylthiazol-4-yl, pyridin-2-yl, pyridin-3-yl, 6-methoxy-pyridin-2-yl, 3-methylpyridin-2-yl, 5-chloro-pyridin-2-yl, 5-trifluoromethylpyridin-2-yl, 2-methylpyridin-3-yl, 5-methylpyridin-3-yl, 5-chloropyridin-3-yl, 6-methylpyridin-3-yl, pyrimidin-2-yl, 5-ethylpyrimidin-2-yl, pyrazin-2-yl, and 5-methylpyrazin-2-yl.

In certain embodiments, $R^2$ is a 5 or 6 membered heteroaryl optionally substituted with one or more groups selected from OH, CN, halogen, $CF_3$, $C_1$-$C_6$ alkyl, —O($C_1$-$C_6$ alkyl), —S($C_1$-$C_6$ alkyl), and $NR^eR^f$. In certain embodiments, $R^2$ is a 5 or 6 membered heteroaryl optionally substituted with halogen, $C_1$-$C_6$ alkyl or —O($C_1$-$C_6$ alkyl). In certain embodiments, $R^2$ is a 5 or 6 membered heteroaryl optionally substituted with halogen, $C_1$-$C_6$ alkyl or —O($C_1$-$C_6$ alkyl), wherein the heteroaryl contains 1 or 2 heteroatoms selected from nitrogen, oxygen and sulfur. In certain embodiments, $R^2$ is a 5 or 6 membered heteroaryl optionally substituted with halogen, $C_1$-$C_6$ alkyl or —O($C_1$-$C_6$ alkyl), wherein the heteroaryl is selected from pyrazole, oxazole, isoxazole, thiazole, pyridine, pyrimidine and pyrazine. In certain embodiments, $R^2$ is a 5 or 6 membered heteroaryl optionally substituted with halogen, wherein the halogen is Cl or F. In certain embodiments, $R^2$ is a 5 or 6 membered heteroaryl optionally substituted with halogen, wherein the halogen is Cl. In certain embodiments, $R^2$ is a 5 or 6 membered heteroaryl optionally substituted with $C_1$-$C_6$ alkyl, wherein the $C_1$-$C_6$ alkyl is methyl. In certain embodiments, $R^2$ is a 5 or 6 membered heteroaryl optionally substituted with —O($C_1$-$C_6$ alkyl), wherein the $C_1$-$C_6$ alkyl is methoxy. In certain embodiments, $R^2$ is selected from pyrazol-4-yl, 1-methyl-1H-pyrazol-3-yl, 2-methyloxazol-4-yl, 5-methylisoxazol-3-yl, 2-methylthiazol-4-yl, pyridin-2-yl, pyridin-3-yl, 6-methoxy-pyridin-2-yl, 3-methylpyridin-2-yl, 5-chloro-pyridin-2-yl, 5-methylpyridin-2-yl, 2-methylpyridin-3-yl, 5-methylpyridin-3-yl, 5-chloropyridin-3-yl, 6-methylpyridin-3-yl, pyrimidin-2-yl, pyrazin-2-yl, and 5-methylpyrazin-2-yl.

In certain embodiments, $R^2$ is an 8 to 10 membered bicyclic heteroaryl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$. In certain embodiments, $R^2$ is an 8 to 10 membered bicyclic heteroaryl optionally substituted with one or more groups selected from OH, CN, halogen, $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl. In certain embodiments, $R^2$ is an 8 to 10 membered bicyclic heteroaryl. In certain embodiments, $R^2$ is an 8 to 10 membered bicyclic heteroaryl containing one or two nitrogen heteroatoms. In certain embodiments, $R^2$ is an 8 to 10 membered bicyclic heteroaryl, wherein the heteroaryl is quinoxaline. In certain embodiments, $R^2$ is quinoxalin-2-yl.

In certain embodiments, $R^2$ is an 8 to 10 membered bicyclic heteroaryl optionally substituted with one or more groups selected from OH, CN, halogen, $CF_3$, $C_1$-$C_6$ alkyl, —O($C_1$-$C_6$ alkyl), —S($C_1$-$C_6$ alkyl), and $NR^eR^f$. In certain embodiments, $R^2$ is an 8 to 10 membered bicyclic heteroaryl. In certain embodiments, $R^2$ is an 8 to 10 membered bicyclic heteroaryl containing two nitrogen heteroatoms. In certain embodiments, $R^2$ is an 8 to 10 membered bicyclic heteroaryl, wherein the heteroaryl is quinoxaline. In certain embodiments, $R^2$ is quinoxalin-2-yl.

In certain embodiments, $R^3$ and $R^4$ are independently selected from hydrogen or $C_1$-$C_4$ alkyl optionally substituted with OH, F, —O($C_1$-$C_3$ alkyl) or $C_3$-$C_6$ cycloalkyl.

In certain embodiments, $R^3$ and $R^4$ are independently selected from hydrogen, methyl, ethyl, isopropyl, isobutyl, $CH_2CH_2OH$, $CH_2CH_2OCH_3$, $CH_2CH_2F$ and cyclopropylmethyl.

In certain embodiments, $R^3$ is selected from hydrogen, methyl, ethyl, isopropyl, isobutyl, $CH_2CH_2OH$, $CH_2CH_2OCH_3$, $CH_2CH_2F$ and cyclopropylmethyl, and $R^4$ is selected from hydrogen and methyl.

In certain embodiments, $R^3$ is selected from hydrogen or $C_1$-$C_4$ alkyl optionally substituted with OH, F, —O($C_1$-$C_3$ alkyl) or $C_3$-$C_6$ cycloalkyl. In certain embodiments, $R^3$ is selected from hydrogen or $C_1$-$C_4$ alkyl optionally substituted with OH, F, —O($C_1$-$C_3$ alkyl) or $C_3$-$C_6$ cycloalkyl, wherein the cycloalkyl is cyclopropyl. In certain embodiments, $R^3$ is selected from hydrogen, methyl, ethyl, isopropyl, isobutyl, $CH_2CH_2OH$, $CH_2CH_2OCH_3$, $CH_2CH_2F$ and cyclopropylmethyl.

In certain embodiments, $R^3$ is selected from hydrogen or $C_1$-$C_4$ alkyl optionally substituted with OH, F or $C_3$-$C_6$ cycloalkyl. In certain embodiments, $R^3$ is selected from hydrogen, methyl, isopropyl, isobutyl, $CH_2CH_2OH$ and cyclopropylmethyl.

In certain embodiments, $R^3$ is selected from hydrogen or $C_1$-$C_4$ alkyl optionally substituted with OH or $C_3$-$C_6$ cycloalkyl. In certain embodiments, $R^3$ is selected from hydrogen or $C_1$-$C_4$ alkyl optionally substituted with OH or $C_3$-$C_6$ cycloalkyl, wherein the cycloalkyl is cyclopropyl. In certain embodiments, $R^3$ is selected from hydrogen, methyl, isopropyl, isobutyl, $CH_2CH_2OH$ and cyclopropylmethyl (—$CH_2$-cyclopropyl).

In certain embodiments, $R^4$ is selected from hydrogen or $C_1$-$C_4$ alkyl optionally substituted with OH, F or $C_3$-$C_6$ cycloalkyl. In certain embodiments, $R^4$ is selected from hydrogen and methyl.

In certain embodiments, $R^4$ is selected from hydrogen and $C_1$-$C_4$ alkyl optionally substituted with OH or $C_3$-$C_6$ cycloalkyl. In certain embodiments, $R^4$ is selected from hydrogen and $C_1$-$C_4$ alkyl. In certain embodiments, $R^4$ is selected from hydrogen and methyl.

In certain embodiments, $R^3$ and $R^4$ together with the atoms to which they are attached form a 5 or 6 membered ring, as shown in the structure:

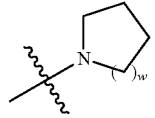

wherein the wavy line represents where the nitrogen attaches to A and w is 1 or 2. As $R^3$ and $R^4$ are both attached to a nitrogen, this 5 or 6 membered ring is a heterocyclic ring.

In certain embodiments, A is selected from a direct bond or $CR^aR^b$. In certain embodiments, $R^a$ is hydrogen. In certain embodiments, $R^b$ is hydrogen or absent.

In certain embodiments, A is a direct bond, as shown in Formula IIIa:

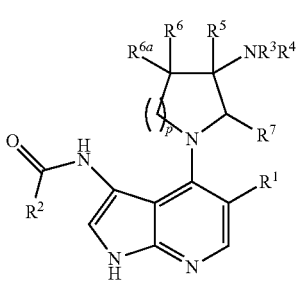

IIIa wherein $R^1$, $R^2$, $R^3$, $R^4$, $R^5$, $R^6$, $R^{6a}$, $R^7$ and p are as defined herein.

In certain embodiments, A is a direct bond and p is 1, as shown in Formula IIIb:

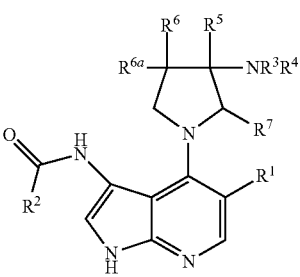

IIIb wherein $R^1$, $R^2$, $R^3$, $R^4$, $R^5$, $R^6$, $R^{6a}$, $R^7$ are as defined herein.

In certain embodiments, A is a direct bond and p is 2, as shown in Formula IIIc:

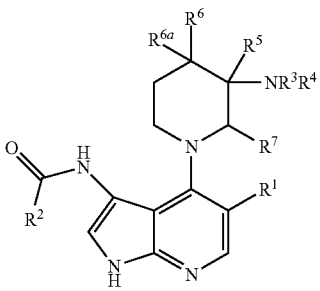

IIIc wherein $R^1$, $R^2$, $R^3$, $R^4$, $R^5$, $R^6$, $R^{6a}$, $R^7$ are as defined herein.

In certain embodiments, A is $CR^aR^b$, as shown in Formula IVa:

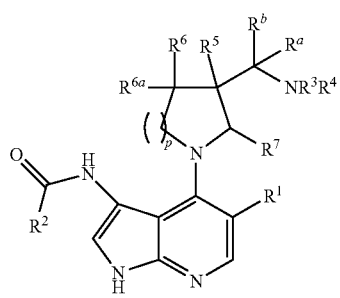

IVa wherein $R^1$, $R^2$, $R^3$, $R^4$, $R^5$, $R^6$, $R^{6a}$, $R^7$ and p are as defined herein.

In certain embodiments, A is $CR^aR^b$ and p is 1, as shown in Formula IVb:

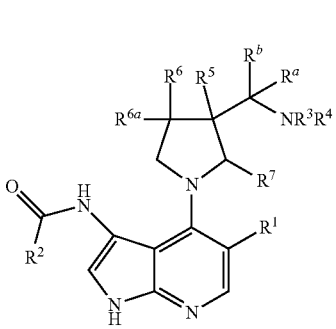

IVb wherein $R^1$, $R^2$, $R^3$, $R^4$, $R^5$, $R^6$, $R^{6a}$, $R^7$, $R^a$ and $R^b$ are as defined herein.

In certain embodiments, $R^4$ and $R^b$ are absent and $R^3$ and $R^a$ together with the atoms to which they are attached form an aromatic 5 or 6 membered ring. As $R^3$ is attached to a nitrogen atom, this aromatic 5 or 6 membered ring is heteroaryl. In certain embodiments, $R^4$ and $R^b$ are absent and $R^3$ and $R^a$ together with the atoms to which they are attached form an aromatic 5 or 6 membered ring, wherein the aromatic ring is heteroaryl and contains 1 nitrogen. In certain embodiments, $R^4$ and $R^b$ are absent and $R^3$ and $R^a$ together with the atoms to which they are attached form an aromatic 5 or 6 membered ring, wherein the aromatic ring is selected from pyrrolyl and pyridinyl. In certain embodiments, $R^4$ and $R^b$ are absent and $R^3$ and $R^a$ together with the atoms to which they are attached form an aromatic 6 membered ring, wherein the aromatic 6 membered ring is pyridinyl. In certain embodiments, $R^4$ and $R^b$ are absent and $R^3$ and $R^a$ together with the atoms to which they are attached form a pyridinyl ring. In certain embodiments, $R^4$ and $R^b$ are absent and $R^3$ and $R^a$ together form pyridin-2-yl.

In certain embodiments, $R^5$ is selected from hydrogen and $CH_3$. In certain embodiments, $R^5$ is hydrogen. In certain embodiments, $R^5$ is $CH_3$.

In certain embodiments, A is $CR^aR^b$, $R^a$ and $R^b$ are hydrogen, and $R^3$ and $R^5$ together with the atoms to which they are attached form a 5 or 6 membered ring, as shown in Formula Va:

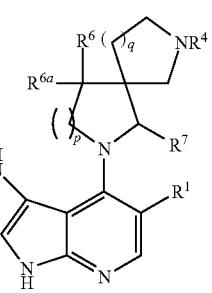

Va wherein $R^1$, $R^2$, $R^4$, $R^6$, $R^{6a}$, $R^7$ and p are as defined herein, and q is 1 or 2. As $R^3$ is attached to a nitrogen atom, this 5 or 6 membered ring is heterocyclic. As $R^3$ and $R^5$ form a ring at a single atom of another ring, the compounds of Formula I and Va contain a spirocyclic ring.

In certain embodiments of Formula Va, p is 1.
In certain embodiments of Formula Va, q is 1.

In certain embodiments of Formula Va, $R^4$, $R^6$, $R^{6a}$ and $R^7$ are hydrogen.

In certain embodiments, A is $CR^aR^b$, $R^a$ and $R^b$ are hydrogen, and $R^3$ and $R^5$ together with the atoms to which they are attached form a 5 membered ring, as shown in Formula Vb:

Vb wherein $R^1$, $R^2$, $R^4$, $R^6$, $R^{6a}$, $R^7$ and p are as defined herein.

In certain embodiments of Formula Vb, p is 1.

In certain embodiments of Formula Vb, $R^4$, $R^6$, $R^{6a}$ and $R^7$ are hydrogen.

In certain embodiments, $R^6$ is selected from hydrogen, F, OH, —OCH$_3$, C$_1$-C$_3$ alkyl and cyclopropyl.

In certain embodiments, $R^6$ is selected from hydrogen, F, OH, —OCH$_3$ and C$_1$-C$_3$ alkyl. In certain embodiments, $R^6$ is hydrogen.

In certain embodiments, $R^6$ is selected from hydrogen, F, —OCH$_3$, methyl and cyclopropyl.

In certain embodiments, $R^6$ is hydrogen.

In certain embodiments, $R^6$ is halogen. In certain embodiments, $R^6$ is F.

In certain embodiments, $R^6$ is —OCH$_3$.

In certain embodiments, $R^6$ is C$_1$-C$_3$ alkyl. In certain embodiments, $R^6$ is methyl.

In certain embodiments, $R^6$ is cyclopropyl.

In certain embodiments, A is a direct bond, $R^{6a}$ is hydrogen and $R^3$ and $R^6$ together with the atoms to which they are attached form a 5 or 6 membered ring, as shown in Formula VIa:

VIa wherein $R^1$, $R^2$, $R^4$, $R^5$, $R^7$ and p are as defined herein, and s is 1 or 2. As $R^3$ is attached to a nitrogen atom, this 5 or 6 membered ring is heterocyclic. As $R^3$ and $R^6$ form a ring at two mutually bonded atoms of another ring, the compounds of Formula I and VIa contain a bicyclic ring.

In certain embodiments of Formula VIa, p is 1 or 2.
In certain embodiments of Formula VIa, p is 1.
In certain embodiments of Formula VIa, p is 2.
In certain embodiments of Formula VIa, s is 1.

In certain embodiments of Formula VIa, $R^4$, $R^5$ and $R^7$ are hydrogen.

In certain embodiments, A is a direct bond, $R^{6a}$ is hydrogen and $R^3$ and $R^6$ together with the atoms to which they are attached form a 5 membered ring, as shown in Formula VIb:

VIb wherein $R^1$, $R^2$, $R^4$, $R^5$, $R^7$ and p are as defined herein.

In certain embodiments of Formula VIb, p is 1 or 2.
In certain embodiments of Formula VIb, p is 1.
In certain embodiments of Formula VIb, p is 2.

In certain embodiments of Formula VIb, $R^4$, $R^5$ and $R^7$ are hydrogen.

In certain embodiments, $R^{6a}$ is selected from hydrogen, F, OH and CH$_3$. In certain embodiments, $R^{6a}$ is hydrogen.

In certain embodiments, $R^{6a}$ is hydrogen.

In certain embodiments, $R^7$ is hydrogen.

In certain embodiments, A is $CR^aR^b$ and $R^3$ and $R^7$ together with the atoms to which they are attached form a 5 or 6 membered ring, as shown in Formula VIIa:

VIIa wherein $R^1$, $R^2$, $R^4$, $R^5$, $R^6$, $R^{6a}$, $R^a$, $R^b$ and p are as defined herein, and t is 1 or 2. As $R^3$ is attached to a nitrogen atom, this 5 or 6 membered ring is heterocyclic. As $R^3$ and $R^7$ form a ring at two mutually bonded atoms of another ring, the compounds of Formula I and VIIa contain a bicyclic ring.

In certain embodiments of Formula VIIa, p is 1.

In certain embodiments of Formula VIIIa, t is 1.

In certain embodiments of Formula VIIIa, $R^4$, $R^5$, $R^6$, $R^{6a}$, $R^a$ and $R^b$ are hydrogen.

In certain embodiments, A is $CR^aR^b$ and $R^3$ and $R^7$ together with the atoms to which they are attached form a 5 membered ring, as shown in Formula VIIb:

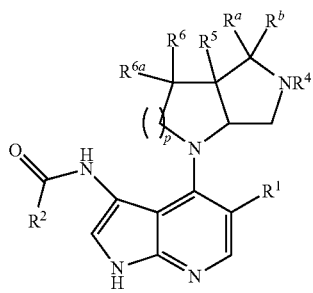

VIIb wherein $R^1$, $R^2$, $R^4$, $R^5$, $R^6$, $R^{6a}$, $R^a$, $R^b$ and p are as defined herein.

In certain embodiments of Formula VIIb, p is 1.

In certain embodiments of Formula VIIb, $R^4$, $R^5$, $R^6$, $R^{6a}$, $R^a$ and $R^b$ are hydrogen.

In certain embodiments, $R^c$ and $R^d$ are independently selected from hydrogen and $C_1$-$C_3$ alkyl.

In certain embodiments, $R^c$ and $R^d$ together with the atom to which they are attached from a 5 or 6 membered ring. As $R^c$ and $R^d$ are attached to a nitrogen atom, this 5 or 6 membered ring is heterocyclic.

In certain embodiments, $R^e$ and $R^f$ are independently selected from hydrogen and $C_1$-$C_3$ alkyl.

In certain embodiments, $R^g$ and $R^h$ are independently selected from hydrogen and $C_1$-$C_3$ alkyl.

In certain embodiments, $R^i$ is $C_1$-$C_3$ alkyl. In certain embodiments, $R^i$ is methyl.

Another embodiment of the present invention provides compounds of Formula IXa:

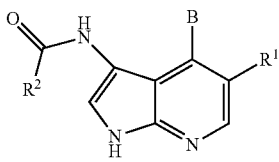

IXa and stereoisomers, tautomers and pharmaceutically acceptable salts thereof, wherein:

$R^1$ is selected from Br, Cl, F, $CF_3$, ethyl, isopropyl, —$OCH_2CH_3$, —$SCH_3$, —$SCH_2CH_3$, —$SCH(CH_3)_2$, cyclopropyl, phenyl and 6-methylpyridin-3-yl;

$R^2$ is selected from ethyl, propyl, isopropyl, isobutyl, cyclopropylmethyl, —$CH_2OH$, —$CH_2OCH_3$, —$CH(CH_3)OCH_3$, —$CH_2CH_2OCH_3$, —$C(CH_3)_2OH$, —$C(cyclopropyl)OCH_3$, —$C(CH_3)_2F$, —$CH_2OCH(CH_3)_2$, cyclopropyl, cyclobutyl, cyclopentyl, tetrahydrofuran-3-yl, 1-methyl-6-oxo-1,6-dihydropyridazin-3-yl, 1-isopropyl-6-oxo-1,6-dihydropyridazin-3-yl, 1-(cyclopropylmethyl)-6-oxo-1,6-dihydropyridazin-3-yl, morpholin-2-yl, pyrimidin-2-yl and 5-ethylpyrimidin-2-yl; and B is selected from the structures:

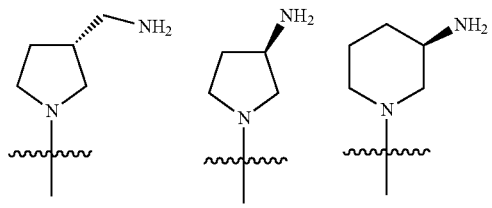

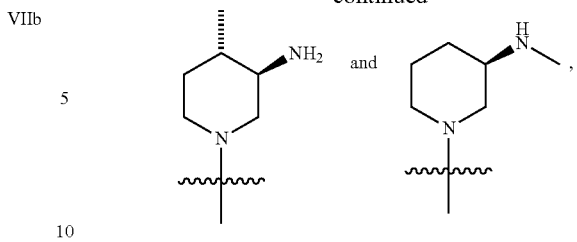

wherein the wavy line represents the point of attachment of B to the pyrrolopyridine of Formula IXa.

In certain embodiments of Formula IXa, $R^1$ is selected from Br, Cl, F, ethyl, isopropyl and —$SCH_3$.

Another embodiment of the present invention provides compounds of Formula IXb:

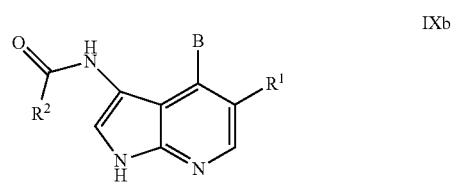

IXb and stereoisomers, tautomers and pharmaceutically acceptable salts thereof, wherein:

$R^1$ is selected from Br, Cl, F, $CF_3$, ethyl, isopropyl, —$OCH_2CH_3$, —$SCH_3$, —$SCH_2CH_3$, —$SCH(CH_3)_2$, cyclopropyl, phenyl and 6-methylpyridin-3-yl;

$R^2$ is selected from ethyl, propyl, isopropyl, isobutyl, cyclopropylmethyl, —$CH_2OH$, —$CH(CH_3)OCH_3$, —$CH_2CH_2OCH_3$, —$C(CH_3)_2OH$, —$C(cyclopropyl)OCH_3$, —$C(CH_3)_2F$, —$CH_2OCH(CH_3)_2$, cyclopropyl, cyclobutyl, cyclopentyl, tetrahydrofuran-3-yl, 1-methyl-6-oxo-1,6-dihydropyridazin-3-yl, 1-isopropyl-6-oxo-1,6-dihydropyridazin-3-yl and 1-(cyclopropylmethyl)-6-oxo-1,6-dihydropyridazin-3-yl; and B is selected from the structures:

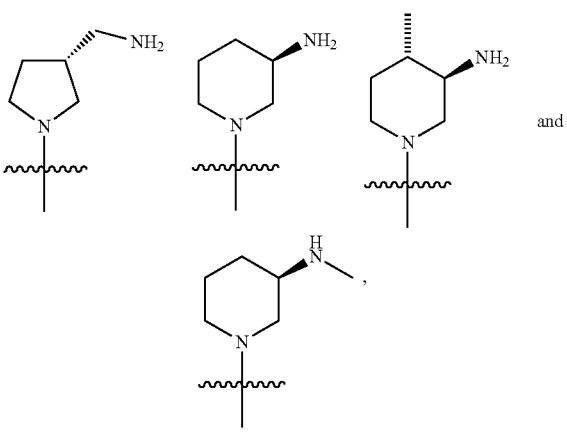

wherein the wavy line represents the point of attachment of B to the pyrrolopyridine of Formula IXb.

In certain embodiments of Formula IXb, $R^1$ is selected from Br, Cl, F, ethyl, isopropyl and —$SCH_3$.

Another embodiment of the present invention provides compounds of Formula IXc:

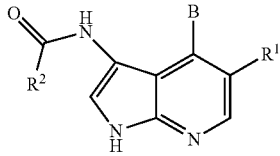

and stereoisomers, tautomers and pharmaceutically acceptable salts thereof, wherein:

$R^1$ is selected from Br, Cl, F, $CF_3$, ethyl, isopropyl, —$OCH_2CH_3$, —$SCH_3$, —$SCH_2CH_3$, —$SCH(CH_3)_2$, cyclopropyl, phenyl and 6-methylpyridin-3-yl;

$R^2$ is selected from ethyl, propyl, isopropyl, isobutyl, cyclopropylmethyl, —$CH_2OH$, —$CH(CH_3)OCH_3$, —$C(CH_3)_2OH$, —$C(cyclopropyl)OCH_3$, —$C(CH_3)_2F$, cyclopropyl, cyclobutyl, cyclopentyl, tetrahydrofuran-3-yl, 1-methyl-6-oxo-1,6-dihydropyridazin-3-yl; and B is selected from the structures:

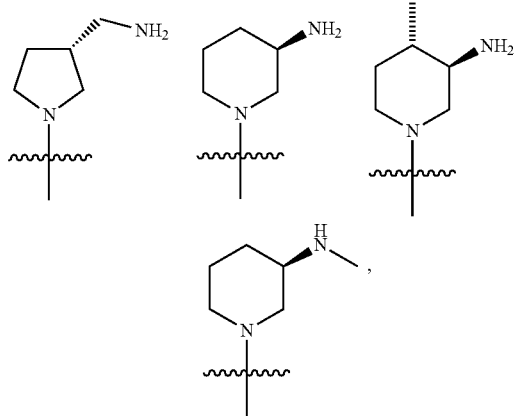

wherein the wavy line represents the point of attachment of B to the pyrrolopyridine of Formula IXc.

In certain embodiments of Formula IXc, $R^1$ is selected from Br, Cl, F, ethyl, isopropyl and —$SCH_3$.

Another embodiment of the present invention provides compounds of Formula IXd:

and stereoisomers, tautomers and pharmaceutically acceptable salts thereof, wherein:

$R^1$ is selected from Br, Cl, F, $CF_3$, ethyl, isopropyl, —$OCH_2CH_3$, —$SCH_3$, —$SCH_2CH_3$, —$SCH(CH_3)_2$, cyclopropyl, phenyl and 6-methylpyridin-3-yl;

$R^2$ is selected from ethyl, isopropyl, and cyclopropyl; and

B is selected from the structures:

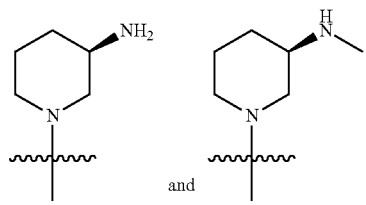

wherein the wavy line represents the point of attachment of B to the pyrrolopyridine of Formula IXd.

In certain embodiments of Formula IXd, $R^1$ is selected from Br, Cl, F, ethyl, isopropyl and —$SCH_3$.

Another embodiment of the present invention provides compounds of Formula X:

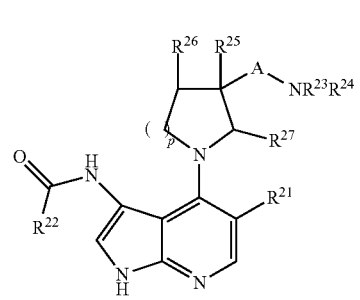

and stereoisomers, tautomers and pharmaceutically acceptable salts thereof, wherein:

A is selected from a direct bond or $CR^aR^b$;

$R^{21}$ is selected from halogen, $C_3$-$C_6$ cycloalkyl and $C_1$-$C_6$ alkyl, wherein the alkyl is optionally substituted with one or more halogen groups;

$R^{22}$ is selected from $C_1$-$C_6$ alkyl, saturated $C_3$-$C_6$ cycloalkyl, phenyl, saturated or partially unsaturated 5 or 6 membered heterocyclic, a 5 or 6 membered heteroaryl, and an 8 to 10 membered bicyclic heteroaryl, wherein the alkyl, cycloalkyl, phenyl, heterocyclic and heteroaryl are optionally substituted with halogen, oxo (except not on phenyl or heteroaryl), $CF_3$, $C_1$-$C_6$ alkyl, —O($C_1$-$C_6$ alkyl) or $C_3$-$C_6$ cycloalkyl;

$R^{23}$ is selected from hydrogen or $C_1$-$C_4$ alkyl optionally substituted with OH or $C_3$-$C_6$ cycloalkyl;

$R^{24}$ is selected from hydrogen and $C_1$-$C_4$ alkyl;

$R^{25}$ is selected from hydrogen and $CH_3$, or

A is $CR^aR^b$, $R^a$ and $R^b$ are hydrogen, and $R^{23}$ and $R^{25}$ together with the atoms to which they are attached form a 5 or 6 membered ring;

$R^{26}$ is selected from hydrogen, or

A is a direct bond and $R^{23}$ and $R^{26}$ together with the atoms to which they are attached form a 5 or 6 membered ring;

$R^{27}$ is selected from hydrogen, or

A is $CR^aR^b$ and $R^{23}$ and $R^{27}$ together with the atoms to which they are attached form a 5 or 6 membered ring;

$R^a$ and $R^b$ are hydrogen, or $R^{24}$ and $R^b$ are absent and $R^{23}$ and $R^a$ together with the atoms to which they are attached form an aromatic 5 or 6 membered ring; and p is 0, 1, 2 or 3.

It will be appreciated that certain compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that certain compounds of Formula I may be used as intermediates for further compounds of Formula I.

It will be further appreciated that the compounds of the present invention may exist in unsolvated as well as solvated forms with pharmaceutically acceptable solvents such as water, ethanol, and the like, and it is intended that the invention embrace both solvated and unsolvated forms.

Synthesis of Compounds

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley Inter-Science® website), or *Beilsteins Handbuch der organischen Chemie*, 4, Aufl. ed. Springer-Verlag, Berlin, including supplements (also available via the Beilstein online database)).

For illustrative purposes, Schemes 1-5 show a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

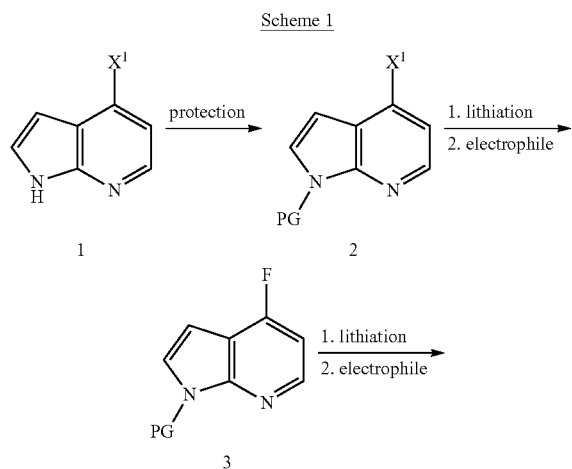

Scheme 1

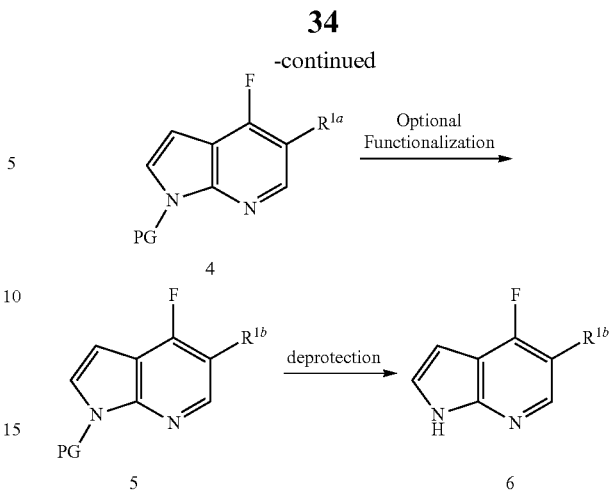

Scheme 1 shows a general scheme for the synthesis of compound 6, wherein $R^{1b}$ is halogen or $CF_3$. Compound 3, wherein PG is a protecting group, such as Boc, CBz, benzyl, phenylsulfonamide or silyl, and $X^1$ is Cl, may be prepared as described in L'Heureux, Alexandre, et al., "Synthesis of functionalized 7-azaindoles via directed ortho-metalations." *Tetrahedron Lett.* 45 (2004): 2317-2319, and Thibault, Carl, et al., "Concise and efficient synthesis of 4-fluoro-1H-pyrrolo [2,3-b]pyridine." *Organic Lett.* 5 (2003): 5023-5025. Compound 3 may be functionalized to install $R^{1a}$ via lithiation under standard conditions (e.g., s-BuLi in an appropriate solvent such as tetrahydrofuran ("THF")) and trapping with a suitable electrophile ($CBr_4$, $I_2$, perbromomethane, N-fluoro-N (phenylsulfonyl)benzenesulfonamide, etc.) to give compound 4, wherein $R^{1a}$ is halogen. Compound 4 may optionally be further functionalized via copper-mediated coupling to provide compound 5. The protecting group may be removed under standard conditions (for example, tetra-N-butylammonium fluoride ("TBAF") to remove a silyl group) to provide compound 6.

In Scheme 1, $R^{1a}$ may also be OH, and $R^{1b}$ may also be $-O(C_1-C_6$ alkyl), wherein the alkyl may be optionally substituted with one or more groups selected from halogen, CN, $CF_3$, $C_1-C_3$ alkyl, $-O(C_1-C_3$ alkyl) and $NR^cR^d$. Compound 3 may be functionalized to install $R^{1a}$ via lithiation under standard conditions and trapping with (1S)-(+)-(10-camphorsulfonyl)oxaziridine gives compound 4, wherein $R^{1a}$ is OH. Compound 4 may optionally be alkylated to provide compound 5, wherein $R^{1b}$ is $-O(C_1-C_6$ alkyl), wherein the alkyl may be optionally substituted with one or more groups selected from halogen, CN, $CF_3$, $C_1-C_3$ alkyl, $-O(C_1-C_3$ alkyl) and $NR^cR^d$.

Scheme 2

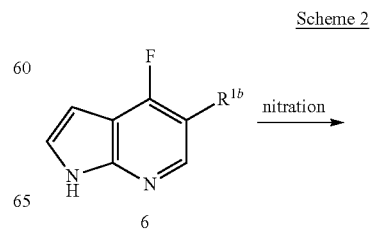

-continued

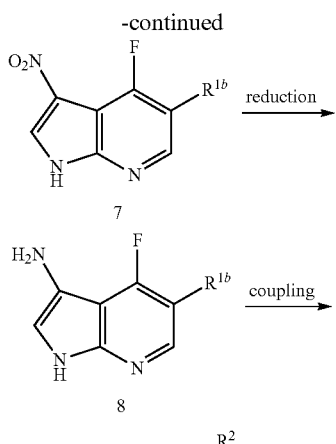

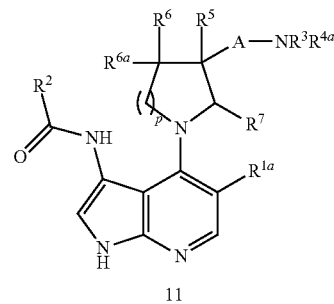

Scheme 3 shows a general scheme for the synthesis of compounds 10 and 11 (both are subsets of Formula I), wherein $R^{1b}$, $R^2$, $R^3$, $R^5$, $R^6$, $R^{6a}$, $R^7$, A and p are as defined herein and $R^{4a}$ is $C_1$-$C_4$ alkyl. Compound 9 can be converted to compound 10 by reaction with an appropriately substituted amine, wherein PG is a protecting group, such as Boc, CBz, benzyl, or $R^4$ as defined herein (when PG is $R^4$ deprotection is not needed), under standard $S_NAr$ reaction conditions. Deprotection of compound 10 using an anhydrous acid (e.g., HCl in dioxane, TFA) produces the free amine. If desired, reductive amination of the amine (using an aldehyde and reducing agent (e.g., NaBH(OAc)$_3$)), or alkylation under standard conditions allows the preparation of the compound 11.

Scheme 2 shows a general scheme for the synthesis of compound 9, wherein $R^{1b}$ and $R^2$ are as defined herein. Nitration of compound 6 can be carried out to give compound 7, which can then be reduced to the amine 8. Coupling of amine 8 with an appropriate acid in the presence of a coupling reagent (such as 2-(1H-benzotriazole-1-yl)-1,1,3,3-tetramethyluronium hexafluorophosphate ("HBTU"), bis(2-oxooxazolidin-3-yl)phosphinic chloride ("BOP-Cl")) or an acid chloride in the presence of a base (such as pyridine, triethylamine, N,N-diisopropylethylamine ("Hunig's base" or "DIEA")) gives compound 9.

Scheme 4

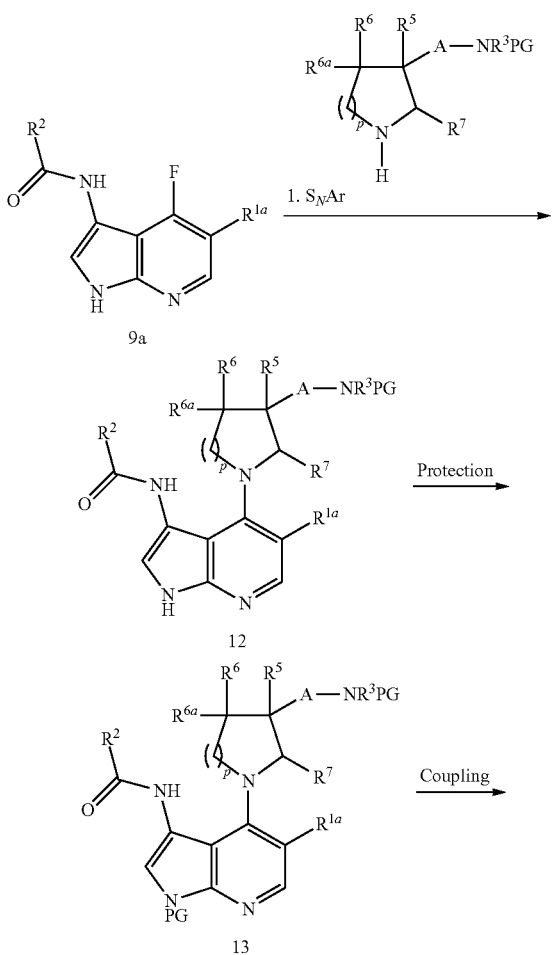

Scheme 3

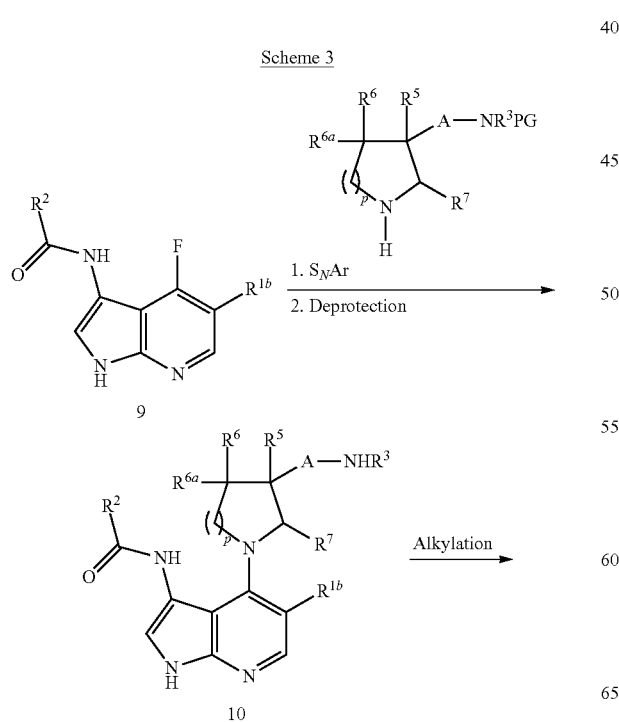

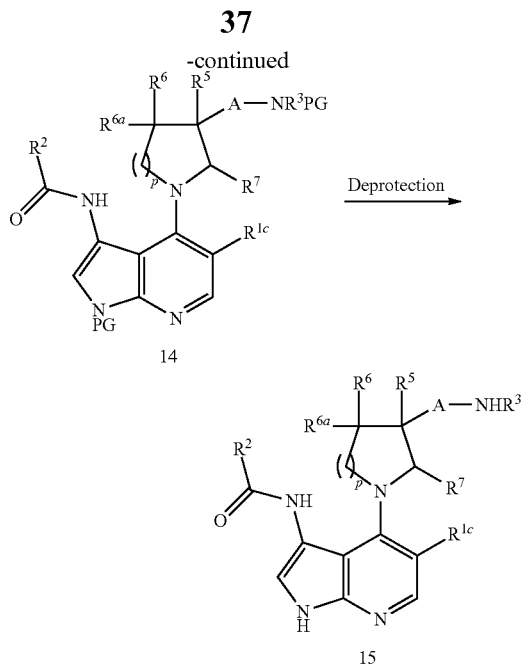

Scheme 4 shows a general scheme for the synthesis of compound 14, wherein $R^2$, $R^3$, $R^5$, $R^6$, $R^{6a}$, $R^7$, A and p are as defined herein, $R^{1c}$ is alkyl, cycloalkyl, aryl or heteroaryl, and PG is a protecting group, such as Boc, CBz, benzyl, or $R^4$ as defined herein. Compound 9a, wherein $R^{1a}$ is as defined herein, can be converted to compound 12 by reaction with an appropriately substituted amine under standard $S_NAr$ reaction conditions. Compound 12 may be protected with standard N-protecting groups (such as tert-butoxycarbonyl, p-methoxybenzyl, etc.) to give compound 13, wherein PG is a protecting group. Compound 14 may then be prepared using an appropriate coupling reaction (such as, but not limited to, a Suzuki, Ullman or Negishi coupling). Compound 14 may then be deprotected with a strong acid (e.g., HCl, trifluoroacetic acid ("TFA"), etc.) to give compound 15.

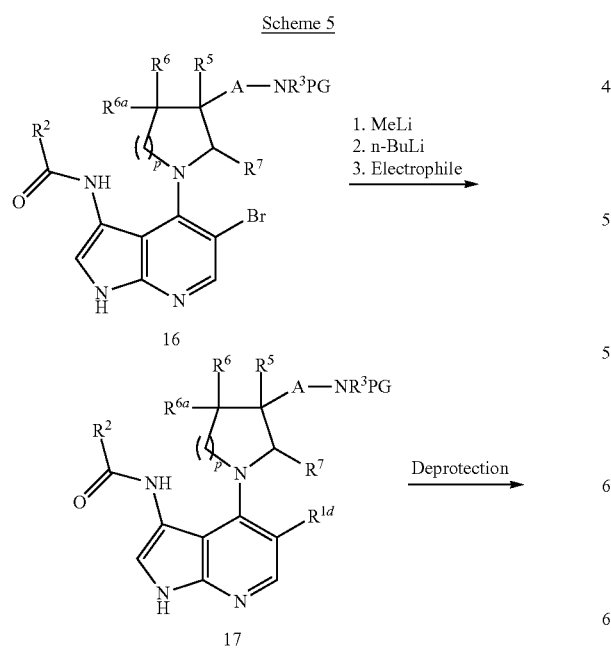

Scheme 5 shows a general method for the synthesis of compound 18, wherein $R^2$, $R^3$, $R^5$, $R^6$, $R^{6a}$, $R^7$, A and p are as defined herein and $R^{1d}$ is hydrogen or a thioether (e.g., —S($C_1$-$C_6$ alkyl)). Compound 16, wherein PG is a protecting group, such as Boc, CBz, benzyl, or $R^4$ as defined herein, may be functionalized to install $R^{1d}$ via deprotonation under standard conditions (e.g., MeLi in an appropriate solvent such as tetrahydrofuran), followed by lithiation under standard conditions (e.g., n-BuLi in an appropriate solvent such as tetrahydrofuran) and trapping with a suitable electrophile such as, but not limited to, a disulfide or ammonium chloride to give compound 17. Compound 17 may then be deprotected with a strong acid (e.g., HCl, TFA, etc.) to give compound 18.

In another embodiment of the present invention, a process for preparing compounds of Formula I (or 10, 11, 15 or 18) is provided, comprising:

(a) reacting a compound of Formula 9:

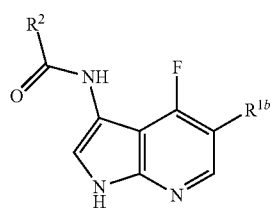

wherein $R^{1b}$ is halogen or $CF_3$; and $R^2$ is selected from $C_1$-$C_6$ alkyl, a saturated or partially unsaturated $C_3$-$C_6$ cycloalkyl, phenyl, a saturated or partially unsaturated 5 or 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclics, heteroaryls and aryl are optionally substituted with one or more groups selected from OH, CN, halogen, oxo (except not on phenyl, aryl or heteroaryl), $CF_3$, $C_1$-$C_6$ alkyl, —O($C_1$-$C_6$ alkyl), —S($C_1$-$C_6$ alkyl), and $NR^eR^f$; and $R^e$ and $R^f$ are independently selected from hydrogen and $C_1$-$C_3$ alkyl;

with an appropriately substituted amine having the formula:

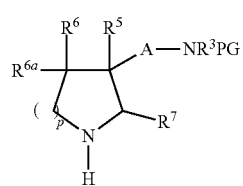

wherein A is selected from a direct bond or CR$^a$R$^b$; R$^3$ is selected from hydrogen or C$_1$-C$_4$ alkyl optionally substituted with OH, F or C$_3$-C$_6$ cycloalkyl; R$^5$ is selected from hydrogen and CH$_3$, or A is CR$^a$R$^b$, R$^a$ and R$^b$ are hydrogen, and R$^3$ and R$^5$ together with the atoms to which they are attached form a 5 or 6 membered ring; R$^6$ is selected from hydrogen, F, OH, —OCH$_3$ and C$_1$-C$_3$ alkyl, or A is a direct bond, R$^{6a}$ is hydrogen and R$^3$ and R$^6$ together with the atoms to which they are attached form a 5 or 6 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; R$^b$ is hydrogen or absent; p is 0, 1, 2 or 3; and PG is a protecting group (such as Boc, CBz, benzyl, or R$^4$, wherein R$^4$ is selected from hydrogen or C$_1$-C$_4$ alkyl optionally substituted with OH, F or C$_3$-C$_6$ cycloalkyl, or R$^3$ and R$^4$ together with the atoms to which they are attached form a 5 or 6 membered ring);

under standard S$_N$Ar reaction conditions to prepare a compound of Formula 10:

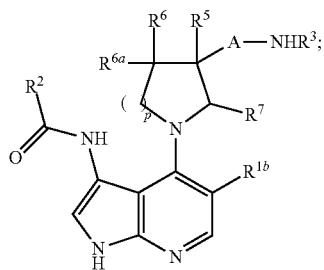

10

(b) alkylating a compound of Formula 10:

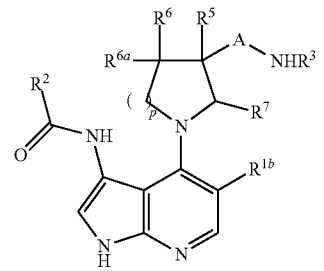

10 wherein R$^{1b}$ is halogen or CF$_3$; R$^2$ is selected from C$_1$-C$_6$ alkyl, a saturated or partially unsaturated C$_3$-C$_6$ cycloalkyl, phenyl, a saturated or partially unsaturated 5 or 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclics, heteroaryls and aryl are optionally substituted with one or more groups selected from OH, CN, halogen, oxo (except not on phenyl, aryl or heteroaryl), CF$_3$, C$_1$-C$_6$ alkyl, —O(C$_1$-C$_6$ alkyl), —S(C$_1$-C$_6$ alkyl), and NR$^e$R$^f$; R$^e$ and R$^f$ are independently selected from hydrogen and C$_1$-C$_3$ alkyl; A is selected from a direct bond or CR$^a$R$^b$; R$^3$ is selected from hydrogen or C$_1$-C$_4$ alkyl optionally substituted with OH, F or C$_3$-C$_6$ cycloalkyl; R$^5$ is selected from hydrogen and CH$_3$, or A is CR$^a$R$^b$, R$^a$ and R$^b$ are hydrogen, and R$^3$ and R$^5$ together with the atoms to which they are attached form a 5 or 6 membered ring; R$^6$ is selected from hydrogen, F, OH, —OCH$_3$ and C$_1$-C$_3$ alkyl, or A is a direct bond, R$^{6a}$ is hydrogen and R$^3$ and R$^6$ together with the atoms to which they are attached form a 5 or 6 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; R$^b$ is hydrogen or absent; and p is 0, 1, 2 or 3;

to provide a compound of Formula 11:

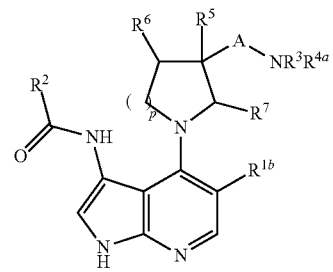

11 wherein R$^{4a}$ is C$_1$-C$_4$ alkyl;

(c) protecting a compound of Formula 12:

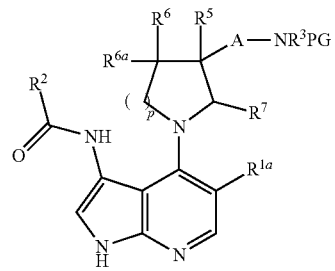

12 wherein R$^{1a}$ is halogen; R$^2$ is selected from C$_1$-C$_6$ alkyl, a saturated or partially unsaturated C$_3$-C$_6$ cycloalkyl, phenyl, a saturated or partially unsaturated 5 or 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclics, heteroaryls and aryl are optionally substituted with one or more groups selected from OH, CN, halogen, oxo (except not on phenyl, aryl or heteroaryl), CF$_3$, C$_1$-C$_6$ alkyl, —O(C$_1$-C$_6$ alkyl), —S(C$_1$-C$_6$ alkyl), and NR$^e$R$^f$; R$^e$ and R$^f$ are independently selected from hydrogen and C$_1$-C$_3$ alkyl; A is selected from a direct bond or CR$^a$R$^b$; R$^3$ is selected from hydrogen or C$_1$-C$_4$ alkyl optionally substituted with OH, F or C$_3$-C$_6$ cycloalkyl; R$^5$ is selected from hydrogen and CH$_3$, or A is CR$^a$R$^b$, R$^a$ and R$^b$ are hydrogen, and R$^3$ and R$^5$ together with the atoms to which they are attached form a 5 or 6 membered ring; R$^6$ is selected from hydrogen, F, OH, —OCH$_3$ and C$_1$-C$_3$ alkyl, or A is a direct bond, R$^{6a}$ is hydrogen and R$^3$ and R$^6$ together with the atoms to which they are attached form a 5 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; $R^b$ is hydrogen or absent; p is 0, 1, 2 or 3; and PG is a protecting group (such as tert-butoxycarbonyl, or p-methoxybenzyl);

performing a coupling reaction; and deprotecting the compound to provide a compound of Formula 15:

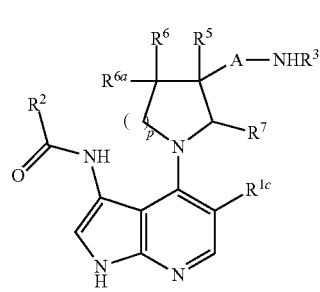

15 wherein $R^{1c}$ is $C_1$-$C_6$ alkyl, $C_3$-$C_6$ cycloalkyl, phenyl or a 5 or 6 membered heteroaryl, wherein the alkyl, cycloalkyl, phenyl or heteroaryl are optionally substituted with one or more groups selected from halogen, CN, $CF_3$, $C_1$-$C_3$ alkyl, —O($C_1$-$C_3$ alkyl) and $NR^cR^d$; and (d) functionalizing a compound of Formula 16:

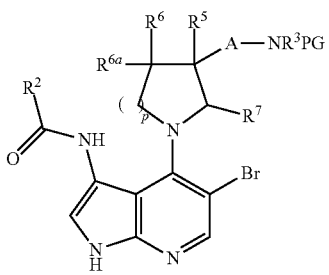

16 wherein $R^2$ is selected from $C_1$-$C_6$ alkyl, a saturated or partially unsaturated $C_3$-$C_6$ cycloalkyl, phenyl, a saturated or partially unsaturated 5 or 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclics, heteroaryls and aryl are optionally substituted with one or more groups selected from OH, CN, halogen, oxo (except not on phenyl, aryl or heteroaryl), $CF_3$, $C_1$-$C_6$ alkyl, —O($C_1$-$C_6$ alkyl), —S($C_1$-$C_6$ alkyl), and $NR^eR^f$; $R^e$ and $R^f$ are independently selected from hydrogen and $C_1$-$C_3$ alkyl; A is selected from a direct bond or $CR^aR^b$; $R^3$ is selected from hydrogen or $C_1$-$C_4$ alkyl optionally substituted with OH, F or $C_3$-$C_6$ cycloalkyl; $R^5$ is selected from hydrogen and $CH_3$, or A is $CR^aR^b$, $R^a$ and $R^b$ are hydrogen, and $R^3$ and $R^5$ together with the atoms to which they are attached form a 5 or 6 membered ring; $R^6$ is selected from hydrogen, F, OH, —$OCH_3$ and $C_1$-$C_3$ alkyl, or A is a direct bond, $R^{6a}$ is hydrogen and $R^3$ and $R^6$ together with the atoms to which they are attached form a 5 membered ring; $R^{6a}$ is selected from hydrogen, F, OH and $CH_3$; $R^7$ is hydrogen, or A is $CR^aR^b$ and $R^3$ and $R^7$ together with the atoms to which they are attached form a 5 or 6 membered ring; $R^a$ is hydrogen, or $R^4$ and $R^b$ are absent and $R^3$ and $R^a$ together with the atoms to which they are attached form an aromatic 5 or 6 membered ring; $R^b$ is hydrogen or absent; p is 0, 1, 2 or 3; PG is a protecting group, such as Boc, CBz, benzyl, or $R^4$; and $R^4$ is selected from hydrogen or $C_1$-$C_4$ alkyl optionally substituted with OH, F or $C_3$-$C_6$ cycloalkyl, or $R^3$ and $R^4$ together with the atoms to which they are attached form a 5 or 6 membered ring;

followed by deprotection to provide a compound of Formula 18:

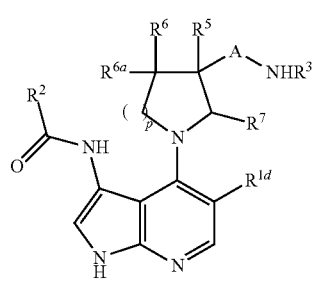

18 wherein $R^{1d}$ is hydrogen or —S($C_1$-$C_6$ alkyl).

In another embodiment of the present invention, a process for preparing compounds of Formula I (or 10, 11, 15 or 18) is provided, comprising:

(a) reacting a compound of Formula 9:

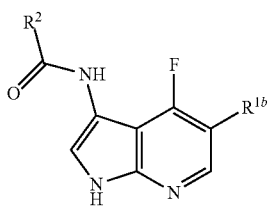

9 wherein $R^{1b}$ is halogen, $CF_3$, and —O($C_1$-$C_6$ alkyl), wherein the alkyl may be optionally substituted with one or more groups selected from halogen, CN, $CF_3$, $C_1$-$C_3$ alkyl, —O($C_1$-$C_3$ alkyl) and $NR^cR^d$; $R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$; $R^c$ and $R^d$ are independently selected from hydrogen and $C_1$-$C_3$ alkyl, or $R^c$ and $R^d$ together with the atom to which they are attached form a 5 or 6 membered ring; $R^e$ and $R^f$ are independently selected from hydrogen and $C_1$-$C_3$ alkyl; $R^g$ and $R^h$ are independently selected from hydrogen and $C_1$-$C_3$ alkyl; and $R^i$ is $C_1$-$C_3$ alkyl;

with an appropriately substituted amine having the formula:

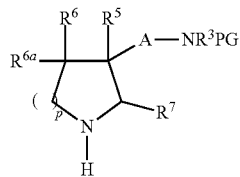

wherein A is selected from a direct bond or CR$^a$R$^b$; R$^3$ is selected from hydrogen or C$_1$-C$_4$ alkyl optionally substituted with OH, F, —O(C$_1$-C$_3$ alkyl) or C$_3$-C$_6$ cycloalkyl; R$^5$ is selected from hydrogen and CH$_3$, or A is CR$^a$R$^b$, R$^a$ and R$^h$ are hydrogen, and R$^3$ and R$^5$ together with the atoms to which they are attached form a 5 or 6 membered ring; R$^6$ is selected from hydrogen, F, OH, —OCH$_3$, C$_1$-C$_3$ alkyl and cyclopropyl, or A is a direct bond, R$^{6a}$ is hydrogen and R$^3$ and R$^6$ together with the atoms to which they are attached form a 5 or 6 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; R$^b$ is hydrogen or absent; p is 0, 1, 2 or 3; and PG is a protecting group (such as Boc, CBz, benzyl, or R$^4$, wherein R$^4$ is selected from hydrogen or C$_1$-C$_4$ alkyl optionally substituted with OH, F, —O(C$_1$-C$_3$ alkyl) or C$_3$-C$_6$ cycloalkyl, or R$^3$ and R$^4$ together with the atoms to which they are attached form a 5 or 6 membered ring);

under standard S$_N$Ar reaction conditions to prepare a compound of Formula 10:

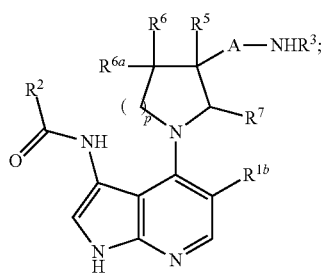

(b) alkylating a compound of Formula 10:

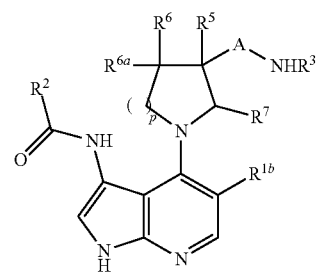

wherein R$^{1b}$ is halogen, CF$_3$, —O(C$_1$-C$_6$ alkyl), wherein the alkyl may be optionally substituted with one or more groups selected from halogen, CN, CF$_3$, C$_1$-C$_3$ alkyl, —O(C$_1$-C$_3$ alkyl) and NR$^c$R$^d$; R$^2$ is selected from C$_1$-C$_6$ alkyl, —O(C$_1$-C$_6$ alkyl), —NH(C$_1$-C$_6$ alkyl), a saturated or partially unsaturated C$_3$-C$_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), CF$_3$, cyclopropyl, cyclopropylmethyl, —SO$_2$R$^i$, C$_1$-C$_6$ alkyl, —O(C$_1$-C$_6$ alkyl), —S(C$_1$-C$_6$ alkyl), NR$^e$R$^f$, and phenyl, wherein the phenyl is optionally substituted with one or more groups selected from OH, CN, halogen, CF$_3$, C$_1$-C$_3$ alkyl, —O(C$_1$-C$_3$ alkyl), and NR$^g$R$^h$; R$^c$ and R$^d$ are independently selected from hydrogen and C$_1$-C$_3$ alkyl, or R$^c$ and R$^d$ together with the atom to which they are attached form a 5 or 6 membered ring; R$^e$ and R$^f$ are independently selected from hydrogen and C$_1$-C$_3$ alkyl; R$^g$ and R$^h$ are independently selected from hydrogen and C$_1$-C$_3$ alkyl; R$^i$ is C$_1$-C$_3$ alkyl; A is selected from a direct bond or CR$^a$R$^b$; R$^3$ is selected from hydrogen or C$_1$-C$_4$ alkyl optionally substituted with OH, F, —O(C$_1$-C$_3$ alkyl) or C$_3$-C$_6$ cycloalkyl; R$^5$ is selected from hydrogen and CH$_3$, or A is CR$^a$R$^b$, R$^a$ and R$^b$ are hydrogen, and R$^3$ and R$^5$ together with the atoms to which they are attached form a 5 or 6 membered ring; R$^6$ is selected from hydrogen, F, OH, —OCH$_3$, C$_1$-C$_3$ alkyl and cyclopropyl, or A is a direct bond, R$^{6a}$ is hydrogen and R$^3$ and R$^6$ together with the atoms to which they are attached form a 5 or 6 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; R$^b$ is hydrogen or absent; and p is 0, 1, 2 or 3;

to provide a compound of Formula 11:

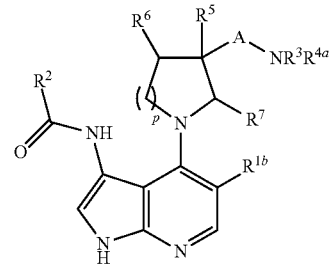

wherein R$^{4a}$ is C$_1$-C$_4$ alkyl;

(c) protecting a compound of Formula 12:

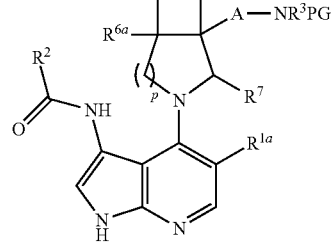

wherein R$^{1a}$ is halogen or OH; R$^2$ is selected from C$_1$-C$_6$ alkyl, —O(C$_1$-C$_6$ alkyl), —NH(C$_1$-C$_6$ alkyl), a saturated or partially unsaturated C$_3$-C$_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), CF$_3$, cyclopropyl, cyclopropylmethyl, —SO$_2$R$^i$, C$_1$-C$_6$ alkyl, —O(C$_1$-C$_6$ alkyl), —S(C$_1$-C$_6$ alkyl), NR$^e$R$^f$, and phenyl, wherein the phenyl is optionally substituted with one or more groups selected from OH, CN, halogen, CF$_3$, C$_1$-C$_3$ alkyl, —O(C$_1$-C$_3$ alkyl), and NR$^g$R$^h$; R$^e$ and R$^f$ are independently selected from hydrogen and C$_1$-C$_3$ alkyl; R$^g$ and R$^h$ are independently selected from hydrogen and C$_1$-C$_3$ alkyl; R$^1$ is C$_1$-C$_3$ alkyl; A is selected from a direct bond or CR$^a$R$^b$; R$^3$ is selected from hydrogen or C$_1$-C$_4$ alkyl optionally substituted with OH, F, —O(C$_1$-C$_3$ alkyl) or C$_3$-C$_6$ cycloalkyl; R$^5$ is selected from hydrogen and CH$_3$, or A is CR$^a$R$^b$, R$^a$ and R$^h$ are hydrogen, and R$^3$ and R$^5$ together with the atoms to which they are attached form a 5 or 6 membered ring; R$^6$ is selected from hydrogen, F, OH, —OCH$_3$, C$_1$-C$_3$ alkyl and cyclopropyl, or A is a direct bond, R$^{6a}$ is hydrogen and R$^3$ and R$^6$ together with the atoms to which they are attached form a 5 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; R$^b$ is hydrogen or absent; p is 0, 1, 2 or 3; and PG is a protecting group (such as tert-butoxycarbonyl, or p-methoxybenzyl);

performing a coupling reaction; and deprotecting the compound to provide a compound of Formula 15:

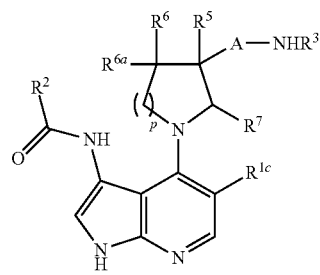

15 wherein R$^{1c}$ is C$_1$-C$_6$ alkyl, C$_3$-C$_6$ cycloalkyl, phenyl or a 5 or 6 membered heteroaryl, wherein the alkyl, cycloalkyl, phenyl or heteroaryl are optionally substituted with one or more groups selected from halogen, CN, CF$_3$, C$_1$-C$_3$ alkyl, —O(C$_1$-C$_3$ alkyl) and NR$^c$R$^d$; and R$^c$ and R$^d$ are independently selected from hydrogen and C$_1$-C$_3$ alkyl, or R$^c$ and R$^d$ together with the atom to which they are attached form a 5 or 6 membered ring; and (d) functionalizing a compound of Formula 16:

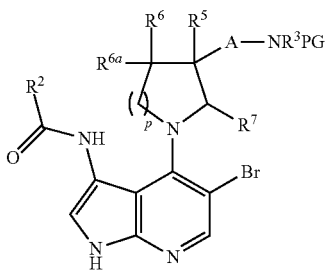

16 wherein R$^2$ is selected from C$_1$-C$_6$ alkyl, —O(C$_1$-C$_6$ alkyl), —NH(C$_1$-C$_6$ alkyl), a saturated or partially unsaturated C$_3$-C$_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), CF$_3$, cyclopropyl, cyclopropylmethyl, —SO$_2$R$^i$, C$_1$-C$_6$ alkyl, —O(C$_1$-C$_6$ alkyl), —S(C$_1$-C$_6$ alkyl), NR$^e$R$^f$, and phenyl, wherein the phenyl is optionally substituted with one or more groups selected from OH, CN, halogen, CF$_3$, C$_1$-C$_3$ alkyl, —O(C$_1$-C$_3$ alkyl), and NR$^g$R$^h$; R$^e$ and R$^f$ are independently selected from hydrogen and C$_1$-C$_3$ alkyl; R$^g$ and R$^h$ are independently selected from hydrogen and C$_1$-C$_3$ alkyl; R$^1$ is C$_1$-C$_3$ alkyl; A is selected from a direct bond or CR$^a$R$^b$; R$^3$ is selected from hydrogen or C$_1$-C$_4$ alkyl optionally substituted with OH, F, —O(C$_1$-C$_3$ alkyl) or C$_3$-C$_6$ cycloalkyl; R$^5$ is selected from hydrogen and CH$_3$, or A is CR$^a$R$^b$, R$^a$ and R$^b$ are hydrogen, and R$^3$ and R$^5$ together with the atoms to which they are attached form a 5 or 6 membered ring; R$^6$ is selected from hydrogen, F, OH, —OCH$_3$, C$_1$-C$_3$ alkyl and cyclopropyl, or A is a direct bond, R$^{6a}$ is hydrogen and R$^3$ and R$^6$ together with the atoms to which they are attached form a 5 membered ring; R$^{6a}$ is selected from hydrogen, F, OH and CH$_3$; R$^7$ is hydrogen, or A is CR$^a$R$^b$ and R$^3$ and R$^7$ together with the atoms to which they are attached form a 5 or 6 membered ring; R$^a$ is hydrogen, or R$^4$ and R$^b$ are absent and R$^3$ and R$^a$ together with the atoms to which they are attached form an aromatic 5 or 6 membered ring; R$^b$ is hydrogen or absent; p is 0, 1, 2 or 3; PG is a protecting group, such as Boc, CBz, benzyl, or R$^4$; and R$^4$ is selected from hydrogen or C$_1$-C$_4$ alkyl optionally substituted with OH, F, —O(C$_1$-C$_3$ alkyl) or C$_3$-C$_6$ cycloalkyl, or R$^3$ and R$^4$ together with the atoms to which they are attached form a 5 or 6 membered ring;

followed by deprotection to provide a compound of Formula 18:

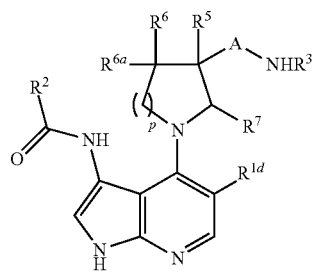

18 wherein R$^{1d}$ is hydrogen or —S(C$_1$-C$_6$ alkyl).

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem. Vol.* 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., Ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr.* Vol. 513 (1990) 375-378). Enriched or purified enantiomers can be distinguished by methods used to distinguish other chiral molecules with asymmetric carbon atoms, such as optical rotation and circular dichroism.

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of Formula I, or a stereoisomer or pharmaceutically acceptable salt thereof. In a further embodiment, the present invention provides a pharmaceutical composition comprising a compound of Formula I, or a stereoisomer or pharmaceutically acceptable salt thereof, together with a pharmaceutically acceptable carrier or excipient.

Methods of Treatment with Compounds of the Invention

The invention includes methods of treating or preventing disease or condition by administering one or more compounds of this invention, or a stereoisomer or pharmaceutically acceptable salt thereof. In one embodiment, a human patient is treated with a compound of the present invention, or a stereoisomer or pharmaceutically acceptable salt thereof, and a pharmaceutically acceptable carrier, adjuvant, or vehicle in an amount to detectably inhibit CHK1 activity.

In another embodiment of the present invention, a method of preventing or treating a disease or disorder modulated by CHK1 and/or CHK2, comprising administering to a mammal in need of such treatment an effective amount of a compound of the present invention is provided.

In another embodiment of the present invention, a method of treating a hyperproliferative disease in a mammal comprising administering a therapeutically effective amount of the compound of the present invention, or a stereoisomer or pharmaceutically acceptable salt thereof, to the mammal is provided.

In another embodiment, a method of treating or preventing cancer, including the below identified conditions, in a mammal in need of such treatment, wherein the method comprises administering to said mammal a therapeutically effective amount of a compound of the present invention, or a stereoisomer or pharmaceutically acceptable salt thereof.

In certain embodiments, the CHK1 inhibitor of the present invention (i.e., a compound of Formula I) is administered in combination with a DNA damaging agent. Generally, the DNA damaging agent will be administered before the CHK1 inhibitor of the present invention. DNA damaging agents include Gemzar® (gemcitabine), Camptosar® (irinotecan or CPT-11), Temodar® (temozolomide), Xeloda® (capecitabine), Hycamtin® (topotecan), cisplatin, Eloxatin® (oxaliplatin), Paraplatin® (carboplatin), camptothecin, ara-C (cytarabine), 5-FU (fluorouracil), Cytoxan® (cyclophosphamide), Etopophos® or Vepesid® (etoposide phosphate), Vumon® (teniposide), Adriamycin PFS® or Adriamycin RDF (doxorubicin), daunorubicin, Alimta® (pemetrexed), and radiation. In certain embodiments, the DNA damaging agent is selected from the group consisting of gemcitabine, irinotecan, temozolomide, capecitabine, camptothecin, cisplatin, ara-C, and 5-FU. In certain embodiments, the DNA damaging agent is selected from gemcitabine, irinotecan, temozolomide and capecitabine. In certain embodiments, the DNA damaging agent is selected from gemcitabine, irinotecan, cisplatin, oxaliplatin, carboplatin and cytarabine. In certain embodiments, the DNA damaging agent is selected from gemcitabine and irinotecan. The DNA damaging agent is administered at its approved or recommended dose.

Because of the ability of a CHK1 inhibitor to potentiate the activity of many anti-cancer agents it is expected that a wide range of tumor types may be treated by the compositions and methods of the invention. These conditions include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast: invasive breast carcinomas (invasive ductal carcinoma and invasive lobular carcinoma), etc.; and Adrenal glands: neuroblastoma. The term hyperproliferative disease includes the above identified conditions. The term "cancerous cell" as provided herein, includes a cell afflicted by any one of the above identified conditions.

In certain embodiments of the present invention, the cancer is selected from colorectal cancer (including Ras mutations), small cell lung cancer, non-small cell lung cancer, glioma, ovarian cancer, metastatic breast cancer, pancreatic cancer, hepatobiliary cancer (including hepatocellular cancer, bile duct cancer and cholangiocarcinoma), gastric cancer, testicular cancer, head and neck squamous cell carcinoma, leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostate cancer.

In certain embodiments of the present invention, the cancer is a solid tumor cancer.

In certain embodiments of the present invention, the cancer is selected from pancreatic cancer, ovarian cancer and colorectal cancer.

In certain embodiments of the present invention, the cancer is selected from colorectal cancer (including Ras mutations), small cell lung cancer, non-small cell lung cancer, and glioma. In certain embodiments, the CHK1 inhibitor is administered in combination with a DNA damaging agent. In a further embodiment, the DNA damaging agent is irinotecan.

In certain embodiments of the present invention, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer. In certain embodiments, the CHK1 inhibitor is administered in combination with a DNA damaging agent. In a further embodiment, the DNA damaging agent is gemcitabine.

In certain embodiments of the present invention, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma. In certain embodiments, the CHK1 inhibitor is administered in combination with a DNA damaging agent. In a further embodiment, the DNA damaging agent is selected from the group consisting of cisplatin, oxaliplatin, and carboplatin.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer. In certain embodiments, the CHK1 inhibitor is administered in combination with a DNA damaging agent. In a further embodiment, the DNA damaging agent is cytarabine.

Another embodiment of the present invention provides the use of a compound of the present invention, or a stereoisomer or pharmaceutically acceptable salt thereof, in the manufacture of a medicament for the treatment of cancer.

In another embodiment, a method of treating or preventing a disease or disorder modulated by CHK1 and/or CHK2, comprising administering to a mammal in need of such treatment an effective amount of a compound of the present invention, or a stereoisomer or pharmaceutically acceptable salt thereof.

In another embodiment, a method of preventing or treating cancer, comprising administering to a mammal in need of such treatment an effective amount of a compound of the present invention, alone or in combination with one or more additional compounds having anti-cancer properties.

CHK1 inhibitors are expected to potentiate the activity of a wide range of anti-cancer agents (or DNA damaging agents), when such agent(s) trigger the CHK1 dependent cell cycle checkpoint.

The invention relates to a composition for the treatment of a hyperproliferative disease in a mammal, comprising a therapeutically effective amount of a compound of the present invention, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

The invention also relates to a method for the treatment of a hyperproliferative disorder in a mammal that comprises administering to said mammal a therapeutically effective amount of a compound of the present invention, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

Another embodiment provides the compounds of the present invention for use in therapy. In a further embodiment, the use also includes the use of a DNA damaging agent.

Another embodiment provides the compounds of the present invention for use in the treatment of a hyperproliferative disease. In a further embodiment, the hyperproliferative disease is cancer, including the above identified conditions. In a further embodiment, the use also includes the use of a DNA damaging agent.

This invention also relates to a pharmaceutical composition for inhibiting abnormal cell growth in a mammal which comprises an amount of a compound of the present invention, or a stereoisomer or a pharmaceutically acceptable salt thereof, in combination with an amount of a chemotherapeutic, wherein the amounts of the compound, stereoisomer or salt and of the chemotherapeutic are together effective in inhibiting abnormal cell growth. Many chemotherapeutics are known in the art. In certain embodiments, the chemotherapeutic is selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and/or prenyl-protein transferase inhibitors.

This invention relates to a method for inhibiting abnormal cell growth in a mammal or treating a hyperproliferative disorder in which the method comprises administering to the mammal an amount of a compound of the present invention, or a stereoisomer or a pharmaceutically acceptable salt thereof, in combination with radiation therapy, wherein the amounts of the compound or salt, in combination with the radiation therapy is effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a compound of the present invention or a stereoisomer or a pharmaceutically acceptable salt thereof, which amount is effective in sensitizing abnormal cells to radiation treatment. The amount of the compound, stereoisomer or salt to be used in this method can be determined according to means for ascertaining effective amounts of such compounds as described herein or by methods know to those skilled in the art.

Another embodiment of the present invention provides the use of a compound of the present invention, or a stereoisomer or pharmaceutically acceptable salt thereof, in the manufacture of a medicament for the treatment of hyperproliferative diseases. In a further embodiment, the hyperproliferative disease may be cancer, including the above identified conditions. In a further embodiment, the use also includes the use of a DNA damaging agent.

In another embodiment of the present invention, use of a compound of the present invention, in the manufacture of a medicament, for use as a CHK1 and/or CHK2 inhibitor in the treatment of a patient undergoing cancer therapy, including the above identified conditions, is provided. In a further embodiment, the use also includes the use of a DNA damaging agent.

Another embodiment of the present invention provides the use of a compound of the present invention in the treatment of a hyperproliferative disease. In a further embodiment, the hyperproliferative disease is cancer, including the above identified conditions. In a further embodiment, the use also includes the use of a DNA damaging agent.

Another embodiment provides the use of a compound of the present invention in the manufacture of a medicament, for use as a CHK1 and/or CHK2 inhibitor in the treatment of a patient undergoing cancer therapy. In a further embodiment, the use also includes the use of a DNA damaging agent.

In another embodiment, a pharmaceutical composition comprising a compound of the present invention for use in the treatment of a hyperproliferative disease is provided.

In another embodiment, a pharmaceutical composition comprising a compound of the present invention for use in the treatment of cancer is provided.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, for example an anti-inflammatory compound that works by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

In order to illustrate the invention, the following Examples are included. However, it is to be understood that these Examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; $CD_3OD$: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Preparative HPLC methods: Some of the final compounds were purified by reverse phase HPLC (0-50% $CH_3CN$ in water) using a Gilson 506C system interface, a Gilson 155 UV/VIS detector, a Gilson 215 Nebula liquid handler/Injector equipped with an 819 injection module, a Gilson 322 pump, and a Waters 25 mm×100 mm YMC ODS-AQ Cartridge 120A Part Number: AQ12S111025RC and a Waters PrepLC 25 mm Radial Compression Module.

LCMS methods: Method 1: This method was run on Agilent 1100 instrument with a Thermo MSQ with a gradient of 5% to 95% organic gradient ($CH_3CN$) with a mobile phase of 10 mM ammonium acetate buffer: 1% isopropyl alcohol in $H_2O$. The column used was a YMC ODS-AQ, 3 um, 120 Angstrom 4.6×50 mm. This method employed a 4 minute run time, and the instrument used was Agilent 1100 instrument with a Thermo MSQ.

Method 2: This method was run on Agilent 1100 instrument with a Thermo MSQ with a gradient of 5% to 95% organic gradient ($CH_3CN$) with a mobile phase of 10 mM ammonium acetate buffer: 1% isopropyl alcohol in $H_2O$. The column used was an YMC ODS-AQ, 3 um, 120 Angstrom 4.6×50 mm. This method employed a 5.5 minute run time, and the instrument used was Agilent 1100 instrument with a Thermo MSQ.

Method 3: This method was run on Thermo Separation Product LC instrument with a LCQ Duo M.S and the column, solvents, gradient and the run time was equal to that of Method 2.

Example A

CHK1 Enzymatic Assay

Compounds were diluted in dimethylsulfoxide ("DMSO") in 3 fold serial dilutions and then added to the reaction to give a final concentration of 1% DMSO. Compounds were tested in an enzymatic assay using human CHK1 kinase domain, amino acids 1 to 273, with 10 additional histidine residues on the carboxy terminus, purified from bacculovirus. The substrate was the fluorescent Omnia peptide S/T11 from Invitrogen. The assay contained 25 mM HEPES pH 7.4, 10 mM MgCl$_2$, 1 mM DTT, 0.01% Triton-X100, 0.5 nM CHK1 enzyme, 2 μM S/T 11 peptide substrate, 60M ATP, test compound, 1% DMSO, in a 25 μL reaction volume. The assay was run at room temperature in white 384 well polypropylene plates (available from Nunc, Inc of Naperville, Ill.) collecting data every 50 seconds for 45 minutes in an Envision plate reader (PerkinElmer, Inc. of Waltham, Mass.), excitation 340 nM, emission 495 nM. The collected data from each well was fit to a straight line and the resulting rates were used to calculate a percent of control. IC$_{50}$ values for each test compound were determined from the percent of control vs. compound concentration plots using a four parameter fit.

Examples 1-184 below were tested in the above assay and found to have an IC$_{50}$ of less than 5 μM. A majority of Examples 1-184 below were tested in the above assay and found to have an IC$_{50}$ of less than 1 μM.

Example B

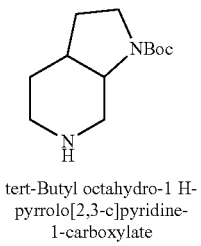 [SMILES: CC(C)(C)OC(=O)N1CCC2CCNCC21]

tert-Butyl octahydro-1 H-
pyrrolo[2,3-c]pyridine-
1-carboxylate

Step A: 1H-Pyrrolo[2,3-c]pyridine (2.50 g, 21.2 mmol) and triethylamine (3.24 mL, 23.3 mmol) were placed in DCM (25 mL) at room temperature. Triethylamine (3.24 mL, 23.3 mmol) was then added, and the reaction was stirred for 30 minutes. The reaction was then poured into water and extracted with DCM. The organic fraction was dried, filtered, and concentrated to give the crude product, which was purified by column chromatography (500:3 DCM:MeOH) to give tert-butyl 1H-pyrrolo[2,3-c]pyridine-1-carboxylate (4.4 g, 95% yield).

Step B: tert-Butyl 1H-pyrrolo[2,3-c]pyridine-1-carboxylate (1.0 g, 4.58 mmol) and PtO$_2$ (0.208 g, 0.916 mmol) were placed in 1:1 EtOH:AcOH (10 mL) and hydrogenated at 50 PSI of H$_2$ for 8 hours (Parr shaker). The reaction was then concentrated, and the crude oil was dissolved in DCM and poured into saturated Na$_2$CO$_3$ and extracted into DCM. The combined organic fractions were dried, filtered, and concentrated to give tert-butyl octahydro-1H-pyrrolo[2,3-c]pyridine-1-carboxylate (0.99 g, 95% yield) as an oil.

Example C

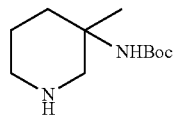

tert-Butyl 3-methylpiperidin-
3-ylcarbamate

Step A: To ethyl piperidine-3-carboxylate (5.0 g, 30.2 mmol) and K$_2$CO$_3$ (4.2 g, 30.2 mmol) in 1:1 THF-water (100 mL) was added benzyl carbonochloridate (4.5 mL, 31.7 mmol) at 0° C. The reaction mixture was stirred at room temperature for 2 hours, and then ether (50 mL) was added. The organic layer was separated, washed with brine and dried over sodium sulfate. After removal of the solvent, the residue was purified by chromatography on silica gel (hexane:ethyl acetate 5:1) to give 1-benzyl 3-ethyl piperidine-1,3-dicarboxylate (7.60 g, 86% yield) as an oil.

Step B: To 1-benzyl 3-ethyl piperidine-1,3-dicarboxylate (3.0 g, 10.3 mmol) in THF (20 mL) was added lithium bis(trimethylsilyl)amide (12.9 mL, 12.9 mmol) in THF at −78° C., and the reaction was stirred at this temperature for 20 minutes. MeI (0.867 mL, 13.9 mmol) was added, and the reaction was warmed to room temperature. After 2 hours at room temperature, the mixture was poured onto saturated ammonium chloride (20 mL) and extracted with ether, washed with brine and dried over sodium sulfate. After removal of the solvent, the residue was purified by chromatography on silica gel (hexane:ethyl acetate 5:1) to give 1-benzyl 3-ethyl 3-methylpiperidine-1,3-dicarboxylate (3.1 g, 98% yield) as an oil.

Step C: To 1-benzyl 3-ethyl 3-methylpiperidine-1,3-dicarboxylate (3.0 g, 10.0 mmol) in ethanol (15 mL) was added LiOH (15.0 mL, 30.1 mmol), and the reaction mixture was stirred at 86° C. for 1 hour. The ethanol was removed, and ether (30 mL) was added. The aqueous layer was separated and acidified with saturated potassium hydrogen sulfate to a pH of about 3 to about 4, extracted with ethyl acetate (50 mL), and washed with brine and dried over sodium sulfate. After removal of the solvent, 1-(benzyloxycarbonyl)-3-methylpiperidine-3-carboxylic acid (2.6 g, 92% yield) was isolated as an oil.

Step D: DPPA (2.4 mL, 11.1 mmol) was added to 1-(benzyloxycarbonyl)-3-methylpiperidine-3-carboxylic acid (2.5 g, 9.2 mmol) and TEA (1.5 mL, 11.1 mmol) in t-BuOH (17.7 mL, 184.6 mmol). The mixture was heated at reflux for 6 hours and then was transferred to a sealed tube and heated at 126° C. for 3 days. The solvent was removed, and then ether (50 mL) and saturated sodium bicarbonate (30 mL) were added. The organic layer was separated, washed with brine, dried over sodium sulfate. After removal of the solvent, the residue was purified by chromatography on silica gel (hexane:ethyl acetate 5:1) to give benzyl 3-(tert-butoxycarbonylamino)-3-methylpiperidine-1-carboxylate (1.4 g, 43% yield) as a solid.

Step E: Benzyl 3-(tert-butoxycarbonylamino)-3-methylpiperidine-1-carboxylate (1.4 g, 4.0 mmol) and 10% Pd/C (0.21 g, 0.2 mmol) in MeOH (20 mL) were stirred under H$_2$ atmosphere (1 atm) for 1 hour. The catalyst was removed by filtration and washed with methanol. The filtrate was concentrated to give tert-butyl 3-methylpiperidin-3-ylcarbamate (0.62 g, 72% yield) as a solid.

Example D

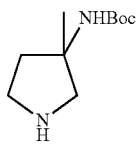

tert-Butyl 3-methylpyrrolidin-
3-ylcarbamate

Step A: To methylpyrrolidine-3-carboxylate hydrochloride (4.00 g, 24.15 mmol) and K$_2$CO$_3$ (6.68 g, 48.3 mmol) in 1:1

THF-water (100 mL) was added benzyl carbonochloridate (3.57 mL, 25.36 mmol) at 0° C. The reaction mixture was stirred at room temperature for 2 hours. Ether (50 mL) was added. The organic layer was separated, washed with brine and dried over sodium sulfate. After removal of the solvent, the residue was purified by chromatography (hexane:ethyl acetate 3:1) to give 1-benzyl 3-methylpyrrolidine-1,3-dicarboxylate (3.45 g, 54% yield) as an oil.

Step B: To 1-benzyl 3-methylpyrrolidine-1,3-dicarboxylate (3.45 g, 13.1 mmol) in THF (20 mL) was added lithium bis(trimethylsilyl)amide (16.4 mL, 16.4 mmol) in THF at −78° C., and the reaction was stirred at this temperature for 20 minutes. MeI (1.10 mL, 17.7 mmol) was added, and the reaction was warmed to room temperature. After 2 hours at room temperature, the mixture was poured onto saturated ammonium chloride (20 mL) and extracted with ether, washed with brine and dried over sodium sulfate. After removal of the solvent, the residue was purified by chromatography (hexane:ethyl acetate 4:1) to give 1-benzyl 3-methyl 3-methylpyrrolidine-1,3-dicarboxylate (2.72 g, 75% yield) as an oil.

Step C: A 3M LiOH solution (14.7 mL, 29.4 mmol) was added to 1-benzyl 3-methyl 3-methylpyrrolidine-1,3-dicarboxylate (2.72 g, 9.81 mmol) in ethanol (15 mL), and the reaction mixture was stirred at 78° C. (bath) for 1 hour. The ethanol was removed, and ether (30 mL) was added. The aqueous layer was separated and acidified with saturated potassium hydrogen sulfate to a pH of about 3 to about 4, extracted with ethyl acetate (50 mL), washed with brine and dried over sodium sulfate. After removal of the solvent, 1-(benzyloxycarbonyl)-3-methylpyrrolidine-3-carboxylic acid (2.56 g, 99% yield) was isolated as an oil.

Step D: DPPA (2.52 mL, 11.67 mmol) was added to 1-(benzyloxycarbonyl)-3-methylpyrrolidine-3-carboxylic acid (2.56 g, 9.72 mmol) and TEA (1.63 mL, 11.7 mmol) in t-BuOH (27.9 mL, 291.7 mmol). The mixture was heated at reflux for 1 hour and then was transferred to a sealed tube and heated at 100° C. (bath) for 24 hours. The solvent was removed, and ether (50 mL) and saturated sodium bicarbonate (30 mL) were added. The organic layer was separated, washed with brine and dried over sodium sulfate. After removal of the solvent, the residue was purified by chromatography (hexane:ethyl acetate 5:1) to give benzyl 3-(tert-butoxycarbonylamino)-3-methylpyrrolidine-1-carboxylate (2.0 g, 61% yield) as an oil.

Step E: Benzyl 3-(tert-butoxycarbonylamino)-3-methylpyrrolidine-1-carboxylate (2.00 g, 5.98 mmol) and 10% Pd/C (0.32 g, 0.30 mmol) in MeOH (20 mL) were stirred under 1 atmosphere of $H_2$ for 1 hour. The catalyst was removed by filtration and washed with methanol. The filtrate was concentrated to give tert-butyl 3-methylpyrrolidin-3-ylcarbamate (1.15 g, 96%) as a solid.

Example E

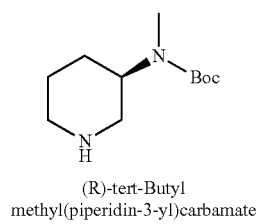

(R)-tert-Butyl methyl(piperidin-3-yl)carbamate

Step A: A solution of (R)-tert-butyl piperidin-3-ylcarbamate (10.00 g, 49.93 mmol) and triethylamine (20.88 mL, 149.8 mmol) in $CH_2Cl_2$ (100 mL) at 0° C. (ice bath) was treated dropwise with benzyl carbonochloridate (10.54 mL, 74.90 mmol) and stirred at 0° C. After 2 hours, the mixture was diluted with $CH_2Cl_2$ (50 mL) and successively washed with ice cold 10% HCl (2×30 mL), water (1×30 mL), saturated $NaHCO_3$ (1×30 mL), and brine (1×30 mL). The organic phase was dried ($MgSO_4$), filtered, and concentrated in vacuo. The residue obtained was purified by flash chromatography on silica gel (Biotage Flash 60) eluting with 20% EtOAc/hexane (3 L). The fractions containing the product were pooled, concentrated in vacuo and dried under high vacuum for 18 hours to provide (R)-benzyl 3-(tert-butoxycarbonylamino)piperidine-1-carboxylate as a solid. LCMS (APCI+) m/z 335 (M+H)+.

Step B: A solution of (R)-benzyl 3-(tert-butoxycarbonylamino)piperidine-1-carboxylate (5.00 g, 14.95 mmol) in dry DMF (50 mL) was added dropwise to a suspension of sodium hydride 60% in mineral oil (0.7176 g, 17.94 mmol) in dry DMF (10 mL). The mixture was stirred at 0° C. for 1 hour and allowed to stir at room temperature for 2 hours. Then the mixture was cooled to 0° C. and treated dropwise with iodomethane (1.024 mL, 16.45 mmol). The reaction mixture was stirred at 0° C. for 1 hour and allowed to warm to room temperature over 18 hours. Water (40 mL) was added, and the mixture was extracted into EtOAc (3×50 mL). The organic layers were combined, washed with water (3×20 mL), dried ($MgSO_4$), filtered, and concentrated in vacuo. The residue obtained was purified by flash chromatography on silica gel (Biotage Flash 40M+) eluting with 20% EtOAc/hexane (1.25 L) to provide (R)-benzyl 3-(tert-butoxycarbonyl(methyl)amino)piperidine-1-carboxylate (4.10 g, 79% yield) as an oil. LCMS (APCI+) m/z 349 (M+H)+.

Step C: A solution of (R)-benzyl 3-(tert-butoxycarbonyl(methyl)amino)piperidine-1-carboxylate (4.00 g, 11.5 mmol) in methanol (10 mL) was slowly added to a suspension of 5% Pd on activated carbon (2.44 g, 1.15 mmol) in EtOH (20 mL). The reaction mixture was evacuated and back filled with $N_2$ (3 cycles). The reaction vessel was then evacuated and back filled with $H_2$ (3 cycles) using a $H_2$ balloon. The mixture was stirred under $H_2$ atmosphere for 1 hour and filtered through a pad of celite, washing with additional 10% MeOH/EtOAc (3×20 mL). The filtrate collected was concentrated in vacuo to provide (R)-tert-butyl methyl(piperidin-3-yl)carbamate (2.01 g, 82% yield) as an oil. LCMS (APCI+) m/z 215 (M+H)+.

Example F

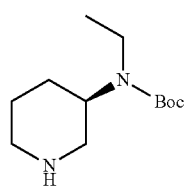

(R)-tert-Butyl ethyl(piperidin-3-yl)carbamate

Step A: A solution of (R)-benzyl 3-(tert-butoxycarbonylamino)piperidine-1-carboxylate (5.00 g, 14.95 mmol, Example E) in dry DMF (50 mL) was added dropwise to a suspension of sodium hydride 60% in mineral oil (0.7176 g, 17.94 mmol) in dry DMF (10 mL). The mixture was stirred at 0° C. for 1 hour and allowed to stir at room temperature for 2 hours. The mixture was then cooled to 0° C. and treated dropwise with iodoethane (1.315 mL, 16.45 mmol). The reaction mixture was stirred at 0° C. for 2 hours and allowed to warm to room temperature over 18 hours. Water (50 mL) was added, and the mixture was extracted into EtOAc (3×70 mL). The organic layers were combined, washed with water (3×20 mL), dried (MgSO$_4$), filtered, and concentrated in vacuo. The resulting residue was purified by flash chromatography on silica gel (Biotage Flash 40M+) eluting with 20% EtOAc/hexane to provide (R)-benzyl 3-(tert-butoxycarbonyl(ethyl) amino)piperidine-1-carboxylate (5.01 g, 92% yield) as an oil. LCMS (APCI+) m/z 363 (M+H)+.

Step B: A solution of (R)-benzyl 3-(tert-butoxycarbonyl (ethyl)amino)piperidine-1-carboxylate (5.00 g, 13.8 mmol) in a mixture of EtOH:MeOH (1:1, 50 mL) was added to a suspension of 10% palladium on activated carbon (1.47 g, 1.38 mmol) in EtOH (20 mL) under N$_2$ atmosphere. The mixture was degassed under N$_2$ (3 cycles) and back filled with H$_2$ (3 cycles) using a H$_2$ balloon. The mixture was then stirred under H$_2$ atmosphere for 4 hours. The reaction mixture was then filtered through a pad of celite washing with 5% MeOH/EtOAc (3×30 mL). The filtrate collected was concentrated in vacuo to provide the crude (R)-tert-butyl ethyl(piperidin-3-yl)carbamate. LCMS (APCI+) m/z 229 (M+H)+.

Example G

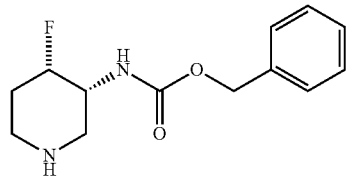

Benzyl-cis-4-fluoropiperidin-3-ylcarbamate

Step A: A solution of m-CPBA (7.53 g, 32.7 mmol) in DCM (10 mL) was added to a solution of tert-butyl 5,6-dihydropyridine-1(2H)-carboxylate (5.00 g, 27.3 mmol) in DCM (20 mL) at 0° C. The reaction was stirred at 0° C. for 15 minutes and then at room temperature for 3 hours. Saturated sodium sulfite solution (20 mL) and saturated sodium bicarbonate solution (30 mL) was added. The organic layer was separated, washed with brine, dried (sodium sulfate) and concentrated in vacuo to give tert-butyl 7-oxa-3-azabicyclo [4.1.0]heptane-3-carboxylate (5.36 g, 99%) as oil.

Step B: A mixture of tert-butyl 7-oxa-3-azabicyclo[4.1.0] heptane-3-carboxylate (5.46 g, 27.4 mmol) and triethylamine trihydrofluoride (4.42 g, 27.4 mmol) in DCE (4 mL) was stirred at 80° C. (bath) for 18 hours. After cooling to room temperature, saturated sodium bicarbonate (20 mL) and DCM (30 mL) were added. The organic phase was separated, washed with brine, dried (sodium sulfate) and concentrated in vacuo. The residue obtained was purified by flash chromatography on silica gel (hexane:ethyl acetate 1:1) to give trans-tert-butyl 4-fluoro-3-hydroxypiperidine-1-carboxylate (3.5 g, 58%) as a solid.

Step C: A mixture of trans-tert-butyl 4-fluoro-3-hydroxypiperidine-1-carboxylate (3.10 g, 14.1 mmol) and 4-methylbenzene-1-sulfonyl chloride (5.39 g, 28.3 mmol) in pyridine (20 mL) was stirred at room temperature for 18 hours. The pyridine was removed in vacuo, and the residue was dissolved in ethyl acetate (30 mL), washed with brine, dried (sodium sulfate) and concentrated in vacuo. The residue obtained was purified by flash chromatography on silica gel (hexane:ethyl acetate 2:1) to give trans-tert-butyl 4-fluoro-3-(tosyloxy)piperidine-1-carboxylate (3.95 g, 75%) as a solid.

Step D: A mixture of trans-tert-butyl 4-fluoro-3-(tosyloxy) piperidine-1-carboxylate (3.95 g, 10.6 mmol) and NaN$_3$ (1.72 g, 26.4 mmol) in DMF (30 mL) was stirred at 128° C. (bath) for 18 hours. After cooling to room temperature, ether (100 mL) was added. The mixture was washed with brine (2×50 mL), dried (sodium sulfate) and concentrated in vacuo. The residue obtained was purified by flash chromatography on silica gel (hexane:ethyl acetate 4:1) to give cis-tert-butyl 3-azido-4-fluoropiperidine-1-carboxylate (1.40 g, 54%).

Step E: A mixture of cis-tert-butyl 3-azido-4-fluoropiperidine-1-carboxylate (1.40 g, 5.73 mmol) and 10% Pd/C (0.61 g, 0.57 mmol) in MeOH (20 mL) was charged 1 atmosphere H$_2$ and stirred at room temperature for 1 hour. The catalyst was removed by filtration and washed with methanol. The filtrate was concentrated in vacuo. The residue obtained was dissolved in pyridine (10 mL) and benzyl carbonochloridate (1.61 mL, 11.46 mmol) was added. The reaction was stirred at room temperature for 2 hours. The pyridine was removed in vacuo, and the residue was dissolved in ethyl acetate (30 mL), washed with brine, dried (sodium sulfate) and concentrated in vacuo. The residue obtained was purified by flash chromatography on silica gel (hexane:ethyl acetate 3:1) to give cis-tert-butyl 3-(benzyloxycarbonylamino)-4-fluoropiperidine-1-carboxylate (0.44 g, 22%) as a solid.

Step F: 4N HCl in dioxane (3.29 mL, 13.2 mmol) was added to a solution of cis-tert-butyl 3-(benzyloxycarbonylamino)-4-fluoropiperidine-1-carboxylate (0.58 g, 1.65 mmol) in DCM (3 mL) at room temperature. The reaction mixture was stirred at room temperature for 2 hours. The solvent was removed in vacuo. The resulting solid was dissolved in water (5 mL) and extracted with ether (10 mL). The resulting aqueous layer was basified with 30% potassium carbonate to a pH of about 10 and extracted with DCM (2×30 mL). The combined organic layer was dried (sodium sulfate) and concentrated in vacuo to give benzyl-cis-4-fluoropiperidin-3-ylcarbamate (0.39 g, 94%) as a solid.

Example H

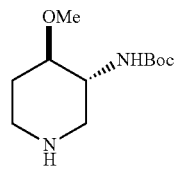

tert-Butyl-trans-4-methoxypiperidin-3-ylcarbamate

Step A: 3-Chlorobenzoperoxoic acid (51.1 g, 228 mmol) was added portion wise to a solution of 5,6-dihydropyridine-1(2H)-carboxylate (33.0 g, 152 mmol) in DCM (200 mL) at 0° C. After 10 minutes at 0° C., the reaction was warmed to room temperature and stirred at room temperature for 4 hours. The reaction mixture was diluted with ether (800 mL), washed with 1N NaOH solution (2×200 mL), saturated N$_2$SO$_3$ solution (2×100 mL), brine (100 mL), dried (sodium sulfate) and concentrated in vacuo to give benzyl 7-oxa-3-azabicyclo[4.1.0]heptane-3-carboxylate (35.0 g, 99%) as an oil.

Step B: A mixture of benzyl 7-oxa-3-azabicyclo[4.1.0] heptane-3-carboxylate (19.0 g, 81.5 mmol), NaN$_3$ (10.6 g, 163 mmol) and NH$_4$Cl (4.36 g, 81.5 mmol) in MeOH (200 mL) and water (40 mL) was stirred at 65° C. (bath) for 20 hours. The reaction mixture was cooled to room temperature, and the methanol was removed in vacuo. The resulting mixture was extracted with ether (2×300 mL). The combined ether layers were washed with brine, dried (sodium sulfate) and concentrated in vacuo to give a mixture of trans-benzyl 4-azido-3-hydroxypiperidine-1-carboxylate and trans-benzyl 3-azido-4-hydroxypiperidine-1-carboxylate (22.0 g, 98%).

Step C: 4-Methylbenzene-1-sulfonyl chloride (31.9 g, 167 mmol) was added dropwise to a mixture of trans-benzyl 4-azido-3-hydroxypiperidine-1-carboxylate, trans-benzyl 3-azido-4-hydroxypiperidine-1-carboxylate (22.0 g, 79.6 mmol) and pyridine (17 mL) in DCM (60 mL) at 0° C. After 5 minutes at 0° C., the reaction mixture was allowed warm to room temperature and stirred at room temperature for 3 days. The solvent was removed in vacuo, and the residue obtained was dissolved in ethyl acetate (300 mL). The mixture was washed with brine, dried (sodium sulfate) and concentrated in vacuo. The residue obtained was purified by flash chromatography on silica gel (hexane:ethyl acetate 3:1) to give a mixture of trans-benzyl 4-azido-3-(tosyloxy)piperidine-1-carboxylate and trans-benzyl 3-azido-4-(tosyloxy)piperidine-1-carboxylate (37 g, 100%).

Step D: $NaBH_4$ (3.41 g, 90.3 mmol) was added portionwise to a solution of $CuSO_4$-$5H_2O$ (10.73 g, 42.98 mmol) in methanol (200 mL) at 0° C. After 5 minutes, a solution of trans-benzyl 4-azido-3-(tosyloxy)piperidine-1-carboxylate and trans-benzyl 3-azido-4-(tosyloxy)piperidine-1-carboxylate (37 g, 85.95 mmol; mixed product from last step) in methanol (100 mL) was added at 0° C. After addition, additional $NaBH_4$ (10.2 g, 270.6 mmol) was added in four portions over the course of 1 hour. After one hour at 0° C., the reaction mixture was filtered through a pad of celite and concentrated in vacuo. The residue obtained was dissolved in DCM (800 mL), washed with water (200 mL), saturated $NH_4Cl$ solution (200 mL), brine (200 mL), dried (sodium sulfate) and concentrated in vacuo. The residue obtained was dissolved in DCM (200 mL) and TEA (24.0 mL, 171.9 mmol) and diethyl phosphorochloridate (12.4 mL, 85.95 mmol) was added at 0° C. The reaction mixture was warmed to room temperature and stirred at room temperature for 30 minutes. Water (50 mL) was added. The organic layer was separated, washed with brine, dried (sodium sulfate) and concentrated in vacuo. The residue obtained was purified by flash chromatography on silica gel (ethyl acetate) to give benzyl 7-(diethoxyphosphoryl)-3,7-diazabicyclo[4.1.0]heptane-3-carboxylate (17.5 g, 55%) as an oil.

Step E: $BF_3$ etherate (1.35 mL, 10.6 mmol) was added to a solution of benzyl 7-(diethoxyphosphoryl)-3,7-diazabicyclo[4.1.0]heptane-3-carboxylate (1.96 g, 5.32 mmol) in methanol (10 mL) at 0° C. and stirred at 0° C. for 2 hours. The solvent was removed in vacuo, ethyl acetate (30 mL) and saturated sodium bicarbonate (20 mL) were added. The organic layer was separated, dried (sodium sulfate) and concentrated in vacuo to give trans-benzyl 3-(diethoxyphosphorylamino)-4-methoxypiperidine-1-carboxylate (2.00 g, 94%) as an oil.

Step F: A mixture of trans-benzyl 3-(diethoxyphosphorylamino)-4-methoxypiperidine-1-carboxylate (2.00 g, 4.99 mmol) and 10% Pd/C (0.27 g, 0.25 mmol) in methanol (30 mL) was charged with 1 atmosphere hydrogen and stirred at room temperature for 1 hour. The catalyst was removed by filtration and washed with methanol (20 mL). The filtrate was concentrated in vacuo to give diethyl trans-4-methoxypiperidin-3-ylphosphoramidate (1.30 g, 98%) as an oil.

Step G: A mixture of diethyl trans-4-methoxypiperidin-3-ylphosphoramidate (1.30 g, 4.88 mmol), benzaldehyde (0.74 mL, 7.32 mmol) and acetic acid (0.56 mL, 9.76 mmol) in methanol (20 mL) was stirred at 0° C. for 30 minutes. $NaCNBH_3$ (0.46 g, 7.32 mmol) was added at 0° C. The resulting solution was warmed to room temperature and stirred at room temperature for 1 hour. The solvent was removed in vacuo and saturated sodium bicarbonate (20 mL) and ethyl acetate (30 mL) were added. The organic layer was separated, washed with brine, dried (sodium sulfate) and concentrated in vacuo to give diethyl trans-1-benzyl-4-methoxypiperidin-3-ylphosphoramidate (1.70 g, 98%), which was used directly in the next step without purification.

Step H: 6N HCl (5.56 mL, 33.4 mmol) was added to a solution of diethyl trans-1-benzyl-4-methoxypiperidin-3-ylphosphoramidate (1.7 g, 4.77 mmol) in dioxane (5 mL) at room temperature and stirred at 66° C. (bath) for 2 hours. The solvent was removed in vacuo, and the residue obtained was dissolved in THF (5 mL) and a 6N NaOH solution (7 mL). $Boc_2O$ (2.08 g, 9.54 mmol) was added, and the reaction mixture was stirred at room temperature for 1 hour. Ethyl acetate (20 mL) was added, and the organic layer was separated, dried (sodium sulfate) and concentrated in vacuo. The residue obtained was purified by flash chromatography on silica gel (hexane:ethyl acetate 3:1) to give tert-butyl trans-1-benzyl-4-methoxypiperidin-3-ylcarbamate (1.37 g, 90%) as an oil.

Step I: A mixture of tert-butyl trans-1-benzyl-4-methoxypiperidin-3-ylcarbamate (1.37 g, 4.28 mmol) and 10% Pd/C (0.46 g, 0.43 mmol) in MeOH (20 mL) was charged with 1 atmosphere hydrogen and stirred at room temperature for 18 hours. The catalyst was removed by filtration and washed with methanol (20 mL). The filtrate was concentrated in vacuo to give tert-butyl trans-4-methoxypiperidin-3-ylcarbamate (0.99 g, 100%) as a solid.

Example I

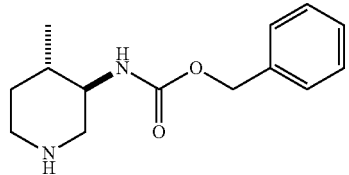

Benzyl-trans-4-methylpiperidin-3-ylcarbamate

Step A: To a suspension of Cu(I)I (0.10 g, 0.54 mmol) in THF (20 mL) was slowly added 1.40M methylmagnesium bromide (15.5 mL, 21.7 mmol) in 3:1 toluene:THF at −30° C. After stirring at that temperature for 15 minutes, a solution of benzyl 7-(diethoxyphosphoryl)-3,7-diazabicyclo[4.1.0]heptane-3-carboxylate (2.00 g, 5.43 mmol, Example H, Step D) in THF (10 mL) was added at −30° C. The mixture was then slowly warmed to 0° C. in 2 hours and stirred at 0° C. for 2 hours. Water (20 mL) was added and extracted with ethyl acetate (2×30 mL), washed with brine, dried (sodium sulfate) and concentrated in vacuo. The residue obtained was purified by flash chromatography on silica gel (ethyl acetate) to give trans-benzyl 3-(diethoxyphosphorylamino)-4-methylpiperidine-1-carboxylate (1.00 g, 48%) as an oil.

Step B: A mixture of trans-benzyl 3-(diethoxyphosphorylamino)-4-methylpiperidine-1-carboxylate (0.95 g, 2.5 mmol) and 10% Pd/C (0.13 g, 0.12 mmol) in methanol (30 mL) was charged with 1 atmosphere hydrogen and stirred at room temperature for 1 hour. The catalyst was removed by filtration and washed with methanol (20 mL). The filtrate was concentrated in vacuo to give diethyl trans-4-methylpiperidin-3-ylphosphoramidate (0.63 g, 100%) as an oil.

Step C: A mixture of diethyl trans-4-methylpiperidin-3-ylphosphoramidate (0.63 g, 2.52 mmol), benzaldehyde (0.38 mL, 3.78 mmol) and acetic acid (0.29 mL, 5.03 mmol) in methanol (20 mL) was stirred at 0° C. for 30 minutes. NaCNBH$_3$ (0.24 g, 3.78 mmol) was added at 0° C. The resulting solution was warmed to room temperature and stirred at room temperature for 1 hour. The solvent was removed in vacuo, and saturated sodium bicarbonate (20 mL) and ethyl acetate (30 mL) were added. The organic layer was separated, washed with brine, dried (sodium sulfate) and concentrated in vacuo to give diethyl trans-1-benzyl-4-methylpiperidin-3-ylphosphoramidate (0.85 g, 99%), which was used directly in the next step without purification.

Step D: 6N HCl (4.1 mL, 25 mmol) was added to a solution of diethyl trans-1-benzyl-4-methylpiperidin-3-ylphosphoramidate (0.85 g, 2.5 mmol) in dioxane (5 mL) at room temperature and stirred at 66° C. (bath) for 2 hours. The solvent was removed in vacuo, and the residue obtained was dissolved in THF (5 mL) and 6N NaOH (7 mL). Boc$_2$O (1.09 g, 5.0 mmol) was added and stirred at room temperature for 1 hour. Ethyl acetate (20 mL) was added, and the organic layer was separated, dried (sodium sulfate) and concentrated in vacuo. The residue obtained was purified by flash chromatography on silica gel (hexane:ethyl acetate 4:1) to give tert-butyl trans-1-benzyl-4-methylpiperidin-3-ylcarbamate (0.64 g, 84%) as a solid.

Step E: A mixture of tert-butyl trans-1-benzyl-4-methylpiperidin-3-ylcarbamate (0.64 g, 2.1 mmol) and 10% Pd/C (0.22 g, 0.21 mmol) in methanol (10 mL) was charged with 1 atmosphere hydrogen and stirred at room temperature for 18 hours. The catalyst was removed by filtration and washed with methanol (20 mL). The filtrate was concentrated in vacuo to give tert-butyl trans-4-methylpiperidin-3-ylcarbamate (0.43 g, 95%) as a solid.

Example J

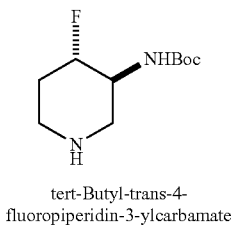 [SMILES: CC(C)(C)OC(=O)N[C@H]1CNCC[C@@H]1F]

tert-Butyl-trans-4-fluoropiperidin-3-ylcarbamate

Step A: BF$_3$ etherate (3.10 mL, 24.4 mmol) was added to a solution of benzyl 7-(diethoxyphosphoryl)-3,7-diazabicyclo[4.1.0]heptane-3-carboxylate (3.00 g, 8.14 mmol; Example H, step D) in DCM (10 mL) at 0° C. The resulting solution was warmed to room temperature and stirred at room temperature for 3 days. The solvent was removed in vacuo, ethyl acetate (30 mL) and saturated sodium bicarbonate (20 mL) were added. The organic layer was separated, dried (sodium sulfate) and concentrated in vacuo. The residue obtained was purified by flash chromatography on silica gel (ethyl acetate) to give trans-benzyl 3-(diethoxyphosphorylamino)-4-fluoropiperidine-1-carboxylate (0.53 g, 17%) as oil.

Step B: A mixture of trans-benzyl 3-(diethoxyphosphorylamino)-4-fluoropiperidine-1-carboxylate (0.54 g, 1.4 mmol) and 10% Pd/C (0.074 g, 0.070 mmol) in methanol (30 mL) was charged with 1 atmosphere hydrogen and stirred at room temperature for 6 hours. The catalyst was removed by filtration and washed with methanol (20 mL). The filtrate was concentrated in vacuo to give diethyl trans-4-fluoropiperidin-3-ylphosphoramidate (0.35 g, 99%) as oil.

Step C: A mixture of diethyl trans-4-fluoropiperidin-3-ylphosphoramidate (0.35 g, 1.38 mmol), benzaldehyde (0.21 mL, 2.07 mmol) and acetic acid (0.16 mL, 2.75 mmol) in methanol (20 mL) was stirred at 0° C. for 30 minutes. NaCNBH$_3$ (0.13 g, 2.07 mmol) was added at 0° C. The resulting solution was warmed to room temperature and stirred at room temperature for 1 hour. The solvent was removed in vacuo, and saturated sodium bicarbonate (20 mL) and ethyl acetate (30 mL) were added. The organic layer was separated, washed with brine, dried (sodium sulfate) and concentrated in vacuo to give diethyl trans-1-benzyl-4-fluoropiperidin-3-ylphosphoramidate (0.47 g, 99%), which was used directly in the next step without purification.

Step D: 6N HCl (4.55 mL, 27.30 mmol) was added to a solution of diethyl trans-1-benzyl-4-fluoropiperidin-3-ylphosphoramidate (0.47 g, 1.37 mmol) in dioxane (5 mL) and stirred at 66° C. (bath) for 2 hours. The solvent was removed in vacuo, and the residue obtained was dissolved in THF (5 mL) and 6N NaOH (7 mL). Boc$_2$O (0.60 g, 2.73 mmol) was added and stirred at room temperature for 1 hour. Ethyl acetate (20 mL) was added, and the organic layer was separated, dried (sodium sulfate) and concentrated in vacuo. The residue obtained was purified by flash chromatography on silica gel (hexane:ethyl acetate=4:1) to give tert-butyl trans-1-benzyl-4-fluoropiperidin-3-ylcarbamate (0.28 g, 67%) as a solid.

Step E: A mixture of tert-butyl trans-1-benzyl-4-fluoropiperidin-3-ylcarbamate (0.28 g, 0.91 mmol) and 10% Pd/C (0.097 g, 0.091 mmol) in MeOH (10 mL) was charged 1 atmosphere of hydrogen and stirred at room temperature for 4 hours. The catalyst was removed by filtration and washed with methanol (20 mL). The filtrate was concentrated in vacuo to give tert-butyl trans-4-fluoropiperidin-3-ylcarbamate (0.19 g, 96%) as oil.

Example K

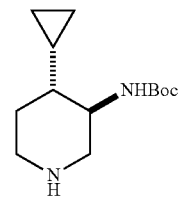

tert-Butyl-trans-4-cyclopropylpiperidin-3-ylcarbamate

Step A: To a suspension of Cu(I)I (0.15 g, 0.77 mmol) in THF (20 mL) was slowly added 0.50M cyclopropylmagnesium bromide (61.2 mL, 30.6 mmol) in THF at −30° C. After stirring at that temperature for 15 minutes, a solution of benzyl 7-(diethoxyphosphoryl)-3,7-diazabicyclo[4.1.0]heptane-3-carboxylate (2.82 g, 7.66 mmol; Example H, Step D) in THF (10 mL) was added at −30° C., and then the mixture was slowly warmed to room temperature and stirred at room temperature for 2 hours. Water (50 mL) was added and extracted with ethyl acetate (2×40 mL), washed with brine, dried (sodium sulfate) and concentrated in vacuo. The residue obtained was purified by flash chromatography on silica gel (ethyl acetate) to give trans-benzyl 4-cyclopropyl-3-(diethoxyphosphorylamino)piperidine-1-carboxylate (1.84 g, 59%).

Step B: A mixture of trans-benzyl 4-cyclopropyl-3-(diethoxyphosphorylamino)piperidine-1-carboxylate (1.84 g, 4.48 mmol) and 10% Pd/C (0.48 g, 0.45 mmol) in methanol (30 mL) was charged with 1 atmosphere hydrogen and stirred at room temperature for 1 hour. The catalyst was removed by filtration and washed with methanol (20 mL). The filtrate was concentrated in vacuo to give diethyl trans-4-cyclopropylpiperidin-3-ylphosphoramidate (1.24 g, 100%) as an oil.

Step C: A mixture of diethyl trans-4-cyclopropylpiperidin-3-ylphosphoramidate (1.24 g, 4.49 mmol), benzaldehyde (0.68 mL, 6.73 mmol) and acetic acid (0.51 mL, 8.98 mmol) in methanol (20 mL) was stirred at 0° C. for 30 minutes. NaCNBH$_3$ (0.42 g, 6.73 mmol) was added at 0° C. The resulting solution was warmed to room temperature and stirred at room temperature for 1 hour. The solvent was removed in vacuo, and saturated sodium bicarbonate (20 mL) and ethyl acetate (30 mL) were added. The organic layer was separated, washed with brine, dried (sodium sulfate) and concentrated in vacuo to give diethyl trans-1-benzyl-4-cyclopropylpiperidin-3-ylphosphoramidate (1.64 g, 100%), which was used directly in the next step without purification.

Step D: 6N HCl (7.46 mL, 44.76 mmol) was added to a solution of diethyl trans-1-benzyl-4-cyclopropylpiperidin-3-ylphosphoramidate (1.64 g, 4.48 mmol) in dioxane (5 mL) and stirred at 66° C. (bath) for 2 hours. The solvent was removed in vacuo, and the residue obtained was dissolved in THF (5 mL) and 6N NaOH (7 mL). Boc$_2$O (1.95 g, 8.95 mmol) was added and stirred at room temperature for 1 hour. Ethyl acetate (20 mL) was added, and the organic layer was separated, dried (sodium sulfate) and concentrated in vacuo. The residue obtained was purified by flash chromatography on silica gel (hexane:ethyl acetate=3:1) to give tert-butyl trans-1-benzyl-4-cyclopropylpiperidin-3-ylcarbamate (1.20 g, 81%) as a solid.

Step E: A mixture of tert-butyl trans-1-benzyl-4-cyclopropylpiperidin-3-ylcarbamate (1.20 g, 3.63 mmol) and 10% Pd/C (0.39 g, 0.36 mmol) in methanol (20 mL) was charged with 1 atmosphere hydrogen and stirred at room temperature for 18 hours. The catalyst was removed by filtration and washed with methanol (20 mL). The filtrate was concentrated in vacuo to give tert-butyl-trans-4-cyclopropylpiperidin-3-ylcarbamate (0.87 g, 100%) as a solid.

Example L

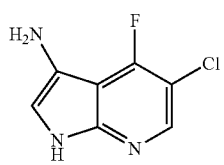

5-Chloro-4-fluoro-1H-pyrrolo[2,3-b]pyridin-3-amine

4-Fluoro-1-(triisopropylsilyl)-1H-pyrrolo[2,3-b]pyridine (3.0 g, 10.258 mmol) was placed in THF (15 mL) at −78° C. s-BuLi (16.12 mL, 22.57 mmol) was then added dropwise and stirred for 30 minutes. Hexachloroethane (6.07 g, 25.6 mmol) in THF (10 mL) was then added rapidly, and the reaction was stirred for an additional 30 minutes. The reaction was quenched with saturated aqueous NH$_4$Cl and extracted into hexanes. The combined organic fractions were dried, filtered and concentrated to give the crude product that was purified by column chromatography (hexanes) to give 5-chloro-4-fluoro-1-(triisopropylsilyl)-1H-pyrrolo[2,3-b]pyridine (2.1 g, 62% yield).

5-Chloro-4-fluoro-1-(triisopropylsilyl)-1H-pyrrolo[2,3-b]pyridine (3.0 g, 9.18 mmol) was placed in THF (15 mL) at 0° C. TBAF (10.094 mL, 10.094 mmol) was added dropwise and stirred for 30 minutes. The reaction was then quenched with saturated aqueous NaHCO$_3$ and extracted into DCM. The combined organic fractions were dried, filtered, and concentrated to give the crude product that was purified by column chromatography (500:6 DCM:MeOH) to give 5-chloro-4-fluoro-1H-pyrrolo[2,3-b]pyridine (1.4 g, 89% yield).

5-Chloro-4-fluoro-1H-pyrrolo[2,3-b]pyridine (1.2 g, 7.0 mmol) was added slowly to fuming nitric acid (10 mL) at 0° C. Upon completion of the addition, the reaction was stirred for 10 minutes, and then quenched with ice. Water was added until a precipitate formed, which was filtered, washed with water and dried to give the product 5-chloro-4-fluoro-3-nitro-1H-pyrrolo[2,3-b]pyridine (1.3 g, 86% yield).

5-Chloro-4-fluoro-3-nitro-1H-pyrrolo[2,3-b]pyridine (1.20 g, 5.57 mmol) was placed in 6M HCl (30 mL). SnCl$_2$ (5.28 g, 27.8 mmol) was then added, and the reaction was stirred for 30 minutes at room temperature. The reaction was then poured into a mixture of 1M NaOH and ice. The resulting suspension was then raised to a pH of 8 and then extracted with 3:1 DCM:i-PrOH. The combined organic fractions were dried, filtered, and concentrated to give the crude product, which was triturated with 10:1 hexanes:DCM to give the product 5-chloro-4-fluoro-1H-pyrrolo[2,3-b]pyridin-3-amine (0.8 g, 77% yield).

Example 1

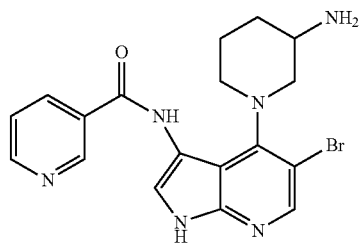

N-(4-(3-Aminopiperidin-1-yl)-5-bromo-1H-pyrrolo[2,3-b]pyridin-3-yl)nicotinamide

Step A: A solution of 3-chlorobenzoperoxoic acid (121 g, 698 mmol) in ethyl acetate ("EtOAc"; 500 mL) was added dropwise over 1 hour to 1H-pyrrolo[2,3-b]pyridine (75.0 g, 635 mmol) in EtOAc (1.5 L) at 0° C. The reaction was stirred for 4 hours at room temperature. The resulting suspension was filtered and dried under high vacuum to provide 1H-pyrrolo[2,3-b]pyridine N-oxide, 3-chlorobenzoic acid salt (135 g, 73% yield) as a solid. This material was dissolved in water (500 mL), and 30% aqueous potassium carbonate was added to bring the pH to about 9 to 10. The reaction was stirred for 1 hour, and then it was cooled to about 0-5° C. The precipitate that formed was filtered and washed with water and then dried under high vacuum to provide 1H-pyrrolo[2,3-b]pyridine N-oxide (42 g, 67% yield) as a solid.

Step B: Tetramethylammonium bromide (72 g, 470 mmol) was added to 1H-pyrrolo[2,3-b]pyridine N-oxide (42 g, 313 mmol) in DMF (500 mL) at 0° C., which was followed by addition of methanesulfonic anhydride (109 g, 626 mmol).

The suspension was warmed to room temperature and stirred at room temperature for 18 hours. Water (200 mL) was added, and the solution was neutralized with addition of 50% NaOH. The resulting solution was then further diluted with water (500 mL) and cooled to 0° C. The precipitate formed was collected, rinsed with water and diluted in $CH_2Cl_2$/MeOH (500 mL, 3:1 v/v). This solution was dried ($MgSO_4$), filtered and concentrated in vacuo to yield 4-bromo-1H-pyrrolo[2,3-b]pyridine (33 g, 53% yield) as a solid. $^1$H NMR (400 MHz, $(CD_3)_2SO$) δ 12.05 (br s, 1H), 8.10 (d, 1H), 7.61 (dd, 1H), 7.34 (d, 1H), 6.43 (dd, 1H); LCMS (APCI+) m/z 196.9, 198.9 (M+H)+, Retention time=2.59 minutes (Method 1).

Step C: Sodium hydride (8.37 g, 209 mmol; 60% oil dispersion) was slowly added to 4-bromo-1H-pyrrolo[2,3-b]pyridine (33.0 g, 167 mmol) in THF (500 mL) at 0° C. The reaction was stirred for 15 minutes. Chlorotriisopropylsilane (38.7 g, 201 mmol) was then added in one portion. The suspension was warmed to room temperature and stirred for 30 minutes. The suspension was then cooled to about 0-5° C. and quenched with saturated aqueous $NH_4Cl$ (about 200 mL). The aqueous phase was extracted with hexanes (3×300 mL), and the combined organic phases were dried ($MgSO_4$) and concentrated in vacuo. The residue was purified by flash chromatography on silica gel eluting with hexanes to yield 4-bromo-1-(triisopropylsilyl)-1H-pyrrolo[2,3-b]pyridine (50 g, 84% yield) as an oil, which solidified upon standing. $^1$H NMR (400 MHz, $CDCl_3$) δ 8.05 (d, 1H), 7.34 (d, 1H), 7.22 (d, Hz, 2H), 6.59 (d, 1H), 1.88-1.80 (m, 3H), 1.11 (d, 18H).

Step D: 4-Bromo-1-(triisopropylsilyl)-1H-pyrrolo[2,3-b]pyridine (50 g, 141.5 mmol) in THF (2 L) at −78° C. was treated dropwise with tert-butyllithium (166.5 mL, 283.0 mmol, 1.7M in pentane). The reaction was then stirred for 15 minutes. N-Fluoro-N-(phenylsulfonyl)benzenesulfonamide (49.08 g, 155.6 mmol) in THF (200 mL) was then added dropwise, and the mixture was stirred at −78° C. After 2 hours, the reaction was quenched at −78° C. with saturated aqueous $NH_4Cl$ (200 mL). The aqueous phase was extracted with hexanes. The combined hexane phases were dried ($MgSO_4$) and passed through a plug of silica gel eluting with hexanes. The combined hexanes fractions were concentrated in vacuo to provide 4-fluoro-1-(triisopropylsilyl)-1H-pyrrolo[2,3-b]pyridine (36.1 g, 87% yield) as an oil. $^1$H NMR (400 MHz, $CDCl_3$) δ 18.18 (dd, 1H), 7.25 (d, 1H), 6.76 (dd, 1H), 1.86-1.81 (m, 3H), 1.13 (d, 18H).

Step E: 4-Fluoro-1-(tri isopropyl silyl)-1H-pyrrolo[2,3-b]pyridine (28.0 g, 95.7 mmol) in THF (600 mL) at −78° C. was treated dropwise with sec-butyllithium (150 mL, 211 mmol; 1.4M in cyclohexane). The reaction was stirred at −78° C. for 30 minutes. Perbromomethane (79.4 g, 239 mmol) in THF (100 mL) was then added dropwise. The reaction was stirred at −78° C. for 1 hour and then quenched with saturated aqueous $NH_4Cl$. The aqueous phase was extracted with hexanes. The combined organic phases were dried ($MgSO_4$) and concentrated in vacuo. The oil obtained was purified by flash chromatography on silica gel eluting with hexanes to provide 5-bromo-4-fluoro-1-(triisopropylsilyl)-1H-pyrrolo[2,3-b]pyridine (30 g, 84% yield) as an oil, which solidified upon standing. $^1$H NMR (400 MHz, $CDCl_3$) δ 8.28 (d, 1H), 7.26 (s, 1H), 6.62 (d, 1H), 1.86-1.78 (m, 3H), 1.11 (d, 18H).

Step F: $TBAF·3H_2O$ (80.8 mL, 80.8 mmol; 1.0M solution in THF) was added to 5-bromo-4-fluoro-1-(triisopropylsilyl)-1H-pyrrolo[2,3-b]pyridine (30.0 g, 80.8 mmol) in THF (200 mL) at room temperature. The reaction was stirred for 20 minutes, and then water (200 mL) and ether (500 mL) were added. The aqueous phase was extracted with ether. The combined organic phases were washed with brine, dried ($MgSO_4$) and concentrated in vacuo. The solid was crystallized from EtOAc to provide 5-bromo-4-fluoro-1H-pyrrolo[2,3-b]pyridine (12.5 g, 72% yield). $^1$H NMR (400 MHz, $CDCl_3$) δ 11.06 (br s, 1H), 8.39 (d, 1H), 7.35 (dd, 1H), 6.60 (dd, 1H); LCMS (APCI+) m/z 214.9, 216.9 (M+H)+, Retention time=2.75 minutes (Method 1).

Step G: 5-Bromo-4-fluoro-1H-pyrrolo[2,3-b]pyridine (10 g, 47 mmol) was added to fuming nitric acid (50 mL) at 0° C., and the reaction was stirred at 0° C. for 30 minutes. Ice (300 mL) was added, and the reaction was allowed to warm to room temperature. The resulting suspension was filtered and dried under high vacuum to provide 5-bromo-4-fluoro-3-nitro-1H-pyrrolo[2,3-b]pyridine (9.2 g, 76% yield) as a solid. $^1$H NMR (400 MHz, $(CD_3)_2SO$) δ 13.63 (br s, 1H), 8.85 (s, 1H), 8.56 (d, 1H).

Step H: Tin (II) chloride (10 g, 54 mmol) was slowly added to 5-bromo-4-fluoro-3-nitro-1H-pyrrolo[2,3-b]pyridine (9.0 g, 35 mmol) in 6N HCl (200 mL) at a temperature of about 0° C. to about 5° C., and the reaction was stirred at room temperature for 2 hours. The reaction pH was raised to 7 by addition of 6N NaOH. The aqueous layer was then extracted with $CHCl_3$/i-PrOH (3:1). The combined organic phases were dried ($MgSO_4$) and concentrated in vacuo to yield 5-bromo-4-fluoro-1H-pyrrolo[2,3-b]pyridin-3-amine (5.1 g, 64% yield) as a solid. $^1$H NMR (400 MHz, $(CD_3)_2SO$) δ 11.18 (br s, 1H), 8.13 (d, 1H), 6.66 (d, 1H), 4.21 (s, 2H); LCMS (APCI+) m/z 229.9, 231.9 (M+H)+, Retention time=2.11 minutes (Method 1).

Step I: A solution of 5-bromo-4-fluoro-1H-pyrrolo[2,3-b]pyridin-3-amine (3.0 g, 13 mmol) in $CH_2Cl_2$ (200 mL) was treated with nicotinic acid (3.2 g, 26 mmol), bis(2-oxooxazolidin-3-yl)phosphinic chloride (6.6 g, 26 mmol) and triethylamine (6.6 g, 65 mmol). The reaction was stirred at room temperature for 1 hour, and then 3M aqueous LiOH (4 mL) was added. The reaction was stirred for 1 hour, and then saturated aqueous $Na_2CO_3$ was added (200 mL). The aqueous phase was extracted with $CH_2Cl_2$ (1×200 mL), and the aqueous phase was filtered. The filtered cake was dried to yield N-(5-bromo-4-fluoro-1H-pyrrolo[2,3-b]pyridin-3-yl)nicotinamide (3.5 g, 80% yield). $^1$H NMR (400 MHz, $(CD_3)_2SO$) δ 9.09 (d, 1H), 8.72 (d, 1H), 8.32 (d, 1H), 8.26 (d, 1H), 7.50 (dd, 1H); LCMS (APCI+) m/z 336.9 (M+H)+, Retention time=2.19 minutes (Method 1).

Step J: A solution of N-(5-bromo-4-fluoro-1H-pyrrolo[2,3-b]pyridin-3-yl)nicotinamide (120 mg, 0.358 mmol) in n-BuOH (5 mL) was treated with tert-butyl piperidin-3-ylcarbamate (359 mg, 1.79 mmol) and stirred at 160° C. for 20 hours in a sealed tube. The mixture was concentrated in vacuo, and the residue was purified by C-18 reverse phase flash chromatography (Biotage SP4 unit, C-18 25M column, 20-80% $CH_3CN$/water gradient; 20 CV) to provide tert-butyl 1-(5-bromo-3-(nicotinamido)-1H-pyrrolo[2,3-b]pyridin-4-yl)piperidin-3-ylcarbamate (60 mg, 32% yield) as a solid. $^1$H NMR (400 MHz, $CDCl_3$) δ 10.10 (br s, 1H), 9.27 (m, 1H), 9.19 (d, 1H), 8.79 (d, 1H), 8.33-8.29 (m, 2H), 8.18 (br s, 1H), 7.51-7.47 (m, 1H), 4.54-4.78 (m, 1H), 3.84-3.69 (m, 1H), 3.64-3.41 (m, 3H), 3.08-2.95 (m, 1H), 2.09-1.96 (m, 1H), 1.92-1.50 (m, 2H), 1.42 (s, 9H); LCMS (APCI+) m/z 515.1, 517.1 (M+H)+, Retention time=2.83 minutes (Method 1).

Step K: A solution of tert-butyl 1-(5-bromo-3-(nicotinamido)-1H-pyrrolo[2,3-b]pyridin-4-yl)piperidin-3-ylcarbamate (50 mg, 0.097 mmol) in TFA (5 mL) was stirred at room temperature for 30 minutes and concentrated in vacuo. The residue was dissolved in minimal methanol, and the solution was added to a 2N HCl ether solution. The precipitate formed was filtered and dried under high vacuum to yield N-(4-(3-aminopiperidin-1-yl)-5-bromo-1H-pyrrolo[2,3-b]pyridin-3-yl)nicotinamide hydrochloride (22 mg, 52% yield). $^1$H NMR (400 MHz, $(CD_3)_2SO$) δ 12.06 (s, 1H), 10.47 (br s, 1H), 9.38 (d, 1H), 8.96 (dd, 1H), 8.75 (d, 1H), 8.28 (s, 1H), 8.24 (br s, 2H), 7.92 (dd, 1H), 7.61 (s, 1H), 3.51-3.45 (m, 1H), 3.38-3.26 (m, 1H), 3.23-3.06 (m, 3H), 1.94-1.84 (m, 1H), 1.67-1.59 (m, 1H), 1.48-1.24 (m, 2H); LCMS (APCI+) m/z 415, 417.0 (M+H)+, Retention time=1.78 minutes (Method 1).

Example 1A

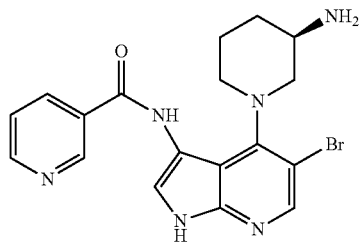

(R)-N-(4-(3-Aminopiperidin-1-yl)-5-bromo-1H-pyrrolo[2,3-b]pyridin-3-yl)nicotinamide Step A: Solid (R)-tert-butyl 1-(5-bromo-3-(nicotinamido)-1H-pyrrolo[2,3-b]pyridin-4-yl)piperidin-3-ylcarbamate (52 mg, 34% yield) was prepared as described in Example 1, Step J, using N-(5-bromo-4-fluoro-1H-pyrrolo[2,3-b]pyridin-3-yl)nicotinamide (100 mg, 0.298 mmol, Example 1, Step I) and substituting (R)-tert-butyl piperidin-3-ylcarbamate (179 mg, 0.895 mmol) for tert-butyl piperidin-3-ylcarbamate.

Step B: Solid (R)—N-(4-(3-Aminopiperidin-1-yl)-5-bromo-1H-pyrrolo[2,3-b]pyridin-3-yl)nicotinamide hydrochloride (12 mg, 33% yield) was prepared as described in Example 1, Step K, substituting (R)-tert-butyl 1-(5-bromo-3-(nicotinamido)-1H-pyrrolo[2,3-b]pyridin-4-yl)piperidin-3-ylcarbamate for tert-butyl 1-(5-bromo-3-(nicotinamido)-1H-pyrrolo[2,3-b]pyridin-4-yl)piperidin-3-ylcarbamate. $^1$H NMR (400 MHz, (CD$_3$)$_2$SO) δ 12.06 (d, 1H), 10.47 (br s, 1H), 9.39 (d, 1H), 8.96 (dd, 1H), 8.79 (d, 1H), 8.28 (s, 1H), 8.24 (br s, 3H), 7.92 (dd, 1H), 7.61 (d, 1H), 3.52-3.44 (m, 1H), 3.37-3.28 (m, 1H), 3.22-3.08 (m, 3H), 1.95-1.85 (m, 1H), 1.67-1.56 (m, 1H), 1.50-1.27 (m, 2H); LCMS (APCI+) m/z 415, 417.0 (M+H)+, Retention time=1.78 minutes (Method 1).

Example 1B

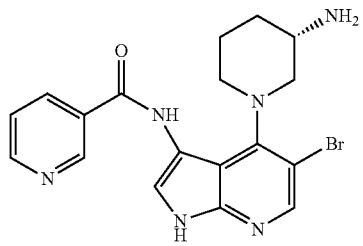

(S)-N-(4-(3-Aminopiperidin-1-yl)-5-bromo-1H-pyrrolo[2,3-b]pyridin-3-yl)nicotinamide Step A: (S)-tert-Butyl 1-(5-bromo-3-(nicotinamido)-1H-pyrrolo[2,3-b]pyridin-4-yl)piperidin-3-ylcarbamate (63 mg, 41%) was prepared as described in Example 1, Step J, using N-(5-bromo-4-fluoro-1H-pyrrolo[2,3-b]pyridin-3-yl)nicotinamide (100 mg, 0.298 mmol, Example 1, Step I) and substituting (S)-tert-butyl piperidin-3-ylcarbamate (179 mg, 0.895 mmol) for tert-butyl piperidin-3-ylcarbamate.

Step B: (S)—N-(4-(3-Aminopiperidin-1-yl)-5-bromo-1H-pyrrolo[2,3-b]pyridin-3-yl)nicotinamide hydrochloride (8 mg, 20% yield) was prepared as described in Example 1, Step K, substituting (S)-tert-butyl 1-(5-bromo-3-(nicotinamido)-1H-pyrrolo[2,3-b]pyridin-4-yl)piperidin-3-ylcarbamate for tert-butyl 1-(5-bromo-3-(nicotinamido)-1H-pyrrolo[2,3-b]pyridin-4-yl)piperidin-3-ylcarbamate. $^1$H NMR (400 MHz, (CD$_3$)$_2$SO) δ 11.93 (d, 1H), 10.14 (br s, 1H), 9.21 (d, 1H), 8.79 (dd, 1H), 8.56-8.41 (m, 1H), 8.22 (s, 1H), 7.99 (br s, 1H), 7.64 (dd, 1H), 3.45-323 (m, 2H), 3.18-2.98 (m, 4H), 1.87-1.51 (m, 1H), 1.48-1.13 (m, 2H); LCMS (APCI+) m/z 415, 417.0 (M+H)+, Retention time=1.78 minutes (Method 1).

Example 2

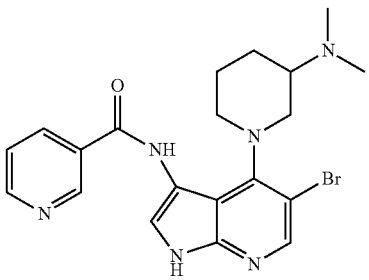

N-(5-Bromo-4-(3-(dimethylamino)piperidin-1-yl)-1H-pyrrolo[2,3-b]pyridin-3-yl)nicotinamide N,N-Dimethylpiperidin-3-amine (115 mg, 0.895 mmol) was added to N-(5-bromo-4-fluoro-1H-pyrrolo[2,3-b]pyridin-3-yl)nicotinamide (100 mg, 0.298 mmol) in n-BuOH. The reaction was stirred at 160° C. for 20 hours in a sealed tube. After concentration, the residue was purified by C-18 reverse phase flash chromatography (Biotage SP4 unit, C-18 25M column, 0-60% CH$_3$CN/water gradient; 20 CV) to yield N-(5-bromo-4-(3-(dimethylamino)piperidin-1-yl)-1H-pyrrolo[2,3-b]pyridin-3-yl)nicotinamide (60 mg, 45.4% yield) as a solid. The solid was dissolved in a minimal amount of methanol, and then the solution was added to 2N HCl in ether. The resulting precipitate was filtered and dried under high vacuum to yield N-(5-bromo-4-(3-(dimethylamino)piperidin-1-yl)-1H-pyrrolo[2,3-b]pyridin-3-yl)nicotinamide hydrochloride as a solid. $^1$H NMR (400 MHz, (CD$_3$)$_2$SO) δ 10.91 (d, 1H), 10.63 (br s, 1H), 9.47 (d, 1H), 8.99 (dd, 1H), 8.90 (d, 1H), 8.30 (s, 1H), 7.98 (dd, 1H), 7.59 (s, 1H), 3.67-3.59 (m, 1H), 3.27-3.06 (m, 3H), 2.76-2.67 (m, 1H), 2.68 (d, 3H), 2.65 (d, 3H), 2.14-2.04 (m, 1H), 1.74-1.66 (m, 1H), 1.59-1.32 (m, 2H); LCMS (APCI+) m/z 443, 445 (M+H)+, Retention time=1.90 minutes (Method 1).

Example 3

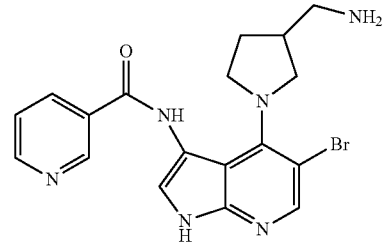

N-(4-(3-(Aminomethyl)pyrrolidin-1-yl)-5-bromo-1H-pyrrolo[2,3-b]pyridin-3-yl)nicotinamide N-(4-(3-(Aminomethyl)pyrrolidin-1-yl)-5-bromo-1H-pyrrolo[2,3-b]pyridin-3-yl)nicotinamide hydrochloride (6 mg, 83% yield) was prepared as described in Example 1, Steps J and K, using N-(5-bromo-4-fluoro-1H-pyrrolo[2,3-b]pyridin-3-yl)nicotinamide (20 mg, 0.060 mmol; Example 1, Step I) and substituting tert-butyl pyrrolidin-3-ylmethylcarbamate (60 mg, 0.30 mmol) for tert-butyl piperidin-3-ylcarbamate. $^1$H NMR (400 MHz, (CD$_3$)$_2$SO) δ 11.91 (d, 1H), 10.27 (s, 1H), 9.18 (d, 1H), 8.62 (dd, 1H), 8.43 (dt, 1H), 8.31 (s, 1H), 7.98 (br s, 3H), 7.76-7.72 (m, 2H), 3.65-3.61 (m, 1H), 3.54-3.44 (m, 2H), 3.27-3.21 (m, 1H), 2.86-2.76 (m, 1H), 2.68-2.52 (m, 2H), 2.12-2.01 (m, 1H), 1.68-1.58 (m, UT); LCMS (APCI+) m/z 415, 417 (M+H)+, Retention time=1.87 minutes (Method 1).

Example 3A

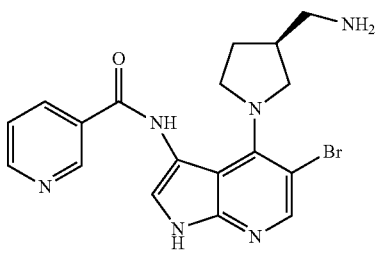

(S)-N-(4-(3-(Aminomethyl)pyrrolidin-1-yl)-5-bromo-1H-pyrrolo[2,3-b]pyridin-3-yl)nicotinamide Solid (S)—N-(4-(3-(aminomethyl)pyrrolidin-1-yl)-5-bromo-1H-pyrrolo[2,3-b]pyridin-3-yl)nicotinamide hydrochloride (160 mg, 86% yield) was prepared as described in Example 1, Steps J and K, using N-(5-bromo-4-fluoro-1H-pyrrolo[2,3-b]pyridin-3-yl)nicotinamide (400 mg, 1.19 mmol; Example 1, Step I) and substituting (R)-tert-butyl pyrrolidin-3-ylmethylcarbamate (717 mg, 3.58 mmol) for tert-butyl piperidin-3-ylcarbamate. $^1$H NMR (400 MHz, (CD$_3$)$_2$SO) δ 11.99 (d, 1H), 10.42 (s, 1H), 9.25 (d, 1H), 8.94 (dd, 1H), 8.61 (dt, 1H), 8.31 (d, 1H), 8.11 (br s, 3H), 7.89 (dd, 1H), 7.70 (d, 1H), 3.65-3.62 (m, 1H), 3.58-3.46 (m, 2H), 3.20-3.26 (m, 1H), 2.85-2.76 (m, 2H), 2.63-2.53 (m, 1H), 2.12-2.01 (m 1H), 1.69-1.60 (m, 1H); LCMS (APCI+) m/z 415, 417 (M+H)+, Retention time=1.87 minutes (Method 1).

Example 3B

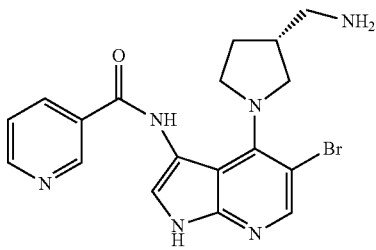

(R)-N-(4-(3-(Aminomethyl)pyrrolidin-1-yl)-5-bromo-1H-pyrrolo[2,3-b]pyridin-3-yl)nicotinamide Solid (R)—N-(4-(3-(aminomethyl)pyrrolidin-1-yl)-5-bromo-1H-pyrrolo[2,3-b]pyridin-3-yl)nicotinamide hydrochloride (64 mg, 13% yield) was prepared as described in Example 1, Steps J and K, using N-(5-bromo-4-fluoro-1H-pyrrolo[2,3-b]pyridin-3-yl)nicotinamide (400 mg, 1.19 mmol) and substituting (S)-tert-butyl pyrrolidin-3-ylmethylcarbamate (717 mg, 3.58 mmol) for tert-butyl piperidin-3-ylcarbamate. $^1$H NMR (400 MHz, (CD$_3$)$_2$SO) δ 11.98 (d, 1H), 10.41 (s, 1H), 9.24 (d, 1H), 8.93 (dd, 1H), 8.59 (dt, 1H), 8.31 (s, 1H), 8.10 (br s, 1H), 7.87 (dd, 1H), 7.71 (d, 1H), 3.68-3.64 (m, 1H0, 3.57-3.46 (m, 2H), 3.30-3.26 (m, 1H), 2.86-2.77 (m, 2H), 2.63-2.55 (m, 1H), 2.11-2.03 (m, 1H), 1.69-1.60 (m, 1H); LCMS (APCI+) m/z 415, 417 (M+H)+, Retention time=1.94 minutes (Method 1).

Example 4

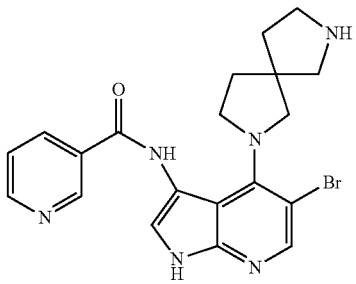

N-(5-Bromo-4-(2,7-diazaspiro[4,4]nonan-2-yl)-1H-pyrrolo[2,3-b]pyridin-3-yl)nicotinamide N-(5-Bromo-4-(2,7-diazaspiro[4.4]nonan-2-yl)-1H-pyrrolo[2,3-b]pyridin-3-yl)nicotinamide hydrochloride (8 mg, 33% yield) was prepared as described in Example 1, Steps J and K, substituting tert-butyl 2,7-diazaspiro[4.4]nonane-2-carboxylate (135 mg, 0.597 mmol) for tert-butyl piperidin-3-ylcarbamate. $^1$H NMR (400 MHz, (CD$_3$)$_2$SO) δ 12.03 (d, 1H), 10.36 (s, 1H), 9.58-9.39 (m, 2H), 9.31 (d, 1H), 8.91 (dd, 1H), 8.63 (dt, 1H), 8.31 (s, 1H), 7.82 (dd, 7.64 (d, 1H), 3.59-3.52 (m, 2H), 3.46 (d, 2H), 3.25-3.20 (m, 2H), 3.14-3.08 (m, 2H), 1.95-1.85 (m, 2H), 1.81-1.68 (m, 2H); LCMS (APCI+) m/z 441, 443 (M+H)+, Retention time=1.87 minutes (Method 1).

Example 5

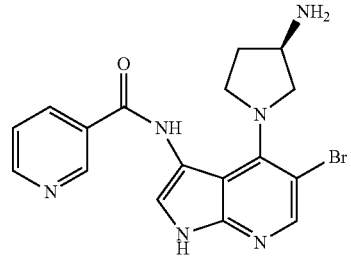

(R)-N-(4-(3-Aminopyrrolidin-1-yl)-5-bromo-1H-pyrrolo[2,3-b]pyridin-3-yl)nicotinamide Step A: (R)-tert-Butyl pyrrolidin-3-ylcarbamate (333 mg, 1.79 mmol) was added to N-(5-bromo-4-fluoro-1H-pyrrolo[2,3-b]pyridin-3-yl)nicotinamide (200 mg, 0.597 mmol) in n-BuOH (3 mL), and the reaction was stirred at 160° C. for 24 hours. The reaction was concentrated to dryness, and then the residue was purified by chromatography (SP4, C-18 25M+ column, gradient of 10-90% CH$_3$CN/water, 30CV) to yield (R)-tert-butyl 1-(5-bromo-3-(nicotinamido)-1H-pyrrolo[2,3-b]pyridin-4-yl)pyrrolidin-3-ylcarbamate (105 mg, 35.1% yield) as a solid.

Step B: (R)-tert-Butyl 1-(5-bromo-3-(nicotinamido)-1H-pyrrolo[2,3-b]pyridin-4-yl)pyrrolidin-3-ylcarbamate (90 mg, 0.18 mmol) was dissolved in TFA (5 mL) and stirred at room temperature for 30 minutes. The reaction was concentrated to dryness and then dissolved in a minimal amount of methanol. The solution was added dropwise to a stirred solution of 4N HCl in dioxane. The resulting solid was filtered and dried under high vacuum to yield (R)—N-(4-(3-aminopyrrolidin-1-yl)-5-bromo-1H-pyrrolo[2,3-b]pyridin-3-yl)nicotinamide hydrochloride (20 mg, 28% yield) as a solid. $^1$H NMR (400 MHz, (CD$_3$)$_2$SO) δ 12.01 (d, 1H), 10.38 (s, 1H), 9.29 (d, 1H), 8.93 (dd, 1H), 8.67 (d, 1H), 8.38 (br s, 3H), 8.30 (s, 1H), 7.88 (dd, 1H), 7.68 (d, 1H), 3.83-3.78 (m, 1H), 3.75-3.67 (m 1H), 3.65-3.59 (m, 1H), 3.58-3.54 (m, 1H), 3.49-3.42 (m, 1H), 2.21-2.13 (m, 1H), 1.95-1.86 (m, 1H); LCMS (APCI+) m/z 401, 403 (M+H)+, Retention time=1.94 minutes (Method 1).

Example 6

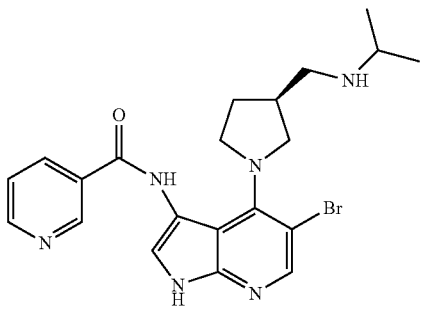

(S)-N-(5-Bromo-4-(3-((isopropylamino)methyl)pyrrolidin-1-yl)-1H-pyrrolo[2,3-b]pyridin-3-yl)nicotinamide DIEA (0.023 mL, 0.133 mmol) was added to a solution of (S)—N-(4-(3-(aminomethyl)pyrrolidin-1-yl)-5-bromo-1H-pyrrolo[2,3-b]pyridin-3-yl)nicotinamide hydrochloride (70 mg, 0.13 mmol; Example 3A) and propan-2-one (77.4 mg, 1.33 mmol) in CH$_2$Cl$_2$:DMF (1:1, 3 mL), followed by the addition of NaBH(OAc)$_3$ (57 mg, 0.26 mmol). The reaction was stirred for 30 minutes. The reaction mixture was then poured into a solution of Na$_2$CO$_3$ and extracted into CH$_2$Cl$_2$. The organic phases were combined, dried (MgSO$_4$), filtered and concentrated in vacuo. The residue was purified by reverse phase HPLC (Gilson system). The isolated product was then dissolved in minimal CH$_2$Cl$_2$ (with MeOH to aid solubility) and added to 1M HCl in ether (10 mL). The solid formed was collected to provide (S)—N-(5-bromo-4-(3-((isopropylamino)methyl)pyrrolidin-1-yl)-1H-pyrrolo[2,3-b]pyridin-3-yl)nicotinamide hydrochloride (40 mg, 53% yield). $^1$H NMR (400 MHz, (CD$_3$)$_2$SO) δ 12.08 (d, 1H), 10.58 (s, 1H), 9.32 (d, 1H), 8.98 (dd, 1H), 8.76 (dt, 1H), 8.32 (s, 1H), 7.99 (dd, 1H), 7.67 (d, 1H), 3.77-3.73 (m, 1H), 3.60-3.52 (m, 2H), 3.39-3.34 (m, 1H), 3.23-3.16 (m, 1H), 2.91-2.85 (m, 2H), 2.73-2.66 (m, 1H), 2.14-2.07 (m, 1H), 1.74-1.64 (m, 1H), 1.22 (d, 6H); LCMS (APCI+) m/z 459.1, 460.1 (M+H)+.

Example 7

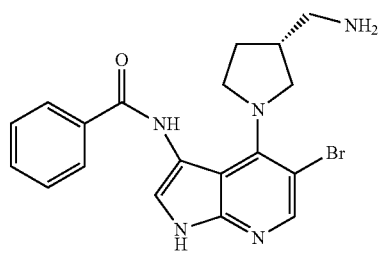

(R)-N-(4-(3-Aminomethyl)pyrrolidin-1-yl)-5-bromo-1H-pyrrolo[2,3-b]pyridin-3-yl)benzamide Step A: N-(5-Bromo-4-fluoro-1H-pyrrolo[2,3-b]pyridin-3-yl)benzamide (10 mg, 7% yield) was prepared as described in Example 1, Step I, using 5-bromo-4-fluoro-1H-pyrrolo[2,3-b]pyridin-3-amine (100 mg, 0.435 mmol) and substituting benzoic acid (112 mg, 0.913 mmol) for nicotinic acid. $^1$H NMR (400 MHz, (CD$_3$)$_2$SO) δ 12.16 (br s, 1H), 10.06 (s, 1H), 8.38 (d, 1H), 7.98 (dd, 1H), 7.64-7.52 (m, 5H); LCMS (APCI+) m/z 333.9 (M+H)+, Retention time=3.11 minutes (Method 2).

Step B: (R)—N-(4-(3-(Aminomethyl)pyrrolidin-1-yl)-5-bromo-1H-pyrrolo[2,3-b]pyridin-3-yl)benzamide hydrochloride (15 mg, 37% yield) was prepared as described in Example 1, Steps J and K, substituting N-(5-bromo-4-fluoro-1H-pyrrolo[2,3-b]pyridin-3-yl)benzamide (75 mg, 0.22 mmol) for N-(5-bromo-4-fluoro-1H-pyrrolo[2,3-b]pyridin-3-yl)nicotinamide and (S)-tert-butyl pyrrolidin-3-ylmethylcarbamate (130 mg, 0.67 mmol) for tert-butyl piperidin-3-ylcarbamate. $^1$H NMR (400 MHz, (CD$_3$)$_2$SO) δ 11.85 (s, 1H), 10.14 (s, 1H), 8.31 (s, 1H), 8.07 (br s, 3H), 7.93 (dd, 2H), 7.78 (d, 1H), 7.64-7.61 (m, 3H), 3.65-3.62 (m, 1H), 3.55-3.47 (m, 2H), 3.30-3.26 (m, 1H), 2.88-2.82 (m, 2H), 2.71-2.63 (m, 1H), 2.18-2.10 (m, 1H), 1.76-1.67 (m, 1H); LCMS (APCI+) m/z 414.0 (M+H)+, Retention time=2.30 minutes (Method 2).

Example 8

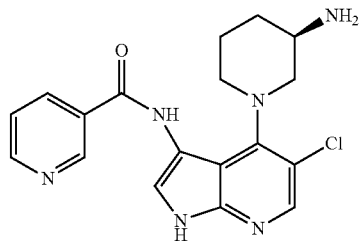

(R)-N-(4-(3-Aminopiperidin-1-yl)-5-chloro-1H-pyrrolo[2,3-b]pyridin-3-yl)nicotinamide Step A: 5-Chloro-4-fluoro-1-(triisopropylsilyl)-1H-pyrrolo[2,3-b]pyridine (2.1 g, 62% yield) was prepared as described in Example 1, Step E, using 4-fluoro-1-(triisopropylsilyl)-1H-pyrrolo[2,3-b]pyridine (3.0 g, 10.26 mmol) and substituting hexachloroethane (6.07 g, 25.64 mmol) for perbromomethane.

Step B: 5-Chloro-4-fluoro-1-(triisopropylsilyl)-1H-pyrrolo[2,3-b]pyridine (3.0 g, 9.2 mmol) in THF (15 mL) at 0° C. was treated dropwise with TBAF (10.1 mL, 10.1 mmol). After 30 minutes, the reaction was quenched with saturated aqueous NaHCO$_3$ and extracted into CH$_2$Cl$_2$. The combined organic fractions were dried (MgSO$_4$), filtered, and concentrated in vacuo. The crude was purified by flash chromatography on silica gel using 1.2% MeOH:CH$_2$Cl$_2$ to provide 5-chloro-4-fluoro-1H-pyrrolo[2,3-b]pyridine (1.4 g, 89% yield).

Step C: 5-Chloro-4-fluoro-3-nitro-1H-pyrrolo[2,3-b]pyridine (1.3 g, 86% yield) was prepared as described in Example 1, Step G, substituting 5-chloro-4-fluoro-1H-pyrrolo[2,3-b]pyridine (1.2 g, 7.0 mmol) for 5-bromo-4-fluoro-1H-pyrrolo[2,3-b]pyridine.

Step D: 5-Chloro-4-fluoro-1H-pyrrolo[2,3-b]pyridin-3-amine (0.8 g, 77% yield) was prepared as described in Example 1, Step H, substituting 5-chloro-4-fluoro-3-nitro-1H-pyrrolo[2,3-b]pyridine (1.20 g, 5.56 mmol) for 5-bromo-4-fluoro-3-nitro-1H-pyrrolo[2,3-b]pyridine. LCMS (APCI+) m/z 186.2 (M+H)+.

Step E: N-(5-Chloro-4-fluoro-1H-pyrrolo[2,3-b]pyridin-3-yl)nicotinamide (0.42 g, 67% yield) was prepared as described in Example 1, Step I, substituting 5-chloro-4-fluoro-1H-pyrrolo[2,3-b]pyridin-3-amine (400 mg, 2.155 mmol) for 5-bromo-4-fluoro-1H-pyrrolo[2,3-b]pyridin-3-amine. LCMS (APCI+) m/z 291.0 (M+H)+, Retention time=2.45 min (Method 2).

Step F: (R)—N-(4-(3-Aminopiperidin-1-yl)-5-chloro-1H-pyrrolo[2,3-b]pyridin-3-yl)nicotinamide hydrochloride (90 mg, 74% yield) was prepared as described in Example 1, Steps J and K, substituting N-(5-chloro-4-fluoro-1H-pyrrolo[2,3-b]pyridin-3-yl)nicotinamide (200 mg, 0.688 mmol) for N-(5-bromo-4-fluoro-1H-pyrrolo[2,3-b]pyridin-3-yl)nicotinamide and (R)-tert-butyl piperidin-3-ylcarbamate (276 mg, 1.38 mmol) for tert-butyl piperidin-3-ylcarbamate. $^1$H NMR (400 MHz, (CD$_3$)$_2$SO) δ 12.01 (d, 1H), 10.39 (s, 1H), 9.35 (s, 1H), 8.92 (dd, 1H), 8.70 (d, 1H), 8.21-8.17 (m, 4H), 7.84 (dd, 1H), 7.63 (s, 1H), 3.54-3.47 (m, 1H), 3.33-3.26 (m, 1H), 3.16-3.09 (m, 3H), 1.91-1.83 (m, 1H), 1.65-1.56 (m, 1H), 1.42-1.32 (m, 2H); LCMS (APCI+) m/z 371 (M+H)+, Retention time=1.95 minutes (Method 2).

Example 9

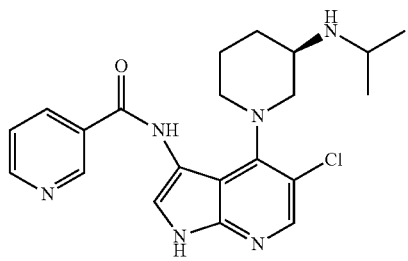

(R)-N-(5-Chloro-4-(3-(isopropylamino)piperidin-1-yl)-1H-pyrrolo[2,3-b]pyridin-3-yl)nicotinamide (R)—N-(5-Chloro-4-(3-(isopropylamino)piperidin-1-yl)-1H-pyrrolo[2,3-b]pyridin-3-yl)nicotinamide hydrochloride (30 mg, 64% yield) was prepared as described in Example 6, using propan-2-one (104 mg, 1.80 mmol) and substituting (R)—N-(4-(3-aminopiperidin-1-yl)-5-chloro-1H-pyrrolo[2,3-b]pyridin-3-yl)nicotinamide hydrochloride (43 mg, 0.089 mmol) for (S)—N-(4-(3-(aminomethyl)pyrrolidin-1-yl)-5-bromo-1H-pyrrolo[2,3-b]pyridin-3-yl)nicotinamide hydrochloride. $^1$H NMR (400 MHz, D$_2$O) δ 9.20-9.19 (m, 1H), 8.88-8.83 (m, 2H), 8.17 (s, 1H), 8.05-7.80 (m, 1H), 7.44-7.43 (m, 1H), 3.86-3.73 (m, 1H), 3.50-3.44 (m, 1H), 3.41-3.31 (m, 2H), 3.18-3.10 (m, 1H), 3.06-2.98 (m, 1H), 2.04-1.95 (m, 1H), 1.69-1.61 (m, 1H), 1.58-1.47 (m, 1H), 1.35-1.25 (m, 1H), 1.14 (d, 3H), 1.10 (d, 3H); LCMS (APCI+) m/z 413.1 (M+H)+, Retention time=2.06 minutes (Method 2).

Example 10

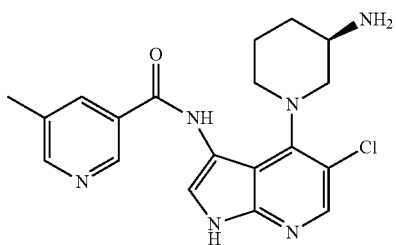

(R)-N-(4-(3-Aminopiperidin-1-yl)-5-chloro-1H-pyrrolo[2,3-b]pyridin-3-yl)-5-methylnicotinamide Step A: N-(5-Chloro-4-fluoro-1H-pyrrolo[2,3-b]pyridin-3-yl)-5-methylnicotinamide (250 mg, 76% yield) was prepared as described in Example 1, Step I, substituting 5-chloro-4-fluoro-1H-pyrrolo[2,3-b]pyridin-3-amine (200 mg, 1.1 mmol) for 5-bromo-4-fluoro-1H-pyrrolo[2,3-b]pyridin-3-amine and 5-methylnicotinic acid (310 mg, 2.26 mmol) for nicotinic acid. $^1$H NMR (400 MHz, (CD$_3$)$_2$SO) δ 8.94 (d, 1H), 8.60 (d, 1H), 8.29-8.23 (m, 1H), 8.14 (s, 1H), 7.65 (s, 1H), 2.40 (s, 3H); LCMS (APCI+) m/z 305 (M+H)+, Retention time=2.66 minutes (Method 2).

Step B: (R)—N-(4-(3-Aminopiperidin-1-yl)-5-chloro-1H-pyrrolo[2,3-b]pyridin-3-yl)-5-methylnicotinamide hydrochloride (70 mg, 19% yield) was prepared as described in Example 1, Steps J and K, substituting N-(5-chloro-4-fluoro-1H-pyrrolo[2,3-b]pyridin-3-yl)-5-methylnicotinamide (230 mg, 0.755 mmol) for N-(5-bromo-4-fluoro-1H-pyrrolo[2,3-b]pyridin-3-yl)nicotinamide and (R)-tert-butyl piperidin-3-ylcarbamate (378 mg, 1.89 mmol) for tert-butyl piperidin-3-ylcarbamate. $^1$H NMR (400 MHz, D$_2$O) δ 8.94 (d, 1H), 8.69 (d, 1H), 8.66 (d, 1H), 8.13 (s, 1H), 7.43 (s, 1H), 3.69-3.62 (m, 1H), 3.37-3.27 (m, 2H), 3.22-3.14 (m, 1H), 3.09-3.01 (m, 1H), 2.47 (s, 3H), 1.92-1.83 (m, 1H), 1.69-1.58 (m, 1H), 1.49-1.31 (m, 2H); LCMS (APCI+) m/z 385.1 (M+H)+, Retention time=2.09 minutes (Method 2).

Example 11

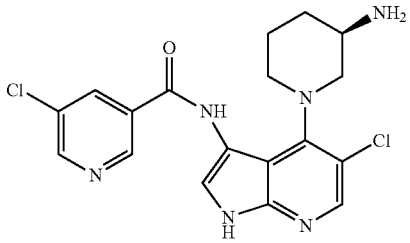

(R)-N-(4-(3-Aminopiperidin-1-yl)-5-chloro-1H-pyrrolo[2,3-b]pyridin-3-yl)-5-chloronicotinamide Step A: 5-Chloro-N-(5-chloro-4-fluoro-1H-pyrrolo[2,3-b]pyridin-3-yl)nicotinamide (320 mg, 91% yield) was prepared as described in Example 1, Step I, substituting 5-chloro-4-fluoro-1H-pyrrolo[2,3-b]pyridin-3-amine (200 mg, 1.1 mmol) for 5-bromo-4-fluoro-1H-pyrrolo[2,3-b]pyridin-3-amine and 5-chloronicotinic acid (357 mg, 2.26 mmol) for nicotinic acid. $^1$H NMR (400 MHz, (CD$_3$)$_2$SO) δ 9.08 (s, 1H), 8.84 (d, 1H), 8.42 (s, 1H), 8.32 (s, 1H), 8.30 (s, 1H); LCMS (APCI+) m/z 326 (M+H)+, Retention time=2.94 minutes (Method 2).

Step B: (R)—N-(4-(3-Aminopiperidin-1-yl)-5-chloro-1H-pyrrolo[2,3-b]pyridin-3-yl)-5-chloronicotinamide hydrochloride (0.13 g, 85% yield) was prepared as described in Example 1, Steps J and K, substituting 5-chloro-N-(5-chloro-4-fluoro-1H-pyrrolo[2,3-b]pyridin-3-yl)nicotinamide (0.35 g, 1.1 mmol) for N-(5-bromo-4-fluoro-1H-pyrrolo[2,3-b]pyridin-3-yl)nicotinamide and (R)-tert-butyl piperidin-3-ylcarbamate (0.647 g, 3.23 mmol) for butyl piperidin-3-ylcarbamate. $^1$H NMR (400 MHz, D$_2$O) δ 8.87 (d, 1H), 8.68 (d, 1H), 8.35-8.30 (m, 1H), 8.15 (s, 1H), 7.43 (s, 1H), 3.81-3.74 (m, 1H), 3.49-3.37 (m, 2H), 3.20-3.13 (m, 1H), 3.11-3.03 (m, 1H), 1.97-1.88 (m, 1H), 1.69-1.61 (m, 1H), 1.53-1.44 (m, 1H), 1.42-1.31 (m, 1H); LCMS (APCI+) m/z 405, 407 (M+H)+, Retention time=2.21 minutes (Method 2).

Example 12

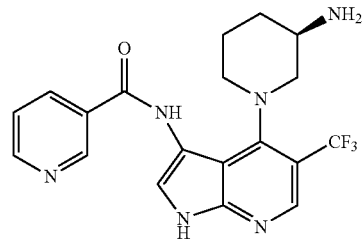

(R)-N-(4-(3-Aminopiperidin-1-yl)-5-(trifluoromethyl)-
1H-pyrrolo[2,3-b]pyridin-3-yl)nicotinamide Step A: 4-Chloro-1H-pyrrolo[2,3-b]pyridine (5.0 g, 32.8 mmol) in THF (50 mL) was cooled to 0° C., and NaH (1.64 g, 41.0 mmol, 60% oil dispersion) was added. After 15 minutes, triisopropylsilylchloride ("TIPS-Cl"; 6.94 mL, 32.8 mmol) was added, and the reaction was stirred at room temperature for 1 hour. A saturated ammonium chloride solution (20 mL) was added, and the mixture was extracted with hexanes (40 mL), washed with brine and dried over sodium sulfate. After removal of the solvent, the residue was purified by chromatography (hexanes) to give 4-chloro-1-(triisopropylsilyl)-1H-pyrrolo[2,3-b]pyridine (10.0 g, 99% yield) as an oil.

Step B: s-BuLi (59.3 mL, 71.2 mmol, 1.4M in cyclohexane) at –78° C. was added to 4-chloro-1-(triisopropyl silyl)-1H-pyrrolo[2,3-b]pyridine (10.0 g, 32.4 mmol) in THF (100 mL), and the reaction was stirred at –78° C. for 30 minutes. $I_2$ (20.5 g, 80.9 mmol) in THF (50 mL) was added, and the reaction was stirred at –78° C. for 20 minutes. A saturated ammonium chloride solution (50 mL) and a saturated sodium sulfite solution (50 mL) were added, and the mixture was extracted with hexanes (200 mL), washed with brine and dried over sodium sulfate. After removal of the solvent, the residue was dissolved in THF (50 mL), and TBAF (32.4 mL, 32.4 mmol) was added. The reaction was stirred at room temperature for 10 minutes, and then water (20 mL) and ethyl acetate (100 mL) were added. The organic layer was separated, washed with brine, and dried over sodium sulfate. After removal of the solvent, the residue was suspended in dichloromethane ("DCM"; 20 mL) and stirred for 10 minutes. The solid formed was collected by filtration to give 4-chloro-5-iodo-1H-pyrrolo[2,3-b]pyridine (6.6 g, 73% yield) as a solid.

Step C: NaH (0.960 g, 24.0 mmol, 60% dispersion in mineral oil) at 0° C. was added to 4-chloro-5-iodo-1H-pyrrolo[2,3-b]pyridine (5.57 g, 20.0 mmol) in dimethylformamide ("DMF"; 40 mL) and stirred at 0° C. for 20 minutes. Benzenesulfonyl chloride (2.82 mL, 22.0 mmol) was added, and the reaction was stirred at room temperature for 2 hours. Water (200 mL) was added and stirred for 10 minutes. The solid formed was collected by filtration, washed with ether, and dried to give 4-chloro-5-iodo-1-(phenylsulfonyl)-1H-pyrrolo[2,3-b]pyridine (8.20 g, 98% yield).

Step D: A mixture of 4-chloro-5-iodo-1-(phenylsulfonyl)-1H-pyrrolo[2,3-b]pyridine (2.0 g, 4.8 mmol), Cu(I)I (0.910 g, 4.78 mmol) and methyl 2,2-difluoro-2-(fluorosulfonyl)acetate (2.1 mL, 16.7 mmol) in DMF (10 mL) was heated at 100° C. for 3 hours. The reaction was cooled to room temperature, diluted with EtOAc (30 mL) and filtered through a plug of celite. The filtrate was washed with water (15 mL), brine (15 mL), dried ($Na_2SO_4$), and concentrated in vacuo. The residue was purified by flash chromatography on silica gel eluting with 1:1 $CH_2Cl_2$/hexanes to provide 4-chloro-1-(phenylsulfonyl)-5-(trifluoromethyl)-1H-pyrrolo[2,3-b]pyridine (1.4 g, 81% yield) as a solid. $^1$H NMR (400 MHz, $(CD_3)_2SO$) δ 8.80 (s, 1H), 8.25 (d, 1H), 8.16 (d, 2H), 7.80-7.76 (m, 1H), 7.69-7.65 (m, 2H), 7.07 (d, 1H); LCMS (APCI+) m/z 360.9, 362.9 (M+H)+.

Step E: A solution of 2M LiOH (19.1 mL, 38.2 mmol) was added to a solution of 4-chloro-1-(phenylsulfonyl)-5-(trifluoromethyl)-1H-pyrrolo[2,3-b]pyridine (4.59 g, 12.7 mmol) in THF (20 mL), and the reaction was stirred at room temperature for 20 hours. The mixture was neutralized to a pH of about 8 with saturated potassium hydrogen sulfate and extracted with ethyl acetate (50 mL). The organic phase was washed with brine, dried ($Na_2SO_4$), filtered and concentrated in vacuo to provide 4-chloro-5-(trifluoromethyl)-1H-pyrrolo[2,3-b]pyridine (2.5 g, 91% yield) as a solid. $^1$H NMR (400 MHz, $(CD_3)_2SO$) δ 12.54 (br s, 1H), 8.59 (s, 1H), 7.82 (d, 1H), 6.71 (d, 1H); LCMS (APCI+) m/z 220.9 (M+H)+.

Step F: 4-Chloro-5-(trifluoromethyl-1H-pyrrolo[2,3-b]pyridine (0.18 g, 0.84 mmol) was added slowly to fuming nitric acid (1.68 mL, 33.5 mmol) at 0° C. and stirred for 10 minutes. Ice (20 g) was added, followed by water (30 mL). The solid formed was collected by filtration to give 4-chloro-3-nitro-5-(trifluoromethyl)-1H-pyrrolo[2,3-b]pyridine (0.20 g, 90% yield) as a solid.

Step G: $SnCl_2$ dihydrate (0.85 g, 3.77 mmol) at a temperature of about 0° C. to about 5° C. was added to 4-chloro-3-nitro-5-(trifluoromethyl)-1H-pyrrolo[2,3-b]pyridine (0.20 g, 0.75 mmol) in 6M HCl (5 mL). The mixture was stirred at room temperature for 2 hours, and was then neutralized to a pH of about 8 with a 6N NaOH solution. The mixture was extracted with $CHCl_3$:IPA (3×30 mL; 3:1) and dried over sodium sulfate. After removal of the solvent, 4-chloro-5-(trifluoromethyl)-1H-pyrrolo[2,3-b]pyridin-3-amine (0.16 g, 89% yield) was isolated as a solid.

Step H: Triethylamine ("TEA"; 0.50 mL, 3.61 mmol) was added to 4-chloro-5-(trifluoromethyl)-1H-pyrrolo[2,3-b]pyridin-3-amine (0.17 g, 0.72 mmol), nicotinic acid (0.18 g, 1.44 mmol) and BOP-Cl (0.37 g, 1.44 mmol) in DCM (10 mL). The mixture was stirred for 30 minutes, and water was added (10 mL). The solid formed was collected by filtration, washed with DCM (10 mL) and dried to give N-(4-chloro-5-(trifluoromethyl)-1H-pyrrolo[2,3-b]pyridin-3-yl)nicotinamide (80 mg, 0.2 mmol, 32% yield) as a solid.

Step I: N-(4-Chloro-5-(trifluoromethyl)-1H-pyrrolo[2,3-b]pyridin-3-yl)nicotinamide (80 mg, 0.2 mmol) and (R)-tert-butyl piperidin-3-ylcarbamate (0.14 g, 0.70 mmol) in n-BuOH (3 mL) were stirred at 143° C. (bath) for 32 hours. The solvent was removed, and the residue was dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 10-80% $CH_3CN$/water gradient; 30 CV) to give a solid. This solid was dissolved in DCM (3 mL), and TFA (0.5 mL) was added. The mixture was stirred at room temperature for 30 minutes. The solvent was removed. The residue was dissolved in DCM (1 mL) and 2N HCl in ether (2 mL) was added. The solid formed was collected by filtration to give (R)—N-(4-(3-aminopiperidin-1-yl)-5-(trifluoromethyl)-1H-pyrrolo[2,3-b]pyridin-3-yl)nicotinamide hydrochloride (0.047 g, 39% yield) as a solid. $^1$H NMR (400 MHz, $(CD_3)_2SO$) δ 12.43 (d, 1H), 10.54 (s, 1H), 9.42 (d, 1H), 8.98 (d, 1H), 8.88 (d, 1H), 8.53 (s, 1H), 8.25 (br s, 3H), 7.97 (dd, 1H), 7.74 (d, 1H), 3.36-3.29 (m, 1H), 3.12-3.05 (m, 2H), 3.04-2.95 (m, 2H), 1.94-1.84 (m, 1H), 1.67-1.57 (m, 1H), 1.54-1.42 (m, 1H), 1.33-1.19 (m, 1H); LCMS (APCI+) m/z 405.1 (M+H)+.

Example 13

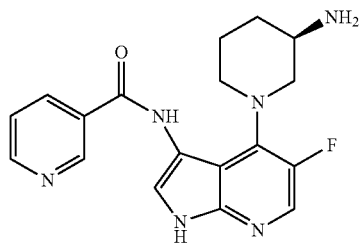

(R)-N-(4-(3-Aminopiperidin-1-yl)-5-fluoro-1H-pyrrolo[2,3-b]pyridin-3-yl)nicotinamide Step A: 4-fluoro-1-(triisopropylsilyl)-1H-pyrrolo[2,3-b]pyridine (2.00 g, 6.84 mmol) in THF (20 mL) was added to s-BuLi (12.5 mL, 15.0 mmol, 1.4M in cyclohexane) at −78° C. for 30 minutes. N-Fluoro-N-(phenylsulfonyl)benzenesulfonamide (5.39 g, 17.1 mmol) in THF (15 mL) was added, and it was stirred at −78° C. for 20 minutes. A saturated ammonium chloride solution (20 mL) was added and extracted with hexanes (50 mL), washed with brine, and dried over sodium sulfate. After removal of the solvent, the residue was dissolved in THF (10 mL), and TBAF (6.84 mL, 6.84 mmol) in THF (6.84 mL, 6.84 mmol) was added. The reaction was stirred at room temperature for 10 minutes, and water (20 mL) and ethyl acetate (30 mL) were added. The organic layer was separated, washed with brine and dried over sodium sulfate. After removal of the solvent, the residue was purified by chromatography (ethyl acetate) to give 4,5-difluoro-1H-pyrrolo[2,3-b]pyridine (0.63 g, 60% yield) as a solid. LCMS (APCI+) m/z 155.1 (M+H)+.

Step B: 4,5-Difluoro-1H-pyrrolo[2,3-b]pyridine (0.63 g, 4.09 mmol) was added slowly to fuming nitric acid (8.18 mL, 164 mmol) at 0° C. and stirred slowly for 5 minutes. Ice (20 g) was added followed by water (40 mL). The solid formed was collected by filtration to give 4,5-difluoro-3-nitro-1H-pyrrolo[2,3-b]pyridine (0.65 g, 80% yield) as a solid.

Step C: SnCl$_2$ dihydrate (3.68 g, 16.3 mmol) at a temperature of about 0° C. to about 5° C. was added to 4,5-difluoro-3-nitro-1H-pyrrolo[2,3-b]pyridine (0.65 g, 3.26 mmol) in 6M HCl (5 mL). The mixture was stirred at room temperature for 30 minutes. The mixture was neutralized to a pH of about 8 with a 6N NaOH solution. The mixture was extracted with CHCl$_3$:IPA (3×30 mL; 3:1) and dried over sodium sulfate. After removal of the solvent, 4,5-difluoro-1H-pyrrolo[2,3-b]pyridin-3-amine (0.45 g, 2.66 mmol, 81% yield) was isolated as a solid.

Step D: Nicotinoyl chloride hydrochloride (0.70 g, 3.90 mmol) was added to 4,5-difluoro-1H-pyrrolo[2,3-b]pyridin-3-amine (0.22 g, 1.30 mmol) in pyridine (5 mL). The reaction was stirred at room temperature for 10 minutes, and then the pyridine was removed. THF (5 mL) and 2N LiOH (3 mL) were added, and the reaction was stirred for 20 minutes. The THF was removed, and water (20 mL) was added. The solid formed was collected by filtration and dried to give N-(4,5-difluoro-1H-pyrrolo[2,3-b]pyridin-3-yl)nicotinamide (0.33 g, 92% yield) as a solid.

Step E: N-(4,5-difluoro-1H-pyrrolo[2,3-b]pyridin-3-yl)nicotinamide (0.21 g, 0.77 mmol), (R)-tert-butyl piperidin-3-ylcarbamate (0.31 g, 1.53 mmol) and DIEA (0.13 mL, 0.77 mmol) in n-BuOH (3 mL) were stirred at 143° C. (bath) for 24 hours. The solvent was removed. The residue was dissolved in ethyl acetate (20 mL), washed with water (10 mL), brine (10 mL), and dried over sodium sulfate. After removal of the solvent, the residue was purified by C-18 reverse phase flash chromatography (Biotage SP4 unit, C-18 25M column, 10-80% CH$_3$CN/water gradient; 30 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-fluoro-1H-pyrrolo[2,3-b]pyridin-3-yl)nicotinamide hydrochloride (0.23 g, 66% yield) as a solid. $^1$H NMR (400 MHz, (CD$_3$)$_2$SO) δ 11.89 (d, 1H), 10.38 (s, 1H), 9.33 (d, 1H), 8.88 (dd, 1H), 8.64 (dt, 1H), 8.18 (s, 1H), 8.17 (br s, 3H), 7.76 (dd, 1H), 7.60 (d, 1H), 3.64-3.56 (m, 1H), 3.25-3.17 (m, 2H), 3.16-3.07 (m, 1H), 3.04-2.95 (m, 1H), 1.87-1.75 (m, 1H), 1.62-1.52 (m, 1H), 1.48-1.38 (m, 1H), 1.35-1.22 (m, 1H); LCMS (APCI+) m/z 355.1 (M+H)+.

Example 14

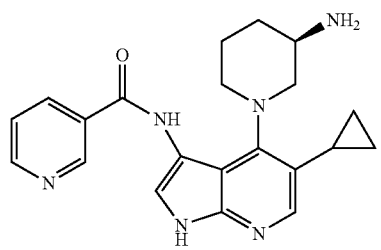

(R)-N-(4-(3-Aminopiperidin-1-yl)-5-cyclopropyl-1H-pyrrolo[2,3-b]pyridin-3-yl)nicotinamide Step A: Triethylamine (0.130 mL, 0.931 mmol), Boc$_2$O (81 mg, 0.373 mmol), and 4-dimethylaminopyridine ("DMAP"; 19 mg, 0.155 mmol) were added to a solution of (R)-tert-butyl 1-(5-bromo-3-(nicotinamido)-1H-pyrrolo[2,3-b]pyridin-4-yl)piperidin-3-ylcarbamate (160 mg, 0.31 mmol, Example 1A) in CH$_2$Cl$_2$ (5 mL) at room temperature, and the reaction was stirred for 30 minutes. The reaction was then poured into water and extracted with CH$_2$Cl$_2$. The organic phase was separated, dried (Na$_2$SO$_4$), filtered, and concentrated in vacuo. The residue was purified by flash chromatography on silica gel eluting with 1.6% CH$_3$OH/CH$_2$Cl$_2$ to provide (R)-tert-butyl 5-bromo-4-(3-(tert-butoxycarbonylamino)piperidin-1-yl)-3-(nicotinamido)-1H-pyrrolo[2,3-b]pyridine-1-carboxylate (170 mg, 89% yield). LCMS (APCI+) m/z 615, 617 (M+H)+, Retention time=4.08 minutes (Method 2).

Step B: A mixture of (R)-tert-butyl 5-bromo-4-(3-(tert-butoxycarbonylamino)piperidin-1-yl)-3-(nicotinamido)-1H-pyrrolo[2,3-b]pyridine-1-carboxylate (170 mg, 0.276 mmol), cyclopropylboronic acid (95 mg, 1.10 mmol), K$_3$PO$_4$ (205 mg, 0.967 mmol), Pd(OAc)$_2$ (6.20 mg, 0.0276 mmol), and tricyclohexylphosphine (9.3 mg, 0.033 mmol) in toluene/water (10:1 mixture, 4.4 mL) was degassed under argon and heated at 80° C. for 15 hours. The reaction mixture was then allowed to cool to room temperature. The mixture was poured into water and extracted with CH$_2$Cl$_2$. The organic phase was dried (Na$_2$SO$_4$), filtered and concentrated in vacuo. The residue was purified by C-18 reverse phase flash chromatography (Biotage SP4 unit, C-18 25M column, 5 to 95% CH$_3$CN/water gradient; 30 CV) to provide (R)-tert-butyl 4-(3-(tert-butoxycarbonylamino)piperidin-1-yl)-5-cyclopropyl-3-(nicotinamido)-1H-pyrrolo[2,3-b]pyridine-1-carboxylate (81 mg, 51% yield). LCMS (APCI+) m/z 577.2 (M+H)+, Retention time=4.01 minutes (Method 2).

Step C: (R)-tert-Butyl 4-(3-(tert-butoxycarbonylamino)piperidin-1-yl)-5-cyclopropyl-3-(nicotinamido)-1H-pyrrolo

[2,3-b]pyridine-1-carboxylate (81 mg, 0.14 mmol) was treated with TFA followed by 2M HCl in ether as described in Example 1, Step K, to provide (R)—N-(4-(3-aminopiperidin-1-yl)-5-cyclopropyl-1H-pyrrolo[2,3-b]pyridin-3-yl)nicotinamide hydrochloride (33 mg, 48% yield). $^1$H NMR (400 MHz, D$_2$O) δ 9.16 (d, 1H), 8.82 (dd, 1H), 8.72 (dt, 1H), 7.95 (s, 1H), 7.92 (dd, 1H), 7.41 (s, 1H), 3.98-3.93 (m, 1H), 3.61-3.53 (m, 1H), 3.32-3.25 (m, 2H), 3.15-3.06 (m, 1H), 1.96-1.85 (m, 2H), 1.64-1.56 (m, 1H), 1.52-1.41 (m, 1H), 1.39-1.27 (m, 1H), 0.98-0.92 (m, 2H), 0.70-0.61 (m, 2H); LCMS (APCI+) m/z 377.2 (M+H)+, Retention time=2.12 minutes (Method 2).

Example 15

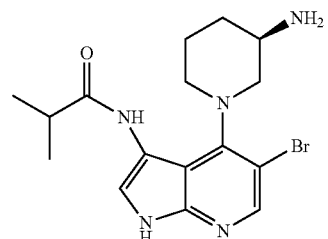

(R)-N-(4-(3-Aminopiperidin-1-yl)-5-bromo-
1H-pyrrolo[2,3-b]pyridin-3-yl)isobutyramide Step A: Isobutyric acid (306 mg, 3.48 mmol), bis(2-oxooxazolidin-3-yl)phosphinic chloride (885 mg, 3.48 mmol) and triethylamine (880 mg, 8.69 mmol) were added to 5-bromo-4-fluoro-1H-pyrrolo[2,3-b]pyridin-3-amine (400 mg, 1.74 mmol) in DCM (200 mL). The reaction was stirred at room temperature for 1 hour, and then 3M aqueous LiOH (4 mL) was added. The reaction as stirred for 1 hour, and then saturated aqueous Na$_2$CO$_3$ was added (200 mL). The aqueous phase was extracted 3 times with DCM (200 mL). Then the combined organic phases were dried over MgSO$_4$ and concentrated to dryness. The residue was purified by C-18 reverse phase flash chromatography (Biotage SP4 unit, C-18 25M column, 20-100% CH$_3$CN/water gradient; 20 CV) to yield N-(5-bromo-4-fluoro-1H-pyrrolo[2,3-b]pyridin-3-yl)isobutyramide (158 mg, 30% yield) as a solid. $^1$H NMR (400 MHz, (CD$_3$)$_2$SO) δ 12.03 (br s, 1H), 9.40 (s, 1H), 8.34 (d, 1H), 7.56 (d, 1H), 2.69-2.62 (m, 1H), 1.12 (d, 6H); LCMS (APCI+) m/z 299.9, 301.9 (M+H)+, Retention time=3.02 minutes (Method 3).

Step B: (R)-tert-Butyl piperidin-3-ylcarbamate (327 mg, 1.63 mmol) was added to N-(5-bromo-4-fluoro-1H-pyrrolo[2,3-b]pyridin-3-yl)isobutyramide (140 mg) in n-BuOH (3 mL), and the reaction was stirred at 160° C. for 24 hours in a sealed tube. The reaction was concentrated to dryness. Then the residue was purified by C-18 reverse phase flash chromatography (Biotage SP4 unit, C-18 25M column, 10-90% gradient CH$_3$CN/water gradient; CV) to yield (R)-tert-butyl 1-(5-bromo-3-isobutyramido-1H-pyrrolo[2,3-b]pyridin-4-yl)piperidin-3ylcarbamate (105 mg, 47% yield) as a solid.

Step C: (R)-tert-Butyl 1-(5-bromo-3-isobutyramido-1H-pyrrolo[2,3-b]pyridin-4-yl)piperidin-3ylcarbamate (90 mg, 0.19 mmol) was dissolved in TFA (5 mL) and stirred for 30 minutes at room temperature. The reaction was concentrated to dryness and dissolved in a minimal amount of methanol. The solution was added dropwise to a stirred solution of 4N HCl in dioxane. The resulting solid was filtered and dried under high vacuum to yield (R)—N-(4-(3-aminopiperidin-1-yl)-5-bromo-1H-pyrrolo[2,3-b]pyridin-3-yl)isobutyramide hydrochloride (65 mg, 91% yield) as a solid. $^1$H NMR (400 MHz, (CD$_3$)$_2$SO) δ 11.78 (d, 1H), 9.26 (s, 1H), 8.26 (br s, 3H), 8.24 (s, 1H), 7.61 (br s, 1H), 3.52-3.27 (m, 4H), 3.12-3.05 (m, 1H), 2.69-2.61 (m, 1H), 2.17-2.10 (m, 1H), 1.91-1.83 (m, 1H), 1.74-1.62 (m, 1H), 1.56-1.45 (m, 1H), 1.16 (d, 6H). LCMS (ACPI+) m/z 380, 382 (M)+, Retention time=1.84 minutes (Method 1).

Example 16

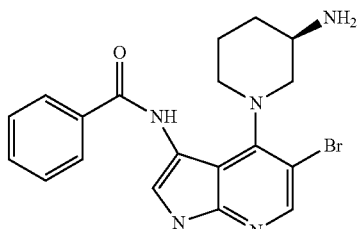

(R)-N-(4-(3-Aminopiperidin-1-yl)-5-bromo-
1H-pyrrolo[2,3-b]pyridin-3-yl)benzamide Step A: (R)-tert-Butyl piperidin-3-ylcarbamate (162 mg, 0.81 mmol) was added to N-(5-bromo-4-fluoro-1H-pyrrolo[2,3-b]pyridin-3-yl)benzamide (90 mg, 0.27 mmol, Example 7, Step A) in n-BuOH (3 mL), and the reaction was stirred at 160° C. for 24 hours in a sealed tube. The reaction was concentrated to dryness. The residue was then purified by chromatography (SP4, C-18 25M+ column, 10-90% CH$_3$CN/water gradient, 30 CV) to yield (R)-tert-butyl 1-(3-benzamido-5-bromo-1H-pyrrolo[2,3-b]pyridin-4-yl)piperidin-3-ylcarbamate (61 mg, 44% yield) as a solid.

Step B: (R)-tert-Butyl 1-(3-benzamido-5-bromo-1H-pyrrolo[2,3-b]pyridin-4-yl)piperidin-3-ylcarbamate was dissolved in TFA (5 mL) and stirred for 30 minutes at room temperature. The reaction was concentrated to dryness and then dissolved in a minimal amount of methanol. The solution was added dropwise to a stirred solution of 2N HCl in ether. The resulting solid was filtered and dried under high vacuum to yield (R)—N-(4-(3-aminopiperidin-1-yl)-5-bromo-1H-pyrrolo[2,3-b]pyridin-3-yl)benzamide hydrochloride (26 mg, 72% yield) as a solid. $^1$H NMR (400 MHz, (CD$_3$)$_2$SO) δ 11.92 (d, 1H), 9.92 (s, 1H), 8.27 (s, 1H), 8.12 (br s, 3H), 8.03 (d, 2H), 7.70 (br s, 1H), 7.64-7.55 (m, 3H), 3.50-3.40 (m, 2H), 3.30-3.19 (m, 2H), 3.13-3.03 (m, 1H), 1.94-1.83 (m, 1H), 1.70-1.61 (m, 1H), 1.51-1.25 (m, 2H); LCMS (APCI+) m/z 414, 416 (M+H)+, Retention time=2.25 minutes (Method 1).

Example 17

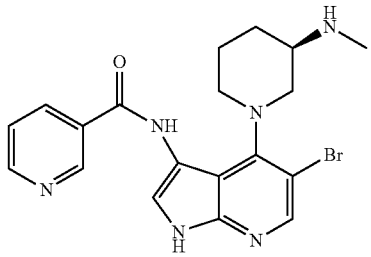

(R)-N-(5-Bromo-4-(3-(methylamino)piperidin-1-yl)-
1H-pyrrolo[2,3-b]pyridin-3-yl)nicotinamide Step A: (R)-tert-Butyl methyl(piperidin-3-yl)carbamate (384 mg, 1.79 mmol) was added to N-(5-bromo-4-fluoro-1H-pyrrolo[2,3-b]pyridin-3-yl)nicotinamide (200 mg, 0.597 mmol, Example 1, Step I) in n-BuOH (3 mL), and the reaction was stirred at 160° C. for 24 hours in a sealed tube. The reaction was concentrated to dryness. The residue was then purified by chromatography (Biotage SP4, C-18 25M+ column, 10-90% CH$_3$CN/water gradient, 30 CV) to yield (R)-tert-butyl 1-(5-bromo-3-(nicotinamido)-1H-pyrrolo[2,3-b]pyridin-4-yl)piperidin-3-yl(methyl)carbamate as a solid.

Step B: (R)-tert-Butyl 1-(5-bromo-3-(nicotinamido)-1H-pyrrolo[2,3-b]pyridin-4-yl)piperidin-3-yl(methyl)carbamate (51 mg, 0.096 mmol) was dissolved in TFA (5 mL) and stirred for 30 minutes at room temperature. The reaction was concentrated to dryness and then dissolved in a minimal amount of methanol. The solution was added dropwise to a stirred solution of 4N HCl in dioxane. The resulting solid was filtered and dried under high vacuum to yield (R)—N-(5-bromo-4-(3-(methylamino)piperidin-1-yl)-1H-pyrrolo[2,3-b]pyridin-3-yl)nicotinamide hydrochloride (33 mg, 80% yield) as a solid. $^1$H NMR (400 MHz, (CD$_3$)$_2$SO) δ 11.99 (d, 1H), 9.30 (d, 1H), 8.99-8.86 (m, 3H), 8.58 (d, 1H), 8.28 (s, 1H), 7.76 (dd, 1H), 7.63 (br s, 1H), 3.59-3.49 (m, 1H), 3.35-3.05 (m, 4H), 2.49 (s, 3H), 2.06-1.90 (m, 1H), 1.71-1.62 (m, 1H), 1.48-1.25 (m, 2H); LCMS (APCI+) m/z 431.0 (M+H)+, Retention time=2.02 minutes (Method 1).

Example 18

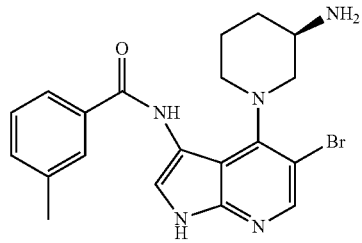

(R)-N-(4-(3-Aminopiperidin-1-yl)-5-bromo-1H-pyrrolo[2,3-b]pyridin-3-yl)-3-methylbenzamide Step A: 5-Bromo-4-fluoro-1H-pyrrolo[2,3-b]pyridin-3-amine (0.250 g, 1.09 mmol), 3-methylbenzoic acid (311 mg, 2.28 mmol), BOP-Cl (581 mg, 2.28 mmol), and triethylamine (0.757 mL, 5.43 mmol) in DCM (5 mL) were stirred at room temperature for 30 minutes. 3M LiOH (3 mL) was then added. The reaction was stirred for an additional 10 minutes and then poured into water. The mixture was then filtered, washed with DCM, washed with 10:1 DCM:MeOH and dried to give N-(5-bromo-4-fluoro-1H-pyrrolo[2,3-b]pyridin-3-yl)-3-methylbenzamide (210 mg, 55.5% yield) as a solid.

Step B: N-(5-Bromo-4-fluoro-1H-pyrrolo[2,3-b]pyridin-3-yl)-3-methylbenzamide (210 mg, 0.60 mmol) and (R)-tert-butyl piperidin-3-ylcarbamate (360 mg, 1.8 mmol) in n-BuOH (3 mL) was stirred at 155° C. in a sealed tube. The reaction was then cooled to room temperature and concentrated to dryness. The crude residue was purified by reverse phase HPLC to give (R)-tert-butyl 1-(5-bromo-3-(3-methylbenzamido)-1H-pyrrolo[2,3-b]pyridin-4-yl)piperidin-3-ylcarbamate (150 mg, 47% yield).

Step C: (R)-tert-Butyl 1-(5-bromo-3-(3-methylbenzamido)-1H-pyrrolo[2,3-b]pyridin-4-yl)piperidin-3-ylcarbamate (123 mg, 0.233 mmol) in DCM (3 mL) at room temperature was treated with TFA (1 mL), and the reaction was stirred for 1 hour. The reaction mixture was then concentrated to dryness. The resulting residue was dissolved in minimal DCM and added to a stirring solution of 1M HCl in ether. The solid formed was filtered, washed with ether and dried to give (R)—N-(4-(3-aminopiperidin-1-yl)-5-bromo-1H-pyrrolo[2,3-b]pyridin-3-yl)-3-methylbenzamide hydrochloride (0.102 g, 87.4% yield). $^1$H NMR (400 MHz, D$_2$O) δ 8.02 (s, 1H), 7.64 (s, 1H), 7.62-7.52 (m, 1H), 7.42-7.38 (m, 3H), 3.49-3.42 (m, 1H), 3.27-3.18 (m, 2H), 3.17-3.06 (m, 2H), 2.29 (s, 3H), 1.81-1.71 (m, 1H), 1.68-1.57 (m, 1H), 1.49-1.26 (m, 2H); LCMS (APCI+) m/z 428, 430 (M+H)+, Retention time=2.68 minutes (Method 2).

Example 19

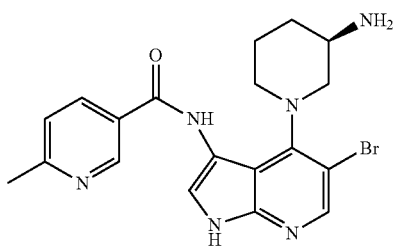

(R)-N-(4-(3-Aminopiperidin-1-yl)-5-bromo-1H-pyrrolo[2,3-b]pyridin-3-yl)-6-methylnicotinamide Step A: A mixture of 5-bromo-4-fluoro-1H-pyrrolo[2,3-b]pyridin-3-amine (250 mg, 1.09 mmol), 6-methylnicotinic acid (313 mg, 2.28 mmol), BOP-Cl (581 mg, 2.28 mmol), and triethylamine (0.757 mL, 5.43 mmol) in DCM (5 mL) was stirred at room temperature for 30 minutes. 3M LiOH (3 mL) was then added. The reaction was stirred for an additional 10 minutes and then poured into water. The mixture was then filtered, washed with DCM, washed with 10:1 DCM:MeOH and dried to give N-(5-bromo-4-fluoro-1H-pyrrolo[2,3-b]pyridin-3-yl)-6-methylnicotinamide (260 g, 68.5% yield) as a solid Step B: N-(5-Bromo-4-fluoro-1H-pyrrolo[2,3-b]pyridin-3-yl)-6-methylnicotinamide (260 mg, 0.745 mmol) and (R)-tert-butyl piperidin-3-ylcarbamate (447 mg, 2.23 mmol) in n-BuOH (3 mL) was heated to 155° C. in a sealed tube. The reaction was then cooled to room temperature and concentrated to dryness. The crude residue was purified by reverse phase HPLC to give (R)-tert-butyl 1-(5-bromo-3-(6-methylnicotinamido)-1H-pyrrolo[2,3-b]pyridin-4-yl)piperidin-3-ylcarbamate (12 mg, 3% yield).

Step C: (R)-tert-Butyl 1-(5-bromo-3-(6-methylnicotinamido)-1H-pyrrolo[2,3-b]pyridin-4-yl)piperidin-3-ylcarbamate (12 mg, 0.023 mmol) in DCM (3 mL) at room temperature was treated with TFA (1 mL). The reaction was stirred for 1 hour and then concentrated to dryness. The resulting residue was dissolved in a minimal amount of DCM and then added to a stirring solution of 1M HCl in ether. The resulting solid was filtered, washed with ether and dried to give (R)—N-(4-(3-aminopiperidin-1-yl)-5-bromo-1H-pyrrolo[2,3-b]pyridin-3-yl)-6-methylnicotinamide hydrochloride (0.004 g, 33% yield) as a solid. $^1$H NMR (400 MHz, D$_2$O) δ 9.02-8.99 (m, 1H), 8.65-8.61 (m, 1H), 8.23 (d, 1H), 7.80 (d, 1H), 7.40 (d, 1H), 3.52-3.46 (m, 1H), 3.36-3.26 (m, 1H), 3.25-3.17 (m 1H), 3.15-3.06 (m 2H), 2.67 (s, 3H), 1.84-1.76 (m, 1H), 1.71-1.61 (m, 1H), 1.46-1.31 (m, 2H); LCMS (APCI+) m/z 429, 431 (M+H)+, Retention time=2.25 minutes (Method 2).

Example 20

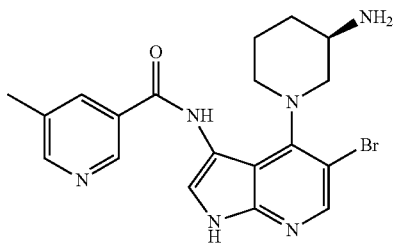

(R)-N-(4-(3-Aminopiperidin-1-yl)-5-bromo-
1H-pyrrolo[2,3-b]pyridin-3-yl)-5-methylnicotinamide Step A: 5-Methylnicotinic acid (477 mg, 3.48 mmol), bis (2-oxooxazolidin-3-yl)phosphinic chloride (885 mg, 3.48 mmol) and triethylamine (880 mg, 8.69 mmol) were added to 5-bromo-4-fluoro-1H-pyrrolo[2,3-b]pyridin-3-amine (400 mg, 1.74 mmol) in DCM (200 mL). The reaction was stirred at room temperature for 1 hour, and then 3M aqueous LiOH (4 mL) was added. The reaction was stirred for 1 hour, and then saturated aqueous Na$_2$CO$_3$ was added (200 mL). The aqueous phase was extracted once with DCM (200 mL), and then the aqueous phase was filtered. The filtered cake was dried to yield N-(5-bromo-4-fluoro-1H-pyrrolo[2,3-b]pyridin-3-yl)-5-methylnicotinamide (228 mg, 37.6% yield) as a solid.

Step B: (R)-tert-Butyl piperidin-3-ylcarbamate (172 mg, 0.859 mmol) was added to N-(5-bromo-4-fluoro-1H-pyrrolo[2,3-b]pyridin-3-yl)-5-methylnicotinamide (100 mg, 0.286 mmol) in n-BuOH (3 mL), and the reaction was stirred at 160° C. for 24 hours in a sealed tube. The reaction was concentrated to dryness, and then the residue was purified by chromatography (SP4, 25M, water/ACN 90/10 to 10/90, 30CV) to yield (R)-tert-butyl 1-(5-bromo-3-(5-methylnicotinamido)-1H-pyrrolo[2,3-b]pyridin-4-yl)piperidin-3-ylcarbamate (47 mg, 31.0% yield) as a solid.

Step C: (R)-tert-Butyl 1-(5-bromo-3-(5-methylnicotinamido)-1H-pyrrolo[2,3-b]pyridin-4-yl)piperidin-3-ylcarbamate (40 mg, 0.076 mmol) was dissolved in TFA (5 mL) and stirred for 30 minutes at room temperature. The reaction was concentrated to dryness and then dissolved in a minimal amount of methanol. The solution was added dropwise to a stirred solution of 4N HCl in dioxane. The resulting solid was filtered and dried under high vacuum to yield (R)—N-(4-(3-aminopiperidin-1-yl)-5-bromo-1H-pyrrolo[2,3-b]pyridin-3-yl)-5-methylnicotinamide hydrochloride (24 mg, 74% yield) as a solid $^1$H NMR (400 MHz, (CD$_3$)$_2$SO) δ 10.29 (br s, 1H), 9.16 (s, 1H), 8.79 (s, 1H), 8.52 (s, 1H), 8.27 (s, 1H), 8.15 (br s, 3H), 7.63 (s, 1H), 3.48-3.27 (m, 2H), 3.26-3.02 (m, 3H), 2.50 (s, 3H), 1.96-1.84 (m, 1H), 1.69-1.59 (m, 1H), 1.51-1.28 (m, 2H); LCMS (APCI+) m/z 429, 431 (M+H)+, Retention time=1.90 min (Method 1).

Example 21

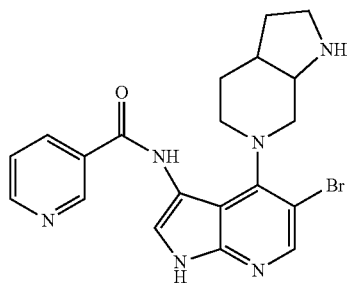

N-(5-Bromo-4-(tetrahydro-1H-pyrrolo[2,3-c]pyridin-6(2H,7H,7aH)-yl)-1H-pyrrolo[2,3-b]pyridin-3-yl)nicotinamide Step A: 1H-Pyrrolo[2,3-c]pyridine (2.50 g, 21.2 mmol) and triethylamine (3.24 mL, 23.3 mmol) were placed in DCM (25 mL) at room temperature. di-tert-Butyl dicarbonate (4.85 g, 22.2 mmol) was then added, and the reaction stirred for 30 minutes. The reaction was then poured into water and extracted with DCM. The organic fraction was dried, filtered, and concentrated. The crude was purified by column chromatography on silica gel (500:3 DCM:MeOH) to give tert-butyl 1H-pyrrolo[2,3-c]pyridine-1-carboxylate (4.4 g, 95.3% yield).

Step B: tert-Butyl 1H-pyrrolo[2,3-c]pyridine-1-carboxylate (1.0 g, 4.58 mmol) and PtO$_2$ (0.208 g, 0.916 mmol) were placed in 1:1 EtOH:AcOH (10 mL) and shaken at 50 PSI under H$_2$ for 8 hours. The reaction was then concentrated. The crude oil was dissolved in DCM, poured into saturated Na$_2$CO$_3$ and extracted into DCM. The organic fraction was dried, filtered, and concentrated to give the product as an oil, tert-butyl octahydro-1H-pyrrolo[2,3-c]pyridine-1-carboxylate (0.99 g, 95.5% yield).

Step C: N-(5-Bromo-4-(tetrahydro-1H-pyrrolo[2,3-c]pyridin-6(2H,7H,7aH)-yl)-1H-pyrrolo[2,3-b]pyridin-3-yl)nicotinamide (0.060 g, 79% yield) was prepared as described in Example 1, Steps J and K, using N-(5-bromo-4-fluoro-1H-pyrrolo[2,3-b]pyridin-3-yl)nicotinamide (0.250 g, 0.746 mmol) and substituting tert-butyl octahydro-1H-pyrrolo[2,3-c]pyridine-1-carboxylate (0.506 g, 2.24 mmol) for tert-butyl piperidin-3-ylcarbamate. $^1$H NMR (400 MHz, D$_2$O) δ 9.14 (d, 1H), 8.82 (dd, 1H), 8.71 (d, 1H), 8.28 (s, 1H), 7.92 (dd, 1H), 7.43 (s, 1H), 3.68-3.63 (m, 1H), 3.54-3.50 (m, 2H), 3.42-3.33 (m, 2H), 3.31-3.21 (m, 2H), 3.09-3.01 (m 1H), 2.27-2.21 (m, 1H), 1.95-1.85 (m, 1H), 1.74-1.65 (m, 2H); LCMS (APCI+) m/z 441, 443 (M+H)+, Retention time=2.04 minutes (Method 2).

Example 22

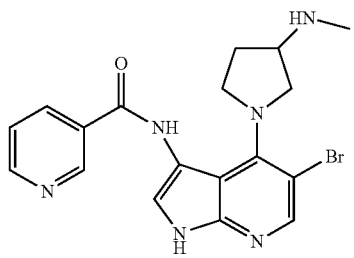

N-(5-Bromo-4-(3-(methylamino)pyrrolidin-1-yl)-
1H-pyrrolo[2,3-b]pyridin-3-yl)nicotinamide N-(5-Bromo-4-fluoro-1H-pyrrolo[2,3-b]pyridin-3-yl) nicotinamide (100 mg, 0.30 mmol), tert-butyl methyl(pyrrolidin-3-yl)carbamate (240 mg, 1.19 mmol) and DIEA (0.0520 mL, 0.30 mmol) in n-BuOH (3 mL) were stirred at 143° C. (bath) for 24 hours. The solvent was removed. The residue was dissolved in ethyl acetate (20 mL), washed with water (10 mL), brine (10 mL), and dried over sodium sulfate. After removal of the solvent, the residue was purified by chromatography (ethyl acetate:MeOH, 10:1) to give a solid. This solid was dissolved in DCM (3 mL), and TFA (0.5 mL) was added. The mixture was stirred at room temperature for 1 hour. The solvent was removed. The residue was dissolved in DCM (1 mL) and 2N HCl in ether (3 mL) was added. The solid formed was collected by filtration to give N-(5-Bromo-4-(3-(methylamino)pyrrolidin-1-yl)-1H-pyrrolo[2,3-b]pyridin-3-yl)nicotinamide (93 mg, 59% yield) as a solid. $^1$H NMR (400 MHz, D$_2$O) δ 9.14 (d, 1H), 8.83 (dd, 1H), 8.71 (dt, 1H), 8.23 (s, 1H), 7.98 (dd, 1H), 7.44 (s, 1H), 4.02-3.96 (m, 1H), 3.76-3.68 (m, 3H), 3.65-3.59 (m, 1H), 2.22-2.13 (m, 1H), 1.93-1.84 (m, 1H); LCMS (APCI+) m/z 415, 417 (M+H)+.

Example 23

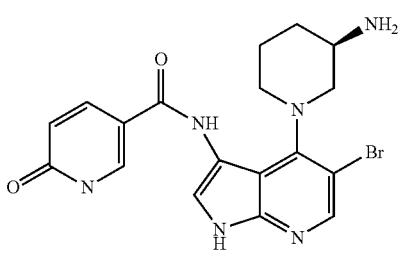

(R)-N-(4-(3-Aminopiperidin-1-yl)-5-bromo-1H-pyrrolo[2,3-b]pyridin-3-yl)-1-methyl-6-oxo-1,6-dihydropyridine-3-carboxamide Step A: TEA (0.61 mL, 4.35 mmol) was added to 5-bromo-4-fluoro-1H-pyrrolo[2,3-b]pyridin-3-amine (0.20 g, 0.87 mmol, Example 1, Step H), 1-methyl-6-oxo-1,6-dihydropyridine-3-carboxylic acid (0.17 g, 1.13 mmol) and BOP-Cl (0.33 g, 1.30 mmol) in DCM (10 mL). The reaction was stirred at room temperature for 1 hour, and then a LiOH solution (3 mL, 2N) was added. The mixture was stirred for 30 minutes, and water (10 mL) was added. The solid formed was collected by filtration, washed with DCM (10 mL) and dried to give N-(5-bromo-4-fluoro-1H-pyrrolo[2,3-b]pyridin-3-yl)-1-methyl-6-oxo-1,6-dihydropyridine-3-carboxamide (0.22 g, 69% yield) as a solid.

Step B: N-(5-Bromo-4-fluoro-1H-pyrrolo[2,3-b]pyridin-3-yl)-1-methyl-6-oxo-1,6-dihydropyridine-3-carboxamide (0.22 g, 0.602 mmol) and (R)-tert-butyl piperidin-3-ylcarbamate (0.362 g, 1.81 mmol) in n-BuOH (2 mL) were stirred at 143° C. (bath) for 24 hours. The solvent was removed, and the residue was dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 10-80% CH$_3$CN/water gradient; 30 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)-1-methyl-6-oxo-1,6-dihydropyridine-3-carboxamide hydrochloride (0.113 g, 36% yield) as a solid. $^1$H NMR (400 MHz, (CD$_3$)$_2$SO) δ 11.94 (s, 1H), 9.74 (s, 1H), 8.62 (s, 8.25 (s, 1H), 8.15 (br s, 3H), 8.06 (d, 1H), 7.51 (s, 1H), 6.49 (d, 1H), 3.44 (m, 1H), 3.32 (m, 1H), 3.20 (m, 2H), 3.07 (m, 1H), 1.93 (m, 1H), 1.66 (m, 1H), 1.49 (m, 1H), 1.35 (m, 1H); LCMS (APCI+) m/z 445 (M+H)+.

Example 24

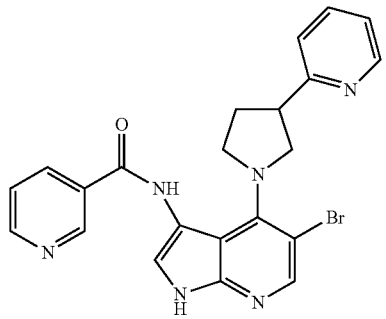

N-(5-Bromo-4-(3-(pyridin-2-yl)pyrrolidin-1-yl)-1H-pyrrolo[2,3-b]pyridin-3-yl)nicotinamide N-(5-Bromo-4-fluoro-1H-pyrrolo[2,3-b]pyridin-3-yl)nicotinamide (100 mg, 0.3 mmol, Example 1, Step I) in n-BuOH (3 mL) and 2-(pyrrolidin-3-yl)pyridine (133 mg, 0.9 mmol) were heated to 160° C. in a sealed tube for 48 hours. After cooling down, the reaction was concentrated to dryness, and the residue purified by C-18 reverse phase flash chromatography (Biotage SP4 unit, C-18 25M column, 10-90% CH$_3$CN/water gradient; 30 CV) to yield N-(5-bromo-4-(3-(pyridin-2-yl)pyrrolidin-1-yl)-1H-pyrrolo[2,3-b]pyridin-3-yl)nicotinamide (29 mg) as a solid. This solid was dissolved in MeOH (1 mL), and then the solution was added dropwise to a 4N HCl solution in dioxane. The resulting solid was collected and dried to yield N-(5-bromo-4-(3-(pyridin-2-yl)pyrrolidin-1-yl)-1H-pyrrolo[2,3-b]pyridin-3-yl)nicotinamide hydrochloride (35 mg, 25% yield) as a solid. $^1$H NMR (400 MHz, (CD$_3$)$_2$SO) δ 12.07 (d, 1H), 10.52 (s, 1H), 9.30 (d, 1H), 8.94-8.91 (m, 1H), 8.72-8.66 (m, 2H), 8.39-8.33 (m, 2H), 7.92-7.76 (m, 3H), 7.71 (d, 1H), 7.20 (br s, 2H), 4.06-3.95 (m, 2H), 3.80-3.67 (m, 3H), 2.48-2.40 (m, 1H), 2.23-2.11 (m, 1H). LCMS (APCI+) m/z 463, 465 (M+H)+, Retention time=2.78 minutes (Method 1).

Example 25

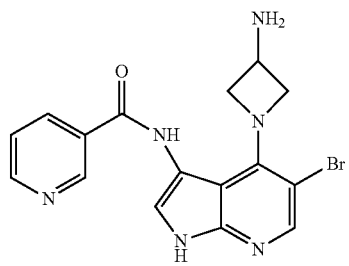

N-(4-(3-Aminoazetidin-1-yl)-5-bromo 1H-pyrrolo[2,3-b]pyridin-3-yl)nicotinamide

Step A: N-(5-Bromo-4-fluoro-1H-pyrrolo[2,3-b]pyridin-3-yl)nicotinamide (100 mg, 0.3 mmol, Example 1, Step I) in n-BuOH (3 mL) and tert-butyl azetidin-3-ylcarbamate (154 mg, 0.9 mmol) were heated to 110° C. in a sealed tube for 24 hours. After cooling down, the reaction was concentrated to dryness, and the residue purified by C-18 reverse phase flash chromatography (Biotage SP4 unit, C-18 25M column, 10-90% CH$_3$CN/water gradient; 30 CV) to yield tert-butyl 1-(5-bromo-3-(nicotinamido)-1H-pyrrolo[2,3-b]pyridin-4-yl)azetidin-3-ylcarbamate (54 mg, 37% yield) as a solid.

Step B: tert-Butyl 1-(5-bromo-3-(nicotinamido)-1H-pyrrolo[2,3-b]pyridin-4-yl)azetidin-3-ylcarbamate (54 mg, 0.11 mmol) was stirred in TFA (3 mL) for 30 minutes, and then the reaction was concentrated to dryness. The residue was dissolved in a minimal amount of methanol, and then it was added dropwise to a 4N HCl dioxane solution. The resulting solid was collected and rinsed with DCM and dried under high vacuum to yield N-(4-(3-aminoazetidin-1-yl)-5-bromo-1H-pyrrolo[2,3-b]pyridin-3-yl)nicotinamide hydrochloride (41 mg, 96% yield) as a solid. $^1$H NMR (400 MHz, (CD$_3$)$_2$SO) δ 12.45 (d, 1H), 10.70 (s, 1H), 8.90 (dd, 1H), 8.68-8.64 (m, 1H), 8.57 (br s, 2H), 8.26 (s, 1H), 7.80 (dd, 1H), 7.40 (d, 1H), 5.76 (br s, 3H), 4.85-4.75 (m, 2H), 4.56-4.50 (m, 2H), 4.00-3.90 (m, 1H). LCMS (APCI+) m/z 387, 389 (M+H)+, Retention time=1.63 minutes (Method 1).

Example 26

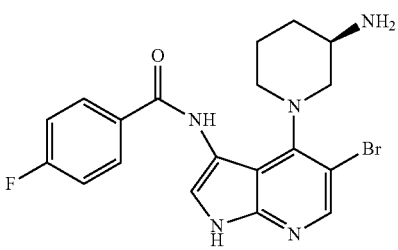

(R)-N-(4-(3-Aminopiperidin-1-yl)-5-bromo-1H-pyrrolo[2,3-b]pyridin-3-yl)-4-fluorobenzamide Step A: 4-Fluorobenzoyl chloride (0.15 mL, 1.30 mmol) was added to 5-bromo-4-fluoro-1H-pyrrolo[2,3-b]pyridin-3-amine (200 mg, 0.87 mmol, Example 1, Step H) in pyridine (5 mL). The reaction was stirred at room temperature for 10 minutes, and then the pyridine was removed. THF (5 mL) and 2N LiOH (3 mL) were added and stirred for 20 minutes. The THF was removed, and water (20 mL) was added. The solid formed was collected by filtration and dried to give N-(5-bromo-4-fluoro-1H-pyrrolo[2,3-b]pyridin-3-yl)-4-fluorobenzamide (0.24 g, 77% yield) as a solid.

Step B: N-(5-Bromo-4-fluoro-1H-pyrrolo[2,3-b]pyridin-3-yl)-4-fluorobenzamide (0.24 g, 0.67 mmol) and (R)-tert-butyl piperidin-3-ylcarbamate (0.40 g, 2.01 mmol) in n-BuOH (2 mL) were stirred at 143° C. (bath) for 24 hours. The solvent was removed, and the residue was dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 20-80% CH$_3$CN/water gradient; 30 CV) to give a solid. The solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)-4-fluorobenzamide hydrochloride (0.14 g, 41% yield) as a solid. $^1$H NMR (400 MHz, (CD$_3$)$_2$SO) δ 11.94 (s, 1H), 9.95 (s, 1H), 8.26 (s, 1H), 8.17-8.9 (m, 6H), 7.65 (br s, 1H), 7.42 (t, 2H), 3.43-3.35 (m, 3.25-3.15 (m, 2H), 3.10-3.04 (m, 1H), 1.92-1.85 (m, 1H), 1.66-1.59 (m, 1H), 1.46-1.28 (m, 2H); LCMS (APCI+) m/z 432 (M+H)+.

Example 27

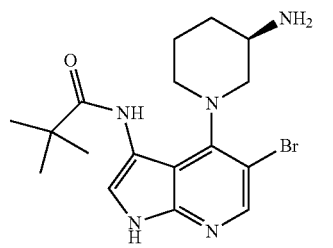

(R)-N-(4-(3-Aminopiperidin-1-yl)-5-bromo-1H-pyrrolo[2,3-b]pyridin-3-yl)pivalamide Step A: Pivaloyl chloride (0.12 mL, 0.98 mmol) was added to 5-bromo-4-fluoro-1H-pyrrolo[2,3-b]pyridin-3-amine (0.15 g, 0.65 mmol) in pyridine (5 mL). The reaction was stirred at room temperature for 10 minutes, and then the pyridine was removed. THF (5 mL) and 2N LiOH (3 mL) were added and stirred for 20 minutes. The THF was removed in vacuo, and water (20 mL) was added to the aqueous residue. The solid formed was collected by filtration and dried to give N-(5-bromo-4-fluoro-1H-pyrrolo[2,3-b]pyridin-3-yl)pivalamide (0.128 g, 62% yield) as a solid.

Step B: N-(5-Bromo-4-fluoro-1H-pyrrolo[2,3-b]pyridin-3-yl)pivalamide (0.128 g, 0.407 mmol) and (R)-tert-butyl piperidin-3-ylcarbamate (0.245 g, 1.22 mmol) in n-BuOH (2 mL) were stirred at 143° C. (bath) for 24 hours. The solvent was removed, and the residue was dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 30-80% CH$_3$CN/water gradient; 30 CV) to give a solid. The solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)pivalamide hydrochloride (66 mg, 32% yield) as a solid. $^1$H NMR (400 MHz, (CD$_3$)$_2$SO) δ 11.78 (s, 1H), 9.03 (s, 1H), 8.25 (s, 1H), 8.18-8.07 (m, 3H), 3.49-3.31 (4H), 3.10-3.03 (m, 1H), 2.17-2.07 (m, 1H), 1.93-1.85 (m, 1H), 1.77-1.65 (m, 1H), 1.55-2.42 (m, 1H), 1.28 (s, 9H); LCMS (APCI+) m/z 394 (M+H)+.

Example 28

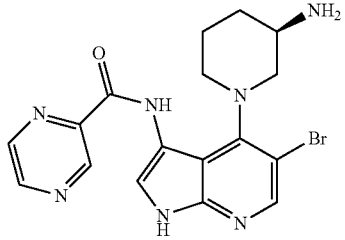

(R)-N-(4-(3-Aminopiperidin-1-yl)-5-bromo-1H-pyrrolo[2,3-b]pyridin-3-yl)pyrazine-2-carboxamide Step A: 5-Bromo-4-fluoro-1H-pyrrolo[2,3-b]pyridin-3-amine (0.200 g, 0.869 mmol, Example 1, Step H), pyrazine-2-carboxylic acid (0.227 g, 1.83 mmol), BOP-Cl (0.465 g, 1.83 mmol), and triethylamine (0.606 ml, 4.35 mmol) were placed in DCM (5 mL) and stirred at room temperature for 30 minutes. 3M LiOH (3 mL) was then added, and the reaction was stirred for an additional 10 minutes and then poured into water. The mixture was then filtered, washed with DCM, and then washed with 10:1 DCM:MeOH and dried to give N-(5-bromo-4-fluoro-1H-pyrrolo[2,3-b]pyridin-3-yl)pyrazine-2-carboxamide (0.180 g, 61% yield) as a solid.

Step B: N-(5-Bromo-4-fluoro-1H-pyrrolo[2,3-b]pyridin-3-yl)pyrazine-2-carboxamide (0.180 g, 0.536 mmol) and (R)-tert-butyl piperidin-3-ylcarbamate (0.322 g, 1.61 mmol) were placed in n-BuOH (2 mL) and heated to 155° C. in a sealed tube. The reaction was then cooled to room temperature and concentrated to dryness. The resulting residue was purified by reverse phase HPLC (5 to 95% ACN in water, Gilson system) to give the product, (R)-tert-butyl 1-(5-bromo-3-(pyrazine-2-carboxamido)-1H-pyrrolo[2,3-b]pyridin-4-yl)piperidin-3-ylcarbamate (0.105 g, 38% yield).

Step C: (R)-tert-Butyl 1-(5-bromo-3-(pyrazine-2-carboxamido)-1H-pyrrolo[2,3-b]pyridin-4-yl)piperidin-3-ylcarbamate (0.060 g, 0.12 mmol) was placed in DCM (3 mL) at room temperature. TFA (1 mL) was then added, and the reaction was stirred at room temperature for 1 hour and then concentrated to dryness. The resulting residue was purified by reverse phase HPLC (0 to 50% ACN in water, Gilson system). The resulting product was then dissolved in minimal DCM (with MeOH to aid solubility) and added to a stirring solution of 1M HCl in ether. The resulting solid was filtered, washed with ether and dried to give (R)—N-(4-(3-aminopiperidin-1-yl)-5-bromo-1H-pyrrolo[2,3-b]pyridin-3-yl)pyrazine-2-carboxamide hydrochloride (0.019 g, 33% yield). $^1$H NMR (400 MHz, D$_2$O) δ 8.69 (s, 1H), 8.57-8.56 (m, 1H), 8.50 (s, 1H), 8.04 (s, 1H), 7.60 (s, 1H), 3.70-3.62 (m, 1H), 3.55-3.50 (m, 1H), 3.42-3.39 (m, 1H), 3.31-3.29 (m, 1H), 2.83-2.80 (m, 1H), 2.19-2.16 (m, 1H), 1.92-1.89 (m, 1H), 1.73-1.69 (m, 1H), 1.49-1.47 (m, 1H); LCMS (APCI+) m/z 416, 418 (M+H)+.

(165 mg, 64% yield) as a solid. $^1$H NMR (400 MHz, (CD$_3$)$_2$SO) δ 12.03 (br s, 1H), 9.76 (s, 1H), 8.34 (d, 1H), 7.59 (s, 1H), 1.93-1.86 (m, 1H), 0.783 (d, 4H); LCMS (APCI+) m/z 298, 300 (M+H)+, Retention time=2.71 min (Method 2).

Step B: N-(5-Bromo-4-fluoro-1H-pyrrolo[2,3-b]pyridin-3-yl)cyclopropanecarboxamide (160 mg, 0.537 mmol) and (R)-tert-butyl piperidin-3-ylcarbamate (537 mg, 2.68 mmol) were processed as described in Example 1, Step J. The crude material was purified by C-18 reverse phase flash chromatography (Biotage SP4 unit, C-18 25M column, 5-80% CH$_3$CN/water gradient; 25 CV) to provide (R)-tert-butyl 1-(5-bromo-3-(cyclopropanecarboxamido)-1H-pyrrolo[2,3-b]pyridin-4-yl)piperidin-3-ylcarbamate (120 mg, 47% yield) as solid. $^1$H NMR (400 MHz, (CD$_3$)$_2$SO) δ 11.57 (d, 1H), 9.61 (s, 1H), 8.14 (s, 1H), 7.52 (br s, 1H), 6.85 (br s, 1H), 3.61-3.48 (m, 1H), 3.25-3.13 (m, 3H), 3.09-3.01 (m, 1H), 1.87-1.80 (m, 1H), 1.77-1.65 (m, 3H), 1.45-1.32 (m, 1H), 1.29 (s, 9H), 0.77 (d, 4H); LCMS (APCI+) m/z 478, 480 (M+H)+, Retention time=3.59 minutes (Method 2).

Step C: (R)-tert-Butyl 1-(5-bromo-3-(cyclopropanecarboxamido)-1H-pyrrolo[2,3-b]pyridin-4-yl)piperidin-3-ylcarbamate (110 mg, 0.230 mmol) in TFA (5 mL) was stirred at room temperature for 30 minutes, and the TFA was removed in vacuo. The oily residue obtained was dissolved in CH$_2$Cl$_2$ (1 mL), and 2M HCl in Et$_2$O was added. The mixture was stirred at ambient temperature for 30 minutes. The solid formed was filtered and triturated with CH$_3$CN to provide (R)—N-(4-(3-aminopiperidin-1-yl)-5-bromo-1H-pyrrolo[2,3-b]pyridin-3-yl)cyclopropanecarboxamide hydrochloride (70 mg, 67% yield). $^1$H NMR (400 MHz, (CD$_3$)$_2$SO) δ 11.82 (s, 1H), 9.65 (s, 1H), 8.26 (br s, 3H), 8.22 (s, 1H), 7.47 (s, 1H), 3.46-3.40 (m, 3H), 3.31-3.23 (m, 1H), 3.12-3.06 (m, 1H), 2.15-2.09 (m, 1H), 1.87-1.80 (m, 2H), 1.76-1.69 (m, 1H), 1.53-1.43 (m, 1H), 0.83-0.81 (m, 4H); LCMS (APCI+) m/z 378.8, 379.9 (M+H)+, Retention time=2.18 minutes (Method 2).

Example 29

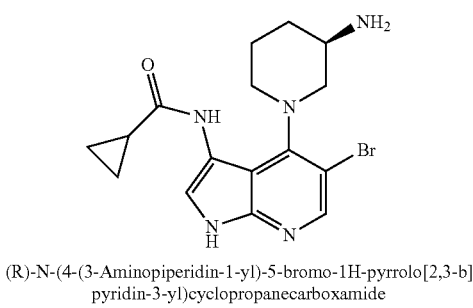 [SMILES: N[C@@H]1CCCN(c2c(Br)cnc3[nH]cc(NC(=O)C4CC4)c23)C1]

(R)-N-(4-(3-Aminopiperidin-1-yl)-5-bromo-1H-pyrrolo[2,3-b]pyridin-3-yl)cyclopropanecarboxamide Step A: A solution of 5-bromo-4-fluoro-1H-pyrrolo[2,3-b]pyridin-3-amine (200 mg, 0.869 mmol) in pyridine (5 mL) at 0° C. was treated dropwise with cyclopropanecarbonyl chloride (118.3 µL, 1.304 mmol). The mixture was stirred at 0° C. for 60 minutes, and then the pyridine was removed in vacuo. The residue obtained was dissolved in THF (10 mL) and treated with lithium hydroxide hydrate (109.5 mg, 2.61 mmol) in water (1 mL). After 30 minutes, the THF was removed under reduced pressure, and water (5 mL) was added to the residue. The solid formed was filtered, washed with additional water and dried to provide N-(5-bromo-4-fluoro-1H-pyrrolo[2,3-b]pyridin-3-yl)cyclopropanecarboxamide Example 30

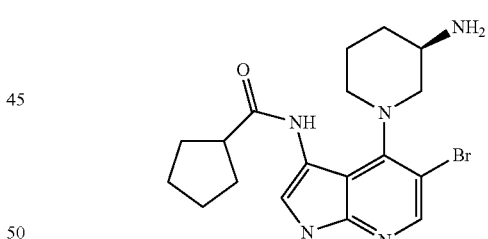

(R)-N-(4-(3-Aminopiperidin-1-yl)-5-bromo-1H-pyrrolo[2,3-b]pyridin-3-yl)cyclopentanecarboxamide Step A: 5-Bromo-4-fluoro-1H-pyrrolo[2,3-b]pyridin-3-amine (200 mg, 0.869 mmol, Example 1, Step H) and cyclopentanecarbonyl chloride (173 mg, 1.30 mmol) were processed as described in Example 29, Step A to provide N-(5-bromo-4-fluoro-1H-pyrrolo[2,3-b]pyridin-3-yl)cyclopentanecarboxamide (210 mg, 74% yield). $^1$H NMR (400 MHz, (CD$_3$)$_2$SO) δ 12.04 (br s, 1H), 8.34 (d, 1H), 7.56 (s, 1H), 2.88-2.80 (m, 1H), 1.89-1.81 (m, 2H), 1.77-1.64 (m, 4H), 1.57-1.53 (m, 2H); LCMS (APCI+) m/z 326, 327.9 (M+H)+, Retention time=3.18 minutes (Method 2).

Step B: A solution of N-(5-bromo-4-fluoro-1H-pyrrolo[2,3-b]pyridin-3-yl)cyclopentanecarboxamide (205 mg, 0.629 mmol) in n-BuOH (5 mL) was treated with (R)-tert-butyl piperidin-3-ylcarbamate (629 mg, 3.14 mmol) and stirred at 160° C. for 18 hours in a sealed tube. The solvent was removed in vacuo, and the residue was dissolved in EtOAc (50 mL) and washed with water (2×10 mL). The organic layer was dried (MgSO$_4$), filtered, and concentrated in vacuo. The residue was purified by C-18 reverse phase flash chromatography (Biotage SP4 unit, C-18 25M column, 5-80% CH$_3$CN/water gradient; 25 CV) to yield a solid, which was crystallized from CH$_3$CN to provide (R)-tert-butyl 1-(5-bromo-3-(cyclopentanecarboxamido)-1H-pyrrolo[2,3-b]pyridin-4-yl)piperidin-3-ylcarbamate (70 mg, 22% yield) as a solid. $^1$H NMR (400 MHz, (CD$_3$)$_2$SO) δ 11.56 (s, 1H), 9.36 (s, 1H), 8.14 (s, 1H), 7.64 (br s, 1H), 6.90 (br s, 1H), 3.56-3.47 (m, 1H), 3.20-3.11 (m, 2H), 3.04-2.97 (m, 1H), 2.81-2.74 (m, 1H), 1.91-1.80 (m, 4H), 1.78-1.70 (m, 3H), 1.67-1.59 (m, 3H), 1.55-1.50 (m, 2H), 1.42-1.34 (m, 1H); LCMS (APCI+) m/z 407.9 [(M-Boc)+H]+, Retention time=4.03 minutes (Method 2).

Step C: A solution of (R)-tert-butyl 1-(5-bromo-3-(cyclopentanecarboxamido)-1H-pyrrolo[2,3-b]pyridin-4-yl)piperidin-3-ylcarbamate (65 mg, 0.13 mmol) in neat TFA (5 mL) was stirred at room temperature for 20 minutes. TFA was then removed in vacuo, and the residue was evaporated from CH$_2$Cl$_2$ (10 mL). The oily residue obtained was dissolved in CH$_2$Cl$_2$ (0.5 mL) and treated with 2M HCl in Et$_2$O. After 30 minutes at room temperature, the solid formed was filtered, washed with additional Et$_2$O and dried to provide (R)—N-(4-(3-aminopiperidin-1-yl)-5-bromo-1H-pyrrolo[2,3-b]pyridin-3-yl)cyclopentanecarboxamide hydrochloride (38 mg, 62% yield) as a solid. $^1$H NMR (400 MHz, (CD$_3$)$_2$SO) δ 11.79 (s, 1H), 9.31 (s, 1H), 8.27 (br s, 1H), 8.23 (s, 1H), 7.59 (br s, 1H), 3.46-3.41 (m, 2H), 3.34-3.27 (m, 2H), 3.11-3.04 (m, 1H), 2.88-2.80 (m, 1H), 2.17-2.11 (m, 1H), 1.94-1.85 (m, 3H), 1.79-1.74 (m, 2H), 1.72-1.65 (m, 3H), 1.60-1.55 (m, 2H), 1.52-1.45 (m, 1H); LCMS (APCI+) m/z 406.0, 408.1 (M+H)+, Retention time=2.42 minutes (Method 2).

Example 31

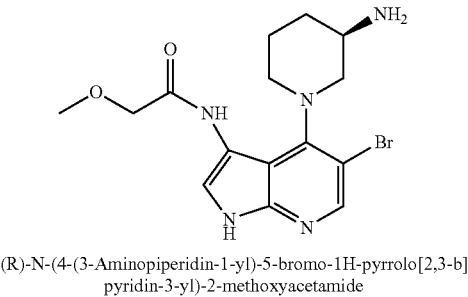 [SMILES: COCC(=O)Nc1c[nH]c2ncc(Br)c(N3CCC[C@@H](N)C3)c12]

(R)-N-(4-(3-Aminopiperidin-1-yl)-5-bromo-1H-pyrrolo[2,3-b]pyridin-3-yl)-2-methoxyacetamide Step A: 2-Methoxyacetic acid (313 mg, 3.5 mmol), bis(2-oxooxazolidin-3-yl)phosphinic chloride (885 mg, 3.5 mmol) and triethylamine (880 mg, 8.7 mmol) were added to 5-bromo-4-fluoro-1H-pyrrolo[2,3-b]pyridin-3-amine (400 mg, 1.7 mmol, Example 1, Step H) in DCM (50 mL). The reaction was stirred at room temperature for 1 hour, and then 3M aqueous LiOH (4 mL) was added. The reaction was stirred for 1 hour, and then saturated aqueous Na$_2$CO$_3$ was added (200 mL). The aqueous phase was extracted 3 times with DCM (200 mL), and then the combined organic phases were dried over MgSO$_4$ and concentrated to dryness. N-(5-bromo-4-fluoro-1H-pyrrolo[2,3-b]pyridin-3-yl)-2-methoxyacetamide (236 mg, 45% yield) was isolated as a solid.

Step B: N-(5-Bromo-4-fluoro-1H-pyrrolo[2,3-b]pyridin-3-yl)-2-methoxyacetamide (100 mg, 0.3 mmol) and (R)-tert-butyl piperidin-3-ylcarbamate (199 mg, 1.0 mmol) in n-BuOH (4 mL) were heated to 160° C. for 18 hours in a sealed tube. After concentration, the residue was purified by C-18 reverse phase flash chromatography (Biotage SP4 unit, C-18 25M column, 10-90% CH$_3$CN/water gradient; 30 CV) to yield (R)-tert-butyl 1-(5-bromo-3-(2-methoxyacetamido)-1H-pyrrolo[2,3-b]pyridin-4-yl)piperidin-3-ylcarbamate (51 mg, 32% yield) as a solid.

Step C: (R)-tert-Butyl 1-(5-bromo-3-(2-methoxyacetamido)-1H-pyrrolo[2,3-b]pyridin-4-yl)piperidin-3-ylcarbamate was stirred in TFA (3 mL) for 30 minutes, and then the reaction was concentrated to dryness. The residue was purified by C-18 reverse phase flash chromatography (Biotage SP4 unit, C-18 12M column, 0-50% CH$_3$CN/water gradient; 20 CV) to yield a solid. The solid was dissolved in a minimal amount of methanol and was added dropwise to a 4N HCl dioxane solution. The resulting solid was collected, rinsed with DCM and dried under high vacuum to yield (R)—N-(4-(3-aminopiperidin-1-yl)-5-bromo-1H-pyrrolo[2,3-b]pyridin-3-yl)-2-methoxyacetamide hydrochloride (22 mg, 55%) as a solid. $^1$H NMR (400 MHz, (CD$_3$)$_2$SO) δ 11.78 (d, 1H), 9.85 (s, 1H), 8.32 (br s, 3H), 8.27 (s, 1H), 7.93 (s, 1H), 4.09 (q, 2H), 3.68-3.58 (m, 1H), 3.53-3.38 (m, 3H), 3.49 (s, 3H), 3.32-3.26 (m, 1H), 3.02-2.96 (m, 1H), 2.24-2.18 (m, 1H), 1.92-1.82 (m, 2H), 1.56-1.46 (m, 1H); LCMS (APCI+) m/z 365, 382 (M)+, Retention time=1.89 minutes (Method 1).

Example 32

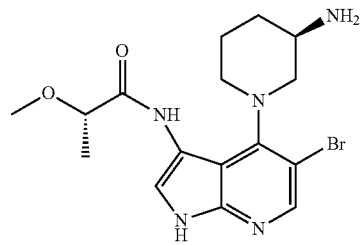

(S)-N-(4-((R)-3-Aminopiperidin-1-yl)-5-bromo-1H-pyrrolo[2,3-b]pyridin-3-yl)-2-methoxypropanamide Step A: (S)-2-Methoxypropanoic acid (181 mg, 1.74 mmol), bis(2-oxooxazolidin-3-yl)phosphinic chloride (443 mg, 1.74 mmol) and triethylamine (440 mg, 4.35 mmol) were added to 5-bromo-4-fluoro-1H-pyrrolo[2,3-b]pyridin-3-amine (200 mg, 0.87 mmol, Example 1, Step H) in DCM (50 mL). The reaction was stirred at room temperature for 1 hour, and then 3M aqueous LiOH (4 mL) was added. The reaction was stirred for 1 hour, and then saturated aqueous Na$_2$CO$_3$ was added (200 mL). The aqueous phase was extracted 3 times with DCM (200 mL), and then the combined organic phases were dried over MgSO$_4$ and concentrated to dryness. The residue was purified by C-18 reverse phase flash chromatography (Biotage SP4 unit, C-18 25M column, 20-100% CH$_3$CN/water gradient; 20 CV) to yield (S)—N-(5-bromo-4-fluoro-1H-pyrrolo[2,3-b]pyridin-3-yl)-2-methoxypropanamide (131 mg, 48% yield) as a solid.

Step B: (S)—N-(5-Bromo-4-fluoro-1H-pyrrolo[2,3-b]pyridin-3-yl)-2-methoxypropanamide (120 mg, 0.38 mmol) and (R)-tert-butyl piperidin-3-ylcarbamate (228 mg, 1.14 mmol) in n-BuOH (4 mL) were heated to 160° C. for 18 hours in a sealed tube. After concentration, the residue was purified by C-18 reverse phase flash chromatography (Biotage SP4 unit, C-18 25M column, 10-90% CH₃CN/water gradient; 30 CV) to yield tert-butyl (R)-1-(5-bromo-3-((S)-2-methoxypropanamido)-1H-pyrrolo[2,3-b]pyridin-4-yl)piperidin-3-ylcarbamate (84 mg, 45% yield) as a solid.

Step C: tert-Butyl (R)-1-(5-bromo-3-((S)-2-methoxypropanamido)-1H-pyrrolo[2,3-b]pyridin-4-yl)piperidin-3-ylcarbamate (84 mg, 0.17 mmol) was stirred in TFA (3 mL) for 30 minutes, and then the reaction was concentrated to dryness. The residue was dissolved in a minimal amount of methanol, and then it was added dropwise to a 4N HCl dioxane solution. The resulting solid was collected and rinsed with DCM and dried under high vacuum to yield (S)—N-(4-((R)-3-aminopiperidin-1-yl)-5-bromo-1H-pyrrolo[2,3-b]pyridin-3-yl)-2-methoxypropanamide hydrochloride (51 mg, 76% yield) as a solid. $^1$H NMR (400 MHz, (CD₃)₂SO) δ 11.79 (d, 1H), 9.89 (s, 1H), 8.40 (br s, 3H), 8.27 (s, 1H), 7.96 (d, 1H), 4.04 (q, 1H), 3.61-3.50 (m, 2H), 3.48-3.36 (m, 1H), 3.46 (s, 3H), 3.34-3.28 (m, 1H), 3.02-2.96 (m, 1H), 2.26-2.18 (m, 1H), 1.92-1.82 (m, 2H), 1.56-1.48 (m, 1H), 1.41 (d, 3H); LCMS (APCI+) m/z 379, 396 (M)+, Retention time=1.95 minutes (Method 1).

Example 33

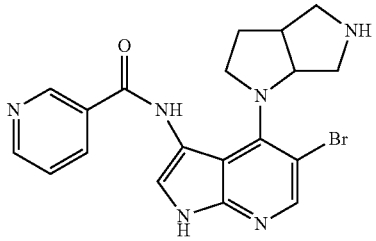

N-(5-Bromo-4-(hexahydropyrrolo[3,4-b]pyrrol-1(2H)-yl)-1H-pyrrolo[2,3-b]pyridin-3-yl)nicotinamide Step A: N-(5-Bromo-4-fluoro-1H-pyrrolo[2,3-b]pyridin-3-yl)nicotinamide (100 mg, 0.3 mmol, Example 1, Step I) and tert-butyl hexahydropyrrolo[3,4-b]pyrrole-5(1H)-carboxylate (190 mg, 0.9 mmol) in n-BuOH (4 mL) were heated to 160° C. for 18 hours in a sealed tube. After concentration, the residue was purified by C-18 reverse phase flash chromatography (Biotage SP4 unit, C-18 25M column, 10-90% CH₃CN/water gradient; 30 CV) to yield tert-butyl 1-(5-bromo-3-(nicotinamido)-1H-pyrrolo[2,3-b]pyridin-4-yl)hexahydropyrrolo[2,3-c]pyrrole-5(1H)-carboxylate as a solid.

Step B: tert-Butyl 1-(5-bromo-3-(nicotinamido)-1H-pyrrolo[2,3-b]pyridin-4-yl)hexahydropyrrolo[2,3-c]pyrrole-5 (1H)-carboxylate (84 mg, 0.16 mmol) was stirred in TFA (3 mL) for 30 minutes, and then the reaction was concentrated to dryness. The residue was dissolved in a minimal amount of methanol, and then it was added dropwise to a 4N HCl dioxane solution. The resulting solid was collected, rinsed with DCM and dried under high vacuum to yield N-(5-bromo-4-(hexahydropyrrolo[3,4-b]pyrrol-1(2H)-yl)-1H-pyrrolo[2,3-b]pyridin-3-yl)nicotinamide hydrochloride (28 mg, 41% yield) as a solid. $^1$H NMR (400 MHz, (CD₃)₂SO) δ 12.15 (d, 1H), 10.69 (s, 1H), 9.55 (br s, 1H), 9.47 (s, 1H), 9.39 (br s, 1H), 9.00 (d, 1H), 8.94 (d, 1H), 8.31 (s, 1H), 7.99 (dd, 1H), 7.57 (d, 1H), 4.92-4.86 (m, 1H), 3.74-3.67 (m, 1H), 3.27-3.19 (m, 2H), 3.14-3.07 (m, 1H), 2.97-2.82 (m, 3H), 1.95-1.85 (m, 1H), 1.69-1.60 (m, 1H); LCMS (APCI+) m/z 427 (M)+, Retention time=1.99 minutes (Method 1).

Example 34

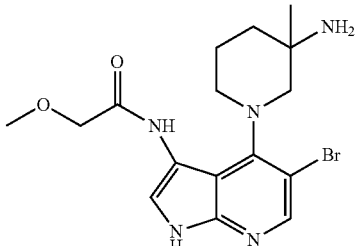

N-(4-(3-Amino-3-methylpiperidin-1-yl)-5-bromo-1H-pyrrolo[2,3-b]pyridin-3-yl)-2-methoxyacetamide Step A: Benzyl carbonochloridate (4.5 mL, 31.7 mmol) at 0° C. was added to ethyl piperidine-3-carboxylate (5.0 g, 30.2 mmol) and K₂CO₃ (4.2 g, 30.2 mmol) in 1:1 THF:water (100 mL). The reaction mixture was stirred at room temperature for 2 hours, and then ether (50 mL) was added. The organic layer was separated, washed with brine and dried over sodium sulfate. After removal of the solvent, the residue was purified by chromatography on silica gel (hexane:ethyl acetate, 5:1) to give 1-benzyl 3-ethyl piperidine-1,3-dicarboxylate (7.60 g 86% yield) as an oil.

Step B: Lithium bis(trimethylsilyl)amide (12.9 mL, 12.9 mmol, 1M solution in THF) at −78° C. was added to 1-benzyl 3-ethyl piperidine-1,3-dicarboxylate (3.0 g, 10.3 mmol) in THF (20 mL), and the reaction was stirred at this temperature for 20 minutes. MeI (0.867 mL, 13.9 mmol) was added, and the reaction was warmed to room temperature. After 2 hours at room temperature, the mixture was poured onto saturated ammonium chloride (20 mL) and extracted with ether, washed with brine and dried over sodium sulfate. After removal of the solvent, the residue was purified by chromatography on silica gel (hexane:ethyl acetate, 5:1) to give 1-benzyl 3-ethyl 3-methylpiperidine-1,3-dicarboxylate (3.1 g, 98% yield) as an oil.

Step C: LiOH (15.0 mL, 30.1 mmol) was added to 1-benzyl 3-ethyl 3-methylpiperidine-1,3-dicarboxylate (3.0 g, 10.0 mmol) in ethanol (15 mL), and the reaction mixture was stirred at 86° C. for 1 hour. The ethanol was removed, and ether (30 mL) was added. The aqueous layer was separated and acidified with saturated potassium hydrogen sulfate to a pH of about 3 to about 4, extracted with ethyl acetate (50 mL), washed with brine and dried over sodium sulfate. After removal of the solvent, 1-(benzyloxycarbonyl)-3-methylpiperidine-3-carboxylic acid (2.6 g, 92% yield) was isolated as an oil.

Step D: Diphenylphosphoryl azide ("DPPA"; 2.4 mL, 11.1 mmol) was added to 1-(benzyloxycarbonyl)-3-methylpiperidine-3-carboxylic acid (2.5 g, 9.2 mmol) and TEA (1.5 mL, 11.1 mmol) in t-BuOH (17.7 mL, 184.6 mmol). The mixture was heated at reflux for 6 hours and then was transferred to a sealed tube and heated at 126° C. for 3 days. The solvent was removed, and then ether (50 mL) and saturated sodium bicarbonate (30 mL) were added. The organic layer was separated, washed with brine, dried over sodium sulfate. After removal of the solvent, the residue was purified by chromatography on silica gel (hexane:ethyl acetate, 5:1) to give benzyl 3-(tert-butoxycarbonylamino)-3-methylpiperidine-1-carboxylate (1.4 g, 43% yield) as a solid.

Step E: Benzyl 3-(tert-butoxycarbonylamino)-3-methylpiperidine-1-carboxylate (1.4 g, 4.0 mmol) and 10% Pd/C (0.21 g, 0.2 mmol) in MeOH (20 mL) were stirred under an $H_2$ atmosphere (1 atm) for 1 hour. The catalyst was removed by filtration and washed with methanol. The filtrate was concentrated to give tert-butyl 3-methylpiperidin-3-ylcarbamate (0.62 g, 72% yield) as a solid.

Step F: N-(5-Bromo-4-fluoro-1H-pyrrolo[2,3-b]pyridin-3-yl)-2-methoxyacetamide (100 mg, 0.331 mmol, Example 31, Step A) and tert-butyl 3-methylpiperidin-3-ylcarbamate (213 mg, 0.993 mmol) in n-BuOH (4 mL) were heated to 160° C. for 48 hours in a sealed tube. After concentration, the residue was purified by C-18 reverse phase flash chromatography (Biotage SP4 unit, C-18 25M column, 10-90% $CH_3CN$/water gradient; 30 CV) to yield N-(4-(3-amino-3-methylpiperidin-1-yl)-5-bromo-1H-pyrrolo[2,3-b]pyridin-3-yl)-2-methoxyacetamide (65 mg, 49% yield) as a solid and tert-butyl 1-(5-bromo-3-(2-methoxyacetamido)-1H-pyrrolo[2,3-b]pyridin-4-yl)-3-methylpiperidin-3-ylcarbamate (32 mg, 19% yield) as an oil.

Step G: N-(4-(3-Amino-3-methylpiperidin-1-yl)-5-bromo-1H-pyrrolo[2,3-b]pyridin-3-yl)-2-methoxyacetamide (65 mg, 0.16 mmol) was dissolved in a minimal amount of methanol and then added to a stirred solution of 4N HCl in dioxane. The resulting solid was filtered and dried under high vacuum to yield N-(4-(3-amino-3-methylpiperidin-1-yl)-5-bromo-1H-pyrrolo[2,3-b]pyridin-3-yl)-2-methoxyacetamide hydrochloride (36 mg, 55% yield) as a solid. $^1$H NMR (400 MHz, $(CD_3)_2SO$) δ 11.90 (d, 1H), 9.38 (s, 1H), 8.26 (s, 1H), 8.24 (br s, 2H), 6.30 (br s, 3H), 4.11 (q, 2H), 3.43 (s, 3H), 3.30-3.21 (m, 1H), 3.20-3.05 (m, 3H), 2.00-1.90 (m, 1H), 1.86-1.75 (m, 3H), 1.46 (s, 3H); LCMS (APCI+) m/z 379, 396 (M)+, Retention time=1.90 minutes (Method 1).

Example 35

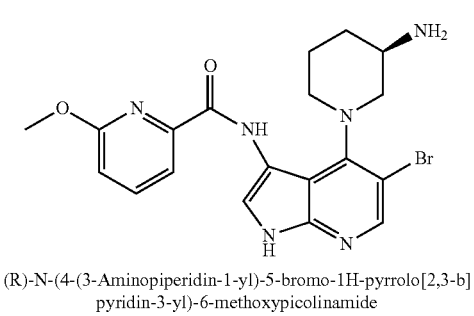 [SMILES: COc1cccc(C(=O)Nc2c[nH]c3ncc(Br)c(N4CCC[C@@H](N)C4)c23)n1]

(R)-N-(4-(3-Aminopiperidin-1-yl)-5-bromo-1H-pyrrolo[2,3-b]pyridin-3-yl)-6-methoxypicolinamide Step A: A solution of 5-bromo-4-fluoro-1H-pyrrolo[2,3-b]pyridin-3-amine (200 mg, 0.869 mmol, Example 1, Step H) in $CH_2Cl_2$ (10 mL) was treated with 6-methoxypicolinic acid (160 mg, 1.04 mmol), bis(2-oxooxazolidin-3-yl)phosphinic chloride (332 mg, 1.30 mmol) and triethylamine (440 mg, 4.35 mmol). The reaction was stirred at room temperature for 1 hour, and then 2M aqueous LiOH (3 mL) was added. The reaction was stirred for 1 hour, and then water was added (10 mL). The solid, which separated, was filtered and washed with $CH_2Cl_2$ (10 mL). The filtered cake was dried to yield N-(5-bromo-4-fluoro-1H-pyrrolo[2,3-b]pyridin-3-yl)-6-methoxypicolinamide (229 mg, 72% yield). $^1$H NMR (400 MHz, $(CD_3)_2SO$) δ 12.17 (s, 1H), 12.25 (s, 1H), 8.40 (d, 1H), 7.96 (dd, 1H), 7.92 (dd. 1H), 7.74 (dd, 1H), 7.11 (dd, 1H), 4.05 (s, 3H); LCMS (APCI+) m/z 365, 366.9 (M+H)+, Retention time=3.75 minutes (Method 2).

Step B: A solution of N-(5-bromo-4-fluoro-1H-pyrrolo[2,3-b]pyridin-3-yl)-6-methoxypicolinamide (228 mg, 0.624 mmol) in n-BuOH (5 mL) was treated with (R)-tert-butyl piperidin-3-ylcarbamate (375 mg, 1.87 mmol) and stirred at 160° C. for 48 hours in a sealed tube. The mixture was concentrated in vacuo, and the residue diluted with water (25 mL) and extracted with EtOAc (3×20 mL). The combined organic extracts were dried over anhydrous magnesium sulfate and filtered. The filtrate was concentrated in vacuo and purified by C-18 reverse phase flash chromatography (Biotage SP4 unit, C-18 25M column, 5-85% $CH_3CN$/water gradient; 25 CV) to provide (R)-tert-butyl 1-(5-bromo-3-(6-methoxypicolinamido)-1H-pyrrolo[2,3-b]pyridin-4-yl)piperidin-3-ylcarbamate (91.5 mg, 27% yield) as a solid. LCMS (APCI+) m/z 445.1, 447.1, 454.1 (M+H)+, Retention time=4.03 minutes (Method 2).

Step C: (R)-tert-Butyl 1-(5-bromo-3-(6-methoxypicolinamido)-1H-pyrrolo[2,3-b]pyridin-4-yl)piperidin-3-ylcarbamate (90 mg, 0.17 mmol) in TFA (3 mL) was stirred at room temperature for 45 minutes and then concentrated in vacuo. The residue was dissolved in minimal methanol, and 2N HCl in ether was added. The precipitate formed was filtered and dried under high vacuum to yield (R)—N-(4-(3-aminopiperidin-1-yl)-5-bromo-1H-pyrrolo[2,3-b]pyridin-3-yl)6-methoxypicolinamide hydrochloride (27 mg, 29% yield). $^1$H NMR (400 MHz, $(CD_3)_2SO$) δ 11.86 (s, 1H), 10.84 (br s, 1H), 8.34 (br s, 2H), 8.29 (s, 1H), 8.80 (d, 2H), 7.81 (d, 1H), 7.26 (d, 1H), 4.04 (s, 3H), 3.96-3.84 (m, 1H), 3.74-3.64 (m, 1H), 3.56-3.46 (m, 1H), 3.40-3.24 (m, 1H), 3.08-3.00 (m, 1H), 2.28-2.12 (m, 2H), 1.84-1.74 (m, 1H), 1.56-1.44 (m, 1H); LCMS (APCI+) m/z 428, 445, 447.0 (M+H)+, Retention time=2.61 minutes (Method 2).

Example 36

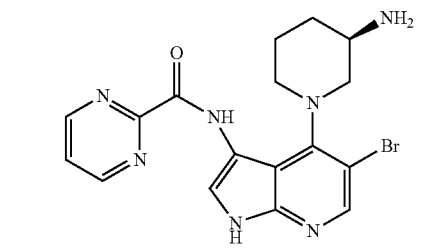

(R)-N-(4-(3-Aminopiperidin-1-yl)-5-bromo-1H-pyrrolo[2,3-b]pyridin-3-yl)pyrimidine-2-carboxamide Step A: A solution of 5-bromo-4-fluoro-1H-pyrrolo[2,3-b]pyridin-3-amine (200 mg, 0.869 mmol, Example 1, Step H) in $CH_2Cl_2$ (10 mL) was treated with pyrimidine-2-carboxylic acid (129 mg, 1.04 mmol), bis(2-oxooxazolidin-3-yl)phosphinic chloride (332 mg, 1.30 mmol) and triethylamine (440 mg, 4.35 mmol). The reaction was stirred at room temperature for 48 hour, and then water (10 mL) was added. The reaction was stirred for 1 hour. The solid which separated was filtered and washed with $CH_2Cl_2$ (10 mL). The filtered cake was dried to yield N-(5-bromo-4-fluoro-1H-pyrrolo[2,3-b]pyridin-3-yl)pyrimidine-2-carboxamide (110 mg, 38% yield). $^1$H NMR (400 MHz, $(CD_3)_2SO$) δ 12.21 (br s, 1H), 10.47 (s, 1H), 9.06 (d, 2H), 8.40 (d, 1H), 7.87 (d, 1H), 7.77 (t, 1H); LCMS (APCI+) m/z 335.9, 337.9 (M+H)+, Retention time=2.70 minutes (Method 2).

Step B: A solution of N-(5-bromo-4-fluoro-1H-pyrrolo[2,3-b]pyridin-3-yl)pyrimidine-2-carboxamide (110 mg, 0.328 mmol) in n-BuOH (5 mL) was treated with (R)-tert-butyl piperidin-3-ylcarbamate (197 mg, 0.982 mmol) and stirred at 160° C. for 48 hours in a sealed tube. The mixture was concentrated in vacuo, and the residue was diluted with water (25 mL) and extracted with EtOAc (3×20 mL). The combined organic extracts were dried over anhydrous magnesium sulfate and filtered. The filtrate was concentrated in vacuo, and the residue purified by C-18 reverse phase flash chromatography (Biotage SP4 unit, C-18 25M column, 5-85% $CH_3CN$/water gradient; 25 CV) to provide (R)-tert-butyl 1-(5-bromo-3-(pyrimidine-2-carboxamido)-1H-pyrrolo[2,3-b]pyridin-4-yl)piperidin-3-ylcarbamate (67.6 mg, 40% yield) as a solid. LCMS (APCI+) m/z 416, 418 (M+H)+, Retention time=3.40 minutes (Method 2).

Step C: (R)-tert-Butyl 1-(5-bromo-3-(pyrimidine-2-carboxamido)-1H-pyrrolo[2,3-b]pyridin-4-yl)piperidin-3-ylcarbamate (67 mg, 0.13 mmol) in TFA (3 mL) was stirred at room temperature for 45 minutes and concentrated in vacuo. The residue was dissolved in minimal methanol, and 2N HCl in ether was added. The precipitate formed was filtered and dried under high vacuum to yield (R)—N-(4-(3-aminopiperidin-1-yl)-5-bromo-1H-pyrrolo[2,3-b]pyridin-3-yl)pyrimidine-2-carboxamide hydrochloride salt (10 mg, 16% yield). $^1$H NMR (400 MHz, $(CD_3)_2SO$) δ 11.87 (s, 1H), 11.38 (br s, 1H), 9.14 (d, 2H), 8.32 (s, 1H), 8.23 (s, 3H), 8.18-8.16 (m, 1H), 7.87-7.81 (m, 1H), 3.96-3.84 (m, 1H), 3.74-3.64 (m, 1H), 3.60-3.50 (m, 1H), 3.40-3.32 (m, 1H), 3.08-3.00 (m, 1H), 2.42-2.32 (m, 1H), 2.18-2.04 (m, 1H), 1.62-1.48 (m, 1H); LCMS (APCI+) m/z 399, 416.0 (M+H)+, Retention time=2.25 minutes (Method 2).

Example 37

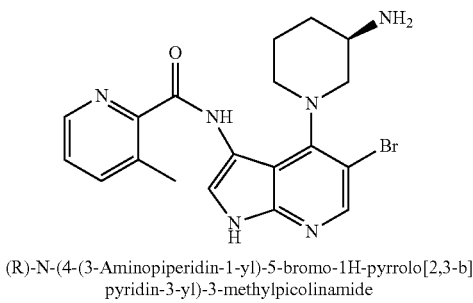 [SMILES: Cc1cccnc1C(=O)Nc1c[nH]c2ncc(Br)c(N3CCC[C@@H](N)C3)c12]

(R)-N-(4-(3-Aminopiperidin-1-yl)-5-bromo-1H-pyrrolo[2,3-b]pyridin-3-yl)-3-methylpicolinamide Step A: A solution of 5-bromo-4-fluoro-1H-pyrrolo[2,3-b]pyridin-3-amine (200 mg, 0.869 mmol, Example 1, Step H) in $CH_2Cl_2$ (10 mL) was treated with 3-methylpicolinic acid (143 mg, 1.04 mmol), bis(2-oxooxazolidin-3-yl)phosphinic chloride (332 mg, 1.30 mmol) and triethylamine (440 mg, 4.35 mmol). The reaction was stirred at room temperature for 1 hour. The mixture was filtered to remove the product, and the filtrate was concentrated in vacuo. The residue was stirred in anhydrous THF (10 mL), treated with 2M LiOH solution (3 mL) and stirred at room temperature for 1 hour. The organic solvent was removed in vacuo, and then water (10 mL) was added. The reaction stirred for 1 hour. The solid, which separated, was filtered and washed with water and $CH_2Cl_2$ (10 mL). The combined filtered cakes were dried to yield N-(5-bromo-4-fluoro-1H-pyrrolo[2,3-b]pyridin-3-yl)-3-methylpicolinamide (197 mg, 65% yield). $^1$H NMR (400 MHz, $(CD_3)_2SO$) δ 12.13 (br s, 1H), 10.42 (s, 1H), 8.56 (d, 1H), 8.39 (d, 1H), 7.87 (d, 1H), 7.84 (d, 1H), 7.55 (dd, 1H) 2.67 (s, 3H); LCMS (APCI+) m/z 349.1, 351 (M+H)+, Retention time=3.42 minutes (Method 3).

Step B: A solution of N-(5-bromo-4-fluoro-1H-pyrrolo[2,3-b]pyridin-3-yl)-3-methylpicolinamide (197 mg, 0.566 mmol) in n-BuOH (5 mL) was treated with (R)-tert-butyl piperidin-3-ylcarbamate (453 mg, 2.263 mmol) and stirred at 160° C. for 48 hours in a sealed tube. The mixture was concentrated in vacuo, and the residue diluted with water (25 mL) and extracted with EtOAc (3×20 mL). The combined organic extracts were dried over anhydrous magnesium sulfate and filtered. The filtrate concentrated in vacuo, and the residue was purified by C-18 reverse phase flash chromatography (Biotage SP4 unit, C-18 25M column, 5-85% $CH_3CN$/water gradient; 25 CV) to provide (R)-tert-butyl 1-(5-bromo-3-(3-methylpicolinamido)-1H-pyrrolo[2,3-b]pyridin-4-yl)piperidin-3-ylcarbamate (83.8 mg, 28% yield) as a solid. LCMS (APCI+) m/z 429.1, 431.1, 531.1 (M+H)+, Retention time=4.32 minutes (Method 2).

Step C: (R)-tert-Butyl 1-(5-bromo-3-(3-methylpicolinamido)-1H-pyrrolo[2,3-b]pyridin-4-yl)piperidin-3-ylcarbamate (83 mg, 0.16 mmol) in TFA (5 mL) was stirred at room temperature for 1.5 hours and concentrated in vacuo. The residue was purified by C-18 reverse phase flash chromatography (Biotage SP4 unit, C-18 12M column, 3-65% $CH_3CN$/water gradient; 14 CV). The residue was dissolved in minimal methanol, and 2N HCl in ether was added. The precipitate formed was filtered and dried under high vacuum to yield (R)—N-(4-(3-aminopiperidin-1-yl)-5-bromo-1H-pyrrolo[2,3-b]pyridin-3-yl)-3-methylpicolinamide hydrochloride (65.9 mg, 78% yield). $^1$H NMR (400 MHz, $(CD_3)_2SO$) δ 11.85 (s, 1H), 11.38 (br s, 1H), 8.69 (d, 1H), 8.38 (br s, 2H), 8.30 (s, 1H), 8.16 (d, 1H), 7.89 (d, 1H), 7.66-7.60 (m, 1H), 3.98-3.84 (m, 1H), 3.78-3.68 (m, 1H), 3.60-3.48 (m, 1H), 3.40-3.32 (m, 1H), 3.08-2.80 (m, 1H), 2.76 (s, 3H), 2.42-2.32 (m, 1H), 2.14-2.00 (m, 1H), 1.90-1.78 (m, 1H) 1.64-1.48 (m, 1H); LCMS (APCI+) m/z 412, 429 (M+H)+, Retention time=2.66 minutes (Method 2).

Example 38

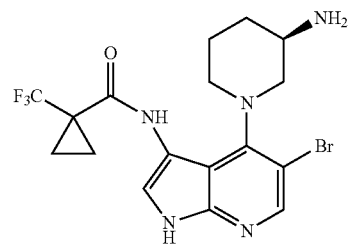

(R)-N-(4-(3-Aminopiperidin-1-yl)-5-bromo-1H-pyrrolo[2,3-b]pyridin-3-yl)-1-(trifluoromethyl)cyclopropanecarboxamide Step A: A solution of 5-bromo-4-fluoro-1H-pyrrolo[2,3-b]pyridin-3-amine (200 mg, 0.869 mmol, Example 1, Step H) in $CH_2Cl_2$ (10 mL) was treated with 1-(trifluoromethyl)cyclopropanecarboxylic acid (161 mg, 1.04 mmol), bis(2-oxooxazolidin-3-yl)phosphinic chloride (332 mg, 1.30 mmol) and triethylamine (440 mg, 4.35 mmol). The reaction was stirred at room temperature for 1 hour. The mixture was concentrated in vacuo. The residue was stirred in anhydrous THF (10 mL), treated with 2M LiOH solution (3 mL) and stirred at room temperature for 1 hour. The organic solvent was removed in vacuo, and then water (10 mL) was added. The reaction was stirred for 1 hour. The solid, which separated, was filtered and washed with water and CH₂Cl₂ (10 mL). The filtered cake was dried to yield N-(5-bromo-4-fluoro-1H-pyrrolo[2,3-b]pyridin-3-yl)-1-(trifluoromethyl)cyclopropanecarboxamide (229.5 mg, 72% yield). ¹H NMR (400 MHz, (CD₃)₂SO) δ 12.15 (br s, 1H), 9.38 (s, 1H), 8.36 (d, 1H), 7.51 (s, 1H), 1.49-1.43 (m, 2H), 1.38-1.33 (m, 2H); LCMS (APCI+) m/z 366, 368 (M+H)+, Retention time=3.32 minutes (Method 3).

Step B: A solution of N-(5-bromo-4-fluoro-1H-pyrrolo[2,3-b]pyridin-3-yl)-1-(trifluoromethyl)cyclopropanecarboxamide (229 mg, 0.627 mmol) in n-BuOH (5 mL) was treated with (R)-tert-butyl piperidin-3-ylcarbamate (505 mg, 2.507 mmol) and stirred at 160° C. for 48 hours in a sealed tube. The mixture was concentrated in vacuo, and the residue diluted with water (25 mL) and extracted with EtOAc (3×20 mL). The combined organic extracts were dried over anhydrous magnesium sulfate and filtered. The filtrate was concentrated in vacuo. The residue was purified by C-18 reverse phase flash chromatography (Biotage SP4 unit, C-18 25M column, 5-85% CH₃CN/water gradient; 25 CV) to provide (R)-tert-butyl 1-(5-bromo-3-(1-(trifluoromethyl)cyclopropanecarboxamido)-1H-pyrrolo[2,3-b]pyridin-4-yl)piperidin-3-ylcarbamate (65 mg, 19% yield) as a solid. LCMS (APCI+) m/z 429.1, 446.1, 492.1, 548.1 (M+H)+, Retention time=3.79 minutes (Method 3).

Step C: (R)-tert-Butyl 1-(5-bromo-3-(1-(trifluoromethyl)cyclopropanecarboxamido)-1H-pyrrolo[2,3-b]pyridin-4-yl)piperidin-3-ylcarbamate (65 mg, 0.12 mmol) in TFA (5 mL) was stirred at room temperature for 1.5 hours and concentrated in vacuo. The residue was purified by C-18 reverse phase flash chromatography (Biotage SP4 unit, C-18 12M column, 3-65% CH₃CN/water gradient; 14 CV). The residue obtained was dissolved in minimal methanol, and 2N HCl in ether was added. The precipitate formed was filtered and dried under high vacuum to yield (R)—N-(4-(3-aminopiperidin-1-yl)-5-bromo-1H-pyrrolo[2,3-b]pyridin-3-yl)-1-(trifluoromethyl)cyclopropanecarboxamide hydrochloride (58 mg, 94% yield). ¹H NMR (400 MHz, (CD₃)₂SO) δ 11.97 (br s, 1H), 9.32 (s, 1H), 8.39 (s, 2H), 8.27 (s, 1H), 7.63 (s, 1H), 3.50-3.22 (m, 4H), 3.15-3.04 (m, 1H), 2.20-2.10 (m, 1H), 1.90-1.78 (m, 1H), 1.76-1.46 (m, 4H), 1.36-1.44 (m, 2H); LCMS (APCI+) m/z 429.2, 446.1, 448.0 (M+H)+, Retention time=2.07 minutes (Method 3).

Example 39

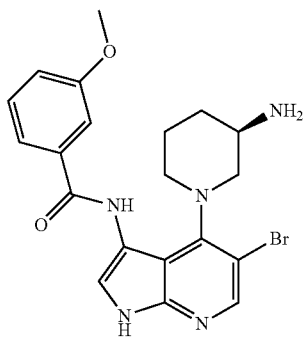

(R)-N-(4-(3-Aminopiperidin-1-yl)-5-bromo-1H-pyrrolo[2,3-b]pyridin-3-yl)-3-methoxybenzamide Step A: 5-Bromo-4-fluoro-1H-pyrrolo[2,3-b]pyridin-3-amine (250 mg, 1.09 mmol, Example 1, Step H), 3-methoxybenzoyl chloride (389 mg, 2.28 mmol), and triethylamine (757 μL, 5.43 mmol) were placed in DCM (5 mL) and stirred at room temperature for 30 minutes. 3M LiOH (3 mL) was added. The reaction was stirred for 10 minutes and then poured onto water. The mixture was then filtered and washed with DCM and water to provide solid N-(5-bromo-4-fluoro-1H-pyrrolo[2,3-b]pyridin-3-yl)-3-methoxybenzamide (219 mg, 55% yield).

Step B: N-(5-Bromo-4-fluoro-1H-pyrrolo[2,3-b]pyridin-3-yl)-3-methoxybenzamide (215 mg, 0.590 mmol) and (R)-tert-butyl piperidin-3-ylcarbamate (414 mg, 2.07 mmol) were placed in n-BuOH (5 mL) and heated to 155° C. for 72 hours. The reaction was then cooled to room temperature and concentrated to dryness. The crude residue was purified by C-18 reverse phase flash chromatography (Biotage Horizon unit, C-18 25M column, 5-90% CH₃CN/water gradient) to give (R)-tert-butyl 1-(5-bromo-3-(3-methoxybenzamido)-1H-pyrrolo[2,3-b]pyridin-4-yl)piperidin-3-ylcarbamate (238 mg, 74% yield).

Step C: (R)-tert-Butyl 1-(5-bromo-3-(3-methoxybenzamido)-1H-pyrrolo[2,3-b]pyridin-4-yl)piperidin-3-ylcarbamate (238 mg, 0.437 mmol) in TFA (2 mL) was stirred for 20 minutes at room temperature and was then concentrated. The residue was purified by C-18 reverse phase flash chromatography (Biotage Horizon unit, C-18 25M column, 0-50% CH₃CN/water with 0.1% TFA) to provide the TFA salt, which was redissolved in 10% MeOH in DCM (2 mL) and added dropwise to a stirred solution of 2M HCl in ether. The resulting precipitate was filtered and dried to provide (R)—N-(4-(3-aminopiperidin-1-yl)-5-bromo-1H-pyrrolo[2,3-b]pyridin-3-yl)-3-methoxybenzamide hydrochloride (96 mg, 42% yield). ¹H NMR (400 MHz, D₂O) δ 8.20 (s, 1H), 7.41 (d, 2H), 7.39 (s, 1H), 7.34 (s, 1H), 7.15 (m, 1H), 3.75 (s, 3H), 3.48 (d, 1H), 3.30-3.05 (m, 4H), 1.78 (m, 1H), 1.62 (m, 1H), 1.46-1.28 (m, 2H); LCMS (APCI+) m/z 447.1 (M+H)+, Retention time=2.36 minutes (Method 2).

Example 40

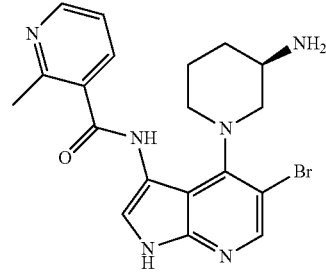

(R)-N-(4-(3-Aminopiperidin-1-yl)-5-bromo-1H-pyrrolo[2,3-b]pyridin-3-yl)-2-methylnicotinamide Step A: 5-Bromo-4-fluoro-1H-pyrrolo[2,3-b]pyridin-3-amine (200 mg, 0.869 mmol, Example 1, Step H), 2-methylnicotinic acid (250 mg, 1.83 mmol), bis(2-oxooxazolidin-3-yl)phosphinic chloride (465 mg, 1.83 mmol), and triethylamine (0.606 mL, 4.35 mmol) were placed in DCM (5 mL) and stirred at room temperature for 90 minutes. 3M LiOH (5 mL) was added. The reaction was stirred for 20 minutes and then was poured onto water. The mixture was then filtered and washed with water and DCM. The filtered solid was dried to give N-(5-bromo-4-fluoro-1H-pyrrolo[2,3-b]pyridin-3-yl)-2-methylnicotinamide (254 mg, 84% yield).

Step B: (R)-tert-Butyl 1-(5-bromo-3-(2-methylnicotinamido)-1H-pyrrolo[2,3-b]pyridin-4-yl)piperidin-3-ylcarbamate (190 mg, 49.3% yield) was prepared according to Example 39, Step B, from N-(5-bromo-4-fluoro-1H-pyrrolo[2,3-b]pyridin-3-yl)-2-methylnicotinamide (254 mg, 0.727 mmol). The reaction was heated for 48 hours instead of 72 hours.

Step C: 4N HCl in dioxane (3 mL) was added to (R)-tert-butyl 1-(5-bromo-3-(2-methylnicotinamido)-1H-pyrrolo[2,3-b]pyridin-4-yl)piperidin-3-ylcarbamate (190 mg, 0.359 mmol) in DCM (3 mL), and the reaction stirred at room temperature for 30 minutes. After concentration, the residue was purified by C-18 reverse phase flash chromatography (Biotage Horizon unit, C-18 25M column, 5-90% CH₃CN/water gradient). The compound was purified again by C-18 reverse phase flash chromatography (Biotage Horizon unit, C-18 25M column, 5-80% CH₃CN/water gradient). The compound was then purified again by C-18 reverse phase flash chromatography (Biotage Horizon unit, C-18 25M column, 0-50% CH₃CN/water with 0.1% TFA) to provide the TFA salt, which was redissolved in 10% MeOH in DCM and added dropwise to a stirred 2N HCl in ether solution. The resulting precipitate was filtered and dried to provide (R)—N-(4-(3-aminopiperidin-1-yl)-5-bromo-1H-pyrrolo[2,3-b]pyridin-3-yl)-2-methylnicotinamide hydrochloride (52.1 mg, 26% yield). $^1$H NMR (400 MHz, D$_2$O) δ 8.66 (dd, 1H), 8.60 (dd, 1H), 8.24 (s, 1H), 7.86 (m, 1H), 7.25 (s, 1H), 3.59 (d, 1H), 3.41 (m, 1H), 3.30-3.15 (m, 3H), 2.76 (s, 3H), 1.92 (m, 1H), 1.77 (m, 1H), 1.47 (m, 2H); LCMS (APCI+) m/z 431.1 (M+H)+, Retention time=2.18 minutes (Method 2).

Example 41

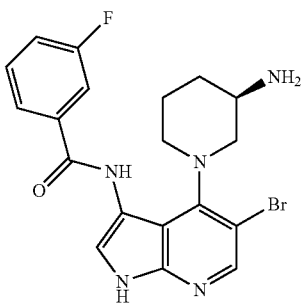

(R)-N-(4-(3-Aminopiperidin-1-yl)-5-bromo-1H-pyrrolo[2,3-b]pyridin-3-yl)-3-fluorobenzamide Step A: 5-Bromo-4-fluoro-1H-pyrrolo[2,3-b]pyridin-3-amine (200 mg, 0.869 mmol, Example 1, Step H), 3-fluorobenzoic acid (256 mg, 1.83 mmol), bis(2-oxooxazolidin-3-yl)phosphinic chloride (465 mg, 1.83 mmol), and triethylamine (0.606 mL, 4.35 mmol) were placed in DCM (5 mL) and stirred at room temperature for 30 minutes. 3M LiOH (3 mL) was then added. The reaction was stirred for 10 minutes and then poured into water. The aqueous layer was extracted several times with DCM, and the combined organic phases were dried, filtered, and concentrated to give N-(5-bromo-4-fluoro-1H-pyrrolo[2,3-b]pyridin-3-yl)-3-fluorobenzamide.

Step B: N-(5-Bromo-4-fluoro-1H-pyrrolo[2,3-b]pyridin-3-yl)-3-fluorobenzamide (306 mg, 0.869 mmol) and (R)-tert-butyl piperidin-3-ylcarbamate (522 mg, 2.61 mmol) were placed in n-BuOH (5 mL) and heated to 155° C. for 42 hours in a sealed tube. The reaction was cooled to room temperature and concentrated to dryness. The crude residue was purified by C-18 reverse phase flash chromatography (Biotage Horizon unit, C-18 25M column, 5-80% CH₃CN/water gradient) to give (R)-tert-butyl 1-(5-bromo-3-(3-fluorobenzamido)-1H-pyrrolo[2,3-b]pyridin-4-yl)piperidin-3-ylcarbamate (125 mg, 27% yield).

Step C: (R)—N-(4-(3-Aminopiperidin-1-yl)-5-bromo-1H-pyrrolo[2,3-b]pyridin-3-yl)-3-fluorobenzamide hydrochloride (41.2 mg, 35% yield) was prepared according Example 39, Step C, from (R)-tert-butyl 1-(5-bromo-3-(3-fluorobenzamido)-1H-pyrrolo[2,3-b]pyridin-4-yl)piperidin-3-ylcarbamate (125 mg, 0.235 mmol). $^1$H NMR (400 MHz, D$_2$O) δ 8.27 (s, 1H), 7.65 (d, 1H), 7.56 (d, 1H), 7.49 (m, 1H), 7.39 (s, 1H), 7.31 (t, 1H), 3.70 (d, 1H), 3.41 (m, 1H), 3.32 (d, 1H), 3.21-3.07 (m, 2H), 1.86 (m, 1H), 1.64 (m, 1H), 1.51 (m, 1H), 1.35 (m, 1H); LCMS (APCI+) m/z 432.0 (M+H)+, Retention time=2.34 minutes (Method 2).

Example 42

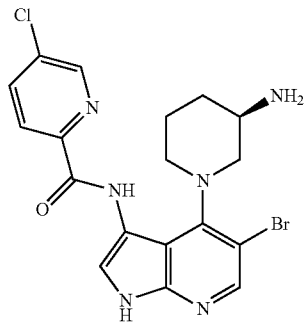

(R)-N-(4-(3-Aminopiperidin-1-yl)-5-bromo-1H-pyrrolo[2,3-b]pyridin-3-yl)-5-chloropicolinamide Step A: TEA (0.61 mL, 4.35 mmol) was added to 5-bromo-4-fluoro-1H-pyrrolo[2,3-b]pyridin-3-amine (200 mg, 0.87 mmol, Example 1, Step H), 5-chloropicolinic acid (160 mg, 1.04 mmol) and BOP-Cl (332 mg, 1.30 mmol) in DCM (5 mL). The reaction was stirred at room temperature for 1 hour, and then a LiOH solution (2 N, 3 mL) was added. The mixture was stirred for 30 minutes, and water (10 mL) was added. The solid formed was collected by filtration, washed with DCM (10 mL) and dried to give N-(5-bromo-4-fluoro-1H-pyrrolo[2,3-b]pyridin-3-yl)-5-chloropicolinamide (240 mg, 73% yield) as a solid.

Step B: N-(5-Bromo-4-fluoro-1H-pyrrolo[2,3-b]pyridin-3-yl)-5-chloropicolinamide (240 mg, 0.64 mmol), (R)-tert-butyl piperidin-3-ylcarbamate (380 mg, 1.91 mmol) and DIEA (0.17 mL, 0.95 mmol) in n-BuOH (2 mL) were stirred at 148° C. (bath) for 40 hours. The solvent was removed, and the residue was dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 30-75% CH₃CN/water gradient; 30 CV) to give a solid. This solid was dissolved in DCM (3 mL) and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)-5-chloropicolinamide hydrochloride (50 mg, 14% yield) as a solid. $^1$H NMR (400 MHz, D$_2$O) δ 8.24 (s, 1H), 8.08 (s, 1H), 7.63 (m, 1H), 7.55-7.58 (m, 2H), 3.59 (m, 1H), 3.42 (m, 1H), 3.35 (m, 1H), 3.27 (m, 1H), 2.77 (m, 1H), 2.11 (m, 1H), 1.87 (m, 1H), 1.68 (m, 1H), 1.40-1.48 (m, 1H); LCMS (APCI+) m/z 451 (M+H)+.

Example 43

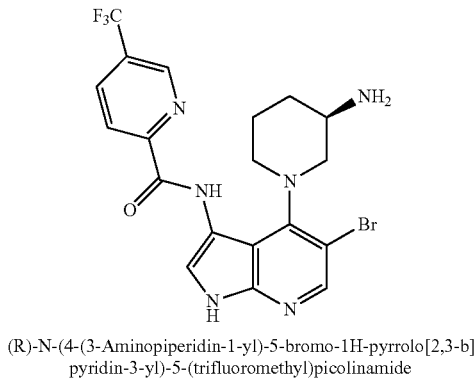 [SMILES: N[C@@H]1CCCN(c2c(Br)cnc3[nH]cc(NC(=O)c4ccc(C(F)(F)F)cn4)c23)C1]

(R)-N-(4-(3-Aminopiperidin-1-yl)-5-bromo-1H-pyrrolo[2,3-b]pyridin-3-yl)-5-(trifluoromethyl)picolinamide Step A: TEA (0.61 mL, 4.35 mmol) was added to 5-bromo-4-fluoro-1H-pyrrolo[2,3-b]pyridin-3-amine (200 mg, 0.87 mmol, Example 1, Step H), 5-(trifluoromethyl)picolinic acid (200 mg, 1.04 mmol) and BOP-Cl (330 mg, 1.30 mmol) in DCM (5 mL). The reaction was stirred at room temperature for 1 hour, and then a LiOH solution (3 mL, 2N) was added. The mixture was stirred for 30 minutes, and water (10 mL) was added. The solid formed was collected by filtration, washed with DCM (10 mL) and dried to give N-(5-bromo-4-fluoro-1H-pyrrolo[2,3-b]pyridin-3-yl)-5-(trifluoromethyl)picolinamide (195 mg, 55% yield) as a solid.

Step B: N-(5-Bromo-4-fluoro-1H-pyrrolo[2,3-b]pyridin-3-yl)-5-(trifluoromethyl)picolinamide (195 mg, 0.48 mmol), (R)-tert-butyl piperidin-3-ylcarbamate (290 mg, 1.45 mmol) and DIEA (0.17 mL, 0.97 mmol) in N-methylpyrrolidone ("NMP"; 2 mL) were stirred at 148° C. (bath) for 18 hours and at 160° C. for 5 hours. Ethyl acetate (20 mL) was added, and the mixture was washed with water (10 mL), brine (10 mL) and dried over sodium sulfate. After removal of the solvent, the residue was purified by C-18 reverse phase flash chromatography (Biotage SP4 unit, C-18 25M column, 45-85% CH$_3$CN/water gradient; 30 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)-5-(trifluoromethyl)picolinamide (24 mg, 8% yield) as a solid. $^1$H NMR (400 MHz, D$_2$O) δ 8.77 (s, 1H), 8.15 (s, 1H), 8.11 (d, 1H), 7.95 (d, 1H), 7.82 (s, 1H), 3.74 (m, 1H), 3.59 (m, 1H), 3.48 (m, 1H), 3.32 (m, 1H), 2.88 (m, 1H), 2.22 (m, 1H), 2.03 (m, 1H), 1.79 (m, 1H), 1.53 (m, 1H); LCMS (APCI+) m/z 483 (M+H)+.

Example 44

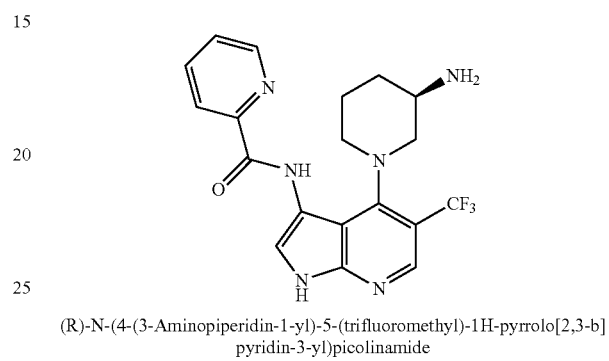

(R)-N-(4-(3-Aminopiperidin-1-yl)-5-(trifluoromethyl)-1H-pyrrolo[2,3-b]pyridin-3-yl)picolinamide Step A: Picolinoyl chloride hydrochloride (270 mg, 1.53 mmol) was added to 4-chloro-5-(trifluoromethyl)-1H-pyrrolo[2,3-b]pyridin-3-amine (240 mg, 1.02 mmol, Example 11, step G) in pyridine (5 mL). The reaction was stirred at 0° C. for 10 minutes, and then the pyridine was removed. THF (5 mL) and 2N LiOH (3 mL) were added and stirred for 20 minutes. The THF was removed, and water (20 mL) was added. The solid formed was collected by filtration and dried to give N-(4-chloro-5-(trifluoromethyl)-1H-pyrrolo[2,3-b]pyridin-3-yl)picolinamide (280 mg, 79% yield) as a solid.

Step B: N-(4-Chloro-5-(trifluoromethyl)-1H-pyrrolo[2,3-b]pyridin-3-yl)picolinamide (280 mg, 0.81 mmol), (R)-tert-butyl piperidin-3-ylcarbamate (490 mg, 2.42 mmol) and DIEA (0.28 mL, 1.61 mmol) in NMP (2 mL) were stirred at 156° C. (bath) for 10 hours. Ethyl acetate (20 mL) was added, the organic layer was washed with water (10 mL), brine (10 mL) and dried over sodium sulfate. After removal of the solvent, the residue was purified by C-18 reverse phase flash chromatography (Biotage SP4 unit, C-18 25M column, 40-80% CH$_3$CN/water gradient; 30 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-(trifluoromethyl)-1H-pyrrolo[2,3-b]pyridin-3-yl)picolinamide hydrochloride (195 mg, 47% yield) as a solid. $^1$H NMR (400 MHz, D$_2$O) δ 8.40 (m, 1H), 8.37 (s, 1H), 7.86 (s, 1H), 7.81 (m, 2H), 7.44 (m, 1H), 3.68 (m, 1H), 3.36 (m, 1H), 2.99 (m, 1H), 2.93 (m, 1H), 2.53 (m, 1H), 2.05 (m, 1H), 1.87 (m, 1H), 1.66 (m, 1H), 1.42 (m, 1H); LCMS (APCI+) m/z 405 (M+H)+.

Example 45

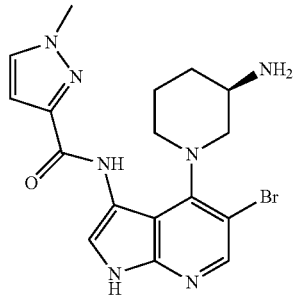

(R)-N-(4-(3-Aminopiperidin-1-yl)-5-bromo-1H-pyrrolo[2,3-b]pyridin-3-yl)-1-methyl-1H-pyrazole-3-carboxamide Step A: TEA (1.21 mL, 8.69 mmol) was added to 5-bromo-4-fluoro-1H-pyrrolo[2,3-b]pyridin-3-amine (400 mg, 1.74 mmol, Example 1, Step H), 1-methyl-1H-pyrazole-3-carboxylic acid (260 mg, 2.09 mmol) and BOP-Cl (60 mg, 2.61 mmol) in DCM (5 mL). The reaction was stirred at room temperature for 1 hour, and then a LiOH solution (3 mL, 2N) was added. The mixture was stirred for 30 minutes, and water (10 mL) was added. The solid formed was collected by filtration, washed with DCM (5 mL) and dried to give N-(5-bromo-4-fluoro-1H-pyrrolo[2,3-b]pyridin-3-yl)-1-methyl-1H-pyrazole-3-carboxamide (30 mg, 66% yield) as a solid.

Step B: N-(5-Bromo-4-fluoro-1H-pyrrolo[2,3-b]pyridin-3-yl)-1-methyl-1H-pyrazole-3-carboxamide (0.190 g, 0.56 mmol), (R)-tert-butyl piperidin-3-ylcarbamate (0.34 g, 1.69 mmol) and DIEA (0.2 mL, 1.12 mmol) in NMP (2 mL) were stirred at 156° C. (bath) for 24 hours. The solvent was removed, and the residue dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 30-70% CH$_3$CN/water gradient; 30 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)-1-methyl-1H-pyrazole-3-carboxamide hydrochloride (0.0096 g, 3% yield) as a solid. $^1$H NMR (400 MHz, D$_2$O) δ 8.22 (s, 1H), 7.73 (s, 1H), 7.60 (d, 1H), 6.70 (d, 1H), 3.86 (s, 3H), 3.70 (m, 1H), 3.52 (m, 1H), 3.40 (m, 2H), 2.98 (m, 1H), 2.12 (m, 1H), 1.94 (m, 1H), 1.76 (m, 1H), 1.48-1.54 (m, 1H); LCMS (APCI+) m/z 418 (M+H)+.

Example 46

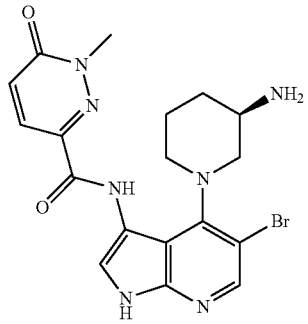

(R)-N-(4-(3-Aminopiperidin-1-yl)-5-bromo-1H-pyrrolo[2,3-b]pyridin-3-yl)-1-methyl-6-oxo-1,6-dihydropyridazine-3-carboxamide Step A: TEA (0.61 mL, 4.35 mmol) was added to 5-bromo-4-fluoro-1H-pyrrolo[2,3-b]pyridin-3-amine (0.20 g, 0.87 mmol, Example 1, Step H), 1-methyl-6-oxo-1,6-dihydropyridazine-3-carboxylic acid (0.16 g, 1.04 mmol) and BOP-Cl (0.29 g, 1.13 mmol) in DCM (5 mL). The reaction was stirred at room temperature for 1 hour, and then a LiOH solution (3 mL, 2N) was added. The mixture was stirred for 30 minutes, and water (10 mL) was added. The solid formed was collected by filtration, washed with DCM (5 mL) and dried to give N-(5-bromo-4-fluoro-1H-pyrrolo[2,3-b]pyridin-3-yl)-1-methyl-6-oxo-1,6-dihydropyridazine-3-carboxamide (0.223 g, 70% yield) as a solid.

Step B: N-(5-Bromo-4-fluoro-1H-pyrrolo[2,3-b]pyridin-3-yl)-1-methyl-6-oxo-1,6-dihydropyridazine-3-carboxamide (0.223 g, 0.61 mmol), (R)-tert-butyl piperidin-3-ylcarbamate (0.366 g, 1.83 mmol) and DIEA (0.21 mL, 1.22 mmol) in NMP (2 mL) were stirred at 156° C. (bath) for 18 hours. The solvent was removed, and the residue was dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 30-70% CH$_3$CN/water gradient; 30 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give (R)—N-(4-(3-aminopiperidin-1-yl)-5-bromo-1H-pyrrolo[2,3-b]pyridin-3-yl)-1-methyl-6-oxo-1,6-dihydropyridazine-3-carboxamide hydrochloride (0.022 g, 6% yield) as a solid. $^1$H NMR (400 MHz, D$_2$O) δ 8.20 (s, 1H), 7.87 (d, 1H), 7.56 (s, 1H), 7.01 (d, 1H), 3.74 (s, 3H), 3.54 (m, 1H), 3.41 (m, 1H), 3.36 (m, 2H), 3.15 (m, 1H), 2.01 (m, 1H), 1.75 (m, 1H), 1.67 (m, 1H), 1.41-1.49 (m, 1H); LCMS (APCI+) m/z 446 (M+H)+.

Example 47

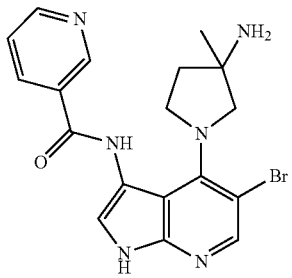

N-(4-(3-Amino-3-methylpyrrolidin-1-yl)-5-bromo-1H-pyrrolo[2,3-b]pyridin-3-yl)nicotinamide Step A: Benzyl carbonochloridate (3.57 mL, 25.36 mmol) at 0° C. was added to methylpyrrolidine-3-carboxylate hydrochloride (4.00 g, 24.15 mmol) and $K_2CO_3$ (6.68 g, 48.3 mmol) in THF:water (100 mL, 1:1). The reaction mixture was stirred at room temperature for 2 hours. Ether (50 mL) was added. The organic layer was separated, washed with brine and dried over sodium sulfate. After removal of the solvent, the residue was purified by chromatography (hexane:ethyl acetate, 3:1) to give 1-benzyl 3-methylpyrrolidine-1,3-dicarboxylate (3.45 g, 54% yield) as an oil.

Step B: Lithium bis(trimethylsilyl)amide (16.4 mL, 16.4 mmol) was added to 1-benzyl 3-methylpyrrolidine-1,3-dicarboxylate (3.45 g, 13.1 mmol) in THF (20 mL) at −78° C., and the reaction was stirred at −78° C. for 20 minutes. MeI (1.10 mL, 17.7 mmol) was added, and the reaction was warmed to room temperature. After 2 hours at room temperature, the mixture was poured onto saturated ammonium chloride (20 mL), extracted with ether, washed with brine and dried over sodium sulfate. After removal of the solvent, the residue was purified by chromatography (hexane:ethyl acetate, 4:1) to give 1-benzyl 3-methyl 3-methylpyrrolidine-1,3-dicarboxylate (2.72 g, 75% yield) as an oil.

Step C: 1-Benzyl 3-methyl 3-methylpyrrolidine-1,3-dicarboxylate (2.72 g, 9.81 mmol) in ethanol (15 mL) was added to a 3M LiOH solution (14.7 mL, 29.4 mmol), and the reaction mixture was stirred at 78° C. (bath) for 1 hour. The ethanol was removed and, ether (30 mL) was added. The aqueous layer was separated and acidified with saturated potassium hydrogen sulfate to a pH of about 3 to about 4, extracted with ethyl acetate (50 mL), washed with brine and dried over sodium sulfate. After removal of the solvent, 1-(benzyloxycarbonyl)-3-methylpyrrolidine-3-carboxylic acid (2.56 g, 99% yield) was isolated as an oil.

Step D: DPPA (2.52 mL, 11.67 mmol) was added to 1-(benzyloxycarbonyl)-3-methylpyrrolidine-3-carboxylic acid (2.56 g, 9.72 mmol) and TEA (1.63 mL, 11.7 mmol) in t-BuOH (27.9 mL, 291.7 mmol). The mixture was heated at reflux for 1 hour, and then was transferred to a sealed tube and heated at 100° C. (bath) for 24 hours. The solvent was removed, and ether (50 mL) and saturated sodium bicarbonate (30 mL) were added. The organic layer was separated, washed with brine and dried over sodium sulfate. After removal of the solvent, the residue was purified by chromatography (hexane:ethyl acetate, 5:1) to give benzyl 3-(tert-butoxycarbonylamino)-3-methylpyrrolidine-1-carboxylate (2.0 g, 61% yield) as an oil.

Step E: Benzyl 3-(tert-butoxycarbonylamino)-3-methylpyrrolidine-1-carboxylate (2.00 g, 5.98 mmol) and 10% Pd/C (0.32 g, 0.30 mmol) in MeOH (20 mL) were stirred under 1 atmosphere of $H_2$ for 1 hour. The catalyst was removed by filtration and washed with methanol. The filtrate was concentrated to give tert-butyl 3-methylpyrrolidin-3-ylcarbamate (1.15 g, 96%) as a solid.

Step F: N-(5-Bromo-4-fluoro-1H-pyrrolo[2,3-b]pyridin-3-yl)nicotinamide (0.085 g, 0.254 mmol, Example 1, Step I), tert-butyl 3-methylpyrrolidin-3-ylcarbamate (0.152 g, 0.76 mmol) and DIEA (0.08 mL, 0.5 mmol) in n-BuOH (2 mL) were stirred at 156° C. (bath) for 6 hours. The solvent was removed, and the residue dissolved in ethyl acetate (20 mL), washed with water (10 mL), brine (10 mL) and dried over sodium sulfate. After removal of the solvent, the residue was purified by C-18 reverse phase flash chromatography (Biotage SP4 unit, C-18 25M column, 10-80% $CH_3CN$/water gradient; 25 CV) to give a solid. This solid was dissolved in DCM (3 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected by filtration to give N-(4-(3-amino-3-methylpyrrolidin-1-yl)-5-bromo-1H-pyrrolo[2,3-b]pyridin-3-yl)nicotinamide hydrochloride (0.072 g, 54% yield) as a solid. $^1$H NMR (400 MHz, $D_2O$) δ 9.16 (s, 1H), 8.84 (d, 1H), 8.78 (d, 1H), 8.22 (s, 1H), 7.98 (m, 1H), 7.40 (s, 1H), 3.80-3.94 (m, 3H), 3.62 (m, 1H), 2.04 (m, 1H), 1.85 (m, 1H), 1.23 (s, 3H); LCMS (APCI+) m/z 415 (M+H)+.

Example 48

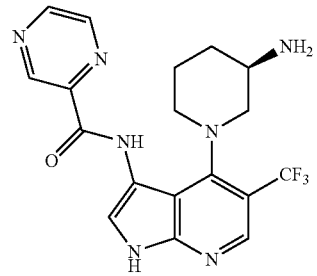

(R)-N-(4-(3-Aminopiperidin-1-yl)-5-bromo-1H-pyrrolo[2,3-b]pyridin-3-yl)quinoxaline-2-carboxamide Step A: 4-Chloro-5-(trifluoromethyl)-1H-pyrrolo[2,3-b]pyridin-3-amine (0.200 g, 0.849 mmol, Example 11, Step G) and pyrazine-2-carboxylic acid (0.221 g, 1.78 mmol) were placed in DCM (5 mL) at room temperature. BOP-Cl (0.454 g, 1.78 mmol) was then added, followed by the addition of triethylamine (0.592 mL, 4.24 mmol). The reaction was stirred for 1 hour. 3M aqueous LiOH (3 mL) was then added, and the reaction was stirred for 10 minutes. Water (10 mL) and DCM (10 mL) were then added, and the reaction was filtered. The resulting solid was slurried with 10:1 DCM:MeOH and filtered to give solid N-(4-chloro-5-(trifluoromethyl)-1H-pyrrolo[2,3-b]pyridin-3-yl)pyrazine-2-carboxamide (0.23 g, 79% yield).

Step B: N-(4-Chloro-5-(trifluoromethyl)-1H-pyrrolo[2,3-b]pyridin-3-yl)pyrazine-2-carboxamide (0.230 g, 0.673 mmol) and (R)-tert-butyl piperidin-3-ylcarbamate (0.404 g, 2.02 mmol) were placed in n-BuOH (3 mL) and heated to 155° C. for 18 hours in a sealed tube. The reaction was then cooled to room temperature and concentrated to dryness. The resulting residue was purified by C-18 reverse phase flash chromatography (Biotage SP4 unit, C-18 25M column, 5-75% $CH_3CN$/water gradient; 25 CV) to give (R)-tert-butyl 1-(3-(pyrazine-2-carboxamido)-5-(trifluoromethyl)-1H-pyrrolo[2,3-b]pyridin-4-yl)piperidin-3-ylcarbamate (0.120 g, 35% yield).

Step C: (R)-tert-Butyl 1-(3-(pyrazine-2-carboxamido)-5-(trifluoromethyl)-1H-pyrrolo[2,3-b]pyridin-4-yl)piperidin-3-ylcarbamate (0.120 g, 0.237 mmol) was placed in DCM (3 mL) at room temperature. TFA (1 mL) was then added, and the reaction was stirred at room temperature for 1 hour. The reaction was then concentrated to dryness to give the crude product, which was purified C-18 reverse phase flash chromatography (Biotage SP4 unit, C-18 25M column, 0-50% $CH_3CN$/water gradient; 25 CV). The purified product was then dissolved in DCM (with minimal MeOH to aid solubility) and added dropwise to a stirring solution of 1M HCl in ether. The resulting solid was filtered, dried and collected to give (R)—N-(4-(3-aminopiperidin-1-yl)-5-(trifluoromethyl)-1H-pyrrolo[2,3-b]pyridin-3-yl)pyrazine-2-carboxamide hydrochloride (0.071 g, 62% yield). $^1$H NMR (400 MHz, $D_2O$) δ 8.84 (s, 1H), 8.59-8.59 (m, 1H), 8.52-8.52 (m, 1H), 8.31 (s, 1H), 7.79 (s, 1H), 3.62-3.54 (m, 1H), 3.37-3.33 (m, 1H), 3.00-2.92 (m, 3H), 2.04-2.01 (m, 1H), 1.85-1.72 (m, 1H), 1.71-1.66 (m, 1H), 1.50-1.40 (m, 1H); LCMS (APCI+) m/z 406 (M+H)+.

Example 49

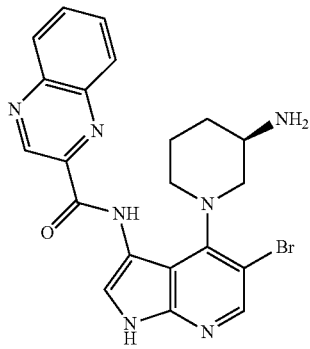

(R)-N-(4-(3-Aminopiperidin-1-yl)-5-bromo-1H-pyrrolo[2,3-b]pyridin-3-yl)quinoxaline-2-carboxamide Step A: 5-Bromo-4-fluoro-1H-pyrrolo[2,3-b]pyridin-3-amine (0.160 g, 0.696 mmol, Example 1, Step H), quinoxaline-2-carboxylic acid (0.254 g, 1.46 mmol), BOP-Cl (0.372 g; 1.46 mmol), and triethylamine (0.352 g, 3.48 mmol) were placed in DCM (5 mL) at room temperature and stirred for 15 hours. 3M aqueous LiOH (3 mL) was then added, and the reaction was stirred for 10 minutes. Water (10 mL) and DCM (10 mL) were then added, and the reaction was filtered. The resulting solid was slurried with 10:1 DCM:MeOH and filtered to give solid N-(5-bromo-4-fluoro-1H-pyrrolo[2,3-b]pyridin-3-yl)quinoxaline-2-carboxamide (0.240 g, 89% yield).

Step B: N-(5-Bromo-4-fluoro-1H-pyrrolo[2,3-b]pyridin-3-yl)quinoxaline-2-carboxamide (0.240 g, 0.621 mmol) and (R)-tert-butyl piperidin-3-ylcarbamate (0.373 g, 1.86 mmol) were placed in n-BuOH (3 mL) and heated to 155° C. for 48 hours in a sealed tube. The reaction was then cooled to room temperature and concentrated to dryness. The resulting residue was purified by reverse phase HPLC (5:75 water:ACN gradient, Gilson system) to give (R)-tert-butyl 1-(5-bromo-3-(quinoxaline-2-carboxamido)-1H-pyrrolo[2,3-b]pyridin-4-yl)piperidin-3-ylcarbamate (0.040 g, 11% yield).

Step C: (R)-tert-Butyl 1-(5-bromo-3-(quinoxaline-2-carboxamido)-1H-pyrrolo[2,3-b]pyridin-4-yl)piperidin-3-ylcarbamate (0.040 g, 0.071 mmol) was placed in DCM (3 mL) at room temperature. TFA (1 mL) was then added. The reaction was stirred at room temperature for 1 hour and concentrated to dryness to give the crude product, which was purified by reverse phase HPLC (0-50% ACN in water, Gilson system). The purified product was then dissolved in DCM (with minimal MeOH to aid solubility) and added dropwise to a stirring solution of 1M HCl in ether. The resulting solid was filtered, dried and collected to give (R)—N-(4-(3-aminopiperidin-1-yl)-5-bromo-1H-pyrrolo[2,3-b]pyridin-3-yl)quinoxaline-2-carboxamide hydrochloride (0.007 g, 18% yield). LCMS (APCI+) m/z 466, 468 (M)+ (Method 2).

Example 50

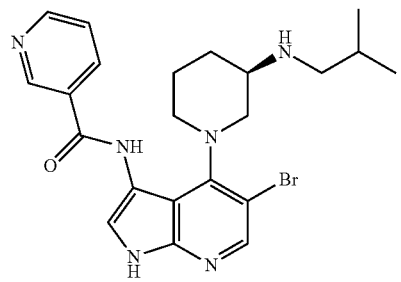

(R)-N-(5-Bromo-4-(3-(isobutylamino)piperidin-1-yl)-1H-pyrrolo[2,3-b]pyridin-3-yl)nicotinamide (R)—N-(4-(3-Aminopiperidin-1-yl)-5-bromo-1H-pyrrolo[2,3-b]pyridin-3-yl)nicotinamide hydrochloride (0.075 g, 0.14 mmol, Example 1A), DIEA (0.100 mL, 0.57 mmol; d 0.742) and trimethyl orthoformate (0.32 mL, 2.9 mmol) were placed in MeOH (3 mL) at room temperature. Isobutyraldehyde (0.026 mL, 0.29 mmol) was then added, and the reaction was stirred at room temperature for 18 hours. $NaBH_4$ (0.014 g, 0.36 mmol) was then added, and the reaction was stirred for 1 hour. The reaction was then poured into water, and extracted with DCM. The combined organic fractions were dried ($MgSO_4$), filtered, and concentrated to give the crude product, which was purified by reverse phase HPLC (0-50% acetonitrile ("ACN") in water, Gilson system). The purified product was then dissolved in DCM (with minimal MeOH to aid solubility) and added dropwise to a stirring solution of 1M HCl in ether. The resulting solid was filtered, dried and collected to give (R)—N-(5-bromo-4-(3-(isobutylamino)piperidin-1-yl)-1H-pyrrolo[2,3-b]pyridin-3-yl)nicotinamide hydrochloride (0.050 g, 60% yield). $^1$H NMR (400 MHz, $D_2O$) δ 9.16-9.16 (m, 1H), 8.83-8.82 (m, 1H), 8.77-8.75 (m, 1H), 8.27 (s, 1H), 7.96-7.93 (m, 1H), 7.42 (s, 1H), 3.78-3.75 (m, 1H), 3.34-3.33 (m, 2H), 3.22-3.17 (m, 1H), 3.09-3.03 (m, 1H), 2.77-2.67 (m, 2H), 2.00-1.97 (m, 1H), 1.81-1.75 (m, 1H), 1.68-1.65 (m, 1H), 1.52-1.49 (m, 1H), 1.35-1.32 (m, 1H), 0.80-0.78 (m, 6H); LCMS (APCI+) m/z 471, 473 (M+H)+.

Example 51

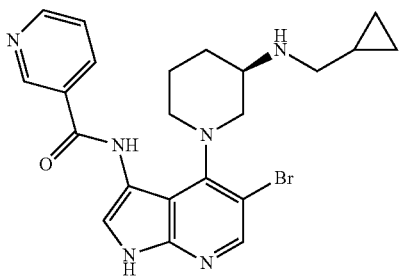

(R)-N-(5-Bromo-4-(3-(cyclopropylmethylamino)piperidin-1-yl)-1H-pyrrolo[2,3-b]pyridin-3-yl)nicotinamide (R)—N-(4-(3-Aminopiperidin-1-yl)-5-bromo-1H-pyrrolo[2,3-b]pyridin-3-yl)nicotinamide hydrochloride (0.075 g, 0.14 mmol, Example 1A), trimethyl orthoformate (0.32 mL, 2.9 mmol), and DIEA (0.100 mL, 0.57 mmol; d 0.742) were placed in MeOH (3 mL). Cyclopropanecarbaldehyde (0.022 mL, 0.29 mmol) was then added, and the reaction was stirred at room temperature for 18 hours. NaBH$_4$ (0.014 g, 0.36 mmol) was then added, and the reaction was stirred for 1 hour. The reaction was then poured into water, and extracted with DCM. The combined organic fractions were dried (MgSO$_4$), filtered, and concentrated to give the crude product, which was purified by reverse phase HPLC (0-50% ACN in water, Gilson system). The purified product was then dissolved in DCM (with minimal MeOH to aid solubility) and added dropwise to a stirring solution of 1M HCl in ether. The resulting solid was filtered, dried and collected to give (R)—N-(5-bromo-4-(3-(cyclopropylmethylamino)piperidin-1-yl)-1H-pyrrolo[2,3-b]pyridin-3-yl)nicotinamide hydrochloride salt (0.050 g, 60% yield). $^1$H NMR (400 MHz, D$_2$O) δ 8.98-8.98 (m, 1H), 8.65-8.64 (m, 1H), 8.52-8.50 (m, 1H), 8.12 (s, 1H), 7.74-7.71 (m, 1H), 7.27 (s, 1H), 3.54-3.51 (m, 1H), 3.18-3.04 (m, 3H), 2.97-2.92 (m, 1H), 2.69-2.55 (m, 2H), 1.82-1.78 (m, 1H), 1.55-1.52 (m, 1H), 1.40-1.30 (m, 1H), 1.21-1.17 (m, 1H), 0.74-0.68 (m, 1H), 0.36-0.32 (m, 2H), 0.05-0.00 (m, 2H); LCMS (APCI+) m/z 469, 471 (M+H)+.

Example 52

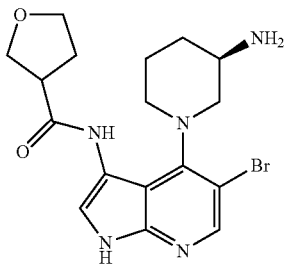

N-(4-((R)-3-Aminopiperidin-1-yl)-5-bromo-1H-pyrrolo[2,3-b]pyridin-3-yl)tetrahydrofuran-3-carboxamide Step A: A mixture of 5-bromo-4-fluoro-1H-pyrrolo[2,3-b]pyridin-3-amine (200 mg, 0.869 mmol, Example 1, Step H), tetrahydrofuran-3-carboxylic acid (202 mg, 1.74 mmol) and triethylamine (606 μL, 4.35 mmol) in CH$_2$Cl$_2$ (10 mL) at room temperature was treated with BOP-Cl (162 mg, 1.74 mmol). The mixture was stirred for 60 minutes, and the solvent was removed in vacuo. The resulting residue was dissolved in THF (10 mL) and treated with lithium hydroxide hydrate (109 mg, 2.61 mmol) in water (1 mL). After 30 minutes, the mixture was concentrated in vacuo, and water (5 mL) was added to the residue. The solid formed was filtered, washed with additional water and dried to provide N-(5-bromo-4-fluoro-1H-pyrrolo[2,3-b]pyridin-3-yl)tetrahydrofuran-3-carboxamide (210 mg, 74% yield) as a solid. $^1$H NMR (400 MHz, (CD$_3$)$_2$SO) δ 12.07 (br s, 1H), 9.65 (s, 1H), 8.35 (d, 1H), 7.59 (s, 1H), 3.95 (t, 1H), 3.81-3.68 (m, 3H), 3.26-3.18 (m, 1H), 2.11-2.05 (m, 2H); LCMS (APCI+) m/z 327.9, 329.9 (M+H)+, Retention time=2.44 min (Method 2).

Step B: A solution of N-(5-bromo-4-fluoro-1H-pyrrolo[2,3-b]pyridin-3-yl)tetrahydrofuran-3-carboxamide (205 mg, 0.625 mmol) in n-BuOH (5 mL) was treated with (R)-tert-butyl piperidin-3-ylcarbamate (626 mg, 3.12 mmol) and stirred at 160° C. for 18 hours in a sealed tube. The solvent was then removed in vacuo, and the residue was dissolved in EtOAc (50 mL) and washed with water (1×10 mL). The organic layer was dried (MgSO$_4$), filtered and concentrated in vacuo. The residue was purified by C-18 flash chromatography (25M+) on Biotage SP4 unit eluting with a gradient of 7-80% CH$_3$CN/water (25 CV) to provide tert-butyl (3R)-1-(5-bromo-3-(tetrahydrofuran-3-carboxamido)-1H-pyrrolo[2,3-b]pyridin-4-yl)piperidin-3-ylcarbamate (65 mg, 20% yield). $^1$H NMR (400 MHz, CDCl$_3$) δ 9.65 (s, 1H), 8.78 (br s, 1H), 8.26 (s, 1H), 8.02 (s, 1H), 4.54-4.47 (m, 1H), 4.05-3.98 (m, 2H), 3.96-3.90 (m, 1H), 3.83-3.72 (m, 1H), 3.70-3.60 (m, 1H), 3.47-3.39 (m, 2H), 3.18-3.09 (m, 2H), 3.07-3.00 (m, 1H), 2.41-2.33 (m, 1H), 2.28-2.16 (m, 1H), 2.03-1.95 (m, 1H), 1.85-1.74 (m, 2H), 1.42 (s, 9H); LCMS (APCI+) m/z 508.1, 510 (M+H)+, Retention time=3.42 minutes (Method 2).

Step C: A solution of tert-butyl (3R)-1-(5-bromo-3-(tetrahydrofuran-3-carboxamido)-1H-pyrrolo[2,3-b]pyridin-4-yl)piperidin-3-ylcarbamate (57 mg, 0.11 mmol) in neat TFA (5 mL) was stirred at room temperature for 30 minutes and concentrated in vacuo. The oily residue was dissolved in a few drops of CH$_2$Cl$_2$ and treated with 2M HCl in Et$_2$O (3 mL). The solid formed was filtered, washed with additional Et$_2$O and purified by C-18 reverse phase column chromatography (Biotage C-18, 12M+) on Biotage SP4 unit eluting with 5%-60% CH$_3$CN/water gradient. The product isolated was dissolved in few drops of 10% MeOH/CH$_2$Cl$_2$ and treated with 2M HCl in Et$_2$O (4 mL). The precipitate formed was filtered, washed with additional Et$_2$O (2×2 mL) followed by CH$_3$CN (1 mL) and dried to provide N-(4-((R)-3-aminopiperidin-1-yl)-5-bromo-1H-pyrrolo[2,3-b]pyridin-3-yl)tetrahydrofuran-3-carboxamide hydrochloride (20 mg, 37% yield) as a solid. $^1$H NMR (400 MHz, (CD$_3$)$_2$SO) δ 11.84 (s, 1H), 9.49 (s, 1H), 8.24 (br s, 4H), 7.57 (s, 1H), 3.84-3.71 (m, 4H), 3.44-3.36 (m, 3H), 3.28-3.21 (m, 2H), 3.11-3.06 (m, 1H), 2.17-2.08 (m, 3H), 1.87-1.80 (m, 1H), 1.76-1.65 (m, 1H), 1.53-1.43 (m, 1H); LCMS (APCI+) m/z 408, 410 (M+H)+, Retention time=1.99 minutes (Method 2).

Example 53

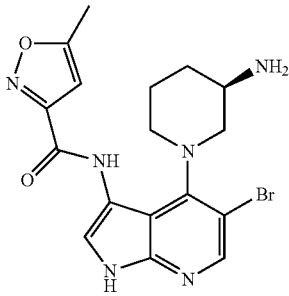

(R)-N-(4-(3-Aminopiperidin-1-yl)-5-bromo-1H-pyrrolo[2,3-b]pyridin-3-yl)-5-methylisoxazole-3-carboxamide Step A: A mixture of 5-bromo-4-fluoro-1H-pyrrolo[2,3-b]pyridin-3-amine (200 mg, 0.869 mmol, Example 1, Step H), 5-methylisoxazole-3-carboxylic acid (221 mg, 1.74 mmol) and triethylamine (606 µL, 4.35 mmol) in $CH_2Cl_2$ (10 mL) at room temperature was treated with BOP-Cl (162 mg, 1.74 mmol). The mixture was stirred at room temperature overnight and additional BOP-Cl (81 mg, 0.87 mmol) and 5-methylisoxazole-3-carboxylic acid (110 mg, 0.87 mmol) were added. The mixture was stirred for an additional 48 hours at room temperature. Next, 2M LiOH (3 mL) was added to the mixture and stirred for 1 hour. The organic solvent was removed in vacuo, and water:$CH_2Cl_2$ (11 mL; 10:1) were added to the aqueous residue. The solid formed was filtered, washed with additional water and dried to provide N-(5-bromo-4-fluoro-1H-pyrrolo[2,3-b]pyridin-3-yl)-5-methylisoxazole-3-carboxamide (210 mg, 71% yield) as a solid. $^1$H NMR (400 MHz, $(CD_3)_2SO$) δ 12.12 (s, 1H), 10.22 (s, 1H), 8.33 9 d, 1H), 7.58 (s, 1H), 2.45 (s, 3H); LCMS (APCI+) m/z 338.9, 340.9 (M+H)+, Retention time=3.16 minutes (Method 2).

Step B: A mixture of N-(5-bromo-4-fluoro-1H-pyrrolo[2,3-b]pyridin-3-yl)-5-methylisoxazole-3-carboxamide (200 mg, 0.590 mmol) and (R)-tert-butyl piperidin-3-ylcarbamate (591 mg, 2.95 mmol) in n-BuOH (5 mL) was stirred at 150° C. for 24 hours in a sealed tube. The reaction mixture was then concentrated in vacuo, and the liquid residue was purified by C-18 reverse phase flash chromatography (Biotage C-18 Flash 25M+) on Biotage SP4 unit eluting with 10-80% $CH_3CN$/water gradient (24 CV). The product isolated was crystallized from MeOH/$CH_3CN$ to provide (R)-tert-butyl 1-(5-bromo-3-(5-methylisoxazole-3-carboxamido)-1H-pyrrolo[2,3-b]pyridin-4-yl)piperidin-3-ylcarbamate (40 mg, 13% yield) as a solid. LCMS (APCI+) m/z 519, 521 (M+H)+, Retention time=4.08 minutes (Method 2).

Step C: A solution of (R)-tert-butyl 1-(5-bromo-3-(5-methylisoxazole-3-carboxamido)-1H-pyrrolo[2,3-b]pyridin-4-yl)piperidin-3-ylcarbamate (38 mg, 0.073 mmol) in neat TFA (2 mL) was stirred at room temperature for 30 minutes and concentrated in vacuo. The residue was dissolved in a few drops of $CH_2Cl_2$ and treated with 2M HCl in $Et_2O$ (2 mL). The solid isolated was purified by C-18 reverse phase chromatography (Biotage C-18, 12M+) on SP4 unit eluting with a gradient of 4-60% $CH_3CN$/water (14 CV). The residue was dissolved in a few drops of $CH_2Cl_2$, and 2M HCl in $Et_2O$ (2 mL) was added. The precipitate formed was filtered, washed with additional $Et_2O$ and dried under high vacuum to provide (R)—N-(4-(3-aminopiperidin-1-yl)-5-bromo-1H-pyrrolo[2,3-b]pyridin-3-yl)-5-methylisoxazole-3-carboxamide hydrochloride (11 mg, 28% yield) as a solid. $^1$H NMR (400 MHz, $(CD_3)_2SO$) δ 11.95 (d, 1H), 10.45 (s, 1H), 8.31 (s, 1H), 8.25 (br s, 3H), 7.97 (s, 6.75 (s, 1H), 3.68-3.58 (m, 2H), 3.53-3.45 (m, 1H), 3.36-3.30 (m, 1H), 3.08-3.02 (m, 1H), 2.53 (s, 3H), 2.21-2.13 (m, 1H), 2.07-1.96 (m, 1H), 1.87-1.81 (m, 1H), 1.55-1.44 (m, 1H); LCMS 402 (APCI+) m/z (M+H)+, Retention time=2.49 minutes (Method 2).

Example 54

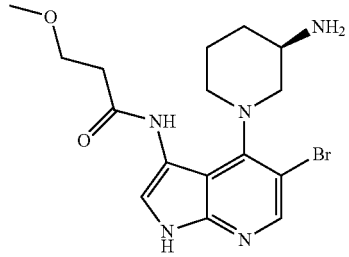

(R)-N-(4-(3-Aminopiperidin-1-yl)-5-bromo-1H-pyrrolo[2,3-b]pyridin-3-yl)-3-methoxypropanamide Step A: A mixture of 5-bromo-4-fluoro-1H-pyrrolo[2,3-b]pyridin-3-amine (200 mg, 0.869 mmol, Example 1, Step H), 3-methoxypropanoic acid (204.2 µL, 2.174 mmol) and triethylamine (605.9 µL, 4.347 mmol) in $CH_2Cl_2$ (10 mL) at room temperature was treated with BOP-Cl (202.7 mg, 2.174 mmol). The mixture was stirred at room temperature for 24 hours. 2M LiOH.$H_2O$ in water (3 mL) was then added and stirred for 30 minutes. The precipitate formed was filtered, washed with $CH_2Cl_2$ (3×2 mL), and dried to provide N-(5-bromo-4-fluoro-1H-pyrrolo[2,3-b]pyridin-3-yl)-3-methoxypropanamide (115 mg, 42% yield) as a solid. $^1$H NMR (400 MHz, $(CD_3)_2SO$) δ 12.05 (br s, 1H), 9.55 (s, 1H), 8.34 (d, 1H), 7.63 (s, 1H), 3.63 (t, 2H), 3.26 (s, 3H), 2.58 (t, 2H); LCMS (APCI+) m/z 317.9 (M+H)+, Retention time=2.57 minutes (Method 2).

Step B: A mixture of N-(5-bromo-4-fluoro-1H-pyrrolo[2,3-b]pyridin-3-yl)-3-methoxypropanamide (110 mg, 0.348 mmol) and (R)-tert-butyl piperidin-3-ylcarbamate (279 mg, 1.39 mmol) in n-BuOH (5 mL) was stirred at 160° C. for 24 hours. The mixture was diluted with EtOAc (100 mL) and washed with brine (1×20 mL). The organic layer was separated, dried ($MgSO_4$), filtered, and concentrated in vacuo. The residue was purified by C-18 reverse phase chromatography (Biotage 25M+ column) on Biotage SP4 unit eluting with 10-85% $CH_3CN$ gradient (25 CV) to provide (R)-tert-butyl 1-(5-bromo-3-(3-methoxypropanamido)-1H-pyrrolo[2,3-b]pyridin-4-yl)piperidin-3-ylcarbamate as a solid. This material was dissolved in TFA (3 mL) and stirred at room temperature for 20 minutes. TFA was then removed in vacuo, and the residue was dissolved in a few drops of methanol and purified by C-18 reverse phase chromatography (Biotage C-18, 12M+ column) on Biotage SP4 unit eluting with 1-50% $CH_3CN$/water gradient (14 CV). The product isolated was dissolved in $CH_2Cl_2$ (1 mL), and 2M HCl in ether (2 mL) was added. The solid was dissolved in MeOH, evaporated from $CH_2Cl_2$ (3×2 mL) and dried under high vacuum to provide (R)—N-(4-(3-aminopiperidin-1-yl)-5-bromo-1H-pyrrolo[2,3-b]pyridin-3-yl)-3-methoxypropanamide hydrochloride (28 mg, 20% yield) as a solid. $^1$H NMR (400 MHz, $(CD_3)_2SO$) δ 11.80 (s, 1H), 9.34 (s, 1H), 8.23 (br s, 4H), 7.57 (br s, 1H), 3.64 (t, 2H), 3.55-3.49 (m, 2H), 3.42-3.55 (m, 2H), 3.27 (s, 3H), 3.08-3.03 (m, 1H), 2.62 (t, 2H), 2.15-2.09 (m, 1H), 1.88-1.81 (m, 1H), 1.75-1.67 (m, 1H), 1.53-1.45 (m, 1H); LCMS (APCI+) m/z 396, 398 (M+H)+, Retention time=2.09 minutes (Method 2).

Example 55

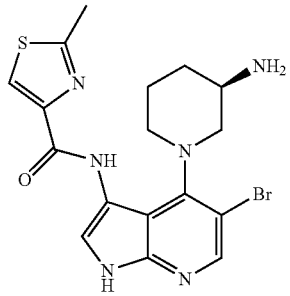

(R)-N-(4-(3-Aminopiperidin-1-yl)-5-bromo-1H-pyrrolo[2,3-b]pyridin-3-yl)-2-methylthiazole-4-carboxamide Step A: A mixture of 5-bromo-4-fluoro-1H-pyrrolo[2,3-b]pyridin-3-amine (200 mg, 0.869 mmol, Example 1, Step H), 2-methylthiazole-4-carboxylic acid (311 mg, 2.17 mmol), and triethylamine (606 µL, 4.35 mmol) in CH$_2$Cl$_2$ (10 mL) at room temperature was treated with BOP-Cl (203 mg, 2.17 mmol). After 1 hour the solid formed was filtered and washed with CH$_2$Cl$_2$ (3×4 mL) to provide N-(5-bromo-4-fluoro-1H-pyrrolo[2,3-b]pyridin-3-yl)-2-methylthiazole-4-carboxamide (210 mg, 68% yield) as a solid. $^1$H NMR (400 MHz, (CD$_3$)$_2$SO) δ 12.14 (s, 1H), 9.83 (s, 1H), 8.38 (d, 1H), 8.26 (s, 1H), 7.74 (d, 1H), 2.77 (s, 3H); LCMS (APCI+) m/z 354.9, 356.9 (M+H)+, Retention time=3.39 minutes (Method 2).

Step B: A mixture of N-(5-bromo-4-fluoro-1H-pyrrolo[2,3-b]pyridin-3-yl)-2-methylthiazole-4-carboxamide (200 mg, 0.563 mmol) and (R)-tert-butyl piperidin-3-ylcarbamate (338 mg, 1.69 mmol) in n-BuOH was stirred at 160° C. in a sealed tube. After 18 hours, additional (R)-tert-butyl piperidin-3-ylcarbamate (113 mg, 0.563 mmol) was added to the mixture and heating at 160° C. was continued for a further 18 hours. The mixture was concentrated in vacuo and purified by C-18 reverse phase column chromatography (Biotage Flash 25 M+ column) on Biotage SP4 unit eluting with a gradient of 10-85% CH$_3$CN/water (25 CV) to provide (R)-tert-butyl 1-(5-bromo-3-(2-methylthiazole-4-carboxamido)-1H-pyrrolo[2,3-b]pyridin-4-yl)piperidin-3-ylcarbamate. This material was dissolved in neat TFA (3 mL), stirred at room temperature for 30 minutes and concentrated in vacuo. The oily residue was dissolved in a few drops of methanol and treated with 2M HCl in ether. The resulting precipitate was concentrated under reduced pressure, and the residue was dissolved in a few drops of methanol and CH$_3$CN was added. The precipitate formed was filtered and dried under high vacuum to provide (R)—N-(4-(3-aminopiperidin-1-yl)-5-bromo-1H-pyrrolo[2,3-b]pyridin-3-yl)-2-methylthiazole-4-carboxamide hydrochloride (25 mg, 10% yield) as a solid. $^1$H NMR (400 MHz, (CD$_3$)$_2$SO) δ 11.87 (s, 1H), 10.64 (s, 1H), 8.34 (br s, 3H), 8.31 (s, 1H), 8.28 (s, 1H), 8.09 (d, 1H), 3.85-3.24 (m, 1H), 3.70-3.57 (m, 2H), 3.35-3.28 (m, 1H), 3.09-3.02 (m, 1H), 2.81 (s, 3H), 2.36-2.27 (m, 2H), 1.94-1.86 (m, 1H), 1.63-1.51 (m, 1H); LCMS (APCI+) m/z 435.0, 437.0 (M+H)+, Retention time=2.54 minutes (Method 2).

Example 56

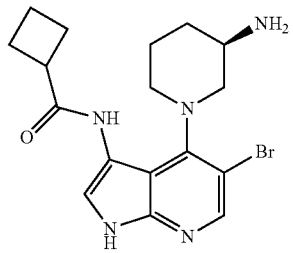

(R)-N-(4-(3-Aminopiperidin-1-yl)-5-bromo-1H-pyrrolo[2,3-b]pyridin-3-yl)cyclobutanecarboxamide Step A: A mixture of 5-bromo-4-fluoro-1H-pyrrolo[2,3-b]pyridin-3-amine (200 mg, 0.869 mmol, Example 1, Step H), cyclobutanecarboxylic acid (218 mg, 2.17 mmol) and triethylamine (606 µL, 4.35 mmol) in CH$_2$Cl$_2$ (10 mL) at room temperature was treated with BOP-Cl (203 mg, 2.17 mmol). The reaction was stirred at room temperature for 42 hours. The reaction mixture was then treated with 2M LiOH.H$_2$O (2 mL) and stirred at room temperature for 18 hours. Water (10 mL) was added to the reaction mixture, and the solid formed was filtered, washed with additional water, and dried to provide N-(5-bromo-4-fluoro-1H-pyrrolo[2,3-b]pyridin-3-yl)cyclobutanecarboxamide (193 mg, 71% yield) as a solid. $^1$H NMR (400 MHz, (CD$_3$)$_2$SO) δ 12.04 (br s, 1H), 9.33 (s, 1H), 8.33 (d, 1H), 7.57 (s, 1H), 3.29-3.24 (m, 1H), 2.25-2.18 (m, 2H), 2.15-2.08 (m, 2H), 1.98-1.88 (m, 1H), 1.86-1.78 (m, 1H); LCMS (APCI+) m/z 311.9, 314.0 (M+H)+, Retention time=2.96 minutes (Method 2).

Step B: A mixture of N-(5-bromo-4-fluoro-1H-pyrrolo[2,3-b]pyridin-3-yl)cyclobutanecarboxamide (188 mg, 0.602 mmol), (R)-tert-butyl piperidin-3-ylcarbamate (362 mg, 1.81 mmol), and triethylamine (168 µL, 1.20 mmol) in n-BuOH (5 mL) was stirred at 160° C. in a sealed tube for 18 hours. The mixture was allowed to cool to room temperature, and was then diluted with EtOAc (100 mL) and washed with brine (2×20 mL). The organic layer was separated, dried (MgSO$_4$), filtered, and concentrated in vacuo. The liquid residue was purified by C-18 reverse phase chromatography (Biotage 25M+) on Biotage SP4 unit eluting with a gradient of 12-85% CH$_3$CN/water (25 CV) to provide (R)-tert-butyl 1-(5-bromo-3-(cyclobutanecarboxamido)-1H-pyrrolo[2,3-b]pyridin-4-yl)piperidin-3-ylcarbamate (90 mg, 30% yield) as a solid. This material was dissolved in neat TFA (3 mL) and stirred at room temperature for 30 minutes. The mixture was then concentrated in vacuo, and the oily residue was dissolved in a few drops of CH$_2$Cl$_2$ and treated with 2M HCl in ether. The solid formed was crystallized from MeOH and CH$_3$CN to provide (R)—N-(4-(3-aminopiperidin-1-yl)-5-bromo-1H-pyrrolo[2,3-b]pyridin-3-yl)cyclobutanecarboxamide hydrochloride (65 mg, 79% yield) as a solid. $^1$H NMR (400 MHz, (CD$_3$)$_2$SO) δ 11.81 (s, 1H), 9.19 (s, 1H), 8.29 (br s, 3H), 8.23 (s, 1H), 7.59 (s, 1H), 3.46-3.37 (m, 2H), 3.35-3.26 (m, 3H), 3.08-3.03 (m, 1H), 2.34-2.24 (m, 2H), 2.18-2.11 (m, 3H), 2.01-1.94 (m, 1H), 1.86-1.80 (m, 2H), 1.70-1.60 (m, 1H), 1.50-1.44 (m, 1H); LCMS (APCI+) m/z 392, 394 (M+H)+, Retention time=2.28 minutes (Method 2).

Example 57

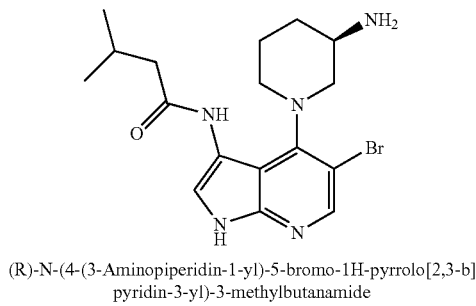 [SMILES: CC(C)CC(=O)Nc1c[nH]c2ncc(Br)c(N3CCC[C@@H](N)C3)c12]

(R)-N-(4-(3-Aminopiperidin-1-yl)-5-bromo-1H-pyrrolo[2,3-b]pyridin-3-yl)-3-methylbutanamide Step A: A mixture of 5-bromo-4-fluoro-1H-pyrrolo[2,3-b]pyridin-3-amine (200 mg, 0.869 mmol, Example 1, Step H), 3-methylbutanoic acid (isovaleric acid) (222 mg, 2.17 mmol) and triethylamine (606 µL, 4.35 mmol) in $CH_2Cl_2$ (10 mL) was processed as described in Example 56, Step A, to provide N-(5-bromo-4-fluoro-1H-pyrrolo[2,3-b]pyridin-3-yl)-3-methylbutanamide (182 mg, 67% yield) as a solid. $^1H$ NMR (400 MHz, $(CD_3)_2SO$) δ 12.04 (s, 1H), 9.46 (s, 1H), 8.34 (d, 1H), 7.56 (s, 1H), 2.20 (d, 2H), 2.11-2.05 (m, 1H), 0.96 (d, 6H); LCMS (APCI+) m/z 314, 316 (M+H)+, Retention time=3.02 minutes (Method 2).

Step B: A mixture of N-(5-bromo-4-fluoro-1H-pyrrolo[2,3-b]pyridin-3-yl)-3-methylbutanamide (177 mg, 0.563 mmol), (R)-tert-butyl piperidin-3-ylcarbamate (339 mg, 1.69 mmol), and triethylamine (157 µL, 1.13 mmol) in n-BuOH (5 mL) was processed as in Example 56, Step B, and the crude was purified by C-18 reverse phase chromatography (Biotage 25M+) on Biotage SP4 unit eluting with a gradient of 15-85% $CH_3CN$/water (25 CV) to provide (R)-tert-butyl 1-(5-bromo-3-(3-methylbutanamido)-1H-pyrrolo[2,3-b]pyridin-4-yl)piperidin-3-ylcarbamate (109 mg, 39% yield) as a solid. LCMS (APCI+) m/z 494, 496 (M+H)+, Retention time=3.92 minutes (Method 2).

Step C: A solution of (R)-tert-butyl 1-(5-bromo-3-(3-methylbutanamido)-1H-pyrrolo[2,3-b]pyridin-4-yl)piperidin-3-ylcarbamate (97 mg, 0.20 mmol) in neat TFA (4 mL) was stirred at room temperature for 30 minutes. TFA was removed in vacuo, and the residue was dissolved in few drops of methanol and treated with 2M HCl in ether (2 mL). The resulting precipitate was concentrated in vacuo, and the oily residue obtained was evaporated from $CH_3CN$ (3×5 mL). The residue obtained was triturated with $CH_3CN$. The resulting solid was filtered, washed with additional $CH_3CN$, and dried under high vacuum to provide (R)—N-(4-(3-aminopiperidin-1-yl)-5-bromo-1H-pyrrolo[2,3-b]pyridin-3-yl)-3-methylbutanamide hydrochloride (89 mg, 97% yield) as a solid. $^1H$ NMR (400 MHz, $(CD_3)_2SO$) δ 11.76 (s, 1H), 9.24 (s, 1H), 8.24 (br s, 3H), 8.17 (s, 1H), 7.50 (s, 1H), 3.41-3.34 (m, 2H), 3.29-3.20 (m, 2H), 3.05-2.99 (m, 1H), 2.21 (d, 2H), 2.10-2.03 (m, 2H), 1.82-1.76 (m, 1H), 1.67-1.61 (m, 1H), 1.48-1.39 (m, 1H), 0.92 (d, 6H); LCMS (APCI+) m/z 394, 396 (M+H)+, Retention time=2.26 minutes (Method 2).

Example 58

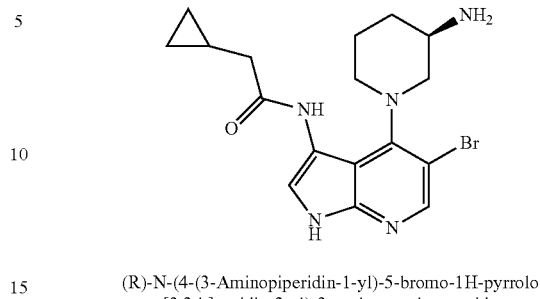

(R)-N-(4-(3-Aminopiperidin-1-yl)-5-bromo-1H-pyrrolo[2,3-b]pyridin-3-yl)-2-cyclopropylacetamide Step A: A mixture of 5-bromo-4-fluoro-1H-pyrrolo[2,3-b]pyridin-3-amine (200 mg, 0.869 mmol, Example 1, Step H), 2-cyclopropylacetic acid (218 mg, 2.17 mmol), triethylamine (606 µL, 4.35 mmol), and BOP-Cl (203 mg, 2.17 mmol) in $CH_2Cl_2$ (10 mL) was stirred at room temperature for 42 hours. Then 2M $LiOH.H_2O$ (3 mL) was added, and the mixture was stirred for 18 hours. The mixture was then diluted with $CH_2Cl_2$ (50 mL). The layers were separated, and the organic layer was dried ($MgSO_4$), filtered, and concentrated in vacuo to provide N-(5-bromo-4-fluoro-1H-pyrrolo[2,3-b]pyridin-3-yl)-2-cyclopropylacetamide (204 mg, 75% yield) as a solid. $^1H$ NMR (400 MHz, $(CD_3)_2SO$) δ 12.04 (s, 1H), 9.40 (s, 1H), 8.34 (d, 1H), 7.61 (s, 1H), 2.24 (d, 2H), 1.10-1.03 (m, 1H), 0.52-0.47 (m, 2H), 0.24-0.20 (m, 1H); LCMS (APCI+) m/z (M+H)+, Retention time=2.92 minutes (Method 2).

Step B: A mixture of N-(5-bromo-4-fluoro-1H-pyrrolo[2,3-b]pyridin-3-yl)-2-cyclopropylacetamide (204 mg, 0.654 mmol), (R)-tert-butyl piperidin-3-ylcarbamate (393 mg, 1.96 mmol), and triethylamine (182 µL, 1.31 mmol) in n-BuOH (5 mL) was processed as in Example 56. The crude was purified by C-18 reverse phase chromatography (Biotage 25M+) on Biotage SP4 unit eluting with a gradient of 15-85% $CH_3CN$/water (25 CV) to provide (R)-tert-butyl 1-(5-bromo-3-(2-cyclopropylacetamido)-1H-pyrrolo[2,3-b]pyridin-4-yl)piperidin-3-ylcarbamate (85 mg, 26% yield) as a solid. LCMS (APCI+) m/z 492, 494 (M+H)+, Retention time=3.75 min (Method 2).

Step C: A solution of (R)-tert-butyl 1-(5-bromo-3-(2-cyclopropylacetamido)-1H-pyrrolo[2,3-b]pyridin-4-yl)piperidin-3-ylcarbamate (80 mg, 0.16 mmol) in neat TFA (3 mL) was stirred at room temperature for 30 minutes. TFA was then removed in vacuo. The oily residue obtained was dissolved in few drops of $CH_2Cl_2$ and treated with 2M HCl in ether (2 mL). The solid formed was filtered, washed with additional $CH_2Cl_2$ (3×3 mL). This material was dissolved in MeOH (0.5 mL), and $CH_3CN$ was added until the mixture became cloudy. The mixture was allowed to stand at room temperature. The solid formed was filtered, washed with additional $CH_3CN$ (2×2 mL), was dried under a stream of nitrogen first and then under high vacuum to provide (R)—N-(4-(3-aminopiperidin-1-yl)-5-bromo-1H-pyrrolo[2,3-b]pyridin-3-yl)-2-cyclopropylacetamide hydrochloride (32 mg, 42% yield) as a solid. $^1H$ NMR (400 MHz, $(CD_3)_2SO$) δ 11.81 (s, 1H), 9.25 (s, 1H), 8.23 (s, 1H), 8.22 (br s, 3H), 7.54 (s, 1H), 3.45-3.38 (m, 2H), 3.36-3.26 (m, 2H), 3.10-3.04 (m, 1H), 2.31 (d, 2H), 2.15-2.08 (m, 1H), 1.86-1.79 (m, 1H), 1.72-1.62 (m, 1H), 1.53-1.45 (m, 1H), 1.13-1.06 (m, 1H), 0.54-0.51 (m, 2H), 0.24-0.21 (m, 2H); LCMS (APCI+) m/z 392.1, 394 (M+H)+, Retention time=2.23 minutes (Method 2).

Example 59

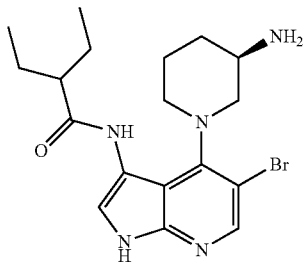

(R)-N-(4-(3-Aminopiperidin-1-yl)-5-bromo-1H-pyrrolo[2,3-b]pyridin-3-yl)-2-ethylbutanamide Step A: A solution of 5-bromo-4-fluoro-1H-pyrrolo[2,3-b]pyridin-3-amine (200 mg, 0.869 mmol, Example 1, Step H) in pyridine at 0° C. was treated dropwise with 2-ethylbutanoyl chloride (176 mg, 1.30 mmol). After 7 hours, 2M LiOH (5 mL) was added to the mixture and stirring was continued at room temperature for 30 minutes. Water (25 mL) was then added, and the solid formed was filtered, washed with water (3×5 mL) and dried to provide N-(5-bromo-4-fluoro-1H-pyrrolo[2,3-b]pyridin-3-yl)-2-ethylbutanamide (235 mg, 82% yield) as a solid. $^1$H NMR (400 MHz, (CD$_3$)$_2$SO) δ 12.06 (s, 1H), 9.46 (s, 1H), 8.34 (d, 1H), 7.53 (s, 1H), 2.30-2.24 (m, 1H), 1.62-1.52 (m, 2H), 1.47-1.41 (m, 2H), 0.90 (t, 6H); LCMS (APCI+) m/z 328, 330 (M+H)+, Retention time=3.20 minutes (Method 2).

Step B: A mixture of N-(5-bromo-4-fluoro-1H-pyrrolo[2,3-b]pyridin-3-yl)-2-ethylbutanamide (225 mg, 0.686 mmol), (R)-tert-butyl piperidin-3-ylcarbamate (412 mg, 2.06 mmol), and N-ethyl-N-isopropylpropan-2-amine (239 μL, 1.37 mmol) in n-BuOH (5 mL) was purged under N$_2$ and stirred at 160° C. in a sealed tube for 16 hours. The solvent was then removed in vacuo, and the liquid residue was purified by C-18 reverse phase column chromatography (Biotage Flash 25M+; C-18) on Biotage SP4 unit eluting with a gradient of 15-90% CH$_3$CN/water (25 CV) to provide (R)-tert-butyl 1-(5-bromo-3-(2-ethylbutanamido)-1H-pyrrolo[2,3-b]pyridin-4-yl)piperidin-3-ylcarbamate (201 mg, 58% yield) as a solid. LCMS (APCI+) m/z 508, 510 (M+H)+, Retention time=4.15 minutes (Method 2).

Step C: A solution of (R)-tert-butyl 1-(5-bromo-3-(2-ethylbutanamido)-1H-pyrrolo[2,3-b]pyridin-4-yl)piperidin-3-ylcarbamate (170 mg, 0.334 mmol) in neat TFA (4 mL) was stirred at room temperature for 30 minutes. TFA was then removed in vacuo, and the oily residue was dissolved in CH$_2$Cl$_2$ and treated with 2M HCl in Et$_2$O. The resulting suspension was concentrated in vacuo and evaporated from CH$_3$CN (3×5 mL). The solid residue obtained was triturated with CH$_3$CN, filtered, washed with additional CH$_3$CN and dried under high vacuum to provide (R)—N-(4-(3-aminopiperidin-1-yl)-5-bromo-1H-pyrrolo[2,3-b]pyridin-3-yl)-2-ethylbutanamide hydrochloride (125 mg, 78% yield) as a solid. $^1$H NMR (400 MHz, (CD$_3$)$_2$SO) δ 11.79 (s, 1H), 9.28 (s, 1H), 8.35 (br s, 3H), 8.25 (s, 1H), 7.71 (br s, 1H), 3.65-3.53 (m, 1H), 3.45-3.37 (m, 2H), 3.36-3.27 (m, 1H), 3.13-3.05 (m, 1H), 2.22-2.13 (m, 2H), 1.97-1.86 (m, 1H), 1.70-1.58 (m, 3H), 1.56-1.47 (m, 3H), 0.93-0.88 (m, 6H); LCMS (APCI+) m/z 408, 410 (M+H)+, Retention time=2.33 minutes (Method 2).

Example 60

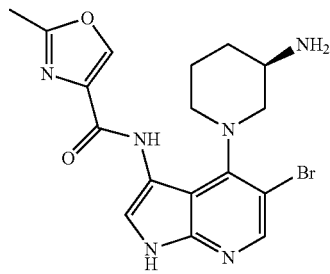

(R)-N-(4-(3-Aminopiperidin-1-yl)-5-bromo-1H-pyrrolo[2,3-b]pyridin-3-yl)-2-methyloxazole-4-carboxamide Step A: A mixture of 5-bromo-4-fluoro-1H-pyrrolo[2,3-b]pyridin-3-amine (200 mg, 0.869 mmol, Example 1, Step H), 2-methyloxazole-4-carboxylic acid (276 mg, 2.17 mmol), triethylamine (606 μL, 4.35 mmol), and BOP-Cl (203 mg, 2.17 mmol) in CH$_2$Cl$_2$ (10 mL) was stirred at room temperature for 4 hours. Next, 2M LiOH.H$_2$O (3 mL) was added, and after 30 minutes water (10 mL) was added. The solid formed was filtered, washed with water (2×5 mL) and dried to provide N-(5-bromo-4-fluoro-1H-pyrrolo[2,3-b]pyridin-3-yl)-2-methyloxazole-4-carboxamide (165 mg, 56% yield) as a solid. $^1$H NMR (400 MHz, (CD$_3$)$_2$SO) δ 12.15 (s, 1H), 9.68 (s, 1H), 8.63 (s, 1H), 8.37 (d, 1H), 7.67 (s, 1H), 2.52 (s, 3H); LCMS (APCI+) m/z 338.9, 341.0 (M+H)+, Retention time=3.21 minutes (Method 2).

Step B: A mixture of N-(5-bromo-4-fluoro-1H-pyrrolo[2,3-b]pyridin-3-yl)-2-methyloxazole-4-carboxamide (160 mg, 0.472 mmol) and (R)-tert-butyl piperidin-3-ylcarbamate (378 mg, 1.89 mmol) in n-BuOH (3 mL) was stirred at 160° C. in a sealed tube. The mixture was allowed to cool to room temperature and concentrated in vacuo. The residue was dissolved in MeOH (1 mL) and purified by C-18 reverse phase flash chromatography (Biotage Flash 25 M+) on SP4 unit eluting with 10-85% CH$_3$CN/water gradient (25 CV) to provide (R)-tert-butyl 1-(5-bromo-3-(2-methyloxazole-4-carboxamido)-1H-pyrrolo[2,3-b]pyridin-4-yl)piperidin-3-ylcarbamate as a solid. This material was treated with neat TFA (3 mL), and after 30 minutes the mixture was concentrated in vacuo. The residue obtained was dissolved in few drops of CH$_2$Cl$_2$ and treated with 2M HCl in ether (3 mL). The solid formed was filtered, washed with additional Et$_2$O and dried under high vacuum to provide (R)—N-(4-(3-aminopiperidin-1-yl)-5-bromo-1H-pyrrolo[2,3-b]pyridin-3-yl)-2-methyloxazole-4-carboxamide hydrochloride (23 mg, 12% yield) as a solid. $^1$H NMR (400 MHz, (CD$_3$)$_2$SO) δ 11.85 (s, 1H), 10.41 (s, 1H), 8.68 (s, 1H), 8.30 (s, 1H), 8.27 (br s, 3H), 8.02 (s, 1H), 4.01-3.99 (m, 1H), 3.69-3.63 (m, 1H), 3.60-3.52 (m, 1H), 3.36-3.29 (m, 1H), 3.06-2.99 (m, 1H), 2.58 (s, 3H), 2.34-2.25 (m, 2H), 1.89-1.82 (m, 1H), 1.59-1.51 (m, 1H); LCMS (APCI+) m/z 419, 421 (M+H)+, Retention time=2.44 minutes (Method 2).

Example 61

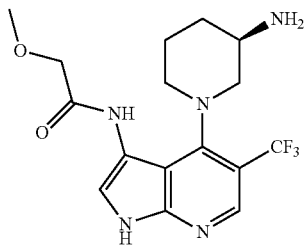

(R)-N-(4-(3-Aminopiperidin-1-yl)-5-(trifluoromethyl)-1H-pyrrolo[2,3-b]pyridin-3-yl)-2-methoxyacetamide Step A: 2-Methoxyacetyl chloride (0.074 mL, 0.76 mmol) was added to a solution of 4-chloro-5-(trifluoromethyl)-1H-pyrrolo[2,3-b]pyridin-3-amine (120 mg, 0.51 mmol, Example 12, Steps A-G) in pyridine (5 mL) at 0° C. The reaction was stirred at 0° C. for 10 minutes, and the pyridine was removed in vacuo. The residue obtained was dissolved in THF (5 mL), treated with 2N LiOH (3 mL) and stirred for 20 minutes. THF was then removed under reduced pressure, and the aqueous slurry obtained was extracted with water (20 mL) and ethyl acetate (50 mL). The organic layer was separated, washed with brine, dried ($Na_2SO_4$) and concentrated in vacuo to provide N-(4-chloro-5-(trifluoromethyl)-1H-pyrrolo[2,3-b]pyridin-3-yl)-2-methoxyacetamide (154 mg, 98% yield) as a solid.

Step B: A mixture of N-(4-chloro-5-(trifluoromethyl)-1H-pyrrolo[2,3-b]pyridin-3-yl)-2-methoxyacetamide (154 mg, 0.501 mmol), (R)-tert-butyl piperidin-3-ylcarbamate (301 mg, 1.50 mmol) and DIEA (0.17 mL, 1.00 mmol) in NMP (2 mL) was stirred at 156° C. for 10 hours. The solvent was removed in vacuo. The residue obtained was dissolved in ethyl acetate (20 mL), washed with water (10 mL) and followed by brine (10 mL). The organic layer was separated, dried ($Na_2SO_4$), and concentrated in vacuo. The residue obtained was purified by C-18 reverse phase flash chromatography (Biotage SP4 unit, C-18, 25M+ column, 30-70% $CH_3CN$/water gradient; 30 CV). The solid isolated was dissolved in DCM (3 mL), and TFA (0.5 mL) was added. The mixture was stirred at room temperature for 1 hour, and the solvent was removed in vacuo. The resulting residue was dissolved in DCM (1 mL) and treated with 2N HCl in ether (3 mL). The solid formed was collected by filtration and dried to give (R)—N-(4-(3-aminopiperidin-1-yl)-5-(trifluoromethyl)-1H-pyrrolo[2,3-b]pyridin-3-yl)-2-methoxyacetamide hydrochloride (61 mg, 27% yield) as a solid. $^1$H NMR (400 MHz, $D_2O$) δ 8.42 (s, 1H), 7.52 (s, 1H), 4.12 (s, 2H), 3.40 (s, 3H), 3.38 (m, 2H), 2.96 (m, 3H), 2.00 (m, 1H), 1.73 (m, 1H), 1.68 (m, 1H), 1.54 (m, 1H); LCMS (APCI+) m/z 372 (M+H)+.

Example 62

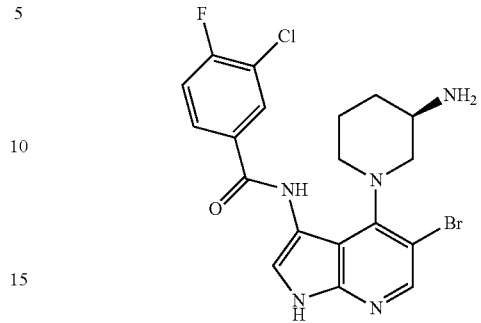

(R)-N-(4-(3-Aminopiperidin-1-yl)-5-bromo-1H-pyrrolo[2,3-b]pyridin-3-yl)-3-chloro-4-fluorobenzamide Step A: A solution of 5-bromo-4-fluoro-1H-pyrrolo[2,3-b]pyridin-3-amine (200 mg, 0.869 mmol, Example 1, Step H), 3-chloro-4-fluorobenzoic acid (319 mg, 1.83 mmol), BOP-Cl (465 mg, 1.83 mmol), and triethylamine (0.606 mL, 4.35 mmol) in DCM (5 mL) at room temperature was stirred for 2 hours. 3M aqueous LiOH (3 mL) was then added, and the mixture was stirred for 10 minutes. Next, water (10 mL) and DCM (10 mL) were added, and the resulting precipitate was filtered. The solid isolated was triturated with 10:1 $CH_2Cl_2$: MeOH and filtered to provide N-(5-bromo-4-fluoro-1H-pyrrolo[2,3-b]pyridin-3-yl)-3-chloro-4-fluorobenzamide (240 mg, 71% yield) as a solid.

Step B: A mixture of N-(5-bromo-4-fluoro-1H-pyrrolo[2,3-b]pyridin-3-yl)-3-chloro-4-fluorobenzamide (240 mg, 0.621 mmol) and (R)-tert-butyl piperidin-3-ylcarbamate (373 mg, 1.86 mmol) in n-BuOH (3 mL) was stirred at 155° C. for 16 hours in a sealed tube. The reaction was then cooled to room temperature and concentrated in vacuo. The resulting residue was purified by reverse phase HPLC (Gilson) to provide (R)-tert-butyl 1-(5-bromo-3-(3-chloro-4-fluorobenzamido)-1H-pyrrolo[2,3-b]pyridin-4-yl)piperidin-3-ylcarbamate (110 mg, 31% yield).

Step C: A solution of (R)-tert-butyl 1-(5-bromo-3-(3-chloro-4-fluorobenzamido)-1H-pyrrolo[2,3-b]pyridin-4-yl)piperidin-3-ylcarbamate (110 mg, 0.194 mmol) in DCM (3 mL) was treated with TFA (1 mL) at room temperature for 1 hour. The mixture was then concentrated in vacuo. The resulting residue was dissolved in a minimal amount of DCM and added to a stirring solution of 1M HCl in ether. The solid obtained was filtered, washed with ether and dried to provide (R)—N-(4-(3-aminopiperidin-1-yl)-5-bromo-1H-pyrrolo[2,3-b]pyridin-3-yl)-3-chloro-4-fluorobenzamide hydrochloride (80 mg, 76% yield). $^1$H NMR (400 MHz, $D_2O$) δ 8.22 (s, 1H), 7.97-7.94 (m, 1H), 7.80-7.77 (m, 1H), 7.38 (s, 1H), 7.32-7.28 (m, 1H), 3.54-3.52 (m, 1H), 3.32-3.30 (m, 1H), 3.25-3.21 (m, 1H), 3.18-3.10 (m, 2H), 1.88-1.80 (m, 1H), 1.68-1.63 (m, 1H), 1.50-1.33 (m, 2H); LCMS (APCI+) m/z 466, 486 (M+H)+.

Example 63

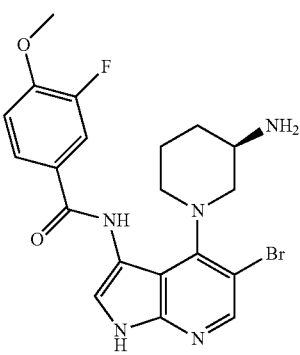

(R)-N-(4-(3-Aminopiperidin-1-yl)-5-bromo-1H-pyrrolo
[2,3-b]pyridin-3-yl)-3-fluoro-4-methoxybenzamide Step A: A mixture of 5-bromo-4-fluoro-1H-pyrrolo[2,3-b]pyridin-3-amine (200 mg, 0.87 mmol, Example 1, Step H), 3-fluoro-4-methoxybenzoic acid (311 mg, 1.83 mmol), BOP-Cl (0.465 g, 1.83 mmol), and triethylamine (0.606 mL, 4.35 mmol) in DCM (5 mL) was processed as described in Example 62, Step A, to provide N-(5-bromo-4-fluoro-1H-pyrrolo[2,3-b]pyridin-3-yl)-3-fluoro-4-methoxybenzamide (300 mg, 90% yield) as a solid. LCMS (APCI+) m/z 381.9, 383.9 (M+H)+, Retention time=3.23 minutes (Method 2).

Step B: A mixture of N-(5-bromo-4-fluoro-1H-pyrrolo[2,3-b]pyridin-3-yl)-3-fluoro-4-methoxybenzamide (300 mg, 0.785 mmol) and (R)-tert-butyl piperidin-3-ylcarbamate (472 mg, 2.36 mmol) in n-BuOH (3 mL) was stirred at 155° C. for 16 hours in a sealed tube. The reaction was then cooled to room temperature and concentrated in vacuo. The resulting residue was purified by reverse phase HPLC (Gilson) to provide (R)-tert-butyl 1-(5-bromo-3-(3-fluoro-4-methoxybenzamido)-1H-pyrrolo[2,3-b]pyridin-4-yl)piperidin-3-ylcarbamate (120 mg, 27% yield).

Step C: (R)-tert-Butyl 1-(5-bromo-3-(3-fluoro-4-methoxybenzamido)-1H-pyrrolo[2,3-b]pyridin-4-yl)piperidin-3-ylcarbamate (150 mg, 0.27 mmol) in DCM (3 mL) was treated with TFA (1 mL), followed by 1M HCl in ether according to the procedure described in Example 62, Step C, to provide (R)—N-(4-(3-aminopiperidin-1-yl)-5-bromo-1H-pyrrolo[2,3-b]pyridin-3-yl)-3-fluoro-4-methoxybenzamide hydrochloride (90 mg, 63% yield). $^1$H NMR (400 MHz, D$_2$O) δ 8.20 (s, 1H), 7.67-7.64 (m, 1H), 7.62-7.59 (m, 1H), 7.35 (s, 1H), 7.18-7.14 (m, 1H), 3.84 (s, 3H), 3.46-3.40 (m, 1H), 3.28-3.18 (m, 2H), 3.12-3.09 (m, 2H), 1.79-1.74 (m, 1H), 1.68-1.61 (m, 1H), 1.46-1.30 (m, 2H); LCMS (APCI+) m/z 462, 464 (M+H)+.

Example 64

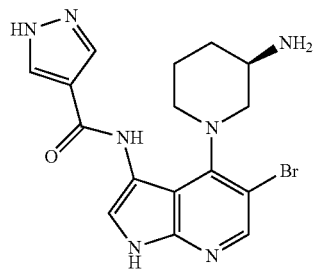

(R)-N-(4-(3-Aminopiperidin-1-yl)-5-bromo-1H-pyrrolo
[2,3-b]pyridin-3-yl)-1H-pyrazole-4-carboxamide Step A: A mixture of 5-bromo-4-fluoro-1H-pyrrolo[2,3-b]pyridin-3-amine (300 mg, 1.30 mmol, Example 1, Step H), 1-(4-methoxybenzyl)-1H-pyrazole-4-carboxylic acid (636 mg, 2.74 mmol), BOP-Cl (697 mg, 2.74 mmol), and triethylamine (0.909 mL, 6.52 mmol) in DCM (5 mL) was processed as described in Example 62, Step A, to provide N-(5-bromo-4-fluoro-1H-pyrrolo[2,3-b]pyridin-3-yl)-1-(4-methoxybenzyl)-1H-pyrazole-4-carboxamide (230 mg, 39% yield).

Step B: A mixture of N-(5-bromo-4-fluoro-1H-pyrrolo[2,3-b]pyridin-3-yl)-1-(4-methoxybenzyl)-1H-pyrazole-4-carboxamide (230 mg, 0.518 mmol) and (R)-tert-butyl piperidin-3-ylcarbamate (311 mg, 1.55 mmol) in n-BuOH (2.5 mL) was heated to 155° C. for 48 hours in a sealed tube. The reaction mixture was then cooled to room temperature and concentrated in vacuo. The resulting residue was purified by reverse phase HPLC (Gilson) to provide (R)-tert-butyl 1-(5-bromo-3-(1-(4-methoxybenzyl)-1H-pyrazole-4-carboxamido)-1H-pyrrolo[2,3-b]pyridin-4-yl)piperidin-3-ylcarbamate (60 mg, 18% yield).

Step C: A solution of (R)-tert-butyl 1-(5-bromo-3-(1-(4-methoxybenzyl)-1H-pyrazole-4-carboxamido)-1H-pyrrolo[2,3-b]pyridin-4-yl)piperidin-3-ylcarbamate (120 mg, 0.192 mmol) in DCM (3 mL) was treated with TFA (1 mL) at room temperature for 30 minutes. The reaction was then concentrated in vacuo and azeotroped with toluene. The resulting residue was dissolved in neat TFA (5 mL) and stirred at 65° C. for 1 hour. The reaction mixture was then concentrated in vacuo, and the residue obtained was purified by reverse phase HPLC (Gilson) to provide (R)—N-(4-(3-aminopiperidin-1-yl)-5-bromo-1H-pyrrolo[2,3-b]pyridin-3-yl)-1H-pyrazole-4-carboxamide hydrochloride (50 mg, 50% yield). $^1$H NMR (400 MHz, D$_2$O) δ 8.26 (s, 1H), 8.12 (s, 2H), 7.33 (s, 1H), 3.67-3.63 (m, 1H), 3.41-3.37 (m, 1H), 3.30-3.27 (m, 1H), 3.19-3.10 (m, 2H), 1.90-1.83 (m, 1H), 1.68-1.65 (m, 1H), 1.55-1.51 (m, 1H), 1.36-1.34 (m, 1H); LCMS (APCI+) m/z 404, 406 (M+H)+.

Example 65

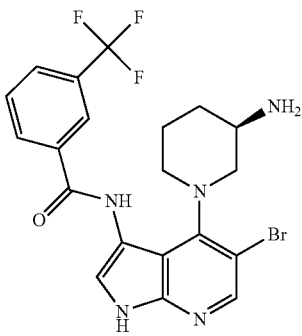

(R)-N-(4-(3-Aminopiperidin-1-yl)-5-bromo-1H-pyrrolo[2,3-b]pyridin-3-yl)-3-(trifluoromethyl)benzamide Step A: A mixture of 5-bromo-4-fluoro-1H-pyrrolo[2,3-b]pyridin-3-amine (200 mg, 0.869 mmol, Example 1, Step H), 3-(trifluoromethyl)benzoic acid (347 mg, 1.83 mmol), BOP-Cl (465 mg, 1.83 mmol), and triethylamine (0.606 mL, 4.35 mmol) in DCM (5 mL) was processed as described in Example 62, Step A, to provide N-(5-bromo-4-fluoro-1H-pyrrolo[2,3-b]pyridin-3-yl)-3-(trifluoromethyl)benzamide (250 mg, 71% yield) as a solid.

Step B: A mixture of N-(5-bromo-4-fluoro-1H-pyrrolo[2,3-b]pyridin-3-yl)-3-(trifluoromethyl)benzamide (250 mg, 0.622 mmol) and (R)-tert-butyl piperidin-3-ylcarbamate (374 mg, 1.87 mmol) in n-BuOH (3 mL) was processed as described in Example 62, Step B, to provide (R)-tert-butyl 1-(5-bromo-3-(3-(trifluoromethyl)benzamido)-1H-pyrrolo[2,3-b]pyridin-4-yl)piperidin-3-ylcarbamate (250 mg, 69% yield).

Step C: (R)-tert-Butyl 1-(5-bromo-3-(3-(trifluoromethyl)benzamido)-1H-pyrrolo[2,3-b]pyridin-4-yl)piperidin-3-ylcarbamate (150 mg, 0.258 mmol) was treated with TFA (1 mL) followed by 1M HCl as described in Example 62, Step C, to provide (R)—N-(4-(3-aminopiperidin-1-yl)-5-bromo-1H-pyrrolo[2,3-b]pyridin-3-yl)-3-(trifluoromethyl)benzamide hydrochloride (0.130 g, 91% yield) as a solid. $^1$H NMR (400 MHz, D$_2$O) δ 8.24 (s, 1H), 8.12 (s, 1H), 8.05-8.04 (d, 1H), 7.88-7.86 (d, 1H), 7.66-7.62 (m, 1H), 7.42 (s, 1H), 3.63-3.60 (m, 1H), 3.36-3.32 (m, 1H), 3.22-3.17 (m, 2H), 3.13-3.08 (m, 1H), 1.84-1.81 (m, 1H), 1.65-1.61 (m, 1H), 1.45-1.42 (m, 1H), 1.34-1.31 (m, 1H); LCMS (APCI+) m/z 482, 484 (M+H)+.

Example 66

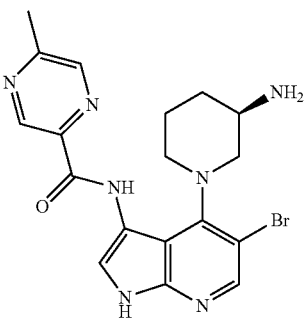

(R)-N-(4-(3-Aminopiperidin-1-yl)-5-bromo-1H-pyrrolo[2,3-b]pyridin-3-yl)-5-methylpyrazine-2-carboxamide Step A: A mixture of 5-bromo-4-fluoro-1H-pyrrolo[2,3-b]pyridin-3-amine (300 mg, 1.30 mmol, Example 1, Step H), 5-methylpyrazine-2-carboxylic acid (378 mg, 2.74 mmol), BOP-Cl (697 mg, 2.74 mmol), and triethylamine (0.909 mL, 6.52 mmol) in DCM (5 mL) was processed as described in Example 62, Step A, to provide N-(5-bromo-4-fluoro-1H-pyrrolo[2,3-b]pyridin-3-yl)-5-methylpyrazine-2-carboxamide (280 mg, 61% yield).

Step B: A mixture of N-(5-bromo-4-fluoro-1H-pyrrolo[2,3-b]pyridin-3-yl)-5-methylpyrazine-2-carboxamide (280 mg, 0.800 mmol) and (R)-tert-butyl piperidin-3-ylcarbamate (480 mg, 2.40 mmol) in n-BuOH (3 mL) was processed as described in Example 62, Step B, to provide crude (R)-tert-butyl 1-(5-bromo-3-(5-methylpyrazine-2-carboxamido)-1H-pyrrolo[2,3-b]pyridin-4-yl)piperidin-3-ylcarbamate without HPLC purification.

Step C: A solution of crude (R)-tert-butyl 1-(5-bromo-3-(5-methylpyrazine-2-carboxamido)-1H-pyrrolo[2,3-b]pyridin-4-yl)piperidin-3-ylcarbamate (75 mg, 0.14 mmol) in DCM (3 mL) was treated with TFA (1 mL) at room temperature. After 1 hour, the mixture was concentrated in vacuo. The resulting residue was dissolved in a minimal amount of DCM and added to a stirring solution of 1M HCl in ether. The resulting solid was filtered, washed with ether and dried to provide (R)—N-(4-(3-aminopiperidin-1-yl)-5-bromo-1H-pyrrolo[2,3-b]pyridin-3-yl)-5-methylpyrazine-2-carboxamide hydrochloride (40 mg, 56% yield). $^1$H NMR (400 MHz, D$_2$O) δ 8.47 (s, 1H), 8.30 (s, 1H), 8.08 (s, 1H), 7.56 (s, 1H), 3.61-3.59 (m, 1H), 3.51-3.46 (m, 1H), 3.42-3.36 (m, 1H), 3.31-3.30 (m, 1H), 2.87-2.84 (m, 1H), 2.40 (s, 3H), 2.16-2.13 (m, 1H), 1.90-1.87 (m, 1H), 1.74-1.71 (m, 1H), 1.49-1.46 (m, 1H); LCMS (APCI+) m/z 430, 432 (M+H)+.

Example 67

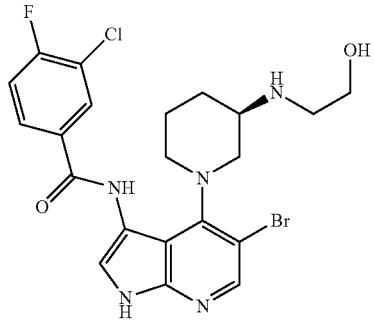

(R)-N-(5-bromo-4-(3-(2-hydroxyethylamino)piperidin-1-yl)-1H-pyrrolo[2,3-b]pyridin-3-yl)-3-chloro-4-fluorobenzamide Step A: 2-(tert-Butyldimethylsilyloxy)acetaldehyde (0.037 mL, 0.19 mmol) was added to a mixture of (R)—N-(4-(3-aminopiperidin-1-yl)-5-bromo-1H-pyrrolo[2,3-b]pyridin-3-yl)-3-chloro-4-fluorobenzamide (70 mg, 0.13 mmol, Example 62), DIEA (0.068 mL, 0.39 mmol), and trimethyl orthoformate (280 mg, 2.6 mmol) in MeOH (3 mL), and the reaction was stirred at room temperature for 18 hours. NaBH$_4$ (9.8 mg, 0.26 mmol) was then added, and the reaction was stirred for 1 hour. The mixture was poured into a saturated solution of NaHCO$_3$, and extracted with CH$_2$Cl$_2$. The combined organic fractions were dried (MgSO$_4$), filtered, and concentrated in vacuo. The residue obtained was purified by column chromatography on silica gel eluting with 2% MeOH:CH$_2$Cl$_2$ to provide (R)—N-(5-bromo-4-(3-(2-(tert-butyldimethylsilyloxy)ethylamino)piperidin-1-yl)-1H-pyrrolo[2,3-b]pyridin-3-yl)-3-chloro-4-fluorobenzamide (32 mg, 39% yield).

Step B: A solution of (R)—N-(5-bromo-4-(3-(2-(tert-butyldimethylsilyloxy)ethylamino)piperidin-1-yl)-1H-pyrrolo[2,3-b]pyridin-3-yl)-3-chloro-4-fluorobenzamide (30 mg, 0.048 mmol) in THF (2 mL) at room temperature was treated with TBAF (0.048 mL, 0.048 mmol) and stirred for 10 minutes. The mixture was then concentrated in vacuo and purified by reverse phases HPLC (Gilson). The residue obtained was dissolved in a minimal amount of DCM and added to a stirring solution of 1M HCl in ether. The solid formed was filtered, washed with ether and dried to give (R)—N-(5-bromo-4-(3-(2-hydroxyethylamino)piperidin-1-yl)-1H-pyrrolo[2,3-b]pyridin-3-yl)-3-chloro-4-fluorobenzamide hydrochloride (0.015 g, 54% yield). $^1$H NMR (400 MHz, D$_2$O) δ 8.19 (s, 1H), 7.98-7.94 (m, 1H), 7.82-7.76 (m, 1H), 7.38 (s, 1H), 7.34-7.29 (m, 1H), 3.64-3.61 (m, 2H), 3.42-2.94 (m, 7H), 1.90-1.82 (m, 1H), 1.70-1.62 (m, 1H), 1.44-1.36 (m, 2H); LCMS (APCI+) m/z 510, 512 (M+H)+.

Example 68

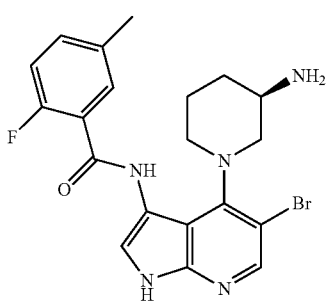

(R)-N-(4-(3-aminopiperidin-1-yl)-5-bromo-1H-pyrrolo
[2,3-b]pyridin-3-yl)-2-fluoro-5-methylbenzamide Step A: A mixture of 5-bromo-4-fluoro-1H-pyrrolo[2,3-b]pyridin-3-amine (200 mg, 0.869 mmol, Example 1, Step H), 2-fluoro-5-methylbenzoic acid (281 mg, 1.83 mmol), BOP-Cl (465 mg, 1.83 mmol), and triethylamine (0.606 mL, 4.35 mmol) in DCM (5 mL) was processed as described in Example 62, Step A, to provide N-(5-bromo-4-fluoro-1H-pyrrolo[2,3-b]pyridin-3-yl)-2-fluoro-5-methylbenzamide (200 mg, 63% yield).

Step B: A mixture of N-(5-bromo-4-fluoro-1H-pyrrolo[2,3-b]pyridin-3-yl)-2-fluoro-5-methylbenzamide (208 mg, 0.568 mmol) and (R)-tert-butyl piperidin-3-ylcarbamate (341 mg, 1.70 mmol) in n-BuOH (2 mL) was processed as described in Example 62, Step B, to provide (R)-tert-butyl 1-(5-bromo-3-(2-fluoro-5-methylbenzamido)-1H-pyrrolo[2,3-b]pyridin-4-yl)piperidin-3-ylcarbamate (120 mg, 39% yield).

Step C: A solution of (R)-tert-butyl 1-(5-bromo-3-(2-fluoro-5-methylbenzamido)-1H-pyrrolo[2,3-b]pyridin-4-yl)piperidin-3-ylcarbamate (120 mg, 0.22 mmol) in DCM (3 mL) was treated with TFA followed by 1M HCl as described in Example 62, Step C, to provide (R)—N-(4-(3-aminopiperidin-1-yl)-5-bromo-1H-pyrrolo[2,3-b]pyridin-3-yl)-2-fluoro-5-methylbenzamide hydrochloride (0.070 g, 61% yield). $^1$H NMR (400 MHz, D$_2$O) δ 8.17 (s, 1H), 7.50-7.48 (m, 1H), 7.45 (s, 1H), 7.33-7.30 (m, 1H), 7.09-7.04 (m, 1H), 3.50-3.48 (m, 1H), 3.31-3.29 (m, 2H), 3.18-3.13 (m, 1H), 3.06-3.03 (m, 1H), 1.86-1.82 (m, 1H), 1.68-1.64 (m, 1H), 1.43-1.41 (m, 2H); LCMS (APCI+) m/z 446, 448 (M+H)+.

Example 69

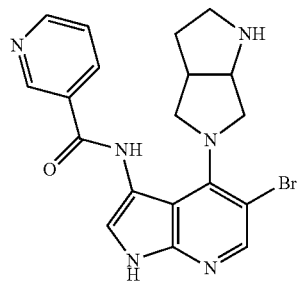

N-(5-bromo-4-(hexahydropyrrolo[3,4-b]pyrrol-5
(1H)-yl)-1H-pyrrolo[2,3-b]pyridin-3-yl)nicotinamide Step A: A mixture of N-(5-bromo-4-fluoro-1H-pyrrolo[2,3-b]pyridin-3-yl)nicotinamide (180 mg, 0.537 mmol, Example 1, Step I), tert-butyl hexahydropyrrolo[3,4-b]pyrrole-1(2H)-carboxylate hydrochloride (334 mg, 1.34 mmol), and DIEA (0.234 mL, 1.34 mmol) in n-BuOH (2 mL) was stirred at 140° C. for 5 hours in a sealed tube. The reaction was then cooled to room temperature and concentrated in vacuo. The residue obtained was purified by reverse phase HPLC (Gilson) to provide tert-butyl 5-(5-bromo-3-(nicotinamido)-1H-pyrrolo[2,3-b]pyridin-4-yl)hexahydropyrrolo[3,4-b]pyrrole-1(2H)-carboxylate (50 mg, 18% yield).

Step B: A solution of tert-butyl 5-(5-bromo-3-(nicotinamido)-1H-pyrrolo[2,3-b]pyridin-4-yl)hexahydropyrrolo[3,4-b]pyrrole-1(2H)-carboxylate (0.070 g, 0.13 mmol) in DCM (3 mL) was treated with TFA (1 mL) followed by 1M HCl in ether as described in Example 62, Step C, to provide N-(5-bromo-4-(hexahydropyrrolo[3,4-b]pyrrol-5(1H)-yl)-1H-pyrrolo[2,3-b]pyridin-3-yl)nicotinamide hydrochloride (20 mg, 28% yield). $^1$H NMR (400 MHz, D$_2$O) δ 9.15 (s, 1H), 8.84-8.83 (m, 1H), 8.78-8.75 (m, 1H), 8.24 (s, 1H), 8.00-7.96 (m, 1H), 7.43 (s, 1H), 4.15-4.11 (m, 1H), 3.97-3.92 (m, 1H), 3.73-3.69 (m, 1H), 3.65-3.61 (m, 1H), 3.54-3.50 (m, 1H), 3.27-3.23 (m, 2H), 2.91-2.87 (m, 1H), 2.00-2.94 (m, 1H), 1.88-1.86 (m, 1H); LCMS (APCI+) m/z 427, 429 (M+H)+.

Example 70

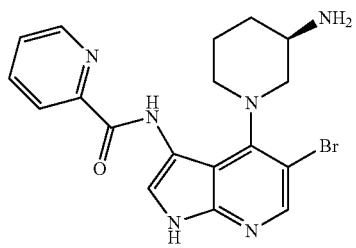

(R)-N-(4-(3-aminopiperidin-1-yl)-5-bromo-1H-pyrrolo
[2,3-b]pyridin-3-yl)picolinamide Step A: Picolinoyl chloride hydrochloride (501 mg, 2.82 mmol) was added to a solution of 5-bromo-4-fluoro-1H-pyrrolo[2,3-b]pyridin-3-amine (324 mg, 1.41 mmol, Example 1, Step H) in pyridine (5 mL). The reaction was stirred at room temperature for 10 minutes, and the pyridine was removed in vacuo. The residue obtained was dissolved in THF (5 mL), treated with 2N LiOH (3 mL), and stirred for 20 minutes. THF was then removed in vacuo, and water (20 mL) was added. The solid formed was collected by filtration and dried to provide N-(5-bromo-4-fluoro-1H-pyrrolo[2,3-b]pyridin-3-yl)picolinamide (389 mg, 82% yield) as a solid. $^1$H NMR (400 MHz, (CD$_3$)$_2$SO) δ 12.17 (br s, 1H), 10.39 (s, 1H), 8.76 (d, 1H), 8.40 (d, 1H), 8.17-8.15 (m, 1H), 8.09 (dt, 1H), 7.87 (d, 1H), 7.71-7.68 (m, 1H).

Step B: N-(5-Bromo-4-fluoro-1H-pyrrolo[2,3-b]pyridin-3-yl)picolinamide (194 mg, 0.579 mmol) and (R)-tert-butyl piperidin-3-ylcarbamate (0.348 g, 1.74 mmol) in n-BuOH (2 mL) was stirred at 149° C. for 24 hours in a sealed tube and concentrated in vacuo. The residue obtained was dissolved in ethyl acetate (20 mL) and successively washed with water (10 mL) and brine (10 mL). The organic layer was dried (MgSO$_4$), filtered, and concentrated in vacuo. The residue obtained was purified by C-18 reverse phase column chromatography (Biotage Flash 25M+) on Biotage SP4 unit eluting with gradient of 10-90% CH$_3$CN/water to provide (R)-tert-butyl 1-(5-bromo-3-(picolinamido)-1H-pyrrolo[2,3-b]pyridin-4-yl)piperidin-3-ylcarbamate. This material was dissolved in DCM (3 mL), treated with TFA (0.5 mL) and stirred at room temperature for 1 hour. The mixture was then concentrated in vacuo. The resulting residue was dissolved in DCM (1 mL) and treated with 2N HCl in ether (3 mL). The solid formed was collected by filtration and dried to give (R)—N-(4-(3-aminopiperidin-1-yl)-5-bromo-1H-pyrrolo[2,3-b]pyridin-3-yl)picolinamide hydrochloride (0.022 g, 0.0419 mmol, 7% yield) as a solid. $^1$H NMR (400 MHz, (CD$_3$)$_2$SO) δ 11.90 (br s, 1H), 11.35 (br s, 1H), 8.87 (d, 1H), 8.36 (br s, 3H), 8.31 (s, 1H), 8.21-8.11 (m, 3H), 7.74 (t, 1H), 4.04-3.94 (m, 1H), 3.76-3.67 (m, 1H), 3.58-3.48 (m, 1H), 3.43-3.34 (m, 1H), 3.08-3.00 (m, 1H), 2.44-2.37 (m, 1H), 2.27-2.14 (m, 1H), 1.90-1.81 (m, 1H), 1.63-1.51 (m, 1H); LCMS (APCI+) m/z 415.1, 417 (M+H)+.

Example 71A

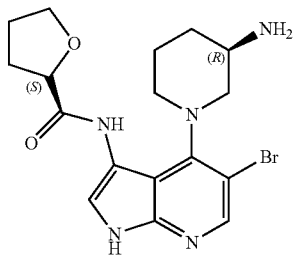

(S)-N-(4-((R)-3-Aminopiperidin-1-yl)-5-bromo-1H-pyrrolo[2,3-b]pyridin-3-yl)tetrahydrofuran-2-carboxamide Step A: A mixture of 5-bromo-4-fluoro-1H-pyrrolo[2,3-b]pyridin-3-amine (200 mg, 0.869 mmol), (S)-tetrahydrofuran-2-carboxylic acid (252 mg, 2.17 mmol), triethylamine (606 μL, 4.35 mmol), and BOP-Cl (203 mg, 2.17 mmol) in CH$_2$Cl$_2$ (10 mL) was stirred at room temperature for 7 hours. 2M LiOH (5 mL) was added then to the mixture and stirred at room temperature for 30 minutes. Water (25 mL) was then added and stirred for an additional 30 minutes. The solid formed was filtered, washed with water (3×5 mL) and dried to provide (S)—N-(5-bromo-4-fluoro-1H-pyrrolo[2,3-b]pyridin-3-yl)tetrahydrofuran-2-carboxamide (202 mg, 70.8% yield) as a solid. LCMS (APCI+) m/z 327.9, 329.9 (M+H)+; Retention time=2.80 minutes (Method 2).

Step B: A mixture of (S)—N-(5-bromo-4-fluoro-1H-pyrrolo[2,3-b]pyridin-3-yl)tetrahydrofuran-2-carboxamide (195 mg, 0.594 mmol), (R)-tert-butyl piperidin-3-ylcarbamate (357 mg, 1.78 mmol), and N-ethyl-N-isopropylpropan-2-amine (207 μL, 1.19 mmol) in n-BuOH (5 mL) were purged under N$_2$ and stirred at 160° C. in a sealed tube for 16 hours. The solvent was then removed in vacuo, and the residue obtained was purified by C-18 reverse phase column chromatography (Biotage Flash 25M+; C-18) on Biotage SP4 unit eluting with a gradient of 15-90% CH$_3$CN/water (25 CV) to provide tert-butyl (R)-1-(5-bromo-3-((S)-tetrahydrofuran-2-carboxamido)-1H-pyrrolo[2,3-b]pyridin-4-yl)piperidin-3-ylcarbamate (150 mg, 0.295 mmol, 49.6% yield) as a solid. LCMS (APCI+) m/z 508.1, 510.1 (M+H)+; Retention time=3.85 minutes (Method 2).

Step C: A solution of tert-butyl (R)-1-(5-bromo-3-((S)-tetrahydrofuran-2-carboxamido)-1H-pyrrolo[2,3-b]pyridin-4-yl)piperidin-3-ylcarbamate (150 mg, 0.295 mmol) in neat TFA (3 mL) was stirred at room temperature for 30 minutes and concentrated in vacuo. The resulting residue was purified by C-18 reverse phase flash chromatography (Biotage C-18, 12M+) on Biotage SP4 unit eluting with a gradient of 1-50% CH$_3$CN/water gradient (14 CV). The product obtained was dissolved in minimal MeOH, diluted with CH$_2$Cl$_2$ (1 mL), and treated with 1M HCl in ether (3 mL). The resulting suspension was concentrated in vacuo and evaporated from CH$_2$Cl$_2$ (3×5 mL). The solid obtained was dried under high vacuum to provide (S)—N-(4-((R)-3-aminopiperidin-1-yl)-5-bromo-1H-pyrrolo[2,3-b]pyridin-3-yl)tetrahydrofuran-2-carboxamide hydrochloride (117 mg, 0.243 mmol, 82.4% yield) as a solid. NMR (400 MHz, (CD$_3$)$_2$SO) δ 11.72 (s, 1H), 9.82 (s, 1H), 8.29 (br s, 3H), 8.21 (s, 1H), 7.89 (s, 1H), 4.39 (t, 1H), 4.02-3.97 (m, 1H), 3.85-3.79 (m, 2H), 3.63-3.55 (m, 1H), 3.42-3.35 (m, 1H), 3.33-3.21 (m, 2H), 2.97-2.89 (m, 1H), 2.27-2.19 (m, 1H), 2.17-2.09 (m, 1H), 1.97-1.92 (m, 1H), 1.89-1.83 (m, 2H), 1.79-1.73 (m, 1H), 1.49-1.40 (m, 1H); LCMS (APCI+) m/z 408, 410.1 (M+H)+; Retention time=2.18 minutes (Method 2).

Example 71B

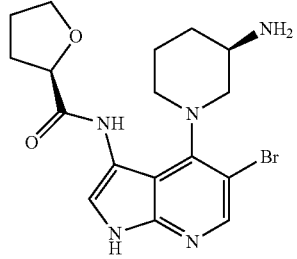

(R)-N-(4-((R)-3-Aminopiperidin-1-yl)-5-bromo-1H-pyrrolo[2,3-b]pyridin-3-yl)tetrahydrofuran-2-carboxamide Step A: A mixture of 5-bromo-4-fluoro-1H-pyrrolo[2,3-b]pyridin-3-amine (200 mg, 0.869 mmol), tetrahydrofuran-2-carboxylic acid (252 mg, 2.17 mmol), triethylamine (606 μL, 4.35 mmol), and BOP-Cl (203 mg, 2.17 mmol) in CH$_2$Cl$_2$ (10 mL) was stirred at room temperature for 7 hours. 2M LiOH (5 mL) was then added to the mixture and stirred at room temperature for 30 minutes. Water (25 mL) was then added to the mixture and stirred for an additional 30 minutes. The solid formed was filtered, washed with water (3×5 mL) and dried to provide N-(5-bromo-4-fluoro-1H-pyrrolo[2,3-b]pyridin-3-yl)tetrahydrofuran-2-carboxamide (230 mg, 80.6% yield) as a solid.

Step B: A mixture of N-(5-bromo-4-fluoro-1H-pyrrolo[2,3-b]pyridin-3-yl)tetrahydrofuran-2-carboxamide (225 mg, 0.686 mmol), (R)-tert-butyl piperidin-3-ylcarbamate (412 mg, 2.06 mmol), and N-ethyl-N-isopropylpropan-2-amine (239 μL, 1.37 mmol) in n-BuOH (5 mL) was purged under N₂ and stirred at 160° C. in a sealed tube for 16 hours. The solvent was then removed in vacuo, and the residue obtained was purified by C-18 reverse phase column chromatography (Biotage Flash 25M+; C-18) on Biotage SP4 unit eluting with a gradient of 15-90% CH₃CN/water (25 CV) to provide tert-butyl (3R)-1-(5-bromo-3-(tetrahydrofuran-2-carboxamido)-1H-pyrrolo[2,3-b]pyridin-4-yl)piperidin-3-ylcarbamate (101 mg, 0.199 mmol, 29.0% yield) as a solid.

Step C: A solution of tert-butyl (3R)-1-(5-bromo-3-(tetrahydrofuran-2-carboxamido)-1H-pyrrolo[2,3-b]pyridin-4-yl)piperidin-3-ylcarbamate in TFA (3 mL) was stirred at room temperature for 30 minutes and then concentrated in vacuo. The residue obtained was purified by C-18 reverse phase chromatography (Biotage Flash 12 M+, C-18) on Biotage SP4 unit eluting with a gradient of 1-50% CH₃CN/water (14 CV). The pure fractions containing the R-isomer (by comparing the retentions times of S-isomer, Example 71A) were pooled, concentrated in vacuo and evaporated from CH₃CN (3×5 mL). The solid residue obtained was dissolved in minimal methanol, diluted with CH₂Cl₂ (1 mL) and treated with 2M HCl in ether (3 mL). The resulting suspension was concentrated in vacuo and evaporated from CH₂Cl₂ (3×5 mL) and dried under high vacuum for 24 hours to provide (R)—N-(4-((R)-3-aminopiperidin-1-yl)-5-bromo-1H-pyrrolo[2,3-b]pyridin-3-yl)tetrahydrofuran-2-carboxamide hydrochloride (16 mg, 21% yield) as a solid. NMR (400 MHz, (CD₃)₂SO) δ 11.72 (s, 1H), 9.83 (s, 1H), 8.21 (s, 1H), 8.16 (br s, 3H), 7.89 (s, 1H), 4.37 (t, 1H), 3.96-3.91 (m, 1H), 3.85-3.79 (m, 1H), 3.55-3.48 (m, 3H), 3.26-3.20 (m, 1H), 2.97-2.91 (m, 1H), 2.28-2.20 (m, 1H), 2.15-2.09 (m, 1H), 1.94-1.81 (m, 5H), 1.48-1.40 (m, 1H); LCMS (APCI+) m/z 408.1, 410.1 (M+H)+, Retention time=2.32 minutes (Method 2).

Example 72

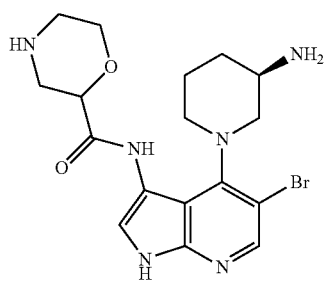

N-(4-((R)-3-Aminopiperidin-1-yl)-5-bromo-1H-pyrrolo[2,3-b]pyridin-3-yl)morpholine-2-carboxamide Step A: A mixture of 5-bromo-4-fluoro-1H-pyrrolo[2,3-b]pyridin-3-amine (350 mg, 1.52 mmol), 4-(tert-butoxycarbonyl)morpholine-2-carboxylic acid (739 mg, 3.20 mmol), BOP-Cl (813 mg, 3.20 mmol), and triethylamine (1.06 mL, 7.61 mmol) in DCM (5 mL) was stirred at room temperature for 1 hour. 3M LiOH (3 mL) was then added, and stirred for an additional 10 minutes. Water (10 mL) and DCM (10 mL) were then added, and the solid formed was filtered. The solid product was washed with DCM (10 mL) and dried to give tert-butyl 2-(5-bromo-4-fluoro-1H-pyrrolo[2,3-b]pyridin-3-ylcarbamoyl)morpholine-4-carboxylate (660 mg, 97.9% yield).

Step B: A mixture of tert-butyl 2-(5-bromo-4-fluoro-1H-pyrrolo[2,3-b]pyridin-3-ylcarbamoyl)morpholine-4-carboxylate (660 mg, 1.49 mmol), (R)-tert-butyl piperidin-3-ylcarbamate (1.49 g, 7.44 mmol), and DIEA (1.30 mL, 7.44 mmol) in n-BuOH (6 mL) was stirred at 120° C. for 36 hours. The reaction was then cooled to room temperature and concentrated in vacuo. The crude residue was purified by reverse phase HPLC (0-50% CH₃CN/water) to give the separated diastereomers of tert-butyl 2-(5-bromo-4-((R)-3-(tert-butoxycarbonylamino)piperidin-1-yl)-1H-pyrrolo[2,3-b]pyridin-3-ylcarbamoyl)morpholine-4-carboxylate in the following yields: diastereomer #1 (70 mg, 7.5%) diastereomer #2 (80 mg, 8.6%).

Step C: A solution of tert-butyl 2-(5-bromo-4-((R)-3-(tert-butoxycarbonylamino)piperidin-1-yl)-1H-pyrrolo[2,3-b]pyridin-3-ylcarbamoyl)morpholine-4-carboxylate diastereomer #1 (70 mg, 0.11 mmol) in DCM (3 mL) at room temperature was treated with TFA (1 mL), and the reaction was stirred for 1 hour. The mixture was concentrated to dryness, and the resulting residue was purified by reverse phase HPLC (0-50% ACN in water). The product isolated was dissolved in minimal DCM (with MeOH to aid solubility) and added to a stirring solution of 1M HCl in ether. The resulting solid was filtered, washed with ether and dried to give N-(4-((R)-3-aminopiperidin-1-yl)-5-bromo-1H-pyrrolo[2,3-b]pyridin-3-yl)morpholine-2-carboxamide hydrochloride diastereomer #1 (50 mg, 84% yield). ¹H NMR (400 MHz, D₂O) δ 8.18 (s, 1H), 7.59 (s, 1H), 4.54-4.48 (m, 1H), 4.21-4.17 (m, 1H), 3.98-3.91 (m, 1H), 3.67-3.64 (m, 1H), 3.47-3.31 (m, 5H), 3.20-3.13 (m, 2H), 3.09-2.98 (m, 1H), 2.11-2.07 (m, 1H), 1.80-1.76 (m, 2H), 1.55-1.53 (m, 1H); LCMS (APCI+) m/z 423, 425 (M+H)+.

Step D: A solution of tert-butyl 2-(5-bromo-4-((R)-3-(tert-butoxycarbonylamino)piperidin-1-yl)-1H-pyrrolo[2,3-b]pyridin-3-ylcarbamoyl)morpholine-4-carboxylate diastereomer #2 (80 mg, 0.13 mmol) in DCM (3 mL) at room temperature was treated with TFA (1 mL). The mixture was stirred at room temperature for 1 hour and concentrated to dryness. The resulting residue was then purified by reverse phase HPLC (0-50% ACN in water). The product isolated was next dissolved in minimal DCM (with MeOH to aid solubility) and added to a stirring solution of 1M HCl in ether. The resulting solid was filtered, washed with ether and dried to give N-(4-((R)-3-aminopiperidin-1-yl)-5-bromo-1H-pyrrolo[2,3-b]pyridin-3-yl)morpholine-2-carboxamide hydrochloride diastereomer #2 (44 mg, 64% yield). ¹H NMR (400 MHz, D₂O) δ 8.18 (s, 1H), 7.57 (s, 1H), 4.55-4.51 (m, 1H), 4.20-4.16 (m, 1H), 3.97-3.90 (m, 1H), 3.67-3.64 (m, 1H), 3.49-3.29 (m, 5H), 3.20-3.08 (m, 2H), 2.95-2.92 (m, 2.09-2.06 (m, 1H), 1.81-1.69 (m, 2H), 1.53-1.49 (m, 1H); LCMS (APCI+) m/z 423, 425 (M+H)+.

Example 73

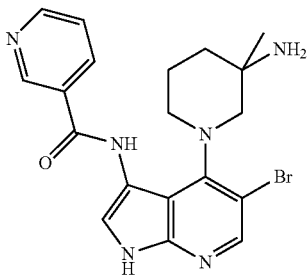

(N-(4-(3-Amino-3-methylpiperidin-1-yl)-5-bromo-1H-pyrrolo[2,3-b]pyridin-3-yl)nicotinamide N-(5-Bromo-4-fluoro-1H-pyrrolo[2,3-b]pyridin-3-yl) nicotinamide (100 mg, 0.298 mmol), tert-butyl 3-methylpiperidin-3-ylcarbamate (192 mg, 0.895 mmol) and DIEA (0.052 mL, 0.298 mmol) in n-BuOH (3 mL) were stirred at 143° C. (bath) for 24 hours. The solvent was removed, and the residue was dissolved in ethyl acetate (20 mL), washed with water (10 mL), brine (10 mL), dried (sodium sulfate), and concentrated in vacuo. The residue obtained was purified by C-18 reverse phase flash chromatography (Biotage SP4 unit, C-18 25M+ column, 10-80% CH$_3$CN/water gradient; 30 CV). The product isolated was dissolved in DCM (2 mL), and TFA (0.5 mL) was added. The mixture was stirred at room temperature for 1 hour. The solvent was then removed. The residue was dissolved in DCM (1 mL), and 2N HCl in ether (3 mL) was added. The solid formed was collected by filtration to give N-(4-(3-amino-3-methylpiperidin-1-yl)-5-bromo-1H-pyrrolo[2,3-b]pyridin-3-yl)nicotinamide hydrochloride (12.8 mg, 7.96% yield) as a solid. $^1$H NMR (400 MHz, (CD$_3$)$_2$SO) δ 12.09 (s, 1H), 10.54 (s, 1H), 9.37 (s, 1H), 8.91 (d, 1H), 8.70 (m, 1H), 8.29 (s, 1H), 8.05 (s, 3H), 7.83 (m, 1H), 7.54 (s, 1H), 3.40 (m, 2H), 3.27 (m, 1H), 3.17 (m, 2H), 1.65 (m, 2H), 1.46 (m, 1H), 2.00 (s, 3H); LCMS (APCI+) m/z 429 (M+H)+.

Example 74

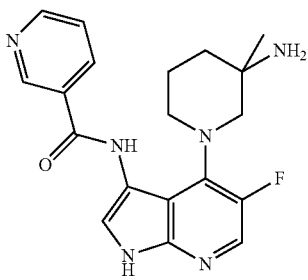

N-(4-(3-Amino-3-methylpiperidin-1-yl)-5-fluoro-1H-pyrrolo[2,3-b]pyridin-3-yl)nicotinamide A mixture of N-(4,5-difluoro-1H-pyrrolo[2,3-b]pyridin-3-yl)nicotinamide (50 mg, 0.18 mmol; Example 13, Step D), tert-butyl 3-methylpiperidin-3-ylcarbamate (78 mg, 0.37 mmol, Example C) and DIEA (0.032 mL, 0.182 mmol) in n-BuOH (1 mL) was stirred at 150° C. (bath) for 24 hours in a sealed tube. The solvent was removed, and the resulting residue was dissolved in ethyl acetate (20 mL), washed with water (10 mL), brine (10 mL), dried (sodium sulfate) and concentrated in vacuo. The residue obtained was purified by C-18 reverse phase flash chromatography (Biotage SP4 unit, C-18 25M column, 10-80% CH$_3$CN/water gradient; 30 CV). The product isolated was dissolved in DCM (2 mL), and TFA (0.5 mL) was added. The mixture was stirred at room temperature for 1 hour. The solvent was removed. The residue was dissolved in MeOH (1 mL), and 2N HCl in ether (3 mL) was added. The solid formed was collected by filtration to give N-(4-(3-amino-3-methylpiperidin-1-yl)-5-fluoro-1H-pyrrolo[2,3-b]pyridin-3-yl)nicotinamide hydrochloride (0.050 g, 56%) as a solid. $^1$H NMR (400 MHz, (CD$_3$)$_2$SO) δ 12.04 (s, 1H), 11.03 (s, 1H), 9.49 (s, 1H), 8.95 (m, 2H), 8.27 (s, 2H), 8.18 (d, 1H), 7.93 (m, 1H), 7.53 (d, 1H), 3.43 (m, 1H), 3.36 (m, 2H), 3.04 (m, 1H), 1.71 (m, 1H), 1.51 (m, 2H), 1.31 (m, 1H), 1.22 (s, 3H). LCMS (APCI+) m/z 369 (M+H)+.

Example 75

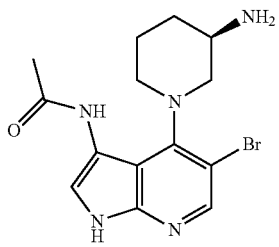

(R)-N-(4-(3-Aminopiperidin-1-yl)-5-bromo-1H-pyrrolo [2,3-b]pyridin-3-yl)acetamide Step A: 5-Bromo-4-fluoro-1H-pyrrolo[2,3-b]pyridin-3-amine (750 mg, 3.26 mmol; Example 1, Step H), TEA (1.4 mL, 9.78 mmol), and Ac$_2$O (0.7 mL, 6.85 mmol) were placed in THF (15 mL) and stirred for 30 minutes. The reaction mixture was filtered, and the solid was dried to provide N-(5-bromo-4-fluoro-1H-pyrrolo[2,3-b]pyridin-3-yl)acetamide (595 mg, 67% yield), which was used without further purification.

Step B: N-(5-Bromo-4-fluoro-1H-pyrrolo[2,3-b]pyridin-3-yl)acetamide (400 mg, 1.47 mmol) and (R)-tert-butyl piperidin-3-ylcarbamate (1.0 g, 5.15 mmol) were placed in n-butanol (4 mL) and heated to 155° C. in a sealed tube for 18 hours. The reaction was then cooled and concentrated. The resulting residue was purified by C-18 reverse phase flash chromatography (Biotage Horizon unit, C-18 25M column, 5-85% CH$_3$CN/water) to give (R)-tert-butyl 1-(3-acetamido-5-bromo-1H-pyrrolo[2,3-b]pyridin-4-yl)piperidin-3-ylcarbamate (543 mg, 77% yield).

Step C: (R)-tert-Butyl 1-(3-acetamido-5-bromo-1H-pyrrolo[2,3-b]pyridin-4-yl)piperidin-3-ylcarbamate (70 mg, 0.15 mmol) was placed in TFA (2 mL) and stirred for 30 minutes. The reaction was then concentrated, and the residue was purified by C-18 reverse phase flash chromatography (Biotage Horizon unit, C-18 12M column, 0-45% CH$_3$CN/water with 0.1% TFA). The product was then dissolved in 10% MeOH in DCM (2 mL) and added dropwise to a stirred solution of 2M HCl in ether. The precipitate was filtered and dried to provide (R)—N-(4-(3-aminopiperidin-1-yl)-5-bromo-1H-pyrrolo[2,3-b]pyridin-3-yl)acetamide hydrochloride (15 mg, 23% yield). $^1$H NMR (400 MHz, D$_2$O) δ 8.21 (s, 1H), 7.26 (s, 1H), 3.58 (d, 1H), 3.49 (s, 1H), 3.25-3.10 (m, 3H), 2.11 (s, 3H), 2.05 (m, 1H), 1.80 (m, 1H), 1.69-1.50 (m, 2H). LCMS (APCI+) m/z 351.9 (M+H)+, Retention time=1.87 minutes (Method 3).

Example 76

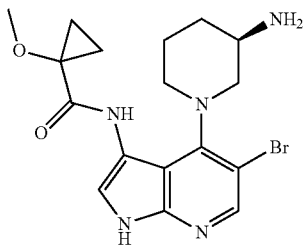

(R)-N-(4-(3-Aminopiperidin-1-yl)-5-bromo-1H-pyrrolo[2,3-b]pyridin-3-yl)-1-methoxycyclopropanecarboxamide Step A: NaH (738 mg, 18.44 mmol; 60% dispersion in oil) was added to a solution of methyl 1-hydroxycyclopropanecarboxylate (1.83 g, 14.18 mmol) in anhydrous THF (15 mL) cooled on an ice bath. The mixture was stirred for 15 minutes then iodomethane (3.22 g, 1.42 mL, 22.69 mmol) was added slowly, and the resulting mixture stirred at ambient temperature for 18 hours. The reaction mixture was quenched with ammonium chloride and extracted with EtOAc (3×20 mL). The combined organic extracts were washed with water, dried over MgSO$_4$, and filtered. The filtrate was evaporated under reduced pressure to give methyl 1-methoxycyclopropanecarboxylate. An aqueous 6N NaOH solution (4 mL) was added to a solution of methyl 1-methoxycyclopropanecarboxylate (1.08 g, 8.3 mmol) in anhydrous THF (5 mL). The mixture was stirred at room temperature for 18 hours, then acidified with aqueous 6N HCl and extracted with EtOAc (3×15 mL). The combined organic layer was dried over MgSO$_4$, filtered and concentrated to give 1-methoxycyclopropanecarboxylic acid (892 mg, 54% yield) as an oil. $^1$H NMR (400 MHz, (CD$_3$)$_2$SO) δ 12.40 (br s, 1H), 3.30 (s, 3H), 1.15-1.10 (m, 2H), 1.08-1.04 (m, 2H).

Step B: Triethylamine (550 mg, 0.757 mL, 5.43 mmol) was slowly added to a mixture of 5-bromo-4-fluoro-1H-indol-3-amine (250 mg, 1.087 mmol, Example 1, step H), 1-methyl-cyclopropanecarboxylic acid (151 mg, 1.30 mmol) and bis(2-oxooxazolidin-3-yl)phosphinic chloride (415 mg, 1.63 mmol) in anhydrous dichloromethane (10 mL). The resulting solution was stirred at room temperature for 3 hours. The mixture was concentrated, and the residue purified by reverse phase chromatography (Biotage SP4 C-18 25M column, 10-75% CH$_3$CN/water, 25CV) to give N-(5-bromo-4-fluoro-1H-pyrrolo[2,3-b]pyridin-3-yl)-1-methoxycyclopropanecarboxamide (216.5 mg, 60%) as a solid. $^1$H NMR (400 MHz, (CD$_3$)$_2$SO) δ 12.04 (br s, 1H), 9.57 (s, 1H), 8.36 (d, 1H), 7.54 (d, 1H), 3.39 (s, 3H), 1.16-1.11 (m, 4H). LCMS (APCI+) m/z 327.9 (M+H)+, Retention time=2.96 minutes.

Step C: (R)-tert-Butyl piperidin-3-ylcarbamate (366 mg, 1.83 mmol) was added to a suspension of N-(5-bromo-4-fluoro-1H-pyrrolo[2,3-b]pyridin-3-yl)-1-methoxycyclopropanecarboxamide (200 mg, 0.61 mmol) in n-BuOH (3 mL). The resulting mixture was heated in a sealed tube at 160° C. for 24 hours. The cooled mixture was diluted with water (40 mL) and extracted with EtOAc (3×20 mL). The combined organic layers were dried over MgSO$_4$ and filtered, and the filtrate was concentrated. The residue was purified by reverse phase chromatography (Biotage SP4, C-18 25M+, 15-85% CH$_3$CN/water, 25CV) to give (R)-tert-butyl 1-(5-bromo-3-(1-methoxycyclopropanecarboxamido)-1H-pyrrolo[2,3-b]pyridin-4-yl)piperidin-3-ylcarbamate (103 mg, 33% yield) as a solid. LCMS (APCI+) m/z 510 (M+2H)+, Retention time=3.84 minutes.

Step D: (R)-tert-Butyl 1-(5-bromo-3-(1-methoxycyclopropanecarboxamido)-1H-pyrrolo[2,3-b]pyridin-4-yl)piperidin-3-ylcarbamate (103 mg, 0.203 mmol) was stirred in trifluoroacetic acid (3 mL) at room temperature for 1.5 hours. The solvent was evaporated in vacuo, and the residue was purified by reverse phase chromatography (Biotage SP4, C-18 12M+, 1-50% CH$_3$CN/water, 16CV). The isolated product was taken up in a minimal volume of methanol and added to a stirred solution of 2N HCl-Et$_2$O. The salt formed was collected by filtration, washed with acetonitrile and dried under vacuum to give (R)—N-(4-(3-aminopiperidin-1-yl)-5-bromo-1H-pyrrolo[2,3-b]pyridin-3-yl)-1-methoxycyclopropanecarboxamide hydrochloride (28 mg, 28% yield) as a solid. $^1$H NMR (400 MHz, D$_2$O) δ 8.30 (s, 1H), 7.36 (s, 1H), 3.75-3.67 (m, 1H), 3.60-3.49 (m, 1H), 3.39-3.33 (m, 3H), 3.30-3.13 (m, 3H), 2.12-2.03 (m, 1H), 1.85-1.76 (m, 1H), 1.74-1.62 (m, 1H), 1.60-1.49 (m, 1H), 1.31-1.13 (m, 4H). LCMS (APCI+) m/z 408, 410 (M+H)+, Retention time=2.14 minutes.

Example 77

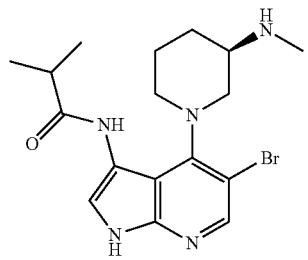

(R)-N-(5-Bromo-4-(3-(methylamino)piperidin-1-yl)-1H-pyrrolo[2,3-b]pyridin-3-yl)isobutyramide Step A: Triethylamine (0.757 mL, 5.43 mmol) was added dropwise to a mixture of 5-bromo-4-fluoro-1H-pyrrolo[2,3-b]pyridin-3-amine (250 mg, 1.087 mmol; Example 1, Step H) and isobutyl chloride (139 mg, 0.137 mL, 1.30 mmol) in dry dichloromethane (10 mL) cooled on an ice-bath, and the solution was stirred at room temperature for 3 hours. The mixture was concentrated. The residue was stirred in THF (10 mL), treated with an aqueous 2N LiOH solution (3 mL), and the resulting mixture was stirred at room temperature for 1 hour. The organic solvent was evaporated in vacuo, and the residue was stirred in water (20 mL). The solid, which separated, was collected by filtration, washed with water and dichloromethane (10 mL), and dried to N-(5-bromo-4-fluoro-1H-pyrrolo[2,3-b]pyridin-3-yl)isobutyramide (228.5 mg, 70% yield) as a solid. $^1$H NMR (400 MHz, (CD$_3$)$_2$SO) δ 12.04 (br s, 1H), 9.41 (s, 1H), 8.34 (d, 1H), 7.56 (s, 1H), 2.72-2.60 (m, 1H), 1.11 (d, 6H). LCMS (APCI+) m/z 299.9 (M+H)+, Retention time=2.80 minutes.

Step B: (R)-tert-Butyl methyl(piperidin-3-yl)carbamate (471 mg, 2.20 mmol; Example E) was added to a suspension of N-(5-bromo-4-fluoro-1H-pyrrolo[2,3-b]pyridin-3-yl)isobutyramide (220 mg, 0.733 mmol) in n-BuOH (2.5 mL). The resulting mixture was heated in a sealed tube at 160° C. for 24 hours. The cooled mixture was diluted with water (40 mL) and extracted with EtOAc (3×20 mL). The combined organic layer was dried over MgSO$_4$, filtered and concentrated. The residue was purified by reverse phase chromatography (Biotage SP4, C-18 25M+, 15-90% CH$_3$CN/water, 25CV) to give (R)-tert-butyl 1-(5-bromo-3-isobutyramido-1H-pyrrolo[2,3-b]pyridin-4-yl)piperidin-3-yl(methyl)carbamate (48 mg, 13% yield) as a solid. LCMS (APCI+) m/z 494.1, 497.1 (M+H)+, Retention time=4.18 minutes.

Step C: (R)-tert-Butyl 1-(5-bromo-3-isobutyramido-1H-pyrrolo[2,3-b]pyridin-4-yl)piperidin-3-yl(methyl)carbamate (65 mg, 0.12 mmol) was stirred in trifluoroacetic acid (3 mL) at room temperature for 1.5 hours. The solvent was evaporated in vacuo, and the residue was purified by reverse phase chromatography (Biotage SP4, C-18 12M+, 2-50% CH3CN/water, 16CV). The isolated product was taken up in a minimal volume of methanol and added to a stirred solution of 2N HCl-Et$_2$O. The salt formed was collected by filtration, washed with acetonitrile and dried under vacuum to give (R)—N-(5-bromo-4-(3-(methylamino)piperidin-1-yl)-1H-pyrrolo[2,3-b]pyridin-3-yl)isobutyramide hydrochloride (29 mg, 64% yield) as a solid. $^1$H NMR (400 MHz, (CD$_3$)$_2$SO) δ 11.81 (br s, 1H), 9.23 (s, 2H), 8.25 (s, 1H), 7.60 (s, 1H), 3.60-3.45 (m, 2H), 3.35-3.20 (m, 2H), 3.15-3.05 (m, 1H), 2.74-2.63 (m, 1H), 2.57 (t, 3H), 2.32-2.20 (m, 1H), 1.95-1.84 (m, 1H), 1.74-1.60 (m, 1H), 1.58-1.43 (m, 1H), 1.16 (d, 6H). LCMS (APCI+) m/z 396.1, 397.1 (M+2H)+, Retention time=2.13 minutes.

Example 78

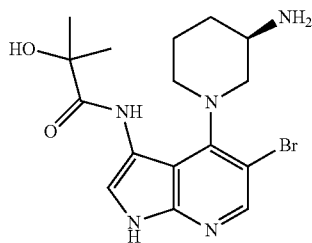

(R)-N-(4-(3-Aminopiperidin-1-yl)-5-bromo-1H-pyrrolo[2,3-b]pyridin-3-yl)-2-hydroxy-2-methylpropanamide Step A: 1-Chloro-2-methyl-1-oxopropan-2-yl acetate (215 mg, 1.30 mmol) in dry dichloromethane (2 mL) was added dropwise to a solution of 5-bromo-4-fluoro-1H-pyrrolo[2,3-b]pyridin-3-amine (250 mg, 1.087 mmol; Example 1, Step H) and triethylamine (550 mg, 0.757 mL, 5.43 mmol) in dry dichloromethane (10 mL) cooled on an ice-bath. The resulting solution was stirred at room temperature for 1 hour. The solvent was evaporated. The residue was then stirred in THF (10 mL), treated with an aqueous 2N LiOH solution (3 mL), and stirred at room temperature for 18 hours. The mixture was evaporated under reduced pressure, and the residue dissolved in EtOAc and washed with water (3×20 mL). The organic layer was dried over MgSO$_4$, filtered and concentrated to give N-(5-bromo-4-fluoro-1H-pyrrolo[2,3-b]pyridin-3-yl)-2-hydroxy-2-methylpropanamide (289 mg, 84% yield) as a solid. $^1$H NMR (400 MHz, (CD$_3$)$_2$SO) δ 12.03 (br s, 1H), 9.27 (s, 1H), 8.36 (d, 1H), 7.69 (d, 1H), 5.84 (s, 1H), 1.37 (s, 6H); LCMS (APCI+) m/z 317.9 (M+H)+, Retention time=2.51 minutes.

Step B: (R)-tert-Butyl piperidin-3-ylcarbamate (538 mg, 2.69 mmol) and N,N-diisopropylethylamine (347 mg, 0.468 mL, 2.69 mmol) were added to a suspension of N-(5-bromo-4-fluoro-1H-pyrrolo[2,3-b]pyridin-3-yl)-2-hydroxy-2-methylpropanamide (283 mg, 0.895 mmol) in n-BuOH (3 mL). The resulting mixture was heated at 150° C. in a sealed tube for 24 hours. The cooled mixture was diluted with water and extracted with EtOAc (3×20 mL). The combined organic layers were dried over MgSO$_4$ and filtered, and the filtrate concentrated to an oil and purified by reverse phase chromatography (Biotage SP4, C-18 25M+, 15-75% CH$_3$CN/water, 25CV) to give (R)-tert-butyl 1-(5-bromo-3-(2-hydroxy-2-methylpropanamido)-1H-pyrrolo[2,3-b]pyridin-4-yl)piperidin-3-ylcarbamate (242 mg, 55% yield) as a solid. LCMS (APCI+) m/z 496.2, 498.2 (M+H)+, Retention time=3.53 minutes.

Step C: (R)-tert-Butyl 1-(5-bromo-3-(2-hydroxy-2-methylpropanamido)-1H-pyrrolo[2,3-b]pyridin-4-yl)piperidin-3-ylcarbamate (242 mg, 0.488 mmol) was stirred at room temperature in trifluoroacetic acid (3 mL) for 1.5 hours. The TFA was evaporated in vacuo, and the residue was purified by reverse phase chromatography (Biotage SP4, C-18 12M+, 2-55% CH$_3$CN/water, 16CV). The isolated product was taken up in a minimal volume of methanol and added to a stirred solution of 2N HCl-Et$_2$O. The salt formed was collected by filtration, washed with acetonitrile and dried under vacuum to give (R)—N-(4-(3-aminopiperidin-1-yl)-5-bromo-1H-pyrrolo[2,3-b]pyridin-3-yl)-2-hydroxy-2-methylpropanamide hydrochloride (200 mg, 87% yield) as a solid. $^1$H NMR (400 MHz, (CD$_3$)$_2$SO) δ 11.71 (br s, 1H), 10.23 (s, 1H), 8.32 (br s, 2H), 8.25 (s, 1H), 7.96 (d, 1H), 3.69-3.48 (m, 3H), 3.34-3.23 (m, 1H), 3.05-2.92 (m, 1H), 2.14-2.05 (m, 2H), 1.86-1.75 (m, 1H), 1.55-1.43 (m, 1H), 1.39 (d, 6H); LCMS (APCI+) m/z 396, 398 (M+H)+, Retention time=2.14 minutes.

Example 79

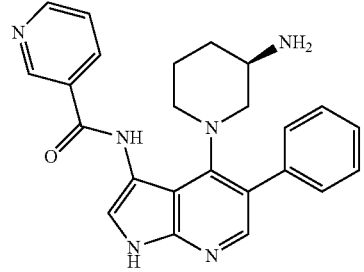

(R)-N-(4-(3-Aminopiperidin-1-yl)-5-phenyl-1H-pyrrolo[2,3-b]pyridin-3-yl)nicotinamide Step A: Phenylboronic acid (28.4 mg, 0.233 mmol), PS-palladium tetrakis (88.2 mg, 0.00970 mmol, 0.10 mmol/1 g) and 2N sodium carbonate (194 µL, 0.388 mmol) were added to (R)-tert-butyl 1-(5-bromo-3-(nicotinamido)-1H-pyrrolo[2,3-b]pyridin-4-yl)piperidin-3-ylcarbamate (100 mg, 0.194 mmol; Example 1A, Step 1) in degassed dioxane (1 mL). The reaction was heated to 150° C. for 1 hour under microwave irradiation. Phenylboronic acid (28.4 mg, 0.233 mmol) and 2N sodium carbonate (194 µL, 0.388 mmol) were added, and the reaction was heated to 150° C. for an additional 2 hours under microwave irradiation and then cooled down and filtered. The filtrate was diluted with DCM, dried with MgSO$_4$, filtered, and concentrated. The resulting residue was purified by reverse phase chromatography (Biotage Horizon, C-18 25M+, 10-90% CH$_3$CN/water) to yield (R)-tert-butyl 1-(3-(nicotinamido)-5-phenyl-1H-pyrrolo[2,3-b]pyridin-4-yl)piperidin-3-ylcarbamate (60 mg, 60% yield) as a solid.

Step B: (R)-tert-Butyl 1-(3-(nicotinamido)-5-phenyl-1H-pyrrolo[2,3-b]pyridin-4-yl)piperidin-3-ylcarbamate (60 mg, 0.12 mmol) in TFA (2 mL) was stirred for 30 minutes. The reaction was concentrated, and the residue was purified by C-18 reverse phase flash chromatography (Biotage Horizon unit, C-18 12S column, 0-45% CH₃CN/water with 0.1% TFA). The resulting solid was dissolved in 10% MeOH in DCM (2 mL) and added dropwise to a stirring solution of 2M HCl in ether. Concentration yielded (R)—N-(4-(3-aminopiperidin-1-yl)-5-phenyl-1H-pyrrolo[2,3-b]pyridin-3-yl)nicotinamide hydrochloride as a solid (24 mg, 39% yield). $^1$H NMR (400 MHz, D$_2$O) δ 9.14 (s, 1H), 8.81 (s, 1H), 8.71 (d, 1H), 7.91 (m, 2H), 7.50-7.31 (m, 6H), 3.56 (m, 1H), 3.26 (m, 1H), 2.89 (m, 1H), 2.45 (m, 2H), 1.69 (m, 1H), 1.36 (m, 1H), 1.25-1.00 (m, 2H). LCMS (APCI+) m/z 413.1 (M+H)+, Retention time=2.25 minutes (Method 3).

Example 80

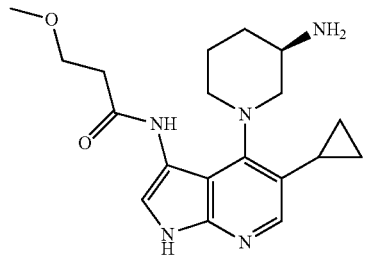

(R)-N-(4-(3-Aminopiperidin-1-yl)-5-cyclopropyl-1H-pyrrolo[2,3-b]pyridin-3-yl)-3-methoxypropanamide Step A: di-tert-Butyl dicarbonate (422 mg, 1.93 mmol), triethylamine (674 µL, 4.83 mmol), and N,N-dimethylpyridin-4-amine (98.4 mg, 0.806 mmol) was added to a solution of (R)-tert-butyl 1-(5-bromo-3-(3-methoxypropanamido)-1H-pyrrolo[2,3-b]pyridin-4-yl)piperidin-3-ylcarbamate (800 mg, 1.61 mmol; Example 54, Step B) in CH₂Cl₂ (15 mL). The mixture was then stirred at room temperature. After 18 hours, additional di-tert-butyl dicarbonate (422 mg, 1.93 mmol) and triethylamine (674 µL, 4.83 mmol) were added, and the mixture was stirred at room temperature for 5 hours. The mixture was then poured into water, and the layers were separated. The aqueous phase was extracted with CH₂Cl₂ (2×30 mL), and the combined organic layers were dried (MgSO₄), filtered, and concentrated in vacuo. The crude was purified by flash chromatography on silica gel (Biotage Flash 40S+, 40% EtOAc/hexane) to provide the (R)-tert-butyl 5-bromo-4-(3-(tert-butoxycarbonylamino)piperidin-1-yl)-3-(3-methoxypropanamido)-1H-pyrrolo[2,3-b]pyridine-1-carboxylate (378 mg, 39% yield) as a solid. LCMS (APCI+) m/z 596.2, 598 (M+H)+.

Step B: A mixture of (R)-tert-butyl 5-bromo-4-(3-(tert-butoxycarbonylamino)piperidin-1-yl)-3-(3-methoxypropanamido)-1H-pyrrolo[2,3-b]pyridine-1-carboxylate (370 mg, 0.620 mmol), cyclopropylboronic acid (213 mg, 2.48 mmol), tricyclohexylphosphine (20.9 mg, 0.0744 mmol), K₃PO₄ (461 mg, 2.17 mmol), and diacetoxypalladium (13.9 mg, 0.0620 mmol) in toluene/water (10:1 mixture, 9 mL) was stirred at 80° C. for 22 hours. The mixture was then diluted with EtOAc (60 mL) and water (10 mL) was added. The layers were separated, and the aqueous layer was extracted with EtOAc (3×20 mL). The combined organic layers were dried (MgSO₄), filtered, and concentrated in vacuo. The oily residue was purified by reverse phase chromatography (Biotage SP4, C-18 25M+, 20%-90% CH₃CN/water, 24CV) to provide (R)-tert-butyl 4-(3-(tert-butoxycarbonylamino)piperidin-1-yl)-5-cyclopropyl-3-(3-methoxypropanamido)-1H-pyrrolo[2,3-b]pyridine-1-carboxylate (77 mg, 22% yield) as a solid. LCMS (APCI+) m/z 558 (M+H)+.

Step C: A solution of (R)-tert-butyl 4-(3-(tert-butoxycarbonylamino)piperidin-1-yl)-5-cyclopropyl-3-(3-methoxypropanamido)-1H-pyrrolo[2,3-b]pyridine-1-carboxylate (70 mg, 0.13 mmol) in neat TFA was stirred at room temperature for 50 minutes and concentrated in vacuo. The residue was dissolved in a mixture of MeOH:CH₂Cl₂ (1:2, 1 mL) and 2M HCl in ether was added. The suspension formed was concentrated in vacuo and rinsed with CH₂Cl₂ (2×2 mL) and triturated with CH₃CN (3 mL). The resulting solid was dried under high vacuum to provide (R)—N-(4-(3-aminopiperidin-1-yl)-5-cyclopropyl-1H-pyrrolo[2,3-b]pyridin-3-yl)-3-methoxypropanamide hydrochloride (15 mg, 33% yield) as a solid. $^1$H NMR (400 MHz, (CD₃)₂SO) δ 12.06 (s, 1H), 9.56 (s, 1H), 8.28 (br s, 3H), 7.94 (s, 1H), 7.41 (d, 1H), 3.82-3.76 (m, 1H), 3.59 (t, 2H), 3.42-3.33 (m, 3H), 3.30-3.27 (m, 1H), 3.22 (s, 3H), 2.60 (t, 2H), 2.10-2.05 (m, 1H), 2.01-1.97 (m, 1H), 1.81-1.75 (m, 1H), 1.70-1.62 (m, 1H), 1.56-1.48 (m, 1H), 1.01-0.95 (m, 2H), 0.75-0.69 (m, 2H). LCMS (APCI+) m/z 358.1 (M+H)+.

Example 81

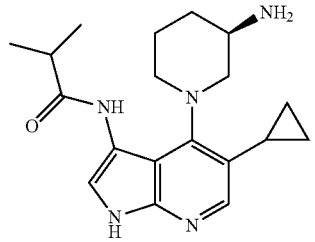

(R)-N-(4-(3-Aminopiperidin-1-yl)-5-cyclopropyl-1H-pyrrolo[2,3-b]pyridin-3-yl)isobutyramide Step A: (R)-tert-Butyl 1-(5-bromo-3-isobutyramido-1H-pyrrolo[2,3-b]pyridin-4-yl)piperidin-3-ylcarbamate (0.300 g, 0.624 mmol; Example 15, Step B) was placed in DCM (8 mL). Boc₂O (0.150 g, 0.687 mmol) and triethylamine (0.261 mL, 1.87 mmol) were then added, followed by the addition of DMAP (0.0381 g, 0.312 mmol). The reaction was stirred for an additional 30 minutes, then poured into water, and extracted with DCM. The combined organic fractions were dried (MgSO₄), filtered, and concentrated to give the crude product, which was purified by chromatography (500:8 DCM:MeOH) to give (R)-tert-butyl 5-bromo-4-(3-(tert-butoxycarbonylamino)piperidin-1-yl)-3-isobutyramido-1H-pyrrolo[2,3-b]pyridine-1-carboxylate (0.33 g, 91% yield).

Step B: (R)-tert-Butyl 5-bromo-4-(3-(tert-butoxycarbonylamino)piperidin-1-yl)-3-isobutyramido-1H-pyrrolo[2,3-b]pyridine-1-carboxylate (0.340 g, 0.586 mmol), cyclopropylboronic acid (0.201 g, 2.34 mmol), K₃PO₄ (0.435 g, 2.05 mmol), Pd(OAc)₂ (0.0131 g, 0.0586 mmol), and P(Cy)₃ (0.0197 g, 0.0703 mmol) were placed in 10:1 toluene:water (4.4 mL total volume) and degassed under argon and then heated to 80° C. for 18 hours. The reaction was then cooled to room temperature, poured into water and extracted with DCM. The organic fraction was dried, filtered, and concentrated to give the crude product that was purified by reverse phase chromatography (Biotage SP4, C-18 25M+, 5-95% CH₃CN/H₂O) to give both (R)-tert-butyl 4-(3-(tert-butoxycarbonylamino)piperidin-1-yl)-5-cyclopropyl-3-isobutyramido-1H-pyrrolo[2,3-b]pyridine-1-carboxylate (0.15 g, 47% yield) and a small amount of (R)-tert-butyl 4-(3-(tert-butoxycarbonylamino)piperidin-1-yl)-3-isobutyramido-1H-pyrrolo[2,3-b]pyridine-1-carboxylate (0.01 g, 3% yield).

Step C: (R)-tert-Butyl 4-(3-(tert-butoxycarbonylamino)piperidin-1-yl)-5-cyclopropyl-3-isobutyramido-1H-pyrrolo[2,3-b]pyridine-1-carboxylate (0.150 g, 0.277 mmol) was placed in DCM (5 mL). TFA (1 mL) was then added, and the reaction was stirred at room temperature for 1 hour and concentrated to dryness. The resulting product was dissolved in minimal DCM (with MeOH to aid solubility) and added to a stirred solution of 1M HCl in ether. The resulting solid was filtered, washed with ether and dried to give (R)—N-(4-(3-aminopiperidin-1-yl)-5-cyclopropyl-1H-pyrrolo[2,3-b]pyridin-3-yl)isobutyramide hydrochloride (0.085 g, 74% yield) as a solid. ¹H NMR (400 MHz, D₂O) δ 7.88 (s, 1H), 7.25 (s, 1H), 3.96-3.93 (m, 1H) 3.53-3.49 (m, 1H) 3.42-3.37 (m, 2H), 3.32-3.27 (m, 1H), 3.22-3.17 (m, 1H), 2.70-3.63 (m, 1H), 2.14-2.12 (m, 1H), 1.89-1.86 (m, 1H), 1.80-1.77 (m, 1H), 1.69-1.66 (m, 1H), 1.54-1.52 (m, 1H), 1.12-1.09 (m, 6H), 0.99-0.96 (m, 2H), 0.66-0.62 (m, 2H); LCMS (APCI+) m/z 342 (M+H)+.

Example 82

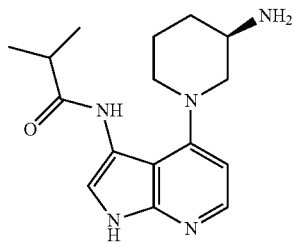

(R)-N-(4-(3-Aminopiperidin-1-yl)-1H-pyrrolo[2,3-b]pyridin-3-yl)isobutyramide (R)-tert-Butyl 4-(3-(tert-butoxycarbonylamino)piperidin-1-yl)-3-isobutyramido-1H-pyrrolo[2,3-b]pyridine-1-carboxylate (0.010 g, 0.020 mmol; Example 81, Step B) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 12M+, 0-50% ACN in water). The resulting product was next dissolved in minimal DCM (with MeOH to aid solubility) and added to a stirred solution of 1M HCl in ether. The resulting solid was filtered, washed with ether and dried to give (R)—N-(4-(3-aminopiperidin-1-yl)-1H-pyrrolo[2,3-b]pyridin-3-yl)isobutyramide hydrochloride (0.002 g, 27% yield). LCMS (APCI+) m/z 302 (M+H)+.

Example 83

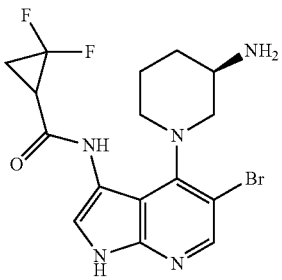

N-(4-((R)-3-Aminopiperidin-1-yl)-5-bromo-1H-pyrrolo[2,3-b]pyridin-3-yl)-2,2-difluorocyclopropanecarboxamide Step A: A mixture of 5-bromo-4-fluoro-1H-pyrrolo[2,3-b]pyridin-3-amine (200 mg, 0.869 mmol; Example 1, Step H), 2,2-difluorocyclopropanecarboxylic acid (212 mg, 1.74 mmol), and triethylamine (606 µL, 4.35 mmol) in CH₂Cl₂ (5 mL) at room temperature was treated with BOP-Cl (162 mg, 1.74 mmol). The mixture was stirred at room temperature for 18 hours. 2M LiOH.H₂O (3 mL) was then added to the mixture and stirred for 30 minutes. Water (10 mL) was added, and the formed solid was filtered, washed with additional water (3×5 mL), and dried to provide N-(5-bromo-4-fluoro-1H-pyrrolo[2,3-b]pyridin-3-yl)-2,2-difluorocyclopropanecarboxamide (158 mg, 54% yield) as a solid. LCMS (APCI+) m/z 334, 336 (M+H)+.

Step B: A sealed tube was charged with N-(5-bromo-4-fluoro-1H-pyrrolo[2,3-b]pyridin-3-yl)-2,2-difluorocyclopropanecarboxamide (150 mg, 0.449 mmol), (R)-tert-butyl piperidin-3-ylcarbamate (270 mg, 1.35 mmol), N-ethyl-N-isopropylpropan-2-amine (235 µL, 1.35 mmol) and n-BuOH (3 mL). Then N₂ was bubbled through the mixture for 5 minutes. The tube was sealed under N₂ and stirred at 120° C. for 5 hours and then at 130° C. for 48 hours. The mixture was concentrated in vacuo, and the residue was purified by reverse phase chromatography (Biotage SP4, C-18 25M+, 15-85% CH₃CN/water, 23 CV) to yield tert-butyl (3R)-1-(5-bromo-3-(2,2-difluorocyclopropanecarboxamido)-1H-pyrrolo[2,3-b]pyridin-4-yl)piperidin-3-ylcarbamate (81 mg, 35% yield) as a solid. LCMS (APCI+) m/z 514.1, 516.1 (M+H)+.

Step C: A solution of tert-butyl (3R)-1-(5-bromo-3-(2,2-difluorocyclopropanecarboxamido)-1H-pyrrolo[2,3-b]pyridin-4-yl)piperidin-3-ylcarbamate (80 mg, 0.16 mmol) in neat TFA (2 mL) was stirred at room temperature for 30 minutes and concentrated in vacuo. The residue was purified by reverse phase chromatography (Biotage SP4, C-18 12M+, 0-40% CH₃CN/water, 14 CV). The residue was dissolved in MeOH (1 mL) and added dropwise to a 2N HCl in ether solution. The resulting solid was filtered and dried to yield N-(4-((R)-3-aminopiperidin-1-yl)-5-bromo-1H-pyrrolo[2,3-b]pyridin-3-yl)-2,2-difluorocyclopropanecarboxamide hydrochloride (15 mg, 20% yield) as a solid. ¹H NMR (400 MHz, (CD₃)₂SO) δ 11.91 (d, 1H), 9.87 (br s, 1H), 8.25 (br s, 3H), 8.23 (s, 1H), 7.52 (s, 1H), 3.49-3.42 (m, 3H), 3.21-3.15 (m, 1H), 3.09-3.02 (m, 2H), 2.12-2.09 (m, 1H), 2.05-1.98 (m, 2H), 1.83-1.75 (m, 2H), 1.54-1.44 (m, 1H). LCMS (APCI+) m/z 414, 416 (M+H)+.

Example 84

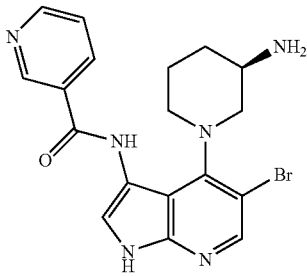

(R)-N-(4-(3-Aminopiperidin-1-yl)-1H-pyrrolo[2,3-b]pyridin-3-yl)nicotinamide (R)-tert-Butyl 1-(5-bromo-3-(nicotinamido)-1H-pyrrolo[2,3-b]pyridin-4-yl)piperidin-3-ylcarbamate (125 mg, 0.243 mmol; Example 1A, Step A) was dissolved in dioxane (20 mL) and cooled to −78° C. MeLi (455 μL, 0.728 mmol) was slowly added, and the reaction was stirred for 10 minutes. n-Butyl lithium (146 μL, 0.364 mmol) was slowly added, and the reaction was stirred for 10 minutes at −78° C. Saturated ammonium chloride was then added, and the mixture was extracted several times with DCM. The layers were separated, dried, filtered, and concentrated. The residue was purified by reverse phase chromatography (Biotage Horizon, C-18 25M+, 0-80% $CH_3CN$/water+10 mM ammonium acetate and 1% IPA). The product was dissolved in TFA (2 mL), stirred for 30 minutes, concentrated and purified by reverse phase chromatography (Biotage Horizon, C-18 12M+, 0-30% $CH_3CN$/water+0.1% TFA). The product was redissolved in 10% MeOH in DCM (2 mL) and added dropwise to a stirred solution of 2M HCl in ether. The reaction was concentrated to give (R)—N-(4-(3-aminopiperidin-1-yl)-1H-pyrrolo[2,3-b]pyridin-3-yl)nicotinamide hydrochloride (18.5 mg, 17% yield). $^1$H NMR (400 MHz, $D_2O$) δ 9.10 (s, 1H), 8.78 (d, 1H), 8.62 (dt, 1H), 7.94 (d, 1H), 7.85 (dd, 1H), 7.39 (s, 1H), 6.78 (d, 1H), 3.89 (d, 1H), 3.72 (d, 1H), 3.33 (m, 1H), 3.21-3.09 (m, 2H), 1.93 (m, 1H), 1.58 (m, 1H), 1.47 (m, 1H), 1.36 (m, 1H). LCMS (APCI+) m/z 337.1 (M+H)+, Retention time=0.43 minutes (Method 3).

Example 85

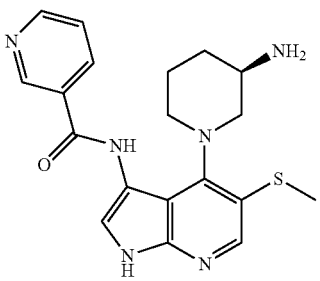

(R)-N-(4-(3-Aminopiperidin-1-yl)-5-(methylthio)-1H-pyrrolo[2,3-b]pyridin-3-yl)nicotinamide Step A: (R)-tert-Butyl 1-(5-bromo-3-(nicotinamido)-1H-pyrrolo[2,3-b]pyridin-4-yl)piperidin-3-ylcarbamate (150 mg, 0.291 mmol; Example 1A, Step A) was dissolved in THF (20 mL) and cooled to −78° C. MeLi (546 μL, 0.873 mmol) was then added slowly, and the reaction was stirred for 10 minutes. n-Butyl lithium (128 μL, 0.320 mmol) was added next, and the reaction was stirred for an additional 10 minutes, followed by the addition of 1,2-dimethyldisulfane (31.5 mg, 0.335 mmol). The reaction was stirred for 30 minutes and then quenched with water. The reaction was extracted several times with DCM. The organic layer was dried, filtered, and concentrated. The resulting residue was purified by reverse phase chromatography (Biotage Horizon, C-18 25M+, 10-85% $CH_3CN$/water) to provide 50% pure (R)-tert-butyl 1-(5-(methylthio)-3-(nicotinamido)-1H-pyrrolo[2,3-b]pyridin-4-yl)piperidin-3-ylcarbamate, which was used without further purification.

Step B: (R)-tert-Butyl 1-(5-(methylthio)-3-(nicotinamido)-1H-pyrrolo[2,3-b]pyridin-4-yl)piperidin-3-ylcarbamate (80 mg, 0.16 mmol) was placed in TFA (2 mL) and stirred for 15 minutes. The reaction was then concentrated and dissolved in 10% MeOH in DCM and then washed with saturated sodium bicarbonate. The organic layer was dried, filtered, and concentrated. The residue was purified by reverse phase prep LC. The product was then dissolved in 10% MeOH in DCM and added to a stirred solution of 2M HCl in ether. The reaction mixture was concentrated to provided (R)—N-(4-(3-aminopiperidin-1-yl)-5-(methylthio)-1H-pyrrolo[2,3-b]pyridin-3-yl)nicotinamide hydrochloride (18.7 mg, 17% yield). $^1$H NMR (400 MHz, $D_2O$) δ 9.10 (s, 1H), 8.78 (d, 1H), 8.61 (dt, 1H), 8.16 (s, 1H), 7.84 (dd, 1H), 7.42 (s, 1H), 3.88 (d, 1H), 3.56 (m, 1H), 3.47 (m, 1H), 3.14 (m, 1H), 3.04 (m, 1H), 2.36 (s, 3H), 1.94 (m, 1H), 1.67 (m, 1H), 1.55 (m, 1H), 1.37 (m, 1H). LCMS (APCI+) m/z 383.1 (M+H)+, Retention time=1.99 minutes (Method 3).

Example 86

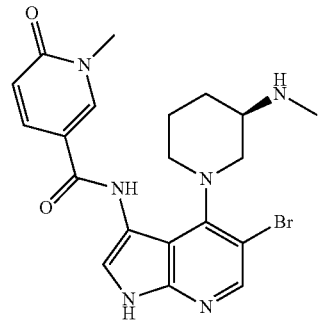

(R)-N-(5-Bromo-4-(3-(methylamino)piperidin-1-yl)-1H-pyrrolo[2,3-b]pyridin-3-yl)-1-methyl-6-oxo-1,6-dihydropyridine-3-carboxamide Step A: A mixture of N-(5-bromo-4-fluoro-1H-pyrrolo[2,3-b]pyridin-3-yl)-1-methyl-6-oxo-1,6-dihydropyridine-3-carboxamide (0.26 g, 0.72 mmol; Example 23, Step A), (R)-tert-butyl methyl(piperidin-3-yl)carbamate (0.46 g, 2.15 mmol) and DIEA (0.38 mL, 2.15 mmol) in n-BuOH (2 mL) was stirred at 143° C. (bath) for 24 hours. The solvent was removed, and the residue was dissolved in THF (2 mL). $Boc_2O$ (0.39 g, 1.79 mmol) was added. The reaction mixture was stirred at room temperature for 3 hours. Ethyl acetate (20 mL) was added, washed with water (10 mL), brine (10 mL), dried (sodium sulfate) and concentrated in vacuo. The residue was purified by reverse phase chromatography (Biotage SP4, C-18 25M+, 10-90% $CH_3CN$/water, 30 CV) to give (R)-tert-butyl 5-bromo-4-(3-(tert-butoxycarbonyl(methyl)amino)piperidin-1-yl)-3-(1-methyl-6-oxo-1,6-dihydropyridine-3-carboxamido)-1H-pyrrolo[2,3-b]pyridine-1-carboxylate (0.072 g, 15%) as a solid. LCMS (APCI+) m/z 659 (M+H)+.

Step B: TFA (0.020 mL, 0.26 mmol) was added to (R)-tert-butyl 5-bromo-4-(3-(tert-butoxycarbonyl(methyl)amino)piperidin-1-yl)-3-(1-methyl-6-oxo-1,6-dihydropyridine-3-carboxamido)-1H-pyrrolo[2,3-b]pyridine-1-carboxylate (0.034 g, 0.052 mmol) in DCM (1 mL). The reaction mixture was stirred at room temperature for 1 hour. The solvent was removed. The residue was dissolved in DCM (1 mL), and 2N HCl in ether (3 mL) was added. The solid formed was collected to give (R)—N-(5-bromo-4-(3-(methylamino)piperidin-1-yl)-1H-pyrrolo[2,3-b]pyridin-3-yl)-1-methyl-6-oxo-1,6-dihydropyridine-3-carboxamide hydrochloride (25 mg, 91%) as a solid. ¹H NMR (400 MHz, D₂O) δ 8.34 (s, 1H), 8.30 (s, 1H), 7.97 (dd, 1H), 7.35 (s, 1H), 6.60 (d, 1H), 3.88 (m, 1H), 3.53 (s, 3H), 3.39 (m, 2H), 3.08 (m, 2H), 2.55 (s, 3H), 2.04 (m, 1H), 1.68 (m, 1H), 1.60 (m, 1H), 1.35 (m, 1H). LCMS (APCI+) m/z 459 (M+H)+.

Example 87

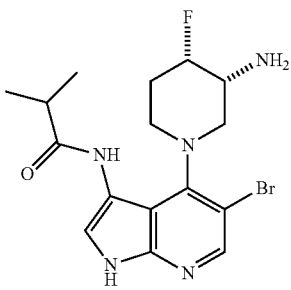

N-(4-cis-3-amino-4-fluoropiperidin-1-yl)-5-bromo-1H-pyrrolo[2,3-b]pyridin-3-yl)isobutyramide A mixture of N-(5-bromo-4-fluoro-1H-pyrrolo[2,3-b]pyridin-3-yl)isobutyramide (0.11 g, 0.37 mmol; Example 15, Step A), benzyl-cis-4-fluoropiperidin-3-ylcarbamate (0.19 g, 0.75 mmol; Example F) and DIEA (0.26 mL, 1.49 mmol) in n-BuOH (2 mL) was stirred at 155° C. (bath) for 22 hours. The solvent was removed, and the residue was dissolved in ethyl acetate (20 mL), washed with water (10 mL), brine (10 mL), dried (sodium sulfate) and concentrated in vacuo. The residue was purified by reverse phase chromatography (Biotage SP4, C-18 25M+, 10-80% CH₃CN/water, 30 CV). The product isolated was dissolved in DCM (3 mL), and TMS-I (0.16 mL, 1.12 mmol) was added. The reaction mixture was stirred at room temperature for 2 hours. The solvent was removed in vacuo, water (10 mL) and ether (30 mL) were added. The aqueous layer was separated, basified with 30% potassium carbonate to a pH of about 9, and extracted with DCM (2×20 mL). The combined organic layers were dried (sodium sulfate) and concentrated in vacuo. The residue was dissolved in DCM (3 mL), and 2N HCl in ether (2 mL) was added. The solid formed was collected to give N-(4-(cis-3-amino-4-fluoropiperidin-1-yl)-5-bromo-1H-pyrrolo[2,3-b]pyridin-3-yl)isobutyramide hydrochloride (36 mg, 21%) as a solid. ¹H NMR (400 MHz, D₂O) δ 8.25 (s, 1H), 7.27 (s, 1H), 3.86 (m, 1H), 3.62 (m, 1H), 3.41 (m, 2H), 3.20 (m, 1H), 2.64 (m, 1H), 2.12 (m, 2H), 1.96 (m 1H), 1.11 (t, 6H). LCMS (APCI+) m/z 398 (M+H)+.

Example 88

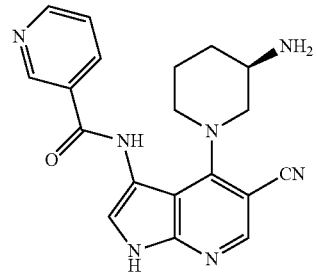

(R)-N-(4-(3-Aminopiperidin-1-yl)-5-cyano-1H-pyrrolo[2,3-b]pyridin-3-yl)nicotinamide Step A: (R)-tert-Butyl 1-(5-bromo-3-(nicotinamido)-1H-pyrrolo[2,3-b]pyridin-4-yl)piperidin-3-ylcarbamate (883 mg, 1.71 mmol; Example 1A, Step A) was placed in DCM (8 mL). Boc₂O (411 mg, 1.88 mmol) and triethylamine (716 μL, 5.14 mmol) were then added, followed by the addition of DMAP (105 mg, 0.857 mmol). The reaction was stirred at room temperature for 1 hour. The reaction was then poured into water and extracted with DCM. The combined organic fractions were dried (MgSO₄), filtered, and concentrated. The residue was purified by silica gel chromatography (0-3% MeOH in DCM) to give (R)-tert-butyl 5-bromo-4-(3-(tert-butoxycarbonylamino)piperidin-1-yl)-3-(nicotinamido)-1H-pyrrolo[2,3-b]pyridine-1-carboxylate (903 mg, 85% yield).

Step B: (R)-tert-Butyl 5-bromo-4-(3-(tert-butoxycarbonylamino)piperidin-1-yl)-3-(nicotinamido)-1H-pyrrolo[2,3-b]pyridine-1-carboxylate (150 mg, 0.244 mmol), Zn(CN)₂ (19 mg, 0.158 mmol), Zn dust (4 mg, 0.0585 mmol), Pd₂dba₃ (4.5 mg, 0.00487 mmol) and dppf (5.4 mg, 0.00975 mmol) were placed in DMA (5 mL) and heated at 90° C. for 24 hours. The reaction was then poured onto water (20 mL) and extracted with ether. The organic layer was separated, washed with brine, and dried over sodium sulfate. After removal of solvent, the residue was purified by reverse phase chromatography (Biotage SP4, C-18 25M+, 5-95% water:ACN). The product was redissolved in 10% MeOH in DCM and added slowly to a stirred solution of 2M HCl in ether (25 mL). The reaction was concentrated to give (R)—N-(4-(3-aminopiperidin-1-yl)-5-cyano-1H-pyrrolo[2,3-b]pyridin-3-yl)nicotinamide hydrochloride (24.8 mg, 22% yield) as a solid. ¹H NMR (400 MHz, D₂O) δ 9.21 (s, 1H), 8.89 (m, 2H), 8.31 (s, 1H), 8.08 (m, 1H), 7.42 (s, 1H), 3.99 (d, 1H), 3.62 (d, 1H), 3.38 (m, 1H), 3.27 (m, 1H), 3.08 (m, 1H), 1.95 (m, 1H), 1.62 (m, 1H), 1.43 (m, 2H). LCMS (APCI+) m/z 362.1 (M+H)+, Retention time=1.78 minutes (Method 3).

Example 89

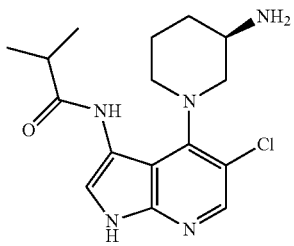

(R)-N-(4-(3-Aminopiperidin-1-yl)-5-chloro-1H-pyrrolo[2,3-b]pyridin-3-yl)isobutyramide Step A: (R)-tert-Butyl 1-(5-bromo-3-isobutyramido-1H-pyrrolo[2,3-b]pyridin-4-yl)piperidin-3-ylcarbamate (0.300 g, 0.624 mmol; Example 15, Step B) was placed in THF (10 mL) and cooled to −78° C. MeLi (1.17 mL, 1.87 mmol) was then added, and the reaction was stirred for 10 minutes. Excess THF (10 mL) was added to aid solubility. n-BuLi (0.525 mL, 1.31 mmol) was then added and stirred for an additional 10 minutes, followed by the addition of a hexachloroethane (0.296 g, 1.25 mmol) solution in THF (3 mL). The reaction was then stirred for an additional 10 minutes at 0° C., poured into water, and extracted into DCM. The organic fractions were dried, filtered, and concentrated to give a crude oil that was purified by reverse phase HPLC (50-75% ACN in water) to give the product (R)-tert-butyl 1-(5-chloro-3-isobutyramido-1H-pyrrolo[2,3-b]pyridin-4-yl)piperidin-3-ylcarbamate (0.100 g, 36.7% yield).

Step B: (R)-tert-Butyl 1-(5-chloro-3-isobutyramido-1H-pyrrolo[2,3-b]pyridin-4-yl)piperidin-3-ylcarbamate (0.100 g, 0.229 mmol) was placed in DCM (3 mL) at room temperature. TFA (1 mL) was then added, and the reaction was stirred at room temperature for 1 hour and concentrated to dryness. The resulting residue was then purified by reverse phase HPLC (0-50% ACN in water). The resulting product was next dissolved in minimal DCM (with MeOH to aid solubility) and added to a stirring solution of 1M HCl in ether. The resulting solid was filtered, washed with ether and dried to give (R)—N-(4-(3-aminopiperidin-1-yl)-5-chloro-1H-pyrrolo[2,3-b]pyridin-3-yl)isobutyramide hydrochloride (0.050 g, 53.3% yield). $^1$H NMR (400 MHz, D$_2$O) δ 8.11 (s, 1H), 7.28 (s, 1H), 3.81-3.78 (m, 1H), 3.52-3.49 (m, 1H), 3.40-3.36 (m, 1H), 3.20-3.15 (m, 2H), 2.66-2.63 (m, 1H), 2.09-2.06 (m, 1H), 1.78-1.77 (m, 1H), 1.65-1.54 (m, 2H), 1.12-0.18 (m, 6H). LCMS (APCI+) m/z 336 (M+H)+.

Example 90

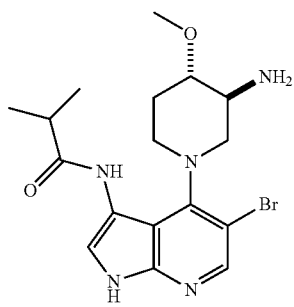

N-(4-(Trans-3-amino-4-methoxypiperidin-1-yl)-5-bromo-1H-pyrrolo[2,3-b]pyridin-3-yl)isobutyramide A mixture of N-(5-bromo-4-fluoro-1H-pyrrolo[2,3-b]pyridin-3-yl)isobutyramide (0.18 g, 0.58 mmol; Example 15, Step A), tert-butyl trans-4-methoxypiperidin-3-ylcarbamate (0.40 g, 1.75 mmol; Example G) and DIEA (0.31 mL, 1.75 mmol) in tert-amyl alcohol (3 mL) was stirred at 146° C. (bath) for 22 hours. The solvent was removed. The resulting residue was dissolved in ethyl acetate (20 mL), washed with water (10 mL), brine (10 mL), dried (sodium sulfate) and concentrated in vacuo. The residue was purified by reverse phase chromatography (Biotage SP4, C-18 25M+, 10-80% CH$_3$CN/water, 30 CV). The isolated product was dissolved in DCM (2 mL), and TFA (0.5 mL) was added. The mixture was stirred at room temperature for 1 hour. The solvent was removed. The residue was dissolved in MeOH (1 mL), and 2N HCl in ether (3 mL) was added. The solid formed was collected to give N-(4-((trans-3-amino-4-methoxypiperidin-1-yl)-5-bromo-1H-pyrrolo[2,3-b]pyridin-3-yl)isobutyramide hydrochloride (0.065 g, 23%) as a solid. $^1$H NMR (400 MHz, D$_2$O) δ 8.22 (s, 1H), 7.29 (s, 1H), 3.74 (m, 1H), 3.39 (m, 3H), 3.32 (s, 3H), 3.25 (m, 2H), 2.63 (m, 1H), 2.25 (m, 1H), 1.51 (m, 1H), 1.11 (t, 6H). LCMS (APCI+) m/z 411 (M+H)+.

Example 90A

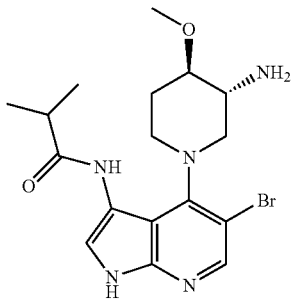

N-(4-((3R,4R)-3-amino-4-methoxypiperidin-1-yl)-5-bromo-1H-pyrrolo[2,3-b]pyridin-3-yl)isobutyramide Chiral separation of Example 90: Chiral OD-H (20 mm×250 mm); 70% hexane, 30% 1:1 ethanol:methanol; flow rate 15 mL/min. $^1$H NMR (400 MHz, D$_2$O) δ 8.23 (s, 1H), 7.29 (s, 1H), 3.80 (m, 1H), 3.41 (m, 3H), 3.32 (s, 3H), 3.23 (m, 2H), 2.64 (m, 1H), 2.25 (m, 1H), 1.51 (m, 1H), 1.11 (t, 6H). LCMS (APCI+) m/z 410 (M+H)+. Enantiomeric excess determined by chiral HPLC (Chiral OD-H (4.6 mm×250 mm); 70% hexane, 30% 1:1 ethanol:methanol; flow rate 0.8 mL/min), 96.2% ee.

Example 90B

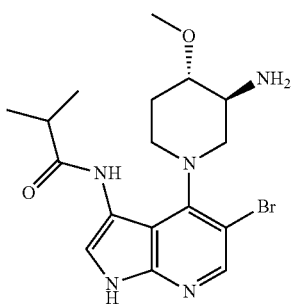

N-(4-((3S,4S)-3-amino-4-methoxypiperidin-1-yl)-5-bromo-1H-pyrrolo[2,3-b]pyridin-3-yl)isobutyramide Chiral separation of Example 90: Chiral OD-H (20 mm×250 mm); 70% hexane, 30% 1:1 ethanol:methanol; flow rate 15 mL/min. $^1$H NMR (400 MHz, D$_2$O) δ 8.22 (s, 1H), 7.28 (s, 1H), 3.74 (m, 1H), 3.40 (m, 3H), 3.32 (s, 3H), 3.24 (m, 2H), 2.63 (m, 1H), 1.90 (m, 1H), 1.50 (m, 1H), 1.11 (t, 6H). LCMS (APCI+) m/z 410 (M+H)+. Enantiomeric excess determined by chiral HPLC (Chiral OD-H (4.6 mm×250 mm); 70% hexane, 30% 1:1 ethanol:methanol; flow rate 0.8 mL/min), 100% ee.

Example 91

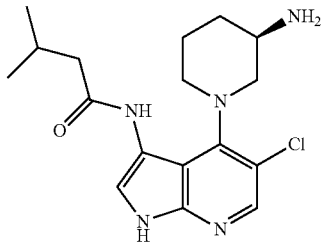

(R)-N-(4-(3-Aminopiperidin-1-yl)-5-chloro-1H-pyrrolo[2,3-b]pyridin-3-yl)-3-methylbutanamide Step A: A 250 mL round bottom flask was charged with 5-chloro-4-fluoro-1H-pyrrolo[2,3-b]pyridin-3-amine (1.6 g, 8.62 mmol; Example 8, Step D), (R)-tert-butyl piperidin-3-ylcarbamate (5.18 g, 25.9 mmol), N-ethyl-N-isopropylpropan-2-amine (4.51 mL, 25.9 mmol), and NMP (15.5 mL). Then $N_2$ was bubbled through the mixture for 5 minutes and stirred at 120° C. under $N_2$ atmosphere for 16 hours to provide the crude (R)-tert-butyl 1-(3-amino-5-chloro-1H-pyrrolo[2,3-b]pyridin-4-yl)piperidin-3-ylcarbamate. LCMS (APCI+) m/z 366.1 (M+H)+.

Step B: Triethylamine (522 μL, 3.83 mmol) was added to an aliquot of (R)-tert-butyl 1-(3-amino-5-chloro-1H-pyrrolo[2,3-b]pyridin-4-yl)piperidin-3-ylcarbamate (200 mg, 0.547 mmol) in NMP (3 mL) at 0° C. under $N_2$ atmosphere. The mixture was then treated dropwise with 3-methylbutanoyl chloride (231 mg, 1.91 mmol) and stirred at 0° C. After 1 hour, the reaction mixture was diluted with $CH_2Cl_2$ (4 mL), and 2M $LiOH.H_2O$ (3 mL) was added. The resulting mixture was stirred at room temperature for 18 hours. The mixture was then diluted with additional $CH_2Cl_2$ (50 mL) and washed with water (3×10 mL). The organic layer was separated, dried ($MgSO_4$), filtered, and concentrated in vacuo. The residue was purified by reverse phase chromatography (Biotage SP4, C-18 40M+, 15-85% $CH_3CN$/water, 40 CV) to provide (R)-tert-butyl 1-(5-chloro-3-(3-methylbutanamido)-1H-pyrrolo[2,3-b]pyridin-4-yl)piperidin-3-ylcarbamate (130 mg, 53% yield) as a solid.

Step C: A solution of (R)-tert-butyl 1-(5-chloro-3-(3-methylbutanamido)-1H-pyrrolo[2,3-b]pyridin-4-yl)piperidin-3-ylcarbamate (128 mg, 0.284 mmol) in neat TFA (3 mL) was stirred at room temperature for 30 minutes and concentrated in vacuo. The oily residue was evaporated from $CH_3CN$ (4×10 mL) to provide (R)—N-(4-(3-aminopiperidin-1-yl)-5-chloro-1H-pyrrolo[2,3-b]pyridin-3-yl)-3-methylbutanamide hydrochloride (95 mg, 79% yield) as a solid. $^1H$ NMR (400 MHz, $(CD_3)_2SO$) δ 11.77 (s, 1H), 9.26 (s, 1H), 8.22 (br s, 3H), 8.12 (s, 1H), 7.58 (br s, 1H), 3.47-3.31 (m, 3H), 3.25-3.17 (m, 1H), 3.13-3.08 (m, 1H), 2.25 (d, 2H), 2.14-2.09 (m, 2H), 1.87-1.81 (m, 1H), 1.74-1.63 (m, 1H), 1.54-1.47 (m, 1H), 0.98 (dd, 6H). LCMS (APCI+) m/z 350 (M+H)+.

Example 92

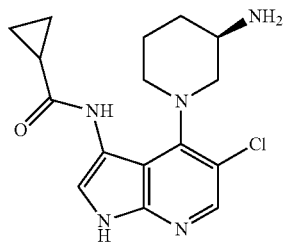

(R)-N-(4-(3-Aminopiperidin-1-yl)-5-chloro-1H-pyrrolo[2,3-b]pyridin-3-yl)cyclopropanecarboxamide Step A: Triethylamine (1018 μL, 7.462 mmol) was added to an aliquot of (R)-tert-butyl 1-(3-amino-5-chloro-1H-pyrrolo[2,3-b]pyridin-4-yl)piperidin-3-ylcarbamate (390 mg, 1.066 mmol; Example 91, Step A) in NMP (3 mL) at 0° C. under $N_2$ atmosphere. The mixture was treated dropwise with cyclopropanecarbonyl chloride (580.4 μL, 6.396 mmol) and stirred at 0° C. for 1 hour. The reaction mixture was then diluted with $CH_2Cl_2$ (4 mL). 2M $LiOH.H_2O$ (9 mL) was added, and the mixture was allowed to stir for 24 hours. The mixture was then diluted with 2% MeOH/EtOAc (100 mL) and washed with water (4×20 mL). The organic layer was separated, dried ($MgSO_4$), filtered, and concentrated in vacuo. The residue obtained was purified by reverse phase chromatography (Biotage SP4, C-18 40M+, 15-85% $CH_3CN$/water, 38 CV) to provide (R)-tert-butyl 1-(5-chloro-3-(cyclopropanecarboxamido)-1H-pyrrolo[2,3-b]pyridin-4-yl)piperidin-3-ylcarbamate as a solid.

Step B: A solution of (R)-tert-butyl 1-(5-chloro-3-(cyclopropanecarboxamido)-1H-pyrrolo[2,3-b]pyridin-4-yl)piperidin-3-ylcarbamate (462 mg, 1.06 mmol) in neat TFA (4 mL) was stirred at room temperature for 30 minutes and concentrated in vacuo. The oily residue obtained was dissolved in $CH_2Cl_2$ (1 mL) and treated with 2M HCl in ether (4 mL). The resulting precipitate was evaporated from $CH_3CN$ (4×10 mL) to provide (R)—N-(4-(3-aminopiperidin-1-yl)-5-chloro-1H-pyrrolo[2,3-b]pyridin-3-yl)cyclopropanecarboxamide hydrochloride (271 mg, 63% yield) as a solid. $^1H$ NMR (400 MHz, $(CD_3)_2SO$) δ 11.79 (d, 1H), 9.65 (s, 1H), 8.25 (br s, 3H), 8.11 (s, 1H), 7.48 (d, 1H), 3.53-3.48 (m, 1H), 3.44-3.31 (m, 2H), 3.23-3.11 (m, 2H), 2.13-2.08 (m, 1H), 1.89-1.80 (m, 2H), 1.75-1.70 (m, 1H), 1.54-1.45 (m, 1140, 0.82 (d, 414). LCMS (APCI+) m/z 334 (M+H)+.

Example 93

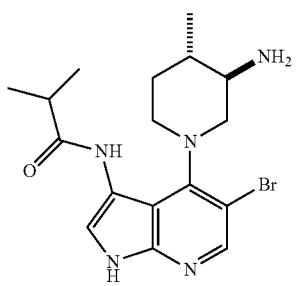

N-(4-(Trans-3-amino-4-methylpiperidin-1-yl)-5-bromo-1H-pyrrolo[2,3-b]pyridin-3-yl)isobutyramide A mixture of N-(5-bromo-4-fluoro-1H-pyrrolo[2,3-b]pyridin-3-yl)isobutyramide (0.20 g, 0.67 mmol; Example 15, Step A), tert-butyl trans-4-methylpiperidin-3-ylcarbamate (0.43 g, 2.00 mmol; Example I) and DIEA (0.35 mL, 2.00 mmol) in n-BuOH (3 mL) was stirred at 146° C. (bath) for 24 hours. The solvent was removed, and the residue was dissolved in ethyl acetate (20 mL), washed with water (10 mL), brine (10 mL), dried (sodium sulfate) and concentrated in vacuo. The residue was purified by reverse phase chromatography (Biotage SP4, C-18 25M+, 10-80% CH$_3$CN/water, 30 CV). The product isolated was dissolved in DCM (2 mL), and TFA (0.5 mL) was added. The mixture was stirred at room temperature for 1 hour. The solvent was removed in vacuo. The residue was purified by reverse phase chromatography (Biotage SP4, C-18 12M+, 0-80% CH$_3$CN/water gradient, 20 CV). The product isolated was dissolved in MeOH (1 mL), and 2N HCl in ether (3 mL) was added. The solid formed was collected to give N-(4-(trans-3-amino-4-methylpiperidin-1-yl)-5-bromo-1H-pyrrolo[2,3-b]pyridin-3-yl)isobutyramide hydrochloride (0.011 g, 4%) as a solid. $^1$H NMR (400 MHz, D$_2$O) δ 8.20 (s, 1H), 7.27 (s, 1H), 3.72 (m, 1H), 3.26 (m, 1H), 3.19 (m, 3H), 2.63 (m, 1H), 1.76 (m, 1H), 1.68 (m, 1H), 1.41 (m, 1H), 1.10 (t, 6H), 1.00 (d, 3H). LCMS (APCI+) m/z 394 (M+H)+.

Example 94

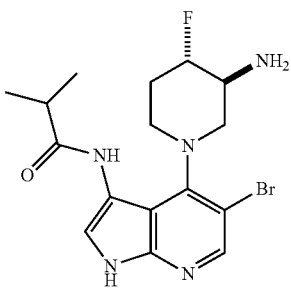

N-(4-(Trans-3-amino-4-fluoropiperidin-1-yl)-5-bromo-1H-pyrrolo[2,3-b]pyridin-3-yl)isobutyramide A mixture of N-(5-bromo-4-fluoro-1H-pyrrolo[2,3-b]pyridin-3-yl)isobutyramide (0.10 g, 0.33 mmol; Example 15, Step A), tert-butyl trans-4-fluoropiperidin-3-ylcarbamate (0.22 g, 1.00 mmol, Example J) and DIEA (0.17 mL, 1.00 mmol) in n-BuOH (3 mL) was stirred at 146° C. (bath) for 40 hours. The solvent was removed, and the residue was dissolved in ethyl acetate (20 mL), washed with water (10 mL), brine (10 mL), dried (sodium sulfate) and concentrated in vacuo. The residue was purified by reverse phase chromatography (Biotage SP4, C-18 25M+, 10-80% CH$_3$CN/water, 20 CV). The product isolated was dissolved in DCM (2 mL), and TFA (0.5 mL) was added. The mixture was stirred at room temperature for 1 hour. The solvent was removed. The residue was dissolved in MeOH (1 mL), and 2N HCl in ether (3 mL) was added. The solid formed was collected to give N-(4-(trans-3-amino-4-fluoropiperidin-1-yl)-5-bromo-1H-pyrrolo[2,3-b]pyridin-3-yl)isobutyramide hydrochloride (0.017 g, 11%) as a solid. $^1$H NMR (400 MHz, D$_2$O) δ 8.24 (s, 1H), 7.27 (s, 1H), 3.83 (m 1H), 3.70 (m, 1H), 3.45 (m, 1H), 3.25 (m, 2H), 2.64 (m, 1H), 2.21 (m, 2H), 1.88 (m, 1H), 1.10 (m, 6H). LCMS (APCI+) m/z 398 (M+H)+.

Example 95

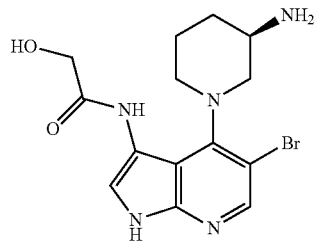

(R)-N-(4-(3-Aminopiperidin-1-yl)-5-bromo-1H-pyrrolo[2,3-b]pyridin-3-yl)-2-hydroxyacetamide Step A: 5-Bromo-4-fluoro-1H-pyrrolo[2,3-b]pyridin-3-amine (0.600 g, 2.61 mmol; Example 1, Step H), 2-acetoxyacetic acid (0.647 g, 5.48 mmol), BOP-Cl (1.39 g, 5.48 mmol), and triethylamine (1.82 mL, 13.0 mmol) were placed in DCM (10 mL) and stirred at room temperature for 1 hour. 3M aqueous LiOH (3 mL) was then added. The reaction was stirred for 2 hours, poured into water, and extracted with DCM. The combined organic fractions were dried (MgSO$_4$), filtered, and concentrated to give the crude product, which was purified by reverse phase chromatography (Biotage SP4, C-18 25M+, 5-95 CH$_3$CN/water) to give N-(5-bromo-4-fluoro-1H-pyrrolo[2,3-b]pyridin-3-yl)-2-hydroxyacetamide (0.400 g, 53% yield).

Step B: N-(5-Bromo-4-fluoro-1H-pyrrolo[2,3-b]pyridin-3-yl)-2-hydroxyacetamide (0.200 g, 0.694 mmol), (R)-tert-butyl piperidin-3-ylcarbamate (0.417 g, 2.08 mmol), and DIEA (0.363 mL, 2.08 mmol) were placed in n-BuOH (2 mL) and heated to 140° C. for 18 hours. The reaction was then cooled to room temperature and concentrated to dryness. The resulting residue was purified by reverse phase chromatography (Biotage SP4, C-18 25M+, 5-75 CH$_3$CN/water) to give (R)-tert-butyl 1-(5-bromo-3-(2-hydroxyacetamido)-1H-pyrrolo[2,3-b]pyridin-4-yl)piperidin-3-ylcarbamate (0.220 g, 68% yield).

Step C: (R)-tert-Butyl 1-(5-bromo-3-(2-hydroxyacetamido)-1H-pyrrolo[2,3-b]pyridin-4-yl)piperidin-3-ylcarbamate (0.220 g, 0.470 mmol) was placed in DCM (3 mL) at room temperature. TFA (1 mL) was then added. The reaction was stirred at room temperature for 1 hour and concentrated to dryness. The residue was purified by reverse phase chromatography (Biotage SP4, C-18 25M+, 5-50 CH$_3$CN/water). The resulting product was next dissolved in minimal DCM (with MeOH to aid solubility) and added to a stirred solution of 1M HCl in ether. The resulting solid was filtered, washed with ether and dried to give (R)—N-(4-(3-aminopiperidin-1-yl)-5-bromo-1H-pyrrolo[2,3-b]pyridin-3-yl)-2-hydroxyacetamide hydrochloride (0.045 g, 22% yield) as a solid. $^1$H NMR (400 MHz, D$_2$O) δ 8.20 (s, 1H), 7.46 (s, 1H), 4.17 (s, 2H), 3.60-3.51 (m, 2H), 3.33-3.28 (m, 1H), 3.22-3.13 (m, 2H), 2.08-2.05 (m, 1H), 1.76-1.72 (m, 2H), 1.54-1.51 (m, 1H). LCMS (APCI+) m/z 368, 370 (M+H)+.

Example 96

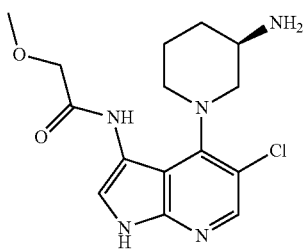

(R)-N-(4-(3-Aminopiperidin-1-yl)-5-chloro-1H-pyrrolo[2,3-b]pyridin-3-yl)-2-methoxyacetamide Step A: An NMP (2 mL) solution of (R)-tert-butyl 1-(3-amino-5-chloro-1H-pyrrolo[2,3-b]pyridin-4-yl)piperidin-3-ylcarbamate (0.200 g, 0.547 mmol; Example 91, Step A), 2-methoxyacetyl chloride (0.302 mL, 3.28 mmol), and triethylamine (0.533 mL, 3.83 mmol) was stirred at room temperature for 1 hour. 3M aqueous LiOH (3 mL) was then added. The reaction was stirred for 10 minutes, poured into water, and extracted with DCM. The combined organic fractions were dried (MgSO$_4$), filtered, and concentrated to give the crude product, which was purified by reverse phase chromatography (Biotage SP4, C-18 25M+, 5-95 CH$_3$CN/water) to give (R)-tert-butyl 1-(5-chloro-3-(2-methoxyacetamido)-1H-pyrrolo[2,3-b]pyridin-4-yl)piperidin-3-ylcarbamate (0.185 g, 77% yield).

Step B: (R)-tert-Butyl 1-(5-chloro-3-(2-methoxyacetamido)-1H-pyrrolo[2,3-b]pyridin-4-yl)piperidin-3-ylcarbamate (0.185 g, 0.422 mmol) was placed in DCM (3 mL) at room temperature. TFA (1 mL) was then added. The reaction was stirred at room temperature for 1 hour and concentrated to dryness. The resulting residue was then purified by reverse phase chromatography (Biotage SP4, C-18 25M+, 5-50 CH$_3$CN/water). The resulting product was next dissolved in minimal DCM (with MeOH to aid solubility) and added to a stirred solution of 1M HCl in ether. The resulting solid was filtered, washed with ether and dried to give (R)—N-(4-(3-aminopiperidin-1-yl)-5-chloro-1H-pyrrolo[2,3-b]pyridin-3-yl)-2-methoxyacetamide hydrochloride (0.170 g, 98% yield) as a solid. $^1$H NMR (400 MHz, D$_2$O) δ 8.10 (s, 1H), 7.41 (s, 1H), 4.09 (s, 2H), 3.71-3.68 (m, 1H), 3.49-3.46 (m, 1H), 3.40 (s, 3H), 3.27-3.13 (m, 3H), 2.11-2.08 (m, 1H), 1.78-1.75 (m, 1H), 1.67-1.65 (m, 1H), 1.54-1.50 (m, 1H). LCMS (APCI+) m/z 338 (M+H)+.

Example 97

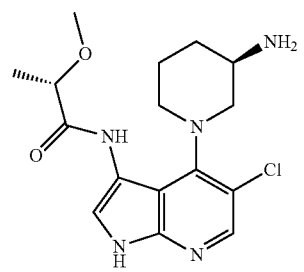

(S)-N-(4-((R)-3-Aminopiperidin-1-yl)-5-chloro-1H-pyrrolo[2,3-b]pyridin-3-yl)-2-methoxypropanamide Step A: An NMP solution (2 mL) of (R)-tert-butyl 1-(3-amino-5-chloro-1H-pyrrolo[2,3-b]pyridin-4-yl)piperidin-3-ylcarbamate (0.200 g, 0.547 mmol; Example 91, Step A), (S)-2-methoxypropanoic acid (0.310 mL, 3.28 mmol), BOP-Cl (0.835 g, 3.28 mmol), and triethylamine (0.533 mL, 3.83 mmol) was stirred for 18 hours. 3M aqueous LiOH (3 mL) was then added. The reaction was stirred for 10 minutes, poured into water, and extracted with DCM. The combined organic fractions were dried (MgSO$_4$), filtered, and concentrated to give the crude product, which was purified by reverse phase chromatography (Biotage SP4, C-18 25M+, 5-95 CH$_3$CN/water) to give the product tert-butyl (R)-1-(5-chloro-3-((S)-2-methoxypropanamido)-1H-pyrrolo[2,3-b]pyridin-4-yl)piperidin-3-ylcarbamate (0.190 g, 77% yield).

Step B: tert-Butyl (R)-1-(5-chloro-3-((S)-2-methoxypropanamido)-1H-pyrrolo[2,3-b]pyridin-4-yl)piperidin-3-ylcarbamate (0.190 g, 0.420 mmol) was placed in DCM (3 mL) at room temperature. TFA (1 mL) was then added. The reaction was stirred at room temperature for 1 hour and concentrated to dryness. The resulting residue was then purified by reverse phase chromatography (Biotage SP4, C-18 25M+, 5-95 CH$_3$CN/water). The resulting product was next dissolved in minimal DCM (with MeOH to aid solubility) and added to a stirred solution of 1M HCl in ether. The resulting solid was filtered, washed with ether and dried to give (S)—N-(4-((R)-3-aminopiperidin-1-yl)-5-chloro-1H-pyrrolo[2,3-b]pyridin-3-yl)-2-methoxypropanamide hydrochloride (0.100 g, 56% yield) as a solid. $^1$H NMR (400 MHz, D$_2$O) δ 8.09 (s, 1H), 7.46 9 s, 1H), 4.05-3.99 (q, 1H), 3.67-3.64 (m, 1H), 3.51-3.49 (m, 1H), 3.37 (s, 3H), 3.26-3.21 (m, 3H), 2.11-2.08 (m, 1H), 1.81-1.77 (m, 1H), 1.72-1.67 (m, 1H), 1.53-1.50 (m, 1H). LCMS (APCI+) m/z 352 (M+H)+.

Example 98

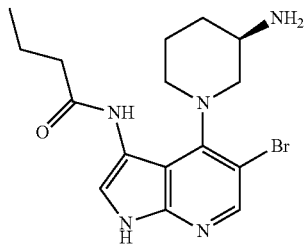

(R)-N-(4-(3-Aminopiperidin-1-yl)-5-bromo-1H-pyrrolo[2,3-b]pyridin-3-yl)butyramide Step A: (R)-tert-Butyl piperidin-3-ylcarbamate (7.84 g, 39.12 mmol) and N,N-diisopropylethylamine (5.06 g, 6.82 mL, 39.12 mmol) were added to a solution of 5-bromo-4-fluoro-1H-pyrrolo[2,3-b]pyridin-3-amine (3.00 g, 13.04 mmol; Example 1, Step H) in NMP (32 mL). The resulting mixture was heated at 120° C. on an oil bath under a nitrogen atmosphere for 18 hours. The crude reaction mixture was used in the next step. LCMS (APCI+) m/z 410 (M+H)+, Retention time=3.32 minutes.

Step B: Butyryl chloride (234 mg, 2.19 mmol) in anhydrous dichloromethane (0.5 mL) was added dropwise to a solution of (R)-tert-butyl 1-(3-amino-5-bromo-1H-pyrrolo[2,3-b]pyridin-4-yl)piperidin-3-ylcarbamate (150 mg, 0.366 mmol) and triethylamine (259 mg, 0.357 mL, 2.56 mmol) in NMP (0.900 mL) cooled on an ice-bath. The mixture was stirred at ambient temperature for 1 hour. The mixture was diluted with THF (10 mL), treated with an aqueous 2N LiOH solution (3 mL) and stirred for 1 hour. The THF was evaporated. The residue was stirred with water (20 mL) and extracted with EtOAc (3×20 mL). The combined organic extracts were dried over MgSO$_4$, filtered and concentrated.

The residue was purified by reverse phase chromatography (Biotage SP4, C-18 25M+, 15-80% CH₃CN/water, 25CV) to give (R)-tert-butyl 1-(5-bromo-3-butyramido-1H-pyrrolo[2,3-b]pyridin-4-yl)piperidin-3-ylcarbamate (176 mg, 100% yield) as a solid. LCMS (APCI+) m/z 482.1, 382, 380 (M+H)+, Retention time=3.80 minutes.

Step C: (R)-tert-Butyl 1-(5-bromo-3-butyramido-1H-pyrrolo[2,3-b]pyridin-4-yl)piperidin-3-ylcarbamate (176 mg, 0.366 mmol) was stirred in TFA (3 mL) at room temperature for 1.5 hours. The solvent was evaporated in vacuo, and the residue purified by reverse phase chromatography (Biotage SP4, C-18 12M+, 2-50% CH₃CN/water, 16CV). The isolated product was taken up in a minimal volume of methanol and added to a stirred solution of 2N HCl-Et₂O. The salt formed was collected by filtration, washed with acetonitrile and dried under vacuum to give (R)—N-(4-(3-aminopiperidin-1-yl)-5-bromo-1H-pyrrolo[2,3-b]pyridin-3-yl)butyramide (110 mg, 66% yield) as a solid. ¹H NMR (400 MHz, D₂O) δ 8.27 (s, 1H), 7.54 (s, 1H), 3.52-3.23 (m, 4H), 3.15-3.05 (m, 1H), 2.38 (t, 2H), 2.19-2.10 (m, 1H), 1.93-1.85 (m, 1H), 1.78-1.60 (m, 3H), 1.58-1.42 (m, 1H), 0.97 (t, 3H). LCMS (APCI+) m/z 380, 383.1 (M+H)+, Retention time=2.38 minutes.

Example 99

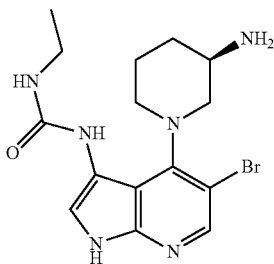

(R)-1-(4-(3-Aminopiperidin-1-yl)-5-bromo-1H-pyrrolo[2,3-b]pyridin-3-yl)-3-ethylurea Step A: (R)-tert-Butyl 1-(3-amino-5-bromo-1H-pyrrolo[2,3-b]pyridin-4-yl)piperidin-3-ylcarbamate (0.150 g, 0.366 mmol; Example 98, Step A) was placed in 1:1 NMP:pyridine (2 mL total volume). Isocyanatoethane (0.146 mL, 1.83 mmol) was then added, and the reaction was stirred at room temperature for 30 minutes and then concentrated. The residue was purified by reverse phase chromatography (Biotage SP4, C-18 12M+, 5:95 ACN in water) to give (R)-tert-butyl 1-(5-bromo-3-(3-ethylureido)-1H-pyrrolo[2,3-b]pyridin-4-yl)piperidin-3-ylcarbamate (0.130 g, 74% yield).

Step B: (R)-tert-Butyl 1-(5-bromo-3-(3-ethylureido)-1H-pyrrolo[2,3-b]pyridin-4-yl)piperidin-3-ylcarbamate (0.130 g, 0.270 mmol) was placed in DCM (3 mL) at room temperature. TFA (1 mL) was then added. The reaction was stirred at room temperature for 1 hour and concentrated to dryness. The residue was then purified by reverse phase chromatography (Biotage SP4, C-18 12M+, 0-50% ACN in water). The resulting product was next dissolved in minimal DCM (with MeOH to aid solubility) and added to a stirring solution of 1M HCl in ether. The resulting solid was filtered, washed with ether and dried to give (R)-1-(4-(3-aminopiperidin-1-yl)-5-bromo-1H-pyrrolo[2,3-b]pyridin-3-yl)-3-ethylurea hydrochloride (0.100 g, 81.5% yield) as a solid. ¹H NMR (400 MHz, D₂O) δ 8.27 (s, 1H), 7.27 (s, 1H), 3.86-3.83 (m, 1H), 3.56-3.54 (m, 1H), 3.48-3.45 (m, 1H), 3.26-3.21 (m, 2H), 3.04-2.99 (m, 2H), 2.09-2.06 (m, 1H), 1.81-1.70 (m, 2H), 1.57-1.55 (m, 1H), 0.94-0.90 (m, 3H). LCMS (APCI+) m/z 381, 383 (M+H)+.

Example 100

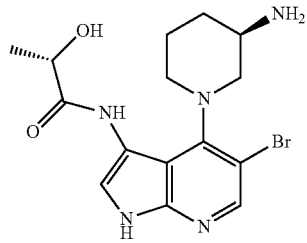

(S)-N-(4-((R)-3-Aminopiperidin-1-yl)-5-bromo-1H-pyrrolo[2,3-b]pyridin-3-yl)-2-hydroxypropanamide Step A: (R)-tert-Butyl 1-(3-amino-5-bromo-1H-pyrrolo[2,3-b]pyridin-4-yl)piperidin-3-ylcarbamate (0.200 g, 0.487 mmol; Example 98, Step A), (S)-2-acetoxypropanoic acid (0.386 g, 2.92 mmol), BOP-Cl (0.745 g, 2.92 mmol), and triethylamine (0.679 mL, 4.87 mmol) were placed in DCM (6 mL) and stirred at room temperature for 18 hours. 3M aqueous LiOH (6 mL) was then added. The reaction was stirred for 10 minutes, poured into water, and extracted with DCM. The combined organic fractions were dried (MgSO₄), filtered, and concentrated to give the crude product, which was purified by reverse phase chromatography (Biotage SP4, C-18 25M+, 5-95 CH₃CN/water) to give tert-butyl (R)-1-(5-bromo-3-((S)-2-hydroxypropanamido)-1H-pyrrolo[2,3-b]pyridin-4-yl)piperidin-3-ylcarbamate (0.120 g, 51% yield).

Step B: tert-Butyl (R)-1-(5-bromo-3-((S)-2-hydroxypropanamido)-1H-pyrrolo[2,3-b]pyridin-4-yl)piperidin-3-ylcarbamate (0.120 g, 0.249 mmol) was placed in DCM (3 mL) at room temperature. TFA (1 mL) was then added. The reaction was stirred at room temperature for 1 hour and concentrated to dryness. The resulting residue was then purified by reverse phase chromatography (Biotage SP4, C-18 25M+, 5-50 CH₃CN/water). The resulting product was next dissolved in minimal DCM (with MeOH to aid solubility) and added to a stirred solution of 1M HCl in ether. The resulting solid was filtered, washed with ether and dried to give (S)—N-(4-((R)-3-aminopiperidin-1-yl)-5-bromo-1H-pyrrolo[2,3-b]pyridin-3-yl)-2-hydroxypropanamide HCl (0.070 g, 62% yield) as a solid. ¹H NMR (400 MHz, D₂O) δ 8.20 (s, 1H), 7.48 (s, 1H), 4.37-4.32 (q, 1H), 3.61-3.55 (m, 2H), 3.31-3.24 (m, 2H), 3.16-3.13 (m, 1H), 2.09-2.05 (m, 1H), 1.77-1.71 (m, 2H), 1.54-1.51 (m, 1H), 1.35-1.33 (d, 3H). LCMS (APCI+) m/z 382, 384 (M+H)+.

Example 101

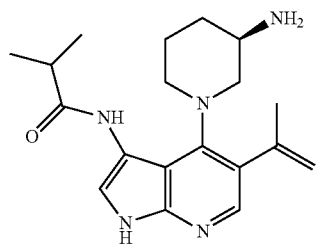

(R)-N-(4-(3-Aminopiperidin-1-yl)-5-(prop-1-en-2-yl)-1H-pyrrolo[2,3-b]pyridin-3-yl)isobutyramide Step A: 4,4,5,5-Tetramethyl-2-(prop-1-en-2-yl)-1,3,2-dioxaborolane (174 mg, 1.03 mmol), PS-palladium tetrakis (470 mg, 0.0517 mmol, 0.10 mmol/1 g) and 2N sodium carbonate (775 μL, 1.55 mmol) were added to (R)-tert-butyl 5-bromo-4-(3-(tert-butoxycarbonylamino)piperidin-1-yl)-3-isobutyramido-1H-pyrrolo[2,3-b]pyridine-1-carboxylate (300 mg, 0.517 mmol; Example 81, Step A) in degassed dioxane (1 mL). The reaction was heated to 120° C. for 1 hour under microwave irradiation. 4,4,5,5-Tetramethyl-2-(prop-1-en-2-yl)-1,3,2-dioxaborolane (174 mg, 1.03 mmol) and 2N sodium carbonate (775 μL, 1.55 mmol) were added, and the reaction was heated to 120° C. for an additional 2 hours. The reaction mixture was then cooled down and filtered. The filtrate was diluted with DCM washed with water. The layers were separated. The organic phase was dried (MgSO$_4$) and concentrated, and the resulting residue was purified by reverse phase chromatography (Biotage SP4, C-18 25M+, 15-100% CH$_3$CN/water) to yield (R)-tert-butyl 4-(3-(tert-butoxycarbonylamino)piperidin-1-yl)-3-isobutyramido-5-(prop-1-en-2-yl)-1H-pyrrolo[2,3-b]pyridine-1-carboxylate (141 mg, 50% yield) as a solid.

Step B: (R)-tert-Butyl 4-(3-(tert-butoxycarbonylamino)piperidin-1-yl)-3-isobutyramido-5-(prop-1-en-2-yl)-1H-pyrrolo[2,3-b]pyridine-1-carboxylate (20 mg, 0.0369 mmol) was placed in TFA (2 mL) and stirred for 30 minutes. The reaction was concentrated and redissolved in 10% MeOH in DCM. This solution was added dropwise to a stirred solution of 2M HCl in ether. The reaction was then concentrated and dried to provide (R)—N-(4-(3-aminopiperidin-1-yl)-5-(prop-1-en-2-yl)-1H-pyrrolo[2,3-b]pyridin-3-yl)isobutyramide hydrochloride (13.8 mg, 90% yield) as a solid. $^1$H NMR (400 MHz, (CD$_3$)$_2$SO) δ 11.96 (s, 1H), 9.36 (s, 1H), 8.21 (br s, 2H), 7.92 (s, 1H), 7.51 (s, 1H), 5.35 (s, 1H), 4.94 (s, 1H), 3.55 (m, 1H), 3.38 (m, 2H), 3.20-3.05 (m, 2H), 2.72 (m, 1H), 2.06 (m, 1H), 1.83 (m, 1H), 1.70 (m, 1H), 1.50 (m, 1H), 1.14 (dd, 6H). LCMS (APCI+) m/z 342.1 (M+H)+, Retention time=2.13 minutes (Method 3).

Example 102

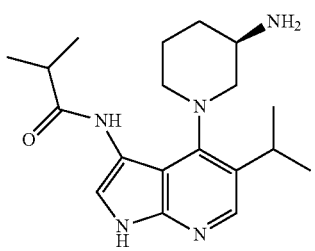

(R)-N-(4-(3-Aminopiperidin-1-yl)-5-isopropyl-1H-pyrrolo[2,3-b]pyridin-3-yl)isobutyramide (R)-tert-Butyl 4-(3-(tert-butoxycarbonylamino)piperidin-1-yl)-3-isobutyramido-5-(prop-1-en-2-yl)-1H-pyrrolo[2,3-b]pyridine-1-carboxylate (125 mg, 0.231 mmol; Example 101, Step A), Pd/C (123 mg, 0.115 mmol), and ethanol (5 mL) were placed under about 1 to 2 atm of hydrogen pressure (balloon) for 24 hours. An extra 0.5 equivalents of Pd/C (61.5 mg, 0.058 mmol) were then added, and the reaction was stirred for an additional 16 hours. The reaction mixture was filtered and concentrated, and the resulting residue was purified by reverse phase chromatography (Gilson, C-18, 0-95% CH$_3$CN/water with 0.1% TFA). The product was then dissolved in 10% MeOH in DCM (2 mL) and added dropwise to a solution of 2M HCl in ether. The reaction was concentrated to give (R)—N-(4-(3-aminopiperidin-1-yl)-5-isopropyl-1H-pyrrolo[2,3-b]pyridin-3-yl)isobutyramide hydrochloride (29.1 mg, 30% yield) as a solid. $^1$H NMR (400 MHz, D$_2$O) δ 8.07 (s, 1H), 7.33 (s, 1H), 3.52 (m, 1H), 3.39 (m, 1H), 3.21 (m, 2H), 3.09 (m, 2H), 2.66 (m, 1H), 2.10 (m, 1H), 1.79 (m, 1H), 1.69 (m, 1H), 1.51 (m, 1H), 1.15 (t, 6H), 1.11 (dd, 6H). LCMS (APCI+) m/z 344.2 (M+H)+, Retention time=2.26 minutes (Method 3).

Example 103

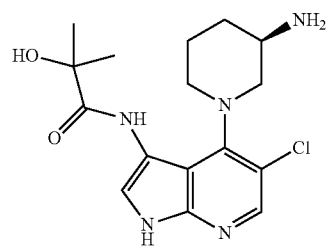

(R)-N-(4-(3-Aminopiperidin-1-yl)-5-chloro-1H-pyrrolo[2,3-b]pyridin-3-yl)-2-hydroxy-2-methylpropanamide Step A: A solution of 1-chloro-2-methyl-1-oxopropan-2-yl acetate (540 mg, 0.469 mL, 3.28 mmol) in anhydrous dichloromethane (2 mL) was added dropwise to a solution of (R)-tert-butyl 1-(3-amino-5-chloro-1H-pyrrolo[2,3-b]pyridin-4-yl)piperidin-3-ylcarbamate (200 mg, 547 mmol; Example 91, Step A) and triethylamine (387 mg, 0.533 mL, 3.83 mmol) in NMP (15 mL) cooled on an ice-bath. The mixture was stirred at ambient temperature for 2 hours. THF (10 mL) was added. The mixture treated with an aqueous solution of 2N LiOH (10 mL) and stirred overnight. The mixture was diluted with water and extracted with EtOAc (3×30 mL). The combined organic extracts were dried over MgSO$_4$, filtered, and concentrated. The residue was purified by reverse phase chromatography (Biotage SP4, C-18 25M+, 20-75% CH$_3$CN/water, 25CV) to give (R)-tert-butyl 1-(5-chloro-3-(2-hydroxy-2-methylpropanamido)-1H-pyrrolo[2,3-b]pyridin-4-yl)piperidin-3-ylcarbamate (221 mg, 89% yield) as a solid. LCMS (APCI+) m/z 452, 454 (M+H)+, Retention time=3.44 minutes.

Step B: (R)-tert-Butyl 1-(5-chloro-3-(2-hydroxy-2-methylpropanamido)-1H-pyrrolo[2,3-b]pyridin-4-yl)piperidin-3-ylcarbamate (221 mg, 0.489 mmol) was stirred in trifluoroacetic acid (3 mL) at room temperature for 1.5 hours. The solvent was evaporated in vacuo, and the residue was purified by reverse phase chromatography (Biotage SP4, C-18 25M+, 2-55% CH$_3$CN/water, 25CV). The isolated product was taken up in a minimal volume of methanol and added to a stirred solution of 2N HCl-Et$_2$O. The salt formed was collected by filtration, washed with acetonitrile and dried under vacuum to give (R)—N-(4-(3-aminopiperidin-1-yl)-5-chloro-1H-pyrrolo[2,3-b]pyridin-3-yl)-2-hydroxy-2-methylpropanamide hydrochloride (103 mg, 50% yield) as a solid. $^1$H NMR (400 MHz, D$_2$O) δ 8.05 (s, 1H), 7.53 (s, 1H), 3.64-3.48 (m, 2H), 3.53-3.22 (m, 1H), 3.24-3.16 (m, 1H), 3.12-3.04 (m, 1H), 2.12-2.04 (m, 1H), 1.80-1.66 (m, 2H), 1.56-1.44 (m, 1H), 1.38 (s, 3H), 1.35 (s, 3H). LCMS (APCI+) m/z 352.1, 354.1 (M+H)+, Retention time=2.02 minutes.

Example 104

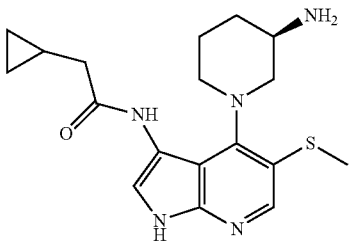

(R)-N-(4-(3-Aminopiperidin-1-yl)-5-(methylthio)-1H-pyrrolo[2,3-b]pyridin-3-yl)-2-cyclopropylacetamide (R)-tert-Butyl 1-(5-bromo-3-(2-cyclopropylacetamido)-1H-pyrrolo[2,3-b]pyridin-4-yl)piperidin-3-ylcarbamate (225 mg, 0.457 mmol; Example 58, Step B) was dissolved in THF (25 mL) and cooled to −78° C. MeLi (1142 μL, 1.83 mmol) was slowly added. The reaction was stirred for 10 minutes. n-Butyl lithium (366 μL, 0.914 mmol) was slowly added. The reaction was stirred for 10 minutes, and then 1,2-dimethyldisulfane (129 mg, 1.37 mmol) was added. The reaction was stirred for 30 minutes and then quenched with water. The reaction mixture was extracted several times with DCM. The organic layer was dried, filtered, and concentrated. The residue was purified by reverse phase chromatography (Gilson, C-18, 0-95% $CH_3CN$/water with 0.1% TFA). The product was then dissolved in 10% MeOH in DCM (2 mL) and added dropwise to a solution of 2M HCl in ether. The reaction was concentrated to give (R)—N-(4-(3-aminopiperidin-1-yl)-5-(methylthio)-1H-pyrrolo[2,3-b]pyridin-3-yl)-2-cyclopropylacetamide hydrochloride (45 mg, 23% yield). $^1H$ NMR (400 MHz, $D_2O$) δ 7.96 (s, 1H), 7.14 (s, 1H), 3.71 (d, 1H), 3.50 (m, 1H), 3.24 (m, 1H), 3.08-2.96 (m, 2H), 2.21 (s, 3H), 2.16 (d, 2H), 1.93 (m, 1H), 1.68 (m, 1H), 1.54-1.39 (m, 2H), 0.83 (m, 1H), 0.37 (m, 2H), 0.01 (m, 2H). LCMS (APCI+) m/z 360.1 (M+H)+, Retention time=2.19 minutes (Method 3).

Example 105

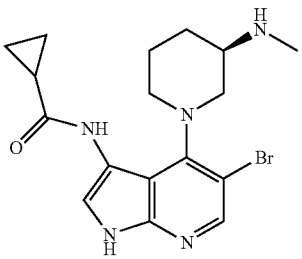

(R)-N-(5-Bromo-4-(3-(methylamino)piperidin-1-yl-1H-pyrrolo[2,3-b]pyridin-3-yl)cyclopropanecarboxamide Step A: A 250 mL round bottom flask was charged with 5-bromo-4-fluoro-1H-pyrrolo[2,3-b]pyridin-3-amine (1.00 g, 4.35 mmol; Example 1, Step H), (R)-tert-butyl methyl (piperidin-3-yl)carbamate (1.86 g, 8.69 mmol), N-ethyl-N-isopropylpropan-2-amine (2.27 mL, 13.0 mmol), and NMP (10.8 mL). Nitrogen was bubbled through the mixture for 5 minutes. The reaction was stirred at 125° C. (oil bath) under positive nitrogen atmosphere for 20 hours to provide the crude (R)-tert-butyl 1-(3-amino-5-bromo-1H-pyrrolo[2,3-b]pyridin-4-yl)piperidin-3-yl(methyl)carbamate.

Step B: A solution of (R)-tert-butyl 1-(3-amino-5-bromo-1H-pyrrolo[2,3-b]pyridin-4-yl)piperidin-3-yl(methyl)carbamate (305 mg, 0.7188 mmol) in NMP (3 mL) was cooled to 0° C. and pyridine (1.5 mL) was added. Then the mixture was treated dropwise with cyclopropanecarbonyl chloride (195.7 μL, 2.156 mmol) and stirred at 0° C. for 30 minutes. 2M $LiOH.H_2O$ (4 mL) was then added, and the mixture was stirred at room temperature. After 48 hours, the mixture was diluted with EtOAc (100 mL) and washed with water (3×20 mL). The organic layer was separated, dried ($MgSO_4$), filtered, and concentrated in vacuo. The residue was purified by reverse phase chromatography (Biotage SP4, C-18 40M+, 15-85% $CH_3CN$/water, 35 CV) to provide (R)-tert-butyl 1-(5-bromo-3-(cyclopropanecarboxamido)-1H-pyrrolo[2,3-b]pyridin-4-yl)piperidin-3-yl(methyl)carbamate hydrochloride (127 mg, 36% yield) as a solid. LCMS (APCI+) m/z 492 (M+H)+.

Step C: A solution of (R)-tert-butyl 1-(5-bromo-3-(cyclopropanecarboxamido)-1H-pyrrolo[2,3-b]pyridin-4-yl)piperidin-3-yl(methyl)carbamate (125 mg, 0.254 mmol) in neat TFA (3 mL) was stirred at room temperature for 30 minutes and concentrated in vacuo. The oily residue was dissolved in $CH_2Cl_2$ and evaporated form $CH_3CN$ (5 mL) to give (R)—N-(5-bromo-4-(3-(methylamino)piperidin-1-yl)-1H-pyrrolo[2,3-b]pyridin-3-yl)cyclopropanecarboxamide hydrochloride (90 mg, 76% yield) as a solid. $^1H$ NMR (400 MHz, $(CD_3)_2SO$) δ 11.81 (s, 1H), 9.62 (s, 1H), 9.21-9.01 (m, 2H), 8.23 (s, 1H), 7.49 (s, 1H), 3.58-3.51 (m, 1H), 3.48-3.22 (m, 3H), 3.10-3.05 (m, 1H), 2.57 (t, 3H), 2.27-2.21 (m, 1H), 1.91-1.82 (m, 2H), 1.78-1.65 (m, 1H), 1.55-1.43 (m, 1H), 0.83 (d, 4H). LCMS (APCI+) m/z 392.1, 394.1 (M+H)+.

Example 106

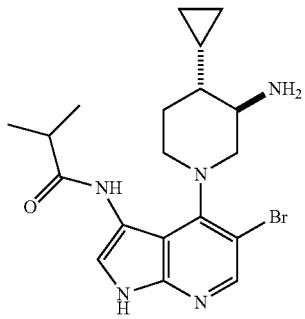

N-(4-(Trans-3-amino-4-cyclopropylpiperidin-1-yl)-5-bromo-1H-pyrrolo[2,3-b]pyridin-3-yl)-isobutyramide A mixture of N-(5-bromo-4-fluoro-1H-pyrrolo[2,3-b]pyridin-3-yl)isobutyramide (0.20 g, 0.67 mmol; Example 15, Step A), tert-butyl-trans-4-cyclopropylpiperidin-3-ylcarbamate (0.48 g, 2.00 mmol; Example K) and DIEA (0.35 mL, 2.00 mmol) in n-BuOH (2 mL) was stirred at 146° C. (bath) for 20 hours. The solvent was removed. The residue was dissolved in ethyl acetate (20 mL), washed with water (10 mL), brine (10 mL), dried (sodium sulfate) and concentrated in vacuo. The residue was purified by reverse phase chromatography (Biotage SP4, C-18 25M+, 20-80% $CH_3CN$/water, 25 CV). The product isolated was dissolved in DCM (2 mL), and TFA (0.5 mL) was added. The mixture was stirred at room temperature for 1 hour. The solvent was removed. The residue was dissolved in DCM (1 mL), and 2N HCl in ether (3 mL) was added. The solid formed was collected to give N-(4-(trans-3-amino-4-cyclopropylpiperidin-1-yl)-5-bromo-1H-pyrrolo[2,3-b]pyridin-3-yl)isobutyramide hydrochloride (0.17 g, 52%) as a solid. $^1$H NMR (400 MHz, D$_2$O) δ 8.21 (s, 1H), 7.26 (s, 1H), 3.81 (m, 1H), 3.48 (m, 1H), 3.38 (m, 1H), 3.11 (m, 2H), 2.60 (m, 1H), 1.88 (m, 1H), 1.82 (m, 1H), 1.52 (m, 1H), 1.16 (m, 1H), 1.07 (t, 6H), 0.77 (m, 1H), 0.39 (m, 1H), 0.14 (m, 1H), 0.11 (m, 1H). LCMS (APCI+) m/z 420 (M+H)+.

Example 107

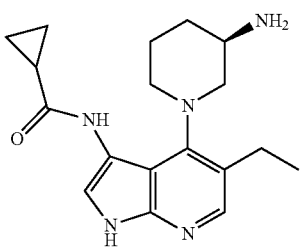

(R)-N-(4-(3-Aminopiperidin-1-yl)-5-ethyl-1H-pyrrolo[2,3-b]pyridin-3-yl)cyclopropanecarboxamide Step A: di-tert-Butyl dicarbonate (150 mg, 0.687 mmol), DMAP (21 mg, 0.172 mmol) and triethylamine (174 mg, 0.239 mL, 1.72 mmol) were added to a solution of (R)-tert-butyl 1-(5-bromo-3-(cyclopropanecarboxamido)-1H-pyrrolo[2,3-b]pyridin-4-yl)piperidin-3-ylcarbamate (274 mg, 0.573 mmol; Example 29, Step B) in anhydrous dichloromethane (6 mL). The resulting mixture was stirred at room temperature under a nitrogen atmosphere for 2 hours. The mixture was concentrated. The residue was taken up in EtOAc, washed with water (3×10 mL) and brine (3×10 mL), dried over MgSO$_4$ and filtered. The filtrate was concentrated under reduced pressure, and the residue was purified by reverse phase chromatography (Biotage SP4, C-18 25M+, 20-95% CH di-tert-butyl dicarbonate (150 mg, 0.687 mmol), DMAP (21 mg, 0.172 mmol) and triethylamine (174 mg, 0.239 mL, 1.72 mmol) CN/water, 25CV) to give (R)-tert-butyl 5-bromo-4-(3-(tert-butoxycarbonylamino)piperidin-1-yl)-3-(cyclopropanecarboxamido)-1H-pyrrolo[2,3-b]pyridine-1-carboxylate (237 mg, 71% yield) as a solid. $^1$H NMR (400 MHz, CDCl$_3$) δ 10.03 (br s, 1H), 8.48 (s, 1H), 8.19 (s, 1H), 3.93-3.73 (m, 1H), 3.67-3.45 (m, 1H), 3.41-3.30 (m, 1H), 3.06-2.99 (m, 1H), 2.27-2.17 (m, 1H), 2.06-1.95 (m, 1H), 1.90-1.77 (m, 1H), 1.63 (s, 9H), 1.60 (s, 1H), 1.42 (s, 9H), 1.22-1.05 (m, 2H), 1.03-0.85 (m, 2H). LCMS (APCI+) m/z 580 (M+2H)+, Retention time=4.53 minutes.

Step B: A solution of (R)-tert-butyl 5-bromo-4-(3-(tert-butoxycarbonyl-amino)piperidin-1-yl)-3-(cyclopropanecarboxamido)-1H-pyrrolo[2,3-b]pyridine-1-carboxylate (200 mg, 0.346 mmol), potassium trifluoro(vinyl)borate (60 mg, 0.449 mmol), PdCl$_2$(dppf) dichloromethane adduct (31 mg, 0.038 mmol) and triethylamine (39 mg, 0.053 mL, 0.38 mmol) in ethanol (6 mL) was heated at 100° C. under nitrogen for 18 hours. The mixture was cooled to room temperature and evaporated under reduced pressure. The residue was purified by reverse phase chromatography (Biotage SP4, C-18 25M+, 20-80% CH$_3$CN/water, 25CV) to give (R)-tert-butyl 4-(3-(tert-butoxycarbonylamino)piperidin-1-yl)-3-(cyclopropanecarboxamido)-5-vinyl-1H-pyrrolo[2,3-b]pyridine-1-carboxylate (64 mg, 35% yield) as a solid. LCMS (APCI+) m/z 526 (M+H)+, Retention time=4.53 minutes.

Step C: 10% Pd/C (65 mg, 0.061 mmol) was added to a solution of (R)-tert-butyl 4-(3-(tert-butoxycarbonylamino)piperidin-1-yl)-3-(cyclopropanecarboxamido)-5-vinyl-1H-pyrrolo[2,3-b]pyridine-1-carboxylate (64 mg, 0.12 mmol) in ethanol (6 mL). The mixture was stirred under a hydrogen atmosphere (balloon) for 3.5 hours. The mixture was filtered through a pad of Celite® and washed with methanol, and the filtrate evaporated in vacuo. The residue was purified by reverse phase chromatography (Biotage SP4, C-18 25M+, 15-80% CH$_3$CN/water, 25CV) to give (R)-tert-butyl 4-(3-(tert-butoxycarbonylamino)piperidin-1-yl)-3-(cyclopropanecarboxamido)-5-ethyl-1H-pyrrolo[2,3-b]pyridine-1-carboxylate (29.4 mg, 46% yield) as a solid. LCMS (APCI+) m/z 528 (M+H)+, Retention time=4.37 minutes.

Step D: (R)-tert-Butyl 4-(3-(tert-butoxycarbonylamino)piperidin-1-yl)-3-(cyclopropanecarboxamido)-5-ethyl-1H-pyrrolo[2,3-b]pyridine-1-carboxylate (29 mg, 0.056 mmol) was stirred at room temperature in trifluoroacetic acid (1.5 mL) for 1.5 hours. The acid was removed in vacuo, and the residue was purified by C-18 flash chromatography (12M+) on a Biotage SP4 eluting with a gradient of 2-50% CH$_3$CN/water (16CV). The isolated product was taken up in a minimal volume of methanol and added to a stirred solution of 2N HCl-Et$_2$O. The salt formed was collected by filtration, washed with acetonitrile and dried under vacuum to give (R)—N-(4-(3-aminopiperidin-1-yl)-5-ethyl-1H-pyrrolo[2,3-b]pyridin-3-yl)cyclopropanecarboxamide hydrochloride (22 mg, 98% yield) as a solid. $^1$H NMR (400 MHz, (CD$_3$)$_2$SO) δ 12.27 (br s, 1H), 9.93 (s, 1H), 8.40 (br s, 1H), 8.11 (s, 1H), 7.47 (d, 1H), 3.73-3.65 (m, 1H), 3.48-3.35 (m, 1H), 3.32-3.10 (m, 3H), 2.78 (q, 2H), 2.20-2.10 (m, 1H), 1.99-1.89 (m, 1H), 1.88-1.80 (m, 1H), 1.78-1.64 (m, 1H), 1.62-1.48 (m, 1H), 1.22 (t, 3H), 0.90-0.75 (m, 4H). LCMS (APCI+) m/z 328.1, 329.1 (M+H)+, Retention time=2.28 minutes.

Example 108

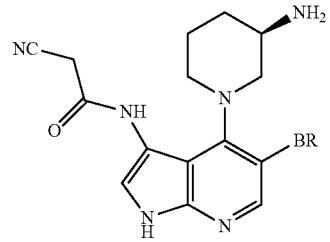

(R)-N-(4-(3-Aminopiperidin-1-yl)-5-bromo-1H-pyrrolo[2,3-b]pyridin-3-yl)-2-cyanoacetamide Step A: 2-Cyanoacetic acid (0.332 g, 3.90 mmol), BOP-Cl (0.993 g, 3.90 mmol), and triethylamine (1.02 mL, 7.31 mmol) were added to an NMP solution (2 mL) of (R)-tert-butyl 1-(3-amino-5-bromo-1H-pyrrolo[2,3-b]pyridin-4-yl)piperidin-3-ylcarbamate (0.200 g, 0.487 mmol; Example 98, Step A). The reaction was then stirred for 18 hours, then poured into water, and extracted with DCM. The combined organic fractions were dried (MgSO$_4$), filtered, and concentrated to give the crude product, which was purified by reverse phase chromatography (Biotage SP4, C-18 25M+, 5-95% CH$_3$CN/water) to give (R)-tert-butyl 1-(5-bromo-3-(2-cyanoacetamido)-1H-pyrrolo[2,3-b]pyridin-4-yl)piperidin-3-ylcarbamate (0.06 g, 26% yield).

Step B: (R)-tert-Butyl 1-(5-bromo-3-(2-cyanoacetamido)-1H-pyrrolo[2,3-b]pyridin-4-yl)piperidin-3-ylcarbamate (0.050 g, 0.10 mmol) was placed in DCM (3 mL) at room temperature. TFA (1 mL) was then added. The reaction was stirred at room temperature for 1 hour and then concentrated to dryness. The resulting residue was then purified by reverse phase chromatography (Biotage SP4, C-18 25M+, 5-50% CH₃CN/water). The resulting product was next dissolved in minimal DCM (with MeOH to aid solubility) and added to a stirring solution of 1M HCl in ether. The resulting solid was filtered, washed with ether and dried to give (R)—N-(4-(3-aminopiperidin-1-yl)-5-bromo-1H-pyrrolo[2,3-b]pyridin-3-yl)-2-cyanoacetamide hydrochloride (0.035 g, 74% yield) as a solid. ¹H NMR (400 MHz, D₂O) δ 8.24 (s, 1H), 7.32 (s, 1H), 3.83 (s, 2H), 3.73-3.70 (m, 1H), 3.56-3.54 (m, 1H), 3.32-3.29 (m, 1H), 3.24-3.13 (m, 2H), 2.10-2.07 (m, 1H), 1.83-1.79 (m, 1H), 1.67-1.55 (m, 2H). LCMS (APCI+) m/z 377, 379 (M+H)+.

Example 109

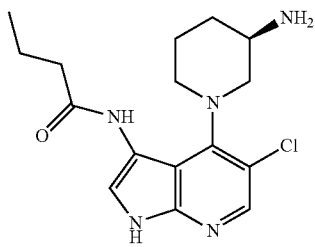

(R)-N-(4-(3-Aminopiperidin-1-yl)-5-chloro-1H-pyrrolo [2,3-b]pyridin-3-yl)butyramide Step A: Butyryl chloride (350 mg, 3.28 mmol) in anhydrous dichloromethane (0.5 mL) was added dropwise to a solution of (R)-tert-butyl 1-(3-amino-5-chloro-1H-pyrrolo[2,3-b]pyridin-4-yl)piperidin-3-ylcarbamate (200 mg, 0.547 mmol; Example 91, Step A) and triethylamine (387 mg, 0.533 mL, 3.83 mmol) in NMP (1.0 mL) cooled on an ice-bath. The resulting mixture was stirred at ambient temperature for 1 hour. The mixture was diluted with THF (10 mL), treated with an aqueous 2N LiOH solution (3 mL) and stirred for 1 hour. The THF was evaporated, and the residue was stirred with water (20 mL) and extracted with EtOAc (3×20 mL). The combined organic extracts were dried over MgSO₄, filtered and concentrated. The residue was purified by reverse phase chromatography (Biotage SP4, C-18 25M+, 15-80% CH₃CN/water, 25CV) to yield (R)-tert-butyl 1-(3-butyramido-5-chloro-1H-pyrrolo[2,3-b]pyridin-4-yl)piperidin-3-ylcarbamate (221 mg, 93% yield) as a solid. LCMS (APCI+) m/z 336.1, 436.1 (M+H)+, Retention time=3.75 minutes.

Step B: (R)-tert-Butyl 1-(3-butyramido-5-chloro-1H-pyrrolo[2,3-b]pyridin-4-yl)piperidin-3-ylcarbamate (221 mg, 0.507 mmol) was stirred in TFA (3 mL) at room temperature for 1.5 hours. The solvent was evaporated in vacuo, and the residue purified by reverse phase chromatography (Biotage SP4, C-18 12M+, 2-50% CH₃CN/water, 16CV). The isolated product was taken up in a minimal volume of methanol and added to a stirred solution of 2N HCl-Et₂O. The salt formed was collected by filtration, washed with acetonitrile and dried under vacuum to give (R)—N-(4-(3-aminopiperidin-1-yl)-5-chloro-1H-pyrrolo[2,3-b]pyridin-3-yl)butyramide (153 mg, 74% yield) as a solid. ¹H NMR (400 MHz, (CD₃)₂SO) δ 11.83 (br s, 1H), 9.32 (s, 1H), 8.35 (br s, 2H), 8.13 (s, 1H), 7.57 (s, 1H), 3.54-3.46 (m, 1H), 3.45-3.30 (m, 2H), 3.27-3.04 (m, 2H), 2.41-2.34 (m, 2H), 2.18-2.09 (m, 1H), 1.91-1.79 (m, 1H), 1.72-1.59 (m, 3H), 1.59-1.39 (m, 1H), 0.96 (t, 3H). LCMS (APCI+) m/z 336.1, 338.1 (M+H)+, Retention time=2.38 minutes.

Example 110

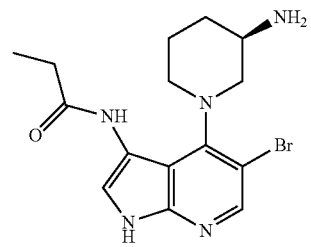

(R)-N-(4-(3-Aminopiperidin-1-yl)-5-bromo-1H-pyrrolo [2,3-b]pyridin-3-yl)propionamide Step A: DCM (2 mL), pyridine (0.5 mL) and propionyl chloride (0.180 g, 1.95 mmol) were added to (R)-tert-butyl 1-(3-amino-5-bromo-1H-pyrrolo[2,3-b]pyridin-4-yl)piperidin-3-ylcarbamate (0.200 g, 0.487 mmol; Example 98, Step A) in NMP (3 mL). The reaction was then stirred for 1 hour at room temperature. 3M aqueous LiOH (3 mL) was then added, and the reaction was stirred for 10 minutes. Water (10 mL) and DCM (10 mL) were then added, and the organic fraction was dried, filtered and concentrated to give the crude product. Purification by reverse phase HPLC (5-95% ACN in water) gave the product (R)-tert-butyl 1-(5-bromo-3-propionamido-1H-pyrrolo[2,3-b]pyridin-4-yl)piperidin-3-ylcarbamate (0.120 g, 52.8% yield).

Step B: (R)-tert-butyl 1-(5-bromo-3-propionamido-1H-pyrrolo[2,3-b]pyridin-4-yl)piperidin-3-ylcarbamate (0.150 g, 0.322 mmol) was placed in DCM (3 mL) at room temperature. TFA (1 mL) was then added. The reaction was stirred at room temperature for 1 hour and concentrated to dryness. The resulting residue was then purified by reverse phase HPLC (0-50% ACN in water). The resulting product was next dissolved in minimal DCM (with MeOH to aid solubility) and added to a stirring solution of 1M HCl in ether. The resulting solid was filtered, washed with ether and dried to give (R)—N-(4-(3-aminopiperidin-1-yl)-5-bromo-1H-pyrrolo[2,3-b] pyridin-3-yl)propionamide hydrochloride (0.110 g, 77.9% yield). ¹H NMR (400 MHz, D₂O) δ 8.24 (s, 1H), 7.27 (s, 1H), 3.74-3.71 (m, 1H), 3.56-3.52 (m, 1H), 3.33-3.30 (m, 1H), 3.20-3.15 (m, 2H), 2.42-2.37 (q, 2H), 2.08-2.06 (m, 1H), 1.80-1.76 (m, 1H), 1.67-1.54 (m, 2H), 1.10-1.06 (t, 3H). LCMS (APCI+) m/z 366, 368 (M+H)+.

Example 111

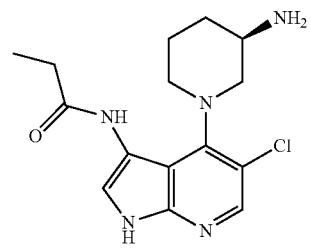

(R)-N-(4-(3-Aminopiperidin-1-yl)-5-chloro-1H-pyrrolo [2,3-b]pyridin-3-yl)-2-propionamide Step A: DCM (2 mL) and pyridine (1 mL) were added to (R)-tert-butyl 1-(3-amino-5-chloro-1H-pyrrolo[2,3-b]pyridin-4-yl)piperidin-3-ylcarbamate (0.3 g, 0.820 mmol;

Example 91, Step A) in NMP (2 mL), and then propionyl chloride (0.228 g, 2.46 mmol) was added. The reaction was then stirred for 1 hour at room temperature, and then 3M aqueous LiOH (3 mL) was added. The reaction was stirred for 10 minutes. Water (10 mL) and DCM (10 mL) were then added, and the organic fraction was dried, filtered and concentrated. Purification of the crude product by reverse phase HPLC (5-95% ACN in water) gave the product (R)-tert-butyl 1-(5-chloro-3-propionamido-1H-pyrrolo[2,3-b]pyridin-4-yl)piperidin-3-ylcarbamate (0.220 g, 63.6% yield).

Step B: (R)-tert-Butyl 1-(5-chloro-3-propionamido-1H-pyrrolo[2,3-b]pyridin-4-yl)piperidin-3-ylcarbamate (0.22 g, 0.521 mmol) was placed in DCM (3 mL) at room temperature. TFA (1 mL) was then added, and the reaction was stirred at room temperature for 1 hour and concentrated to dryness. The resulting residue was then purified by reverse phase HPLC (0-50% ACN in water). The resulting product was next dissolved in minimal DCM (with MeOH to aid solubility) and added to a stirring solution of 1M HCl in ether. The resulting solid was filtered, washed with ether and dried to give (R)—N-(4-(3-aminopiperidin-1-yl)-5-chloro-1H-pyrrolo[2,3-b]pyridin-3-yl)propionamide hydrochloride (0.190 g, 92.3% yield). $^1$H NMR (400 MHz, D$_2$O) δ 8.14 (s, 1H), 7.28 (s, 1H), 3.88-3.84 (m, 1H), 3.54-3.37 (m, 2H), 3.19-3.13 (m, 2H), 2.42-2.37 (q, 2H), 2.11-2.08 (m, 1H), 1.80-1.76 (m, 1H), 1.66-1.54 (m, 2H), 1.10-1.06 (t, 3H). LCMS (APCI+) m/z 322 (M+H)+.

Example 112

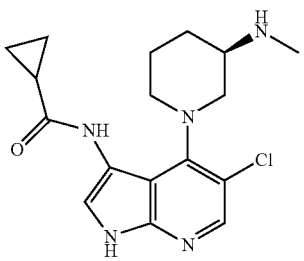

(R)-N-(5-Chloro-4-(3-(methylamino)piperidin-1-yl)-1H-pyrrolo[2,3-b]pyridin-3-yl)cyclopropanecarboxamide Step A: 5-Chloro-4-fluoro-1H-pyrrolo[2,3-b]pyridin-3-amine (0.60 g, 3.2 mmol; Example 8, Step D), (R)-tert-butyl methyl(piperidin-3-yl)carbamate (2.1 g, 9.7 mmol) and DIEA (1.7 mL, 9.7 mmol, d 0.742) were placed in NMP (6 mL) and heated to 120° C. for 20 hours. The reaction was then cooled to room temperature, and the crude NMP solution of (R)-tert-butyl 1-(3-amino-5-chloro-1H-pyrrolo[2,3-b]pyridin-4-yl)piperidin-3-yl(methyl)carbamate was used in the next step without further purification.

Step B: Pyridine (1 mL) and cyclopropanecarbonyl chloride (0.413 g, 3.95 mmol) were added to (R)-tert-butyl 1-(3-amino-5-chloro-1H-pyrrolo[2,3-b]pyridin-4-yl)piperidin-3-yl(methyl)carbamate (0.300 g, 0.790 mmol) in NMP (2 mL), and the reaction was stirred at room temperature for 1 hour. 3M aqueous LiOH (3 mL) was then added, and the reaction was stirred for 10 minutes. Water (10 mL) and DCM (10 mL) were then added, and the organic fraction was separated, dried, filtered, and concentrated. The crude residue was purified by reverse phase chromatography (Biotage SP4, C-18 25M+, 5-95% CH$_3$CN/water) to give (R)-tert-butyl 1-(5-chloro-3-(cyclopropanecarboxamido)-1H-pyrrolo[2,3-b]pyridin-4-yl)piperidin-3-yl(methyl)carbamate (0.170 g, 48% yield).

Step C: (R)-tert-Butyl 1-(5-chloro-3-(cyclopropanecarboxamido)-1H-pyrrolo[2,3-b]pyridin-4-yl)piperidin-3-yl(methyl)carbamate (0.150 g, 0.335 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 12M+, 0-50% CH$_3$CN/water). The resulting product was next dissolved in minimal DCM (with MeOH to aid solubility) and added to a stirred solution of 1M HCl in ether. The resulting solid was filtered, washed with ether and dried to give (R)—N-(5-chloro-4-(3-(methylamino)piperidin-1-yl)-1H-pyrrolo[2,3-b]pyridin-3-yl)cyclopropanecarboxamide hydrochloride (0.120 g, 85% yield) as a solid. $^1$H NMR (400 MHz, D$_2$O) δ 8.12 (s, 1H), 7.27 (s, 1H), 3.87-3.84 (m, 1H), 3.42-3.37 (m, 2H), 3.22-3.17 (m, 2H), 2.60 (s, 3H), 2.18-2.15 (m, 1H), 1.82-1.67 (m, 3H), 1.56-1.53 (m, 1H), 0.91-0.80 (m, 4H). LCMS (APCI+) m/z 348 (M+H)+.

Example 113

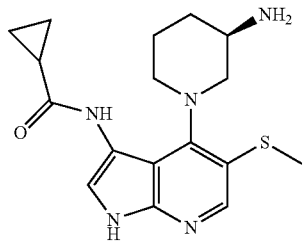

(R)-N-(4-(3-Aminopiperidin-1-yl)-5-(methylthio)-1H-pyrrolo[2,3-b]pyridin-3-yl)cyclopropanecarboxamide (R)-tert-Butyl 1-(5-bromo-3-(cyclopropanecarboxamido)-1H-pyrrolo[2,3-b]pyridin-4-yl)piperidin-3-ylcarbamate (820 mg, 1.71 mmol; Example 15, Step B) was dissolved in THF (35 mL) and cooled to −78° C. MeLi (4285 μL, 6.86 mmol) was slowly added, and the reaction was stirred for 10 minutes. n-Butyl lithium (1714 μL, 4.29 mmol) was slowly added, and the reaction was stirred for 1 minute. 1,2-Dimethyldisulfane (646 mg, 6.86 mmol) was then added. The reaction was stirred for 30 minutes and then quenched with water. The aqueous phase was extracted several times with DCM. The combined organic layers were dried (MgSO$_4$), filtered, and concentrated. The residue was purified by C-18 reverse phase flash chromatography (Gilson prep LC, eluting with 5-95 gradient water:ACN with 0.1% TFA over 20 minutes). The resulting solid was dissolved in TFA (2 mL) and stirred for 20 minutes. The reaction mixture was then concentrated, and the residue dissolved in 10% MeOH in DCM and added to a stirring solution of 2M HCl in ether. Concentration gave (R)—N-(4-(3-aminopiperidin-1-yl)-5-(methylthio)-1H-pyrrolo[2,3-b]pyridin-3-yl)cyclopropanecarboxamide hydrochloride (177 mg, 24.7% yield) as a solid. $^1$H NMR (400 MHz, D$_2$O) δ 8.10 (s, 1H), 7.27 (s, 1H), 3.84 (m, 1H), 3.61 (m, 1H), 3.39 (m, 1H), 3.18 (m, 2H), 2.34 (s, 3H), 2.08 (m, 1H), 1.86-1.53 (m, 4H), 0.92-0.77 (m, 4H). LCMS (APCI+) m/z 346.1 (M+H)+, Retention time=1.97 minutes (Method 3).

Example 114

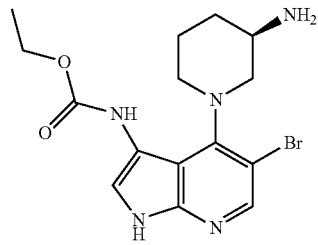

(R)-Ethyl 4-(3-aminopiperidin-1-yl)-5-bromo-1H-pyrrolo[2,3-b]pyridin-3-ylcarbamate Step A: (R)-tert-Butyl 1-(3-amino-5-bromo-1H-pyrrolo[2,3-b]pyridin-4-yl)piperidin-3-ylcarbamate (0.200 g, 0.487 mmol; Example 98, Step A) and triethylamine (0.204 mL, 1.46 mmol) were placed in DCM (5 mL), followed by the addition of diethyl dicarbonate (0.237 g, 1.46 mmol). The reaction was stirred at room temperature for 1 hour. The reaction was then poured into water and extracted with EtOAc. The combined organic fractions were dried (MgSO$_4$), filtered, and concentrated to give the crude product, which was purified by reverse phase chromatography (Biotage SP4, C-18 25M+, 5-95% CH$_3$CN/water) to give (R)-tert-butyl 1-(5-bromo-3-(ethoxycarbonylamino)-1H-pyrrolo[2,3-b]pyridin-4-yl)piperidin-3-ylcarbamate (0.130 g, 55% yield).

Step B: (R)-tert-Butyl 1-(5-bromo-3-(ethoxycarbonylamino)-1H-pyrrolo[2,3-b]pyridin-4-yl)piperidin-3-ylcarbamate (0.120 g, 0.249 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 12M+, 0-50% CH$_3$CN/water). The resulting product was next dissolved in minimal DCM (with MeOH to aid solubility) and added to a stirred solution of 1M HCl in ether. The resulting solid was filtered, washed with ether and dried to give (R)-ethyl 4-(3-aminopiperidin-1-yl)-5-bromo-1H-pyrrolo[2,3-b]pyridin-3-ylcarbamate hydrochloride (0.090 g, 79% yield) as a solid. $^1$H NMR (400 MHz, D$_2$O) δ 8.23 (s, 1H), 7.28 (s, 1H), 4.11-4.06 (q, 2H), 3.78-3.75 (m, 1H), 3.53-3.49 (m, 1H), 3.40-3.43 (m, 1H), 3.27-3.18 (m, 2H), 2.09-2.06 (m, 1H), 1.81-1.69 (m, 2H), 1.60-1.54 (m, 1H), 1.19-1.16 (t, 3H). LCMS (APCI+) m/z 382, 384 (M+H)+.

Example 115

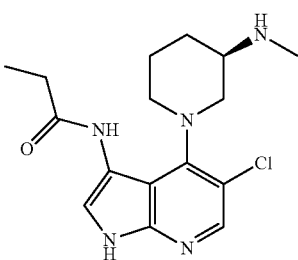

(R)-N-(5-Chloro-4-(3-(methylamino)piperidin-1-yl)-1H-pyrrolo[2,3-b]pyridin-3-yl)propionamide Step A: (R)-tert-Butyl 1-(3-amino-5-chloro-1H-pyrrolo[2,3-b]pyridin-4-yl)piperidin-3-yl(methyl)carbamate (0.300 g, 0.790 mmol; Example 112, Step A) in NMP (2 mL), pyridine (1 mL) and propionyl chloride (0.365 g, 3.95 mmol) were stirred at room temperature for 1 hour. 3M aqueous LiOH (3 mL) was then added, and the reaction was stirred for 10 minutes. Water (10 mL) and DCM (10 mL) were then added, and the organic fraction was separated, dried, filtered, and concentrated. The crude residue was purified by reverse phase chromatography (Biotage SP4, C-18 25M+, 0-95% CH$_3$CN/water) to give (R)-tert-butyl 1-(5-chloro-3-propionamido-1H-pyrrolo[2,3-b]pyridin-4-yl)piperidin-3-yl(methyl)carbamate (0.160 g, 46% yield).

Step B: (R)-tert-Butyl 1-(5-chloro-3-propionamido-1H-pyrrolo[2,3-b]pyridin-4-yl)piperidin-3-yl(methyl)carbamate (0.180 g, 0.413 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 12M+, 0-50% CH$_3$CN/water). The resulting product was dissolved in minimal DCM (with MeOH to aid solubility) and added to a stirred solution of 1M HCl in ether. The resulting solid was filtered, washed with ether and dried to give (R)—N-(5-chloro-4-(3-(methylamino)piperidin-1-yl)-1H-pyrrolo[2,3-b]pyridin-3-yl)propionamide hydrochloride (0.150 g, 89% yield) as a solid. $^1$H NMR (400 MHz, D$_2$O) δ 8.13 (s, 1H), 7.28 (s, 1H), 3.87-3.84 (m, 1H), 3.42-3.37 (m, 2H), 3.20-3.14 (m, 2H), 2.59 (s, 3H), 2.42-2.37 (q, 2H), 1.15-2.13 (m, 1H), 1.79-1.75 (m, 1H), 1.65-1.52 (m, 2H), 1.10-1.06 (t, 3H). LCMS (APCI+) m/z 336 (M+H)+.

Example 116

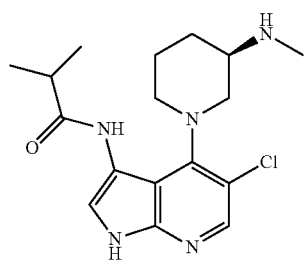

(R)-N-(5-Chloro-4-(3-(methylamino)piperidin-1-yl)-1H-pyrrolo[2,3-b]pyridin-3-yl)isobutyramide Step A: Pyridine (1 mL) and isobutyryl chloride (0.421 g, 3.95 mmol) were added to (R)-tert-butyl 1-(3-amino-5-chloro-1H-pyrrolo[2,3-b]pyridin-4-yl)piperidin-3-yl(methyl)carbamate (0.300 g, 0.790 mmol; Example 112, Step A) in NMP (2 mL), and the reaction was stirred at room temperature for 1 hour. 3M aqueous LiOH (3 mL) was then added, and the reaction was stirred for 10 minutes. Water (10 mL) and DCM (10 mL) were then added, and the organic layer was separated, dried, filtered and concentrated. The crude residue was purified by reverse phase chromatography (Biotage SP4, C-18 12M+, 5-95% CH$_3$CN/water) to give (R)-tert-butyl 1-(5-chloro-3-isobutyramido-1H-pyrrolo[2,3-b]pyridin-4-yl)piperidin-3-yl(methyl)carbamate (0.180 g, 51% yield).

Step B: (R)-tert-Butyl 1-(5-chloro-3-isobutyramido-1H-pyrrolo[2,3-b]pyridin-4-yl)piperidin-3-yl(methyl)carbamate (0.180 g, 0.400 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 12M+, 0-50% CH$_3$CN/water). The resulting product was next dissolved in minimal DCM (with MeOH to aid solubility) and added to a stirred solution of 1M HCl in ether. The resulting solid was filtered, washed with ether and dried to give (R)—N-(5- chloro-4-(3-(methylamino)piperidin-1-yl)-1H-pyrrolo[2,3-b]pyridin-3-yl)isobutyramide hydrochloride (0.150 g, 89% yield) as a solid. ¹H NMR (400 MHz, D₂O) δ 8.16 (s, 1H), 7.28 (s, 1H), 4.01-3.98 (m, 1H), 3.49-3.37 (m, 2H), 3.21-3.11 (m, 2H), 2.69-2.65 (m, 1H), 2.60 (s, 3H), 2.19-2.16 (m, 1H), 1.82-1.78 (m, 1H), 1.64-1.51 (m, 2H), 1.12-1.08 (m, 6H). LCMS (APCI+) m/z 350 (M+H)+.

Example 117

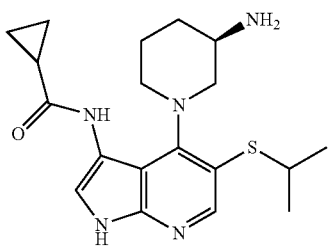

(R)-N-(4-(3-Aminopiperidin-1-yl)-5-(isopropylthio)-1H-pyrrolo[2,3-b]pyridin-3-yl)cyclopropanecarboxamide (R)-tert-Butyl 1-(5-bromo-3-(cyclopropanecarboxamido)-1H-pyrrolo[2,3-b]pyridin-4-yl)piperidin-3-ylcarbamate (150 mg, 0.314 mmol; Example 29, Step B), (9,9-dimethyl-9H-xanthene-4,5-diyl)bis(diphenylphosphine) (18.1 mg, 0.0314 mmol), Pd₂dba₃ (14.4 mg, 0.0157 mmol), propane-2-thiol (71.6 mg, 0.941 mmol), and N-ethyl-N-isopropylpropan-2-amine (109 μL, 0.627 mmol) were placed in dioxane (1 mL) and heated to 150° C. under microwave irradiation for 2 hours. DCM and water were then added to the reaction mixture. The layers were separated, and the organic was washed with 1M NaOH. The organic layer was dried, filtered, and concentrated. The residue was purified by reverse phase chromatography (Biotage SP4, C-18 25M+, 5-95% CH₃CN/water). The product was then dissolved in TFA (2 mL) and stirred for 15 minutes. The reaction was concentrated, and the resulting residue was dissolved in 10% MeOH in DCM and then added dropwise to a stirred solution of 2M HCl in ether. The reaction was concentrated to provide (R)—N-(4-(3-aminopiperidin-1-yl)-5-(isopropylthio)-1H-pyrrolo[2,3-b]pyridin-3-yl)cyclopropanecarboxamide hydrochloride (72 mg, 51% yield) as a solid. ¹H NMR (400 MHz, D₂O) δ 8.21 (s, 1H), 7.27 (s, 1H), 3.91 (d, 1H), 3.65 (m, 1H), 3.52 (d, 1H), 3.27-3.09 (m, 3H), 2.15 (m, 1H), 1.81-1.70 (m, 3H), 1.57 (m, 1H), 1.08 (dd, 6H), 0.94-0.80 (m, 4H). LCMS (APCI+) m/z 374.1 (M+H)+, Retention time=2.38 minutes (Method 3).

Example 118

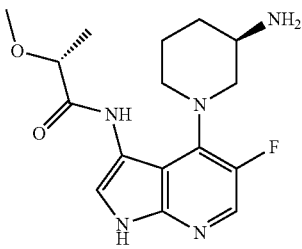

(R)-N-(4-((R)-3-Aminopiperidin-1-yl)-5-fluoro-1H-pyrrolo[2,3-b]pyridin-3-yl)-2-methoxypropanamide Step A: TEA (0.82 mL, 5.91 mmol) was added to a mixture of 4,5-difluoro-1H-pyrrolo[2,3-b]pyridin-3-amine (0.20 g, 1.18 mmol; Example 13, Step C), (R)-2-methoxypropanoic acid (0.25 g, 2.37 mmol) and BOP-Cl (0.60 g, 2.37 mmol) in DCM (5 mL) at room temperature. The reaction was stirred at room temperature for 1 hour, and then a 2N LiOH solution (3 mL) was added. The mixture was stirred at room temperature for 30 minutes, and water (10 mL) and ethyl acetate (30 mL) were added. The organic layer was separated, washed with brine, dried (sodium sulfate) and concentrated in vacuo. The residue obtained was purified by chromatography on silica gel (hexane:ethyl acetate 1:2) to give (R)—N-(4,5-difluoro-1H-pyrrolo[2,3-b]pyridin-3-yl)-2-methoxypropanamide (0.21 g, 70%) as a solid.

Step B: A mixture of (R)—N-(4,5-difluoro-1H-pyrrolo[2,3-b]pyridin-3-yl)-2-methoxypropanamide (0.21 g, 0.82 mmol), (R)-tert-butyl piperidin-3-ylcarbamate (0.33 g, 1.65 mmol) and DIEA (0.43 mL, 2.47 mmol) in n-BuOH (2 mL) was stirred at 140° C. (bath) for 12 hours. The solvent was removed, and the residue was dissolved in ethyl acetate (20 mL), washed with water (10 mL), brine (10 mL), dried (sodium sulfate) and concentrated in vacuo. The residue obtained was purified by reverse phase chromatography (Biotage SP4, C-18 25M+, 10-80% CH₃CN/water gradient, 25 CV). The product isolated was dissolved in DCM (2 mL), and TFA (0.5 mL) was added. The mixture was stirred at room temperature for 1 hour. The solvent was removed. The residue was dissolved in DCM (1 mL) and 2N HCl in ether (3 mL) was added. The solid formed was collected to give (R)—N-(4-((R)-3-aminopiperidin-1-yl)-5-fluoro-1H-pyrrolo[2,3-b]pyridin-3-yl)-2-methoxypropanamide hydrochloride (0.31 g, 93%) as a solid. ¹H NMR (400 MHz, D₂O) δ 8.08 (d, 1H), 7.38 (s, 1H), 4.02 (m, 1H), 3.80 (m, 1H), 3.46 (m, 2H), 3.37 (s, 3H), 3.30 (m, 1H), 3.20 (m, 1H), 2.07 (m, 1H), 1.76 (m, 1H), 1.62 (m, 2H), 1.33 (d, 3H). LCMS (APCI+) m/z 336 (M+H)+.

Example 119

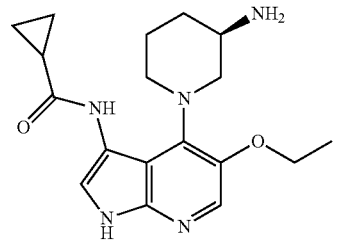

(R)-N-(4-(3-Aminopiperidin-1-yl)-5-ethoxy-1H-pyrrolo[2,3-b]pyridin-3-yl)cyclopropanecarboxamide Step A: sec-Butyllithium (27 mL, 38 mmol; 1.4M in cyclohexane) was added dropwise to 4-fluoro-1-(triisopropylsilyl)-1H-pyrrolo[2,3-b]pyridine (5.0 g, 17 mmol; Example 1, Step D) in THF (200 mL) at −78° C., and the reaction was stirred for 30 minutes. (1S)-(+)-(10-Camphorsulfonyl)oxaziridine (9.4 g, 41 mmol) in THF (40 mL) was added rapidly, and the reaction was stirred at −78° C. for 30 minutes. A solution of saturated ammonium chloride (50 mL) was added, and the reaction mixture was allowed to reach room temperature. After one hour, the aqueous phase was extracted with AcOEt, dried over MgSO₄ and concentrated to a solid, which was triturated in ether. The solid (most of the camphor side product) was filtered off, and the filtrate was concentrated and purified by reverse phase chromatography (Biotage SP4, C-18 40M+, water/ACN 40/60→0/100, 12 CV) to yield 4-fluoro-1-(triisopropylsilyl)-1H-pyrrolo[2,3-b]pyridin-5-ol (2.6 g, 49% yield) as a paste.

Step B: Potassium carbonate (3.49 g, 25.3 mmol) and bromoethane (1.10 g, 10.1 mmol) were added to 4-fluoro-1-(triisopropylsilyl)-1H-pyrrolo[2,3-b]pyridin-5-ol (2.6 g, 8.43 mmol) in DMF (5 mL). The reaction was heated to 60° C. in a sealed tube for 24 hours and then filtered. After concentration, the filtrate was purified by reverse phase chromatography (Biotage SP4, C-18 25M+, water/ACN, 90/10→10/90, 20CV) to yield 5-ethoxy-4-fluoro-1H-pyrrolo[2,3-b]pyridine (360 mg, 12% yield) as a solid.

Step C: Cold (about 0 to about 5° C.) fuming nitric acid (10 mL) was added to 5-ethoxy-4-fluoro-1H-pyrrolo[2,3-b]pyridine (340 mg, 0.944 mmol). The reaction was stirred at 0° C. for 15 minutes and then ice was added. The resulting solid was filtered and dried to yield 5-ethoxy-4-fluoro-3-nitro-1H-pyrrolo[2,3-b]pyridine (165 mg, 78% yield) as a solid.

Step D: Tin chloride (674 mg, 3.55 mmol) was added to 5-ethoxy-4-fluoro-3-nitro-1H-pyrrolo[2,3-b]pyridine (160 mg, 0.711 mmol) in 6N HCl (5 mL) at about 0 to about 5° C., and then the reaction was stirred at 0 to about 5° C. for 2 hours. The solution was neutralized by addition of 6N NaOH and then extracted with CHCl$_3$/IPA (3:1). The combined organic phases were dried over MgSO$_4$ and concentrated to leave 5-ethoxy-4-fluoro-1H-pyrrolo[2,3-b]pyridin-3-amine (120 mg, 86% yield) as a solid.

Step E: Cyclopropanecarbonyl chloride (63.1 μL, 0.676 mmol) was added dropwise to 5-ethoxy-4-fluoro-1H-pyrrolo[2,3-b]pyridin-3-amine (120 mg, 0.615 mmol) in pyridine (5 mL) at 0° C. The reaction was stirred at about 0 to about 5° C. for 2 hours and then concentrated to dryness. Water (10 mL) was added and extracted with CHCl$_3$/IPA (3:1). The combined organic phases were dried over MgSO$_4$ and concentrated to yield N-(5-ethoxy-4-fluoro-1H-pyrrolo[2,3-b]pyridin-3-yl)cyclopropanecarboxamide (90 mg, 55% yield) as a solid.

Step F: (R)-tert-Butyl piperidin-3-ylcarbamate (205 mg, 1.0 mmol) was added to N-(5-ethoxy-4-fluoro-1H-pyrrolo[2,3-b]pyridin-3-yl)cyclopropanecarboxamide (90 mg, 0.34 mmol) in n-butanol (2 mL). The reaction was stirred at 160° C. for 24 hours in a sealed tube. After cooling down and concentration, the residue was purified by reverse phase chromatography (Biotage SP4, C-18 25M+, water/ACN 90/10→10/90, 30CV) to yield (R)-tert-butyl 1-(3-(cyclopropanecarboxamido)-5-ethoxy-1H-pyrrolo[2,3-b]pyridin-4-yl)piperidin-3-ylcarbamate (39 mg) as a solid.

Step G: TFA (3 mL) was added to (R)-tert-butyl 1-(3-(cyclopropanecarboxamido)-5-ethoxy-1H-pyrrolo[2,3-b]pyridin-4-yl)piperidin-3-ylcarbamate (39 mg, 0.088 mmol), and the reaction was stirred at room temperature for 30 minutes. After concentration, the residue was dissolved in MeOH (0.5 mL) and added to a 2N solution of HCL in ether. The resulting solid was collected and dried to yield (R)—N-(4-(3-aminopiperidin-1-yl)-5-ethoxy-1H-pyrrolo[2,3-b]pyridin-3-yl)cyclopropanecarboxamide hydrochloride (28 mg, 93% yield) as a solid. $^1$H NMR (400 MHz, (CD$_3$)$_2$SO) δ 11.80 (s, 1H), 9.85 (s, 1H), 8.43 (s, 1H), 8.25 (s, 2H), 8.00 (s, 1H), 7.40 (s, 1H), 4.05 (q, 2H), 3.68-3.12 (m, 4H), 2.06-1.45 (m, 5H), 1.36 (t, 3H), 1.02 (t, 1H), 0.80-0.70 (m, 4H). LCMS (APCI+) m/z 344.1 (M+H)+.

Example 120

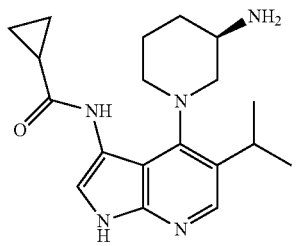

(R)-N-(4-(3-Aminopiperidin-1-yl)-5-isopropyl-1H-pyrrolo[2,3-b]pyridin-3-yl)cyclopropanecarboxamide Step A: 4,4,5,5-Tetramethyl-2-(prop-1-en-2-yl)-1,3,2-dioxaborolane (436 mg, 2.59 mmol), PS-tetrakis(triphenylphosphine)palladium (786 mg, 0.0864 mmol, 0.10 mmol/1 g) and 2N sodium carbonate (1296 μL, 2.59 mmol) were added to (R)-tert-butyl 5-bromo-4-(3-(tert-butoxycarbonylamino)piperidin-1-yl)-3-(cyclopropanecarboxamido)-1H-pyrrolo[2,3-b]pyridine-1-carboxylate (500 mg, 0.864 mmol; Example 107, Step A) in degassed dioxane (1 mL). The reaction was heated to 120° C. for an hour under microwave irradiation. The reaction was then heated to 150° C. for 30 minutes. The reaction was filtered and extracted with DCM. The organic layer was concentrated, and the resulting residue was purified by reverse phase chromatography (Gilson, C-18, 5-95% CH$_3$CN/water) to yield (R)-tert-butyl 1-(3-(cyclopropanecarboxamido)-5-(prop-1-en-2-yl)-1H-pyrrolo[2,3-b]pyridin-4-yl)piperidin-3-ylcarbamate (236 mg, 62% yield).

Step B: (R)-tert-Butyl 1-(3-(cyclopropanecarboxamido)-5-(prop-1-en-2-yl)-1H-pyrrolo[2,3-b]pyridin-4-yl)piperidin-3-ylcarbamate (236 mg, 0.53 mmol), 2,2,2-trifluoroacetate (290 mg, 0.524 mmol) and 10% Pd/C (558 mg, 0.524 mmol) were placed in ethanol (10 mL). The reaction was then hydrogenated at about 1 to about 2 atm (balloon) at room temperature for 18 hours. The reaction was filtered through a plug of celite and concentrated. The residue was purified by reverse phase chromatography (Gilson, C-18, 5-95% CH$_3$CN/water). The product was then dissolved in TFA and stirred for 15 minutes. The reaction was concentrated, and the resulting residue was dissolved in 10% MeOH in DCM and added to a stirred solution of 2M HCl in ether. The reaction was concentrated, and the resulting residue was purified by reverse phase chromatography (Gilson, C-18, 0-60% CH$_3$CN/water). The product was then dissolved in 10% MeOH in DCM and added to a stirred solution of 2M HCl in ether. The reaction was concentrated to give (R)—N-(4-(3-aminopiperidin-1-yl)-5-isopropyl-1H-pyrrolo[2,3-b]pyridin-3-yl)cyclopropanecarboxamide hydrochloride (21 mg, 10% yield) as a solid. $^1$H NMR (400 MHz, D$_2$O) δ 8.07 (s, 1H), 7.32 (s, 1H), 3.57 (d, 1H), 3.39 (m, 1H), 3.30-3.05 (m, 4H), 2.12 (m, 1H), 1.77 (m, 3H), 1.53 (m, 1H), 1.16 (d, 6H), 0.93-0.82 (m, 4H). LCMS (APCI+) m/z 342.1 (M+H)+, Retention time=2.37 minutes (Method 3).

Example 121

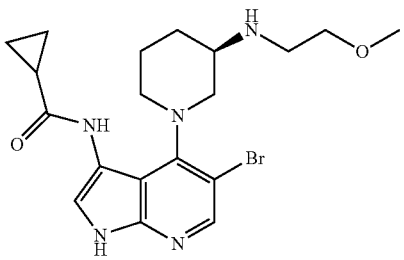

(R)-N-(5-Bromo-4-(3-(2-methoxyethylamino)piperidin-1-yl)-
1H-pyrrolo[2,3-b]pyridin-3-yl)cyclopropanecarboxamide (R)—N-(4-(3-Aminopiperidin-1-yl)-5-bromo-1H-pyrrolo[2,3-b]pyridin-3-yl)cyclopropanecarboxamide hydrochloride (0.100 g, 0.222 mmol; Example 29, Step C), 1-bromo-2-methoxyethane (0.0246 mL, 0.266 mmol), and DIEA (0.154 mL, 0.887 mmol, d 0.742) were placed in DMF (2 mL) and heated to 80° C. for 18 hours. The reaction was then poured into water and extracted with EtOAc. The combined organic fractions were dried (MgSO$_4$), filtered, and concentrated to give the crude product, which was purified by reverse phase chromatography (Biotage SP4, C-18 25M+, 20-50% CH$_3$CN/water). The product was next dissolved in minimal DCM (with MeOH to aid solubility) and added to a stirring solution of 1M HCl in ether. The resulting solid was filtered, washed with ether and dried to give (R)—N-(5-bromo-4-(3-(2-methoxyethylamino)piperidin-1-yl)-1H-pyrrolo[2,3-b]pyridin-3-yl)cyclopropanecarboxamide (0.03 g, 30%). $^1$H NMR (400 MHz, D$_2$O) δ 8.23 (s, 1H), 7.26 (s, 1H), 3.77-3.74 (m, 1H), 3.54-3.50 (m, 3H), 3.28-3.11 (m, 5H), 3.18 (s, 3H), 2.19-2.12 (m, 1H), 1.82-1.61 (m, 4H), 0.90-0.82 (m, 4H). LCMS (APCI+) m/z 436, 438 (M+H)+.

Example 122

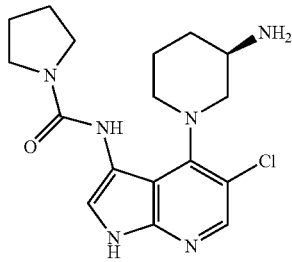

(R)-N-(4-(3-Aminopiperidin-1-yl)-5-chloro-1H-
pyrrolo[2,3-b]pyridin-3-yl)pyrrolidine-1-carboxamide Step A: (R)-tert-Butyl piperidin-3-ylcarbamate (1619 mg, 8.08 mmol) was added to a mixture of 5-chloro-4-fluoro-1H-pyrrolo[2,3-b]pyridin-3-amine (500 mg, 2.69 mmol; Example 8, Step D) and N-ethyl-N-isopropylpropan-2-amine (1408 µL, 8.08 mmol) in NMP (6.75 mL). N$_2$ was bubbled through the mixture for 5 minutes, and the reaction was stirred at 120° C. under N$_2$ for 24 hours. The mixture was allowed to cool, was diluted with 20% EtOAc/Et$_2$O (200 mL) and washed with water (5×50 mL). The organic layer was then dried over MgSO$_4$, filtered, and concentrated in vacuo to provide the crude (R)-tert-butyl 1-(3-amino-5-chloro-1H-pyrrolo[2,3-b]pyridin-4-yl)piperidin-3-ylcarbamate. LCMS (APCI+) m/z 366 (M+H)+.

Step B: Di(1H-imidazol-1-yl)methanone (2185 mg, 13.5 mmol) was added to a stirring solution of crude (R)-tert-butyl 1-(3-amino-5-chloro-1H-pyrrolo[2,3-b]pyridin-4-yl)piperidin-3-ylcarbamate (986 mg, 2.70 mmol) in THF (10 mL), and the mixture was stirred at room temperature. After 18 hours, the reaction mixture was concentrated in vacuo. The residue obtained was dissolved in EtOAc (100 mL) and washed with water (4×20 mL) and brine (1×20 mL). The organic layer was separated, dried (MgSO$_4$), filtered, and concentrated in vacuo. The residue obtained was purified by reverse phase chromatography (Biotage SP4, C-18 25M+, 15-85% CH$_3$CN/water). The product was extracted from the aqueous phase into EtOAc (3×50 mL). The combined organic layers were washed with water (2×10 mL), dried (MgSO$_4$), filtered, and concentrated in vacuo to provide (R)-tert-butyl 1-(5-chloro-3-(pyrrolidine-1-carboxamido)-1H-pyrrolo[2,3-b]pyridin-4-yl)piperidin-3-ylcarbamate (920 mg, 74% yield) as a solid. LCMS (APCI+) m/z 463.1 (M+H)+.

Step C: A solution of (R)-tert-butyl 1-(5-chloro-3-(pyrrolidine-1-carboxamido)-1H-pyrrolo[2,3-b]pyridin-4-yl)piperidin-3-ylcarbamate (130 mg, 0.281 mmol) in neat TFA (4 mL) was stirred at room temperature for 10 minutes, and then the TFA was removed in vacuo. The resulting oily residue was dissolved in CH$_3$OH (5 mL) and evaporated from CH$_3$CN (2×5 mL) to provide (R)—N-(4-(3-aminopiperidin-1-yl)-5-chloro-1H-pyrrolo[2,3-b]pyridin-3-yl)pyrrolidine-1-carboxamide hydrochloride (112 mg, 91% yield) as a solid. $^1$H NMR (400 MHz, (CD$_3$)$_2$SO) δ 1.68 (br s, 1H), 8.25 (s, 3H), 8.10 (s, 1H), 7.85 (s, 1H), 7.42 (d, 1H), 3.51-3.45 (m, 1H), 3.44-3.36 (m, 4H), 3.34-3.22 (m, 3H), 3.16-3.07 (m, 1H), 2.09-2.01 (m, 1H), 1.90-1.87 (m, 4H), 1.80-1.72 (m, 1H), 1.67-1.41 (m, 2H). LCMS (APCI+) m/z 363 (M+H)+.

Example 123

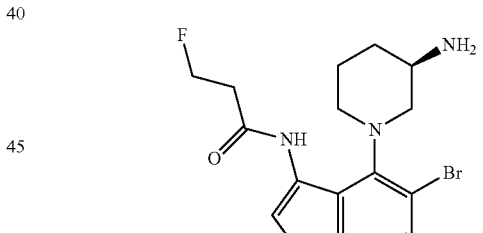

(R)-N-(4-(3-Aminopiperidin-1-yl)-5-bromo-
1H-pyrrolo[2,3-b]pyridin-3-yl)-3-fluoropropanamide Step A: (R)-tert-Butyl 1-(3-amino-5-bromo-1H-pyrrolo[2,3-b]pyridin-4-yl)piperidin-3-ylcarbamate (0.280 g, 0.682 mmol; Example 98, Step A), 3-fluoropropanoic acid (0.314 g, 3.41 mmol), BOP-Cl (0.869 g, 3.41 mmol), and triethylamine (0.761 mL, 5.46 mmol) were placed in DCM (5 mL) and stirred for 1 hour. 3M aqueous LiOH (5 mL) was then added. The reaction was stirred for 1 hour, poured into water, and extracted with DCM. The combined organic fractions were dried (MgSO$_4$), filtered, and concentrated to give the crude product, which was purified by reverse phase chromatography (Biotage SP4, C-18 25M+, 5-95% CH$_3$CN/water) to give (R)-tert-butyl 1-(5-bromo-3-(3-fluoropropanamido)-1H-pyrrolo[2,3-b]pyridin-4-yl)piperidin-3-ylcarbamate (0.050 g, 15% yield).

Step B: (R)-tert-Butyl 1-(5-bromo-3-(3-fluoropropanamido)-1H-pyrrolo[2,3-b]pyridin-4-yl)piperidin-3-ylcarbamate (50 mg, 0.103 mmol) was placed in DCM (3 mL) at room temperature. TFA (1 mL) was then added, and the reaction was stirred at room temperature for 1 hour and concentrated to dryness. The residue was then purified by reverse phase chromatography (Biotage SP4, C-18 25M+, 0-50% CH$_3$CN/water). The resulting product was next dissolved in minimal DCM (with MeOH to aid solubility) and added to a stirred solution of 1M HCl in ether. The resulting solid was filtered, washed with ether and dried to give the product (R)—N-(4-(3-aminopiperidin-1-yl)-5-bromo-1H-pyrrolo[2,3-b]pyridin-3-yl)-3-fluoro-propanamide hydrochloride (0.018 g, 38% yield) as a solid. $^1$H NMR (400 MHz, D$_2$O) δ 8.24 (s, 1H), 7.29 (s, 1H), 4.77-4.73 (m, 1H), 4.66-4.65 m, 1H), 3.73-3.70 (m, 1H), 3.54-3.50 (m, 1H), 3.32-3.29 (m, 1H), 3.21-3.16 (m, 2H), 2.85-2.84 (m, 1H), 2.79-2.77 (m, 1H), 2.04-2.02 (m, 1H), 1.79-1.76 (m, 1H), 1.67-1.65 (m, 1H), 1.56-1.53 (m, 1H). LCMS (APCI+) m/z 384, 386 (M+H)+.

Example 124

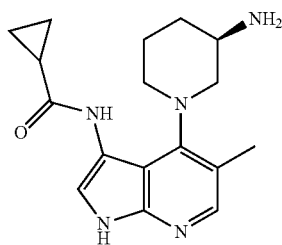

(R)-N-(4-(3-Aminopiperidin-1-yl)-5-methyl-1H-pyrrolo[2,3-b]pyridin-3-yl)cyclopropanecarboxamide Step A: Triethylamine (551 µL, 3.96 mmol) was added to a suspension of (R)—N-(4-(3-aminopiperidin-1-yl)-5-bromo-1H-pyrrolo[2,3-b]pyridin-3-yl)cyclopropanecarboxamide hydrochloride salt (357 mg, 0.791 mmol; Example 29, Step C) in CH$_2$Cl$_2$ (15 mL) at room temperature. The resulting solution was treated with di-tert-butyl dicarbonate (363 mg, 1.66 mmol), followed by N,N-dimethylpyridin-4-amine (9.67 mg, 0.0791 mmol) and stirred at room temperature. After 18 hours, the mixture was diluted with CH$_2$Cl$_2$ (100 mL) and washed with water (3×20 mL). The organic phase was separated, dried (MgSO$_4$), filtered, and concentrated in vacuo. The residue was purified by silica gel chromatography (Biotage, 40S+, 20% EtOAc/hexane) to provide (R)-tert-butyl 5-bromo-4-(3-(tert-butoxycarbonylamino)piperidin-1-yl)-3-(cyclopropanecarboxamido)-1H-pyrrolo[2,3-b]pyridine-1-carboxylate (173 mg, 38% yield) as a solid. LCMS (APCI+) m/z 578.1. 580.1 (M+H)+.

Step B: A solution of (R)-tert-butyl 5-bromo-4-(3-(tert-butoxycarbonylamino)piperidin-1-yl)-3-(cyclopropanecarboxamido)-1H-pyrrolo[2,3-b]pyridine-1-carboxylate (175 mg, 0.303 mmol) in dioxane (5 mL) at room temperature was treated with potassium carbonate (107 mg, 0.771 mmol), Pd(PPh$_3$)$_4$ (31.5 mg, 0.0272 mmol), and 2,4,6-trimethyl-1,3,5,2,4,6-trioxatriborinane (34.2 mg, 0.272 mmol). N$_2$ was bubbled through the mixture for 5 minutes, and the mixture was heated at reflux for 24 hours under N$_2$ atmosphere. The mixture was then diluted with EtOAc (20 mL) and washed with water (1×5 mL). The organic layer was separated, dried (MgSO$_4$), filtered, and concentrated in vacuo. The residue obtained was purified by reverse phase chromatography (Biotage SP4, C-18 25M+, 40-95% CH$_3$CN/water, 24 CV) to provide (R)-tert-butyl 4-(3-(tert-butoxycarbonylamino)piperidin-1-yl)-3-(cyclopropanecarboxamido)-5-methyl-1H-pyrrolo[2,3-b]pyridine-1-carboxylate (86 mg, 55% yield) as a solid. LCMS (APCI+) m/z 514.1 (M+H)+.

Step C: TFA (3 mL) was added to solid (R)-tert-butyl 4-(3-(tert-butoxycarbonylamino)piperidin-1-yl)-3-(cyclopropanecarboxamido)-5-methyl-1H-pyrrolo[2,3-b]pyridine-1-carboxylate (70 mg, 0.14 mmol), and the mixture was stirred at room temperature for 30 minutes. TFA was then removed in vacuo, and the resulting oily residue was dissolved in MeOH (1 drop) and CH$_2$Cl$_2$ (2 mL). This solution was treated with 2M HCl in ether (3 mL). The precipitate formed was concentrated in vacuo and the residue was evaporated from CH$_3$CN (3×5 mL) and dried under high vacuum for 24 hours to provide (R)—N-(4-(3-aminopiperidin-1-yl)-5-methyl-1H-pyrrolo[2,3-b]pyridin-3-yl)cyclopropanecarboxamide hydrochloride (48 mg, 91% yield) as a solid. $^1$H NMR (400 MHz, (CD$_3$)$_2$SO) δ 12.27 (br s, 1H), 9.94 (s, 1H), 8.38 (br s, 3H), 8.09 (s, 1H), 7.43 (d, 1H), 3.78-3.71 (m, 1H), 3.44-3.29 (m, 2H), 3.26-3.16 (m, 2H), 2.40 (s, 3H), 2.18-2.09 (m, 1H), 1.94-1.86 (m, 1H), 1.85-1.79 (m, 1H), 1.74-1.62 (m, 1H), 1.59-1.49 (m, 1H), 0.88-0.79 (m, 4H). LCMS (APCI+) m/z 314 (M+H)+.

Example 125

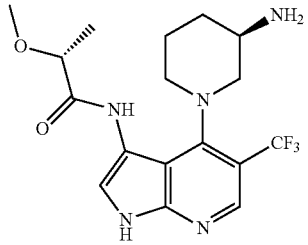

(R)-N-(4-((R)-3-Aminopiperidin-1-yl)-5-(trifluoromethyl)-1H-pyrrolo[2,3-b]pyridin-3-yl)-2-methoxypropanamide Step A: Triethylamine (430 mg, 0.592 mL, 4.25 mmol) was slowly added to a mixture of 4-chloro-5-(trifluoromethyl)-1H-pyrrolo[2,3-b]pyridin-3-amine (200 mg, 0.849 mmol; Example 12, Step G), (R)-2-methoxypropanoic acid (106 mg, 1.02 mmol) and bis(2-oxooxazolidin-3-yl)phosphinic chloride (238 mg, 0.934 mmol) in anhydrous dichloromethane (10 mL). The resulting mixture was stirred at room temperature for 16 hours. The mixture was concentrated, and the residue stirred in THF (5 mL) and treated with water (20 mL). The solid, which separated, was collected by filtration and washed with water then dried under vacuum to yield (R)—N-(4-chloro-5-(trifluoromethyl)-1H-pyrrolo[2,3-b]pyridin-3-yl)-2-methoxypropanamide (263 mg, 96% yield) as a solid. $^1$H NMR (400 MHz, (CD$_3$)$_2$SO) δ 12.49 (br s, 1H), 9.48 (s, 1H), 8.59 (s, 1H), 7.89 (d, 1H), 3.93 (q, 1H), 3.41 (s, 3H), 1.36 (d, 3H).

Step B: (R)-tert-Butyl piperidin-3-ylcarbamate (456 mg, 2.28 mmol) and N,N-diisopropylethylamine (294 mg, 0.396 mL, 2.28 mmol) were added to a suspension of (R)—N-(4-chloro-5-(trifluoromethyl)-1H-pyrrolo[2,3-b]pyridin-3-yl)-2-methoxypropanamide (244 mg, 0.759 mmol) in n-BuOH (3 mL). The resulting mixture was heated in a sealed tube under a nitrogen atmosphere at 160° C. for 24 hours. The cooled mixture was diluted with water and extracted with EtOAc (3×20 mL). The combined organic layer was dried over MgSO₄ and filtered, and the filtrate was concentrated to an oil, which was purified by reverse phase chromatography (Biotage SP4, C-18 25M+, 15-80% CH₃CN/water, 25CV) to give tert-butyl (R)-1-(3-((R)-2-methoxypropanamido)-5-(trifluoromethyl)-1H-pyrrolo[2,3-b]pyridin-4-yl)piperidin-3-ylcarbamate (151 mg, 41%) as a solid. LCMS (APCI+) m/z 386.1, 486.1 (M+H)+, Retention time=3.85 minutes.

Step C: (R)-1-(3-((R)-2-Methoxypropanamido)-5-(trifluoromethyl)-1H-pyrrolo[2,3-b]pyridin-4-yl)piperidin-3-ylcarbamate (152 mg, 0.292 mmol) was stirred in trifluoroacetic acid (3 mL) at room temperature for 1.5 hours. The solvent was evaporated in vacuo, and the residue was purified by reverse phase chromatography (Biotage SP4, C-18 25M+, 10-60% CH₃CN/water, 25CV). The isolated product was taken up in a minimal volume of methanol and added to a stirred solution of 2N HCl-Et₂O. The salt formed was collected by filtration, washed with acetonitrile and dried under vacuum to give (R)—N-(4-((R)-3-aminopiperidin-1-yl)-5-(trifluoromethyl)-1H-pyrrolo[2,3-b]pyridin-3-yl)-2-methoxypropanamide hydrochloride (76 mg, 53% yield) as a solid. ¹H NMR (400 MHz, D₂O) δ 8.54 (s, 1H), 8.07 (s, 1H), 4.03-4.0 (m, 1H), 3.46 (s, 3H), 3.43-3.33 (m, 2H), 3.14-3.06 (m, 2H), 3.05-2.96 (m, 1H), 2.22-2.12 (m, 1H), 1.90-1.82 (m, 1H), 1.56-1.47 (m, 1H), 1.42 (d, 3H). LCMS (APCI+) m/z 386, 387 (M+H)+, Retention time=2.30 minutes.

Example 126

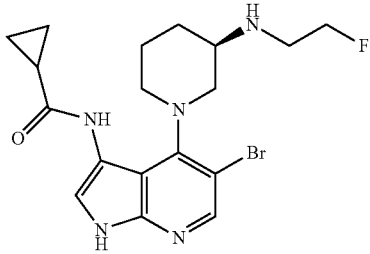

(R)-N-(5-Bromo-4-(3-(2-fluoroethylamino)piperidin-1-yl)-1H-pyrrolo[2,3-b]pyridin-3-yl)cyclopropanecarboxamide (R)—N-(4-(3-Aminopiperidin-1-yl)-5-bromo-1H-pyrrolo[2,3-b]pyridin-3-yl)cyclopropanecarboxamide hydrochloride (0.112 g, 0.248 mmol; Example 29, Step C), 1-bromo-2-fluoroethane (0.0222 mL, 0.298 mmol) and DIEA (0.173 mL, 0.993 mmol, d 0.742) were placed in DMF (2 mL) and heated to 80° C. for 36 hours. The reaction was then cooled to room temperature, poured into water, and extracted with EtOAc. The combined organic fractions were dried (MgSO₄), filtered, and concentrated to give the crude product, which was purified by reverse phase chromatography (Biotage SP4, C-18 40M+, 5-50% water:ACN). The product was next dissolved in minimal DCM (with MeOH to aid solubility) and added to a stirring solution of 1M HCl in ether. The resulting solid was filtered, washed with ether and dried to give (R)—N-(5-bromo-4-(3-(2-fluoroethylamino)piperidin-1-yl)-1H-pyrrolo[2,3-b]pyridin-3-yl)cyclopropanecarboxamide hydrochloride (0.018 g, 15% yield) as a solid. ¹H NMR (400 MHz, D₂O) δ 8.23 (s, 1H), 7.26 (s, 1H), 4.69-4.67 (m, 1H), 4.56-4.55 (m, 1H), 3.84-3.81 (m, 1H), 3.57-3.54 (m, 1H), 3.42-3.16 (m, 5H), 2.22-2.19 (m, 1H), 1.80-1.73 (m, 3H), 1.57-1.55 (m, 1H), 0.90-0.80 (m, 4H). LCMS (APCI+) m/z 424, 426 (M+H)+.

Example 127

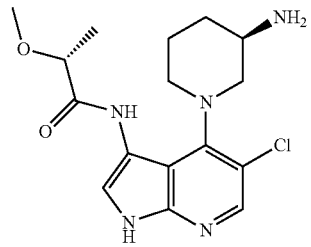

(R)-N-(4-((R)-3-Aminopiperidin-1-yl)-5-chloro-1H-pyrrolo[2,3-b]pyridin-3-yl)-2-methoxypropanamide NMP (4 mL), DIEA (2.47 g, 19.1 mmol), (R)-2-methoxypropanoic acid (1.42 g, 13.7 mmol), and BOP-Cl (3.48 g, 13.7 mmol) were added to a solution of crude (R)-tert-butyl 1-(3-amino-5-chloro-1H-pyrrolo[2,3-b]pyridin-4-yl)piperidin-3-ylcarbamate (1.00 g, 2.73 mmol; Example 91, Step A) in NMP (3.3 mL). The reaction was stirred for 30 minutes. 3M LiOH (25 mL) was then added, and the reaction was stirred at room temperature for 18 hours. Water and DCM were added to the reaction mixture, and the layers were separated. The organic layer was dried, filtered, and concentrated. The resulting residue was purified by reverse phase chromatography (Biotage SP4, C-18 40M+, 5-95% water:ACN) to provide (R)—N-(4-((R)-3-aminopiperidin-1-yl)-5-chloro-1H-pyrrolo[2,3-b]pyridin-3-yl)-2-methoxypropanamide hydrochloride (655 mg, 56% yield) as a solid. ¹H NMR (400 MHz, D₂O) δ 8.03 (s, 1H), 7.50 (s, 1H), 3.99 (q, 1H), 3.58 (m, 1H), 3.46 (m, 1H), 3.37 (s, 3H), 3.29 (m, 1H), 3.15 (m, 1H), 3.00 (m, 1H), 2.09 (m, 1H), 1.80-1.60 (m, 2H), 1.51 (m, 1H), 1.34 (d, 3H). LCMS (APCI+) m/z 352.0 (M+H)+, Retention time=2.28 minutes (Method 3).

Example 128

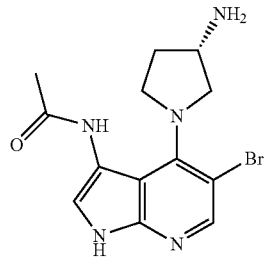

(S)-N-(4-(3-Aminopyrrolidin-1-yl)-5-bromo-1H-pyrrolo[2,3-b]pyridin-3-yl)acetamide Step A: 5-Bromo-4-fluoro-1H-pyrrolo[2,3-b]pyridin-3-amine (750 mg, 3.26 mmol; Example 1, Step H), TEA (1363 μL, 9.78 mmol), and Ac₂O (646 μL, 6.85 mmol) were placed in THF (15 mL) at room temperature and stirred for 30 minutes. The reaction was then filtered, and the solid product was dried to provide N-(5-bromo-4-fluoro-1H-pyrrolo[2,3-b]pyridin-3-yl)acetamide (595 mg, 2.19 mmol, 67% yield).

Step B: N-(5-Bromo-4-fluoro-1H-pyrrolo[2,3-b]pyridin-3-yl)acetamide (0.190 g, 0.698 mmol), DIEA (0.365 mL, 2.10 mmol), and (S)-tert-butyl pyrrolidin-3-ylcarbamate (0.390 g, 2.10 mmol) were placed in n-BuOH (2 mL) and heated to 135° C. for 8 hours. The reaction was then cooled to room temperature and concentrated to dryness. The residue was purified by silica gel chromatography (500:18 DCM:MeOH) to give (S)-tert-butyl 1-(3-acetamido-5-bromo-1H-pyrrolo[2,3-b]pyridin-4-yl)pyrrolidin-3-ylcarbamate (0.240 g, 78% yield).

Step C: (S)-tert-Butyl 1-(3-acetamido-5-bromo-1H-pyrrolo[2,3-b]pyridin-4-yl)pyrrolidin-3-ylcarbamate (0.250 g, 0.570 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 25M+, 0-50% water:ACN). The resulting product was next dissolved in minimal DCM (with MeOH to aid solubility) and added to a stirring solution of 1M HCl in ether. The resulting solid was filtered, washed with ether and dried to give (S)—N-(4-(3-aminopyrrolidin-1-yl)-5-bromo-1H-pyrrolo[2,3-b]pyridin-3-yl)acetamide hydrochloride (0.21 g, 90% yield) as a solid. $^1$H NMR (400 MHz, D$_2$O) δ 8.17 (s, 1H), 7.24 (s, 1H), 4.10-4.05 (m, 1H), 3.95-3.84 (m, 2H), 3.79-3.70 (m, 2H), 2.37-2.32 (m, 1H), 2.07 (s, 3H), 2.02-1.96 (m, 2H). LCMS (APCI+) m/z 338, 340 (M+H)+.

Example 129

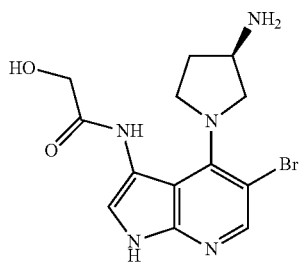

(R)-N-(4-(3-Aminopyrrolidin-1-yl)-5-bromo-1H-pyrrolo[2,3-b]pyridin-3-yl)-2-hydroxyacetamide Step A: 5-Bromo-4-fluoro-1H-pyrrolo[2,3-b]pyridin-3-amine (0.600 g, 2.61 mmol; Example 1, Step H), 2-acetoxyacetic acid (0.647 g, 5.48 mmol), BOP-Cl (1.39 g, 5.48 mmol), and triethylamine (1.82 mL, 13.0 mmol) were placed in DCM (10 mL) and stirred at room temperature for 1 hour. 3M aqueous LiOH (3 mL) was then added. The reaction was stirred for 2 hours, poured into water, and extracted with DCM. The combined organic fractions were dried (MgSO$_4$), filtered, and concentrated to give the crude product, which was purified by reverse phase chromatography (Biotage SP4, C-18 25M+, 5-95% CH$_3$CN/water) to give N-(5-bromo-4-fluoro-1H-pyrrolo[2,3-b]pyridin-3-yl)-2-hydroxyacetamide (0.400 g, 53% yield).

Step B: N-(5-Bromo-4-fluoro-1H-pyrrolo[2,3-b]pyridin-3-yl)-2-hydroxyacetamide (0.200 g, 0.694 mmol), (R)-tert-butyl pyrrolidin-3-ylcarbamate (0.388 g, 2.08 mmol), and DIEA (0.121 mL, 0.694 mmol, d 0.742) were placed in n-BuOH and heated to 135° C. for 8 hours. The reaction was then cooled to room temperature and concentrated to dryness. The resulting residue was purified by reverse phase chromatography (Biotage SP4, C-18 25M+, 5-75% CH$_3$CN/water) to give the product (R)-tert-butyl 1-(5-bromo-3-(2-hydroxyacetamido)-1H-pyrrolo[2,3-b]pyridin-4-yl)pyrrolidin-3-ylcarbamate (0.150 g, 48% yield).

Step C: (R)-tert-Butyl 1-(5-bromo-3-(2-hydroxyacetamido)-1H-pyrrolo[2,3-b]pyridin-4-yl)pyrrolidin-3-ylcarbamate (0.150 g, 0.330 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 25M+, 0-50% CH$_3$CN/water). The resulting product was next dissolved in minimal DCM (with MeOH to aid solubility) and added to a stirred solution of 1M HCl in ether. The resulting solid was filtered, washed with ether and dried to give (R)—N-(4-(3-aminopyrrolidin-1-yl)-5-bromo-1H-pyrrolo[2,3-b]pyridin-3-yl)-2-hydroxyacetamide hydrochloride (0.120 g, 85% yield) as a solid. $^1$H NMR (400 MHz, D$_2$O) δ 8.17 (s, 1H), 7.46 (s, 1H), 4.13 (s, 2H), 4.01-3.93 (m, 11-10, 3.91-3.88 (m, 1H), 3.68-3.61 (m, 1H), 3.60-3.53 (m, 2H), 2.41-2.38 (m, 1H), 2.05-2.02 (m, 1H). LCMS (APCI+) m/z 354, 356 (M+H)+.

Example 130

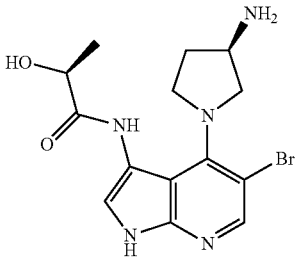

(S)-N-(4-((R)-3-Aminopyrrolidin-1-yl)-5-bromo-1H-pyrrolo[2,3-b]pyridin-3-yl)-2-hydroxypropanamide Step A: 5-Bromo-4-fluoro-1H-pyrrolo[2,3-b]pyridin-3-amine (0.350 g, 1.52 mmol; Example 1, Step H), (S)-2-acetoxypropanoic acid (0.422 g, 3.20 mmol), BOP-Cl (0.813 g, 3.20 mmol), and triethylamine (1.06 mL, 7.61 mmol) were placed in DCM (5 mL) and stirred for 1 hour. 3M aqueous LiOH (3 mL) was then added, and the reaction was stirred for 1 hour and then poured into water and extracted with DCM. The combined organic fractions were dried (MgSO$_4$), filtered, and concentrated to give the crude product, which was purified by reverse phase chromatography (Biotage SP4, C-18 25M+, 0-60% CH$_3$CN/water) to give (S)—N-(5-bromo-4-fluoro-1H-pyrrolo[2,3-b]pyridin-3-yl)-2-hydroxypropanamide (0.040 g, 9% yield).

Step B: (S)—N-(5-Bromo-4-fluoro-1H-pyrrolo[2,3-b]pyridin-3-yl)-2-hydroxypropanamide (0.040 g, 0.13 mmol), (R)-tert-butyl pyrrolidin-3-ylcarbamate (0.074 g, 0.40 mmol) and DIEA (0.069 mL, 0.40 mmol, d 0.742) were placed in n-BuOH (1 mL) and heated to 135° C. for 8 hours. The reaction was then cooled to room temperature and concentrated to dryness. The resulting residue was purified by reverse phase chromatography (Biotage SP4, C-18 25M+, 0-60% CH$_3$CN/water) to give tert-butyl (R)-1-(5-bromo-3-((S)-2-hydroxypropanamido)-1H-pyrrolo[2,3-b]pyridin-4-yl)pyrrolidin-3-ylcarbamate (0.040 g, 65% yield).

Step C: tert-Butyl (R)-1-(5-bromo-3-((S)-2-hydroxypropanamido)-1H-pyrrolo[2,3-b]pyridin-4-yl)pyrrolidin-3-ylcarbamate (0.040 g, 0.085 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 25M+, 0-50% CH$_3$CN/water). The resulting product was next dissolved in minimal DCM (with MeOH to aid solubility) and added to a stirring solution of 1M HCl in ether. The resulting solid was filtered, washed with ether and dried to give (S)—N-(4-((R)-3-aminopyrrolidin-1-yl)-5-bromo-1H-pyrrolo[2,3-b]pyridin-3-yl)-2-hydroxypropanamide hydrochloride (0.022 g, 58% yield). $^1$H NMR (400 MHz, D$_2$O) δ 8.16 (s, 1H), 7.50 (s, 1H), 4.32-4.30 (q, 1H), 4.03-4.00 (m, 1H), 3.89-3.84 (m, 1H), 3.66-3.63 (m, 1H), 3.59-3.55 (m, 1H), 3.48-3.46 (m, 1H), 2.42-2.39 (m, 1H), 2.07-2.04 (m, 1H), 1.34-1.32 (d, 3H); LCMS (APCI+) m/z 368, 370 (M+H)+.

Example 131

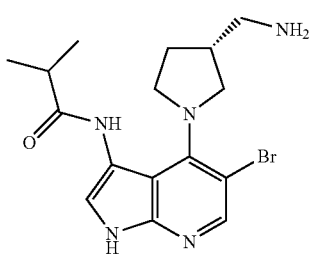

(R)-N-(4-(3-(Aminomethyl)pyrrolidin-1-yl)-5-bromo-1H-pyrrolo[2,3-b]pyridin-3-yl)isobutyramide Step A: A solution of isobutyl chloride (500 mg, 0.492 mL, 4.695 mmol) in anhydrous dichloromethane (2 mL) was added dropwise to a solution of 5-bromo-4-fluoro-1H-pyrrolo[2,3-b]pyridin-3-amine (900 mg, 3.912 mmol; Example 1, Step H) and triethylamine (1.78 g, 2.73 mL, 19.56 mmol) in anhydrous dichloromethane (30 mL) cooled on an ice-bath. The mixture was stirred at ambient temperature for 1.5 hours. The mixture was evaporated under reduced pressure. The residue was stirred in THF (30 mL), treated with an aqueous 2N LiOH solution (8 mL) and stirred for 2 hours. The solvent was evaporated in vacuo, and the residue was stirred in water (30 mL). The solid, which separated, was collected by filtration, washed with water and dichloromethane (10 mL) and dried under vacuum to yield N-(5-bromo-4-fluoro-1H-pyrrolo[2,3-b]pyridin-3-yl)isobutyramide (778.5 mg, 66% yield) as a solid. $^1$H NMR (400 MHz, (CD$_3$)$_2$SO) δ 12.04 (br s, 1H), 9.41 (s, 1H), 8.34 (d, 1H), 7.56 (s, 1H), 2.72-2.60 (m, 1H), 1.11 (d, 6H). LCMS (APCI+) m/z 299.9 (M+)+, Retention time=2.80 minutes.

Step B: (S)-tert-Butyl pyrrolidin-3-ylmethylcarbamate (505 mg, 2.52 mmol) was added to a suspension of N-(5-bromo-4-fluoro-1H-pyrrolo[2,3-b]pyridin-3-yl)isobutyramide (252 mg, 0.84 mmol) and N,N-diisopropylethylamine (326 mg, 0.439 mL, 2.52 mmol) in n-BuOH (2.5 mL). The resulting mixture was heated in a sealed tube under nitrogen at 160° C. for 18 hours. The cooled mixture was diluted with water and extracted with EtOAc (3×20 mL). The combined organic layer was dried over MgSO$_4$ and filtered, and the filtrate was concentrated to an oil and purified by reverse phase chromatography (Biotage SP4, C-18 25M+, 20-85% CH$_3$CN/water, 25CV) to give (R)-tert-butyl (1-(5-bromo-3-isobutyramido-1H-pyrrolo[2,3-b]pyridin-4-yl)pyrrolidin-3-yl)methylcarbamate (245 mg, 61% yield) as a solid. LCMS (APCI+) m/z 480.1, 482.1 (M+H)+, Retention time=3.66 minutes.

Step C: (R)-tert-Butyl (1-(5-bromo-3-isobutyramido-1H-pyrrolo[2,3-b]pyridin-4-yl)pyrrolidin-3-yl)methylcarbamate (245 mg, 0.510 mmol) was stirred in TFA (3 mL) at room temperature for 1.5 hours. The solvent was evaporated in vacuo, and the residue purified by reverse phase chromatography (Biotage SP4, C-18 25M+, 2-55% CH$_3$CN/water, 25CV). The isolated product was taken up in a minimal volume of methanol and added to a stirred solution of 2N HCl-Et$_2$O. The salt formed was collected by filtration, washed with acetonitrile and dried under vacuum to give (R)—N-(4-(3-(aminomethyl)pyrrolidin-1-yl)-5-bromo-1H-pyrrolo[2,3-b]pyridin-3-yl)isobutyramide hydrochloride (128 mg, 55% yield) as a solid. $^1$H NMR (400 MHz, (CD$_3$)$_2$SO) δ 11.74 (br s, 1H), 9.32 (s, 1H), 8.27 (s, 1H), 8.15 (br s, 1H), 7.63 (d, 1H), 3.68-3.61 (m, 1H), 3.57-3.43 (m, 2H), 3.31-3.24 (m, 1H), 3.03-2.92 (m, 2H), 2.80-2.60 (m, 2H), 2.30-2.20 (m, 1H), 1.93-1.80 (m, 1H), 1.16 (d, 6H). LCMS (APCI+) m/z 380, 382.1 (M+H)+, Retention time=2.11 minutes.

Example 132A

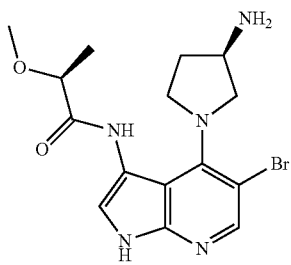

(S)-N-(4-((R)-3-Aminopyrrolidin-1-yl)-5-bromo-1H-pyrrolo[2,3-b]pyridin-3-yl)-2-methoxypropanamide Step A: 5-Bromo-4-fluoro-1H-pyrrolo[2,3-b]pyridin-3-amine (0.5 g, 2.17 mmol; Example 1, Step H), (S)-2-methoxypropanamide (0.471 g, 4.56 mmol), BOP-Cl (1.16 g, 4.56 mmol), and triethylamine (1.51 mL, 10.9 mmol) were placed in DCM (10 mL) and stirred for 18 hours at room temperature, then poured into water, and extracted with DCM. The combined organic fractions were dried (MgSO$_4$), filtered, and concentrated to give the crude product, which was purified by reverse phase chromatography (Biotage SP4, C-18 25M+, 5-95% CH$_3$CN/water) to give (S)—N-(5-bromo-4-fluoro-1H-pyrrolo[2,3-b]pyridin-3-yl)-2-methoxypropanamide (0.6 g, 87% yield).

Step B: (S)—N-(5-Bromo-4-fluoro-1H-pyrrolo[2,3-b]pyridin-3-yl)-2-methoxypropanamide (0.6 g, 1.9 mmol), (R)-tert-butyl pyrrolidin-3-ylcarbamate (1.1 g, 5.7 mmol), and DIEA (0.99 mL, 5.7 mmol) were placed in n-BuOH (4 mL) and heated at 135° C. for 12 hours. The reaction was cooled to room temperature, concentrated, and purified by silica gel chromatography (500:15 DCM:MeOH) to give tert-butyl (R)-1-(5-bromo-3-((S)-2-methoxypropanamido)-1H-pyrrolo[2,3-b]pyridin-4-yl)pyrrolidin-3-ylcarbamate (0.55 g, 60% yield).

Step C: tert-Butyl (R)-1-(5-bromo-3-((S)-2-methoxypropanamido)-1H-pyrrolo[2,3-b]pyridin-4-yl)pyrrolidin-3-ylcarbamate (0.41 g, 0.85 mmol) was placed in DCM (3 mL) at room temperature. TFA (1 mL) was then added, and the reaction was stirred at room temperature for 1 hour and concentrated to dryness. The resulting residue was then purified by reverse phase chromatography (Biotage SP4, C-18 25M+, 0-50% CH$_3$CN/water). The resulting product was next dissolved in minimal DCM (with MeOH to aid solubility) and added to a stirring solution of 1M HCl in ether. The resulting solid was filtered, washed with ether and dried to give (S)—N-(4-((R)-3-aminopyrrolidin-1-yl)-5-bromo-1H-pyrrolo[2, 3-b]pyridin-3-yl)-2-methoxypropanamide hydrochloride (0.35 g, 90% yield) as a solid. $^1$H NMR (400 MHz, D$_2$O) δ 8.17 (s, 1H), 7.39 (s, 1H), 4.03-3.96 (m, 3H), 3.95-3.79 (m, 1H), 3.73-3.69 (m, 1H), 3.60-3.53 (m, 1H), 3.36 (s, 3H), 2.40-2.35 (m, 1H), 2.07-2.02 (m, 1H), 1.31-1.29 (d, 3H). LCMS (APCI+) m/z 382, 384 (M+H)+.

Example 132B

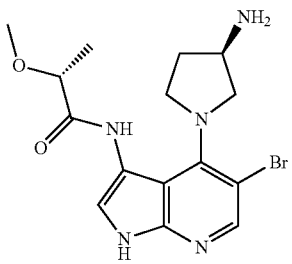

(R)-N-(4-((R)-3-aminopyrrolidin-1-yl)-5-bromo-1H-pyrrolo[2,3-b]pyridin-3-yl)-2-methoxypropanamide Step A: 5-Bromo-4-fluoro-1H-pyrrolo[2,3-b]pyridin-3-amine (0.5 g, 2.17 mmol; Example 1, Step H), (R)-2-methoxypropanoic acid (0.475 g, 4.56 mmol), BOP-Cl (1.16 g, 4.56 mmol), and triethylamine (1.51 mL, 10.9 mmol) were placed in DCM (5 mL) and stirred at room temperature for 1 hour. 3M aqueous LiOH (3 mL) was then added. The reaction was stirred for 10 minutes, then poured into water, and extracted with DCM. The combined organic fractions were dried (MgSO$_4$), filtered, and concentrated to give the crude product, which was purified by silica gel chromatography (500:15 DCM:MeOH) to give (R)—N-(5-bromo-4-fluoro-1H-pyrrolo[2,3-b]pyridin-3-yl)-2-methoxypropanamide.

Step B: (R)—N-(5-Bromo-4-fluoro-1H-pyrrolo[2,3-b]pyridin-3-yl)-2-methoxypropanamide (0.6 g, 1.9 mmol), (R)-tert-butyl pyrrolidin-3-ylcarbamate (1.1 g, 5.7 mmol), and DIEA (0.99 mL, 5.7 mmol, d 0.742) were place in n-BuOH (4 mL) and heated at 135° C. for 12 hours. The reaction was cooled to room temperature, concentrated, and purified by silica gel chromatography (500:15 DCM:MeOH) to give tert-butyl (R)-1-(5-bromo-3-((R)-2-methoxypropanamido)-1H-pyrrolo[2,3-b]pyridin-4-yl)pyrrolidin-3-ylcarbamate (0.56 g, 61% yield).

Step C: tert-Butyl (R)-1-(5-bromo-3-((R)-2-methoxypropanamido)-1H-pyrrolo[2,3-b]pyridin-4-yl)pyrrolidin-3-ylcarbamate (0.150 g, 0.311 mmol) was placed in DCM (3 mL) at room temperature. TFA (1 mL) was then added, and the reaction was stirred at room temperature for 1 hour and concentrated to dryness. The resulting residue was then purified by reverse chromatography (Biotage SP4, C-18 25M+, 0-50% CH$_3$CN/water). The resulting product was next dissolved in minimal DCM (with MeOH to aid solubility) and added to a stirring solution of 1M HCl in ether. The resulting solid was filtered, washed with ether and dried to give (R)—N-(4-((R)-3-aminopyrrolidin-1-yl)-5-bromo-1H-pyrrolo[2,3-b]pyridin-3-yl)-2-methoxypropanamide hydrochloride (0.110 g, 78% yield) as a solid. $^1$H NMR (400 MHz, D$_2$O) δ 8.16 (s, 1H), 7.44 (s, 1H), 3.99-3.96 (m, 2H), 3.91-3.87 (m, 1H), 3.71-3.64 (m, 2H), 3.57-3.53 (m, 1H), 3.36 (s, 3H), 2.44-2.39 (m, 1H), 2.06-2.02 (m, 1H), 1.31-1.29 (d, 3H). LCMS (APCI+) m/z 382, 384 (M+H)+.

Example 133

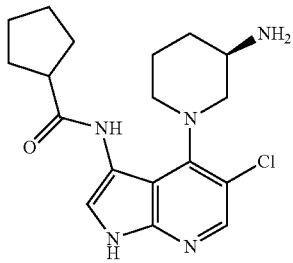

(R)-N-(4-(3-aminopiperidin-1-yl)-5-chloro-1H-pyrrolo[2,3-b]pyridin-3-yl)cyclopentanecarboxamide Step A: 5-Chloro-4-fluoro-3-nitro-1H-pyrrolo[2,3-b]pyridine (1.00 g, 4.6 mmol) and platinum-0.5% Fe (0.452 g, 0.06 mmol) were suspended in THF (12.4 mL) with IPA (6.2 mL). The mixture was hydrogenated at 20 psi for 20 hours, and then the catalyst was removed by filtration. The filtrate was concentrated to dryness, and 5-chloro-4-fluoro-1H-pyrrolo[2,3-b]pyridin-3-amine (923 mg, 107% yield) was isolated as a solid.

Step B: N-Ethyl-N-isopropylpropan-2-amine (279 mg, 2.16 mmol) followed by cyclopentanecarbonyl chloride (143 mg, 1.08 mmol) were added dropwise to 5-chloro-4-fluoro-1H-pyrrolo[2,3-b]pyridin-3-amine (200 mg, 1.08 mmol) in THF (10 mL) at 0° C. The reaction mixture was stirred at 0° C. for 1 hour and then concentrated to dryness. The residue was triturated in water and then filtered. The solid was washed with ACN and dried under vacuum to provide N-(5-chloro-4-fluoro-1H-pyrrolo[2,3-b]pyridin-3-yl)cyclopentanecarboxamide (186 mg, 61% yield) as a solid.

Step C: (R)-tert-Butyl piperidin-3-ylcarbamate (192 mg, 0.96 mmol) was added to N-(5-chloro-4-fluoro-1H-pyrrolo[2,3-b]pyridin-3-yl)cyclopentanecarboxamide (90 mg, 0.32 mmol) in s-BuOH (2 mL), and the reaction mixture was heated to 130° C. for 30 hours in a sealed tube. After cooling down, the reaction was concentrated to dryness, dissolved in AcOEt (10 mL) and washed with 10% aqueous citric acid and brine. The aqueous phase was diluted with hexanes (10 mL) and passed through a short plug of silica gel. The silica gel was rinsed with AcOEt/hexanes (1/1, 100 mL), and the combined organic phases were concentrated in vacuo. The resulting solid was crystallized from AcOEt to yield (R)-tert-butyl 1-(5-chloro-3-(cyclopentanecarboxamido)-1H-pyrrolo[2,3-b]pyridin-4-yl)piperidin-3-ylcarbamate (85 mg, 58% yield) as a solid.

Step D: (R)-tert-Butyl 1-(5-chloro-3-(cyclopentanecarboxamido)-1H-pyrrolo[2,3-b]pyridin-4-yl)piperidin-3-ylcarbamate (80 mg, 0.17 mmol) was stirred in 4N HCl in IPA (5 mL) at about 30-40° C. for 24 hours. The reaction was concentrated to dryness to yield (R)—N-(4-(3-aminopiperidin-1-yl)-5-chloro-1H-pyrrolo[2,3-b]pyridin-3-yl)cyclopentanecarboxamide hydrochloride (72 mg, 115% yield) as a solid.

Example 134

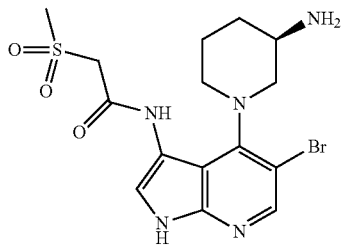

(R)-N-(4-(3-aminopiperidin-1-yl)-5-bromo-1H-pyrrolo[2,3-b]pyridin-3-yl)-2-(methylsulfonyl)acetamide Step A: 2-(Methylsulfonyl)acetic acid (601 mg, 4.35 mmol), bis(2-oxooxazolidin-3-yl)phosphinic chloride (1107 mg, 4.35 mmol) and triethylamine (1100 mg, 10.9 mmol) were added to 5-bromo-4-fluoro-1H-pyrrolo[2,3-b]pyridin-3-amine (500 mg, 2.17 mmol) in DCM (100 mL). The reaction was stirred at room temperature for 1 hour, and then 2N aqueous Na$_2$CO$_3$ (50 mL) was added. The resulting suspension was filtered, and the solid was rinsed with DCM and water. After drying, N-(5-bromo-4-fluoro-1H-pyrrolo[2,3-b]pyridin-3-yl)-2-(methylsulfonyl)acetamide (503 mg, 66.1% yield) was obtained as a solid.

Step B: N-(5-Bromo-4-fluoro-1H-pyrrolo[2,3-b]pyridin-3-yl)-2-(methylsulfonyl)acetamide (300 mg, 0.857 mmol) and (R)-tert-butyl piperidin-3-ylcarbamate (515 mg, 2.57 mmol) in s-BuOH (5 mL) were heated to 135° C. in a sealed tube for 24 hours. After cooling down, the residue was concentrated and purified by reverse phase chromatography (SP4, 25M, water/ACN 80/20→0/100, 30 CV) to yield (R)-tert-butyl 1-(5-bromo-3-(2-(methylsulfonyl)acetamido)-1H-pyrrolo[2,3-b]pyridin-4-yl)piperidin-3-ylcarbamate (306 mg, 67.3% yield) as a solid.

Step C: (R)-tert-Butyl 1-(5-bromo-3-(2-(methylsulfonyl)acetamido)-1H-pyrrolo[2,3-b]pyridin-4-yl)piperidin-3-ylcarbamate (300 mg, 0.566 mmol) was dissolved in TFA (10 mL) and stirred at room temperature for 1 hour. The reaction was concentrated to dryness, dissolved in MeOH (4 mL), and then added to a stirred 2N HCl in ether solution. The resulting precipitate was filtered and dried to yield (R)—N-(4-(3-aminopiperidin-1-yl)-5-bromo-1H-pyrrolo[2,3-b]pyridin-3-yl)-2-(methylsulfonyl)acetamide hydrochloride (98 mg, 40.3% yield) as a solid. $^1$H NMR (400 MHz, (CD$_3$)$_2$SO) δ 11.95 (s, 1H), 9.87 (s, 1H), 8.18-8.26 (m, 4H), 7.50 (s, 1H), 4.47 (dd, 2H), 3.43-3.35 (m, 2H), 3.23 (m, 1H), 3.14 (s, 3H), 3.02 (m, 2H), 2.04 (m, 1H), 1.72 (m, 2H), 1.50 (m, 1H). LCMS (APCI+) m/z 432.3 (M+2H)+.

Example 135

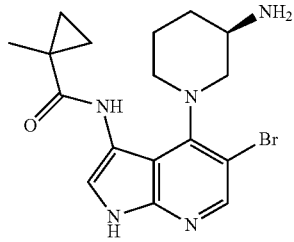

(R)-N-(4-(3-aminopiperidin-1-yl)-5-bromo-1H-pyrrolo[2,3-b]pyridin-3-yl)-1-methylcyclopropanecarboxamide Step A: 1-Methylcyclopropanecarboxylic acid (435 mg, 4.35 mmol), bis(2-oxooxazolidin-3-yl)phosphinic chloride (553 mg, 2.17 mmol) and triethylamine (1100 mg, 10.9 mmol) were added to 5-bromo-4-fluoro-1H-pyrrolo[2,3-b]pyridin-3-amine (500 mg, 2.17 mmol) in DCM (100 mL). The reaction was stirred at room temperature for 1 hour, and then 2N aqueous Na$_2$CO$_3$ was added (50 mL). The resulting suspension was filtered, and the solid was rinsed with DCM and water. After drying, N-(5-bromo-4-fluoro-1H-pyrrolo[2,3-b]pyridin-3-yl)-1-methylcyclopropanecarboxamide (464 mg, 68.4% yield) was obtained as a solid.

Step B: N-(5-Bromo-4-fluoro-1H-pyrrolo[2,3-b]pyridin-3-yl)-1-methylcyclopropanecarboxamide (464 mg, 1.49 mmol) and (R)-tert-butyl piperidin-3-ylcarbamate (298 mg, 1.49 mmol) in s-BuOH (5 mL) were heated to 135° C. in a sealed tube for 24 hours. After cooling down, the residue was concentrated and purified by reverse phase chromatography (SP4, 25M, water/ACN 80/20→0/100, 30 CV) to yield (R)-tert-butyl 1-(5-bromo-3-(1-methylcyclopropanecarboxamido)-1H-pyrrolo[2,3-b]pyridin-4-yl)piperidin-3-ylcarbamate (382 mg, 52.2% yield) as a solid.

Step C: (R)-tert-Butyl 1-(5-bromo-3-(1-methylcyclopropanecarboxamido)-1H-pyrrolo[2,3-b]pyridin-4-yl)piperidin-3-ylcarbamate (380 mg, 0.772 mmol) was dissolved in TFA (10 mL) and stirred at room temperature for 1 hour. The reaction was concentrated to dryness, dissolved in MeOH (4 mL), and then added to a stirring 2N HCl in ether solution. The resulting precipitate was filtered and dried to yield (R)—N-(4-(3-aminopiperidin-1-yl)-5-bromo-1H-pyrrolo[2,3-b]pyridin-3-yl)-1-methylcyclopropanecarboxamide hydrochloride (150 mg, 49.5% yield) as a solid. $^1$H NMR (400 MHz, (CD$_3$)$_2$SO) δ 11.78 (s, 1H), 9.06 (s, 1H), 8.27 (br s, 2H), 8.19 (s, 1H), 7.55 (s, 1H), 3.40-3.26 (m, 4H), 3.04 (m, 1H), 2.08 (m, 1H), 1.80-1.60 (m, 2H), 1.46 (m, 1H), 1.42 (s, 3H), 1.06 (m, 2H), 0.63 (m, 2H). LCMS (APCI+) m/z 392.3 (M).

Example 136

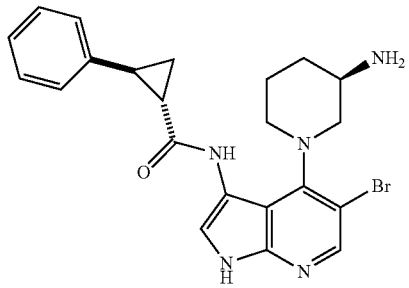

trans-N-(4-((R)-3-aminopiperidin-1-yl)-5-bromo-1H-pyrrolo[2,3-b]pyridin-3-yl)-2-phenylcyclopropanecarboxamide Step A: trans-2-Phenylcyclopropanecarboxylic acid (705 mg, 4.35 mmol), bis(2-oxooxazolidin-3-yl)phosphinic chloride (1107 mg, 4.35 mmol) and triethylamine (1100 mg, 10.9 mmol) were added to 5-bromo-4-fluoro-1H-pyrrolo[2,3-b]pyridin-3-amine (500 mg, 2.17 mmol) in DCM (100 mL). The reaction was stirred at room temperature for 1 hour, and then 2N aqueous Na$_2$CO$_3$ was added (50 mL). The resulting suspension was filtered and the solid rinsed with DCM and water. After drying, trans-N-(5-bromo-4-fluoro-1H-pyrrolo[2,3-b]pyridin-3-yl)-2-phenylcyclopropanecarboxamide (503 mg, 61.8% yield) was obtained as a solid.

Step B: trans-N-(5-Bromo-4-fluoro-1H-pyrrolo[2,3-b]pyridin-3-yl)-2-phenylcyclopropanecarboxamide (500 mg, 1.34 mmol) and (R)-tert-butyl piperidin-3-ylcarbamate (1338 mg, 6.68 mmol) in s-BuOH (5 mL) were heated to 135° C. in a sealed tube for 24 hours. After cooling down, the residue was concentrated and purified by reverse phase chromatography (SP4, 25M, water/ACN 80/20→0/100, 30 CV) to yield tert-butyl (R)-1-(5-bromo-3-(trans-2-phenyl cyclopropanecarboxamido)-1H-pyrrolo[2,3-b]pyridin-4-yl)piperidin-3-ylcarbamate (359 mg, 48.5% yield) as a solid.

Step C: tert-Butyl (R)-1-(5-bromo-3-(trans-2-phenylcyclopropanecarboxamido)-1H-pyrrolo[2,3-b]pyridin-4-yl)piperidin-3-ylcarbamate (350 mg, 0.631 mmol) was dissolved in TFA (10 mL) and stirred at room temperature for 1 hour. The reaction was concentrated to dryness, dissolved in MeOH (4 mL), and then added to a stirring 2N HCl in ether solution. The resulting precipitate was filtered and dried to yield trans-N-(4-((R)-3-aminopiperidin-1-yl)-5-bromo-1H-pyrrolo[2,3-b]pyridin-3-yl)-2-phenylcyclopropanecarboxamide hydrochloride (230 mg, 80.2% yield) as a solid (mixture of diastereoisomers). $^1$H NMR (400 MHz, (CD$_3$)$_2$SO) δ 11.84 (d, 1H), 9.71 (d, 1H), 8.25 (br s, 3H), 8.17 (s, 1H), 7.28-7.22 (m, 2H), 7.18-7.12 (m, 3H), 3.50-3.30 (m, 4H), 3.20-3.00 (m, 2H), 2.35 (m, 0.5H), 2.16 (m, 0.5H), 2.0-1.85 (m, 1H), 1.70-1.26 (m, 5H). LCMS (APCI+) m/z 454.4 (M).

Example 137

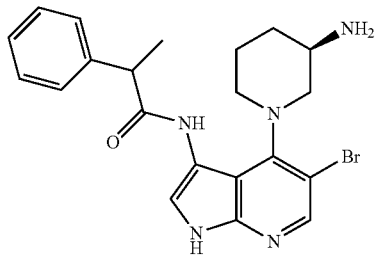

N-(4-((R)-3-aminopiperidin-1-yl)-5-bromo-1H-pyrrolo[2,3-b]pyridin-3-yl)-2-phenylpropanamide Step A: 2-Phenylpropanoic acid (653 mg, 4.35 mmol), bis(2-oxooxazolidin-3-yl)phosphinic chloride (1107 mg, 4.35 mmol) and triethylamine (1100 mg, 10.9 mmol) were added to 5-bromo-4-fluoro-1H-pyrrolo[2,3-b]pyridin-3-amine (500 mg, 2.17 mmol) in DCM (100 mL). The reaction was stirred at room temperature for 1 hour, and then 2N aqueous Na$_2$CO$_3$ (50 mL) was added. The resulting suspension was filtered, and the solid was rinsed with DCM and water. After drying, N-(5-bromo-4-fluoro-1H-pyrrolo[2,3-b]pyridin-3-yl)-2-phenylpropanamide (384 mg, 48.8% yield) was obtained as a solid.

Step B: N-(5-Bromo-4-fluoro-1H-pyrrolo[2,3-b]pyridin-3-yl)-2-phenylpropanamide (170 mg, 0.469 mmol) and (R)-tert-butyl piperidin-3-ylcarbamate (282 mg, 1.41 mmol) in s-BuOH (5 mL) were heated to 135° C. in a sealed tube for 24 hours. After cooling down, the residue was concentrated and purified by reverse phase chromatography (SP4, 25M, water/ACN 80/20→0/100, 30 CV) to yield tert-butyl (3R)-1-(5-bromo-3-(2-phenylpropanamido)-1H-pyrrolo[2,3-b]pyridin-4-yl)piperidin-3-ylcarbamate (142 mg, 55.8% yield) as a solid.

Step C: tert-Butyl (3R)-1-(5-bromo-3-(2-phenylpropanamido)-1H-pyrrolo[2,3-b]pyridin-4-yl)piperidin-3-ylcarbamate (140 mg, 0.258 mmol) was dissolved in TFA (10 mL) and stirred at room temperature for 1 hour. The reaction was concentrated to dryness, dissolved in MeOH (4 mL), and then added to a stirring 2N HCl in ether solution. The resulting precipitate was filtered and dried to yield N-(4-((R)-3-aminopiperidin-1-yl)-5-bromo-1H-pyrrolo[2,3-b]pyridin-3-yl)-2-phenylpropanamide hydrochloride (100 mg, 87.6% yield) as a solid. $^1$H NMR (400 MHz, (CD$_3$)$_2$SO) δ 11.82 (d, 1H), 9.35 (d, 1H), 8.30 (br s, 2H), 8.22 (d, 1H), 7.63 (d, 1H), 7.44-7.25 (m, 5H), 4.03-3.90 (m, 1H), 3.45-2.75 (m, 6H), 2.09-1.94 (m, 1H), 1.70-1.35 (m, 3H), 1.45 (dd, 3H). LCMS (APCI+) m/z 442.4 (M).

Example 138

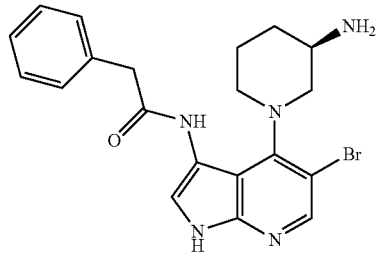

(R)-N-(4-(3-aminopiperidin-1-yl)-5-bromo-1H-pyrrolo[2,3-b]pyridin-3-yl)-2-phenylacetamide Step A: 2-Phenylacetic acid (592 mg, 4.35 mmol), bis(2-oxooxazolidin-3-yl)phosphinic chloride (1107 mg, 4.35 mmol) and triethylamine (1100 mg, 10.9 mmol) were added to 5-bromo-4-fluoro-1H-pyrrolo[2,3-b]pyridin-3-amine (500 mg, 2.17 mmol) in DCM (100 mL). The reaction mixture was stirred at room temperature for 1 hour, and then 2N aqueous Na$_2$CO$_3$ (50 mL) was added. The resulting suspension was filtered, and the solid was rinsed with DCM and water. After drying, N-(5-bromo-4-fluoro-1H-pyrrolo[2,3-b]pyridin-3-yl)-2-phenylacetamide (606 mg, 80.1% yield) was obtained as a solid.

Step B: N-(5-Bromo-4-fluoro-1H-pyrrolo[2,3-b]pyridin-3-yl)-2-phenylacetamide (300 mg, 0.86 mmol) and (R)-tert-butyl piperidin-3-ylcarbamate (518 mg, 2.58 mmol) in s-BuOH (5 mL) were heated to 135° C. in a sealed tube for 24 hours. After cooling down, the residue was concentrated and purified by reverse phase chromatography (SP4, 25M, water/ACN 80/20→0/100, 30 CV) to yield (R)-tert-butyl 1-(5-bromo-3-(2-phenylacetamido)-1H-pyrrolo[2,3-b]pyridin-4-yl)piperidin-3-ylcarbamate (320 mg, 70% yield) as a solid.

Step C: (R)-tert-Butyl 1-(5-bromo-3-(2-phenylacetamido)-1H-pyrrolo[2,3-b]pyridin-4-yl)piperidin-3-ylcarbamate (310 mg, 0.587 mmol) was dissolved in TFA (10 mL) and stirred at room temperature for 1 hour. The reaction was concentrated to dryness, dissolved in MeOH (4 mL), and then added to a stirring 2N HCl in ether solution. The resulting precipitate was filtered and dried to yield (R)—N-(4-(3-aminopiperidin-1-yl)-5-bromo-1H-pyrrolo[2,3-b]pyridin-3-yl)-2-phenylacetamide hydrochloride (280 mg, 111% yield) as a solid. $^1$H NMR (400 MHz, (CD$_3$)$_2$SO) δ 11.82 (s, 1H), 9.47 (s, 1H), 8.30-8.20 (m, 3H), 7.58 (s, 1H), 7.40-7.34 (m, 4H), 7.30-7.25 (m, 1H), 3.77 (s, 2H), 3.46-3.18 (m, 4H), 3.00 (d, 1H), 2.05 (d, 1H), 1.72 (m, 1H), 1.58-1.38 (m, 2H). LCMS (APCI+) m/z 428.4 (M).

Example 139

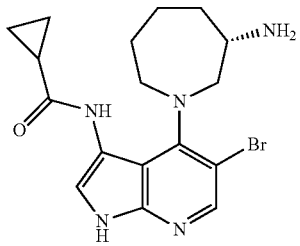

(S)-N-(4-(3-aminoazepan-1-yl)-5-bromo-1H-pyrrolo[2,3-b]pyridin-3-yl)cyclopropanecarboxamide Step A: (S)-tert-Butyl azepan-3-ylcarbamate (431 mg, 2.01 mmol; commercially available or Moon, Sung-Hwan, et al.

"An Efficient Conversion of Chiral α-Amino Acids to Enantiomerically Pure 3-Amino Cyclic Amines." *Synthetic Communications*. Vol. 28, No. 21 (1998): pp. 3919-3926) was added to N-(5-bromo-4-fluoro-1H-pyrrolo[2,3-b]pyridin-3-yl)cyclopropanecarboxamide (200 mg, 0.671 mmol) in n-BuOH (3 mL), and the reaction was heated for 18 hours to 160° C. in a sealed tube. After concentration, the residue was purified by chromatography (SP4, 25M, water/ACN 100/0→0/100, 40CV) to yield (S)-tert-butyl 1-(5-bromo-3-(cyclopropanecarboxamido)-1H-pyrrolo[2,3-b]pyridin-4-yl)azepan-3-ylcarbamate (30 mg, 9% yield) as a solid.

Step B: (S)-tert-Butyl 1-(5-bromo-3-(cyclopropanecarboxamido)-1H-pyrrolo[2,3-b]pyridin-4-yl)azepan-3-ylcarbamate (30 mg, 0.061 mmol) was stirred in TFA (5 mL) for 1 hour. After concentration, the residue was dissolved in a minimal amount of methanol and then added dropwise to a 2N HCl solution in ether. The resulting solid was collected and dried to yield (S)—N-(4-(3-aminoazepan-1-yl)-5-bromo-1H-pyrrolo[2,3-b]pyridin-3-yl)cyclopropanecarboxamide hydrochloride (16 mg, 67% yield) as a solid. $^1$H NMR (400 MHz, (CD$_3$)$_2$SO) δ 12.09 (s, 1H), 10.12 (s, 1H), 9.48 (br s, 2H), 8.25 (s, 1H), 7.32 (d, 1H), 3.30-3.00 (m, 4H), 2.09-1.55 (m, 8H), 0.90-0.75 (m, 4H). LCMS (APCI+) m/z 392.0 (M).

Example 140

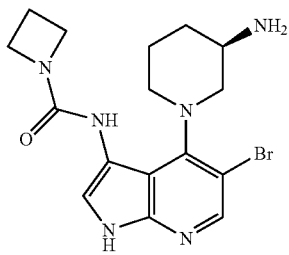

(R)-N-(4-(3-aminopiperidin-1-yl)-5-bromo-1H-pyrrolo[2,3-b]pyridin-3-yl)azetidine-1-carboxamide Step A: Di(1H-imidazol-1-yl)methanone (3.2 g, 19 mmol) was added to (R)-tert-butyl 1-(3-amino-5-bromo-1H-pyrrolo[2,3-b]pyridin-4-yl)piperidin-3-ylcarbamate (2.0 g, 4.9 mmol; Example 98, Step A) in THF (100 mL), and the reaction mixture was stirred at room temperature for 18 hours. The reaction solution was used as is. Azetidine (113 mg, 1.98 mmol) was added to (R)-tert-butyl 1-(5-bromo-3-(1H-imidazole-1-carboxamido)-1H-pyrrolo[2,3-b]pyridin-4-yl)piperidin-3-ylcarbamate (200 mg, 0.397 mmol) in THF (20 mL), and the reaction was stirred for 18 hours. The reaction was concentrated to dryness and then purified by reverse phase chromatography (SP4, 25M, water/ACN 90/10→0/100, 30 CV) to yield (R)-tert-butyl 1-(3-(azetidine-1-carboxamido)-5-bromo-1H-pyrrolo[2,3-b]pyridin-4-yl)piperidin-3-ylcarbamate (90 mg, 46.0% yield) as a solid.

Step B: (R)-tert-Butyl 1-(3-(azetidine-1-carboxamido)-5-bromo-1H-pyrrolo[2,3-b]pyridin-4-yl)piperidin-3-ylcarbamate (74 mg, 0.15 mmol) was dissolved in TFA (3 mL) and stirred at room temperature for 1 hour. After concentration, the residue was dissolved in MeOH (1 mL) and added dropwise to a 2N HCl in ether solution. The resulting solid was filtered and dried to yield (R)—N-(4-(3-aminopiperidin-1-yl)-5-bromo-1H-pyrrolo[2,3-b]pyridin-3-yl)azetidine-1-carboxamide hydrochloride (43 mg, 73% yield) as a solid. $^1$H NMR (400 MHz, (CD$_3$)$_2$SO) δ 11.84 (s, 1H), 8.30 (s, 2H), 8.23 (s, 1H), 7.74 (s, 1H), 7.40 (d, 1H), 3.66 (dd, 2H), 3.54-3.42 (m, 2H), 3.26-3.10 (m, 5H), 2.10-2.04 (m, 1H), 1.90-1.72 (m, 4H), 1.52 (br s, 1H). LCMS (APCI+) m/z 394.4 (M+H).

Example 141

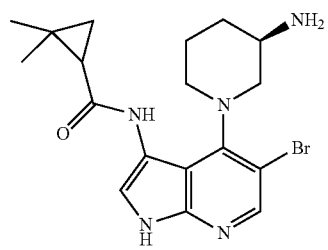

N-(4-((R)-3-aminopiperidin-1-yl)-5-bromo-1H-pyrrolo[2,3-b]pyridin-3-yl)-2,2-dimethylcyclopropanecarboxamide Step A: 2,2-Dimethylcyclopropanecarboxylic acid (0.992 g, 8.69 mmol), bis(2-oxooxazolidin-3-yl)phosphinic chloride (2.21 g, 8.69 mmol) and triethylamine (2.20 g, 21.7 mmol) were added to 5-bromo-4-fluoro-1H-pyrrolo[2,3-b]pyridin-3-amine (1 g, 4.35 mmol) in DCM (100 mL). The reaction was stirred at room temperature for 1 hour, and then 2N aqueous Na$_2$CO$_3$ was added. The mixture was filtered, and the solid rinsed with water and dried to yield N-(5-bromo-4-fluoro-1H-pyrrolo[2,3-b]pyridin-3-yl)-2,2-dimethylcyclopropanecarboxamide (672 mg, 47.4% yield) as a solid.

Step B: N-(5-bromo-4-fluoro-1H-pyrrolo[2,3-b]pyridin-3-yl)-2,2-dimethylcyclopropanecarboxamide (500 mg, 1.53 mmol) and (R)-tert-butyl piperidin-3-ylcarbamate (921 mg, 4.60 mmol) in s-BuOH (10 mL) were stirred at 130° C. for 18 hours. The reaction was concentrated and purified by reverse phase chromatography (SP4, 25M, water/ACN 90/10→0/100, 30 CV) to yield tert-butyl (1R)-3-(5-bromo-3-(2,2-dimethylcyclopropanecarboxamido)-1H-pyrrolo[2,3-b]pyridin-4-yl)cyclohexylcarbamate (360 mg, 46.5% yield) as a solid.

Step C: tert-Butyl (1R)-3-(5-bromo-3-(2,2-dimethylcyclopropanecarboxamido)-1H-pyrrolo[2,3-b]pyridin-4-yl)cyclohexylcarbamate (341 mg, 0.675 mmol) was dissolved in TFA (5 mL) and stirred at room temperature for 1 hour. After concentration, the residue was dissolved in MeOH (2 mL) and added dropwise to a 2N HCl in ether solution. The resulting solid was filtered and dried to yield N-(4-((3R)-3-aminocyclohexyl)-5-bromo-1H-pyrrolo[2,3-b]pyridin-3-yl)-2,2-dimethylcyclopropanecarboxamide hydrochloride (237 mg, 86.7% yield) as a solid (mixture 1/1 diastrereoisomers). $^1$H NMR (400 MHz, (CD$_3$)$_2$SO) δ 11.78 (s, 0.5H), 11.73 (s, 0.5H), 9.48 (s, 0.5H), 9.41 (s, 0.5H), 8.36-8.26 (m, 3H), 8.18 (s, 0.5H), 8.17 (s, 0.5H), 7.48 (s, 0.5H), 7.44 (s, 0.5H), 3.55-3.0 (m, 6H), 2.12-2.04 (m, 1H), 1.84-1.40 (m, 4H), 1.14-1.08 (m, 6H), 0.96 (m, 1H), 0.90 (s, 1H). LCMS (APCI+) m/z 406.4 (M+H).

Example 142

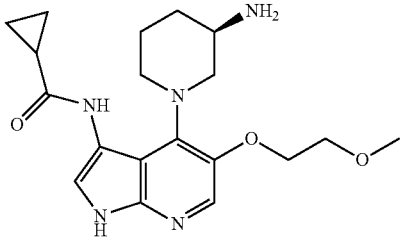

(R)-N-(4-(3-aminopiperidin-1-yl)-5-(2-methoxyethoxy)-1H-pyrrolo[2,3-b]pyridin-3-yl)cyclopropanecarboxamide Step A: 1-Bromo-2-methoxyethane (0.586 g, 4.21 mmol) and potassium carbonate (1.16 g, 8.43 mmol) to 4-fluoro-1-(triisopropylsilyl)-1H-pyrrolo[2,3-b]pyridin-5-ol (1.3 g, 4.21 mmol; Example 119, Step A) in DMF (13 mL). The reaction was heated to 65° C. in a sealed tube for 18 hours, cooled down and then filtered. The filtrate was concentrated and purified by reverse chromatography (SP4, 25M, water/ACN 90/10→0/100, 30CV) to yield 4-fluoro-5-(2-methoxyethoxy)-1H-pyrrolo[2,3-b]pyridine (440 mg, 49.7% yield) as an oil.

Step B: 4-Fluoro-5-(2-methoxyethoxy)-1H-pyrrolo[2,3-b]pyridine (440 mg, 2.09 mmol) was added to $HNO_3$ fuming (4 mL) at 0-5° C., and the reaction was stirred for 15 minutes. Ice was added, and the resulting solid was filtered and dried to yield 4-fluoro-5-(2-methoxyethoxy)-3-nitro-1H-pyrrolo[2,3-b]pyridine (360 mg, 67% yield) as a solid.

Step C: $SnCl_2$ (1337 mg, 7.05 mmol) was added to 4-fluoro-5-(2-methoxyethoxy)-3-nitro-1H-pyrrolo[2,3-b]pyridine (360 mg, 1.41 mmol) in 6N HCl (10 mL) at 0-5° C., and the reaction was stirred at 0-5° C. for 1 hour. The solution was neutralized by addition of 6N NaOH and then extracted with $CHCl_3$/IPA 3/1. The combined organic phases were dried over $MgSO_4$ and concentrated to leave 4-fluoro-5-(2-methoxyethoxy)-1H-pyrrolo[2,3-b]pyridin-3-amine (300 mg, 95% yield) as an oil.

Step D: (R)-tert-Butyl piperidin-3-ylcarbamate (307 mg, 1.53 mmol) was added to N-(4-fluoro-5-(2-methoxyethoxy)-1H-pyrrolo[2,3-b]pyridin-3-yl)cyclopropanecarboxamide (150 mg, 0.511 mmol) in s-BuOH (3 mL), and the reaction was stirred at 150° C. for 24 hours in a sealed tube. After cooling down and concentration, the residue was purified by reverse phase chromatography (SP4, 25M, water/ACN 90/10→0/100, 30 CV) to yield (R)-tert-butyl 1-(3-(cyclopropanecarboxamido)-5-(2-methoxyethoxy)-1H-pyrrolo[2,3-b]pyridin-4-yl)piperidin-3-ylcarbamate (113 mg, 46.7% yield) as a solid.

Step E: (R)-tert-Butyl 1-(3-(cyclopropanecarboxamido)-5-(2-methoxyethoxy)-1H-pyrrolo[2,3-b]pyridin-4-yl)piperidin-3-ylcarbamate (0.110 g, 0.232 mmol) was dissolved in 5N HCl (2.32 mL, 11.6 mmol) in IPA and stirred at room temperature for 2 hours. The reaction was concentrated to dryness, suspended in acetonitrile (5 mL) and stirred at room temperature for 30 minutes. The resulting precipitate was filtered and dried to yield (R)—N-(4-(3-aminopiperidin-1-yl)-5-(2-methoxyethoxy)-1H-pyrrolo[2,3-b]pyridin-3-yl)cyclopropanecarboxamide hydrochloride (0.094 g, 90.7% yield) as a solid. $^1H$ NMR (400 MHz, $D_2O$) δ 7.82 (s, 1H), 7.21 (s, 1H), 4.13 (m, 2H), 3.75-3.81 (m, 3H), 3.47 (m, 2H), 3.30 (s, 3H), 3.22 (m, 2H), 2.07 (m, 1H), 1.74 (m, 2H), 1.57-1.65 (m, 2H), 0.88 (m, 2H), 0.93 (m 2H). LCMS (APCI+) m/z 374.2 (M+H).

Examples 143-184 shown in Table 1 can also be made according to the above described methods.

TABLE 1

| Ex # | Structure | Name | NMR/LCMS |
|---|---|---|---|
| 143 | 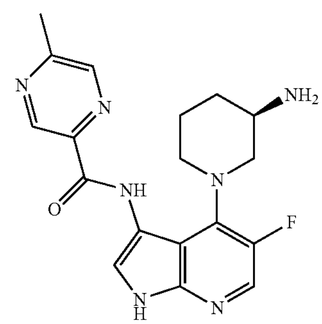 [SMILES: Cc1cnc(C(=O)Nc2c[nH]c3ncc(F)c(N4CCC[C@@H](N)C4)c23)cn1] | (R)-N-(4-(3-Aminopiperidin-1-yl)-5-fluoro-1H-pyrrolo[2,3-b]pyridin-3-yl)-5-methylpyrazine-2-carboxamide | $^1H$ NMR (400 MHz, $D_2O$) δ 8.81 (s, 1H), 8.44 (s, 1H), 8.05 (d, 1H), 7.57 (s, 1H), 3.68-3.65 (m, 1H), 3.50-3.45 (m, 1H), 3.35-3.32 (m, 1H), 3.21-3.17 (m, 1H), 3.12-3.08 (m, 1H), 2.47 (s, 3H), 2.01-1.99 (m, 1H), 1.67-1.65 (m, 2H), 1.49-1.47 (m, 1H); LCMS (APCI+) m/z 370 (M + H)+ |
| 144 | 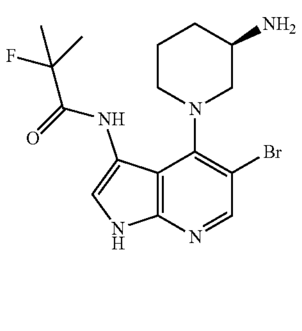 [SMILES: CC(C)(F)C(=O)Nc1c[nH]c2ncc(Br)c(N3CCC[C@@H](N)C3)c12] | (R)-N-(4-(3-Aminopiperidin-1-yl)-5-bromo-1H-pyrrolo[2,3-b]pyridin-3-yl)-2-fluoro-2-methylpropanamide | $^1H$ NMR (400 MHz, $(CD_3)_2SO$) δ 11.85 (br s, 1H), 9.99 (s, 1H), 8.31 (br s, 2H), 8.29 (s, 1H), 7.91 (s, 1H), 3.70-3.45 (m, 2H), 3.35-3.26 (m, 2H), 3.10-3.0 (m, 1H), 2.16-2.08 (m, 1H), 1.92-1.72 (m, 2H), 1.67 (d, 3H), 1.61 (d, 3H), 1.56-1.40 (m, 1H); LCMS (APCI+) m/z 400 (M + 2H)+, Retention time = 2.26 minutes |

TABLE 1-continued

| Ex # | Structure | Name | NMR/LCMS |
|---|---|---|---|
| 145 | 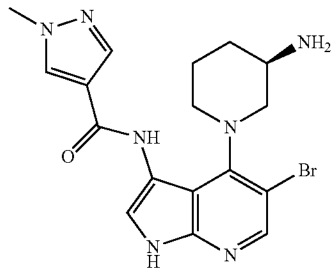 [SMILES: Cn1cc(C(=O)Nc2c[nH]c3ncc(Br)c(N4CCC[C@@H](N)C4)c23)cn1] | (R)-N-(4-(3-Aminopiperidin-1-yl)-5-bromo-1H-pyrrolo[2,3-b]pyridin-3-yl)-1-methyl-1H-pyrazole-4-carboxamide | $^1$H NMR (400 MHz, D$_2$O) δ 8.29 (s, 1H), 8.09 (s, 1H), 7.93 (s, 1H), 7.34 (s, 1H), 3.85-3.83 (m, 1H), 3.81 (s, 3H), 3.50-3.43 (m, 2H), 3.15-3.12 (m, 2H), 1.96-1.93 (m, 1H), 1.69-1.57 (m, 2H), 1.38-1.35 (m, 1H); LCMS (APCI+) m/z 418, 420 (M + H)+ |
| 146 | 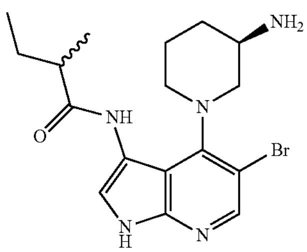 [SMILES: CCC(C)C(=O)Nc1c[nH]c2ncc(Br)c(N3CCC[C@@H](N)C3)c12] | (R)-N-(4-(3-Aminopiperidin-1-yl)-5-bromo-1H-pyrrolo[2,3-b]pyridin-3-yl)-2-methylbutanamide | $^1$H NMR (400 MHz, (CD$_3$)$_2$SO) δ 11.74 (s, 1H), 9.22 (s, 1H), 8.29-8.11 (m, 4H), 7.58 (s, 1H), 3.45-3.17 (m, 5H), 3.07-2.92 (m, 1H), 2.10-1.92 (m, 1H), 1.86-1.24 (m, 5H), 1.08 (m, 3H), 0.85 (m, 3H); LCMS (APCI+) m/z 394, 396 (M + H)+ |
| 147 | 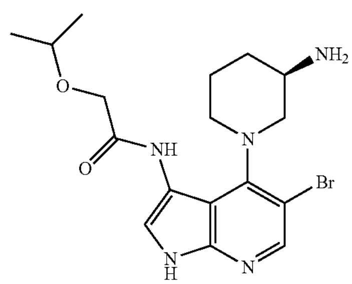 [SMILES: CC(C)OCC(=O)Nc1c[nH]c2ncc(Br)c(N3CCC[C@@H](N)C3)c12] | (R)-N-(4-(3-Aminopiperidin-1-yl)-5-bromo-1H-pyrrolo[2,3-b]pyridin-3-yl)-2-isopropoxyacetamide | $^1$H NMR (400 MHz, (CD$_3$)$_2$SO) δ 11.81 (s, 1H), 9.38 (s, 1H), 8.28 (br s, 3H), 8.26 (s, 1H), 7.95 (brs, 1H), 4.12(s, 2H), 3.84-3.77 (m, 1H), 3.64-3.55 (m, 1H), 3.53-3.45 (m, 1H), 3.42-3.34 (m, 1H), 3.31-3.26 (m, 1H), 3.05-2.99 (m, 1H), 2.18-2.12 (m, 1H), 1.93-1.84 (m, 2H), 1.55-1.45 (m, 1H), 1.24 (dd, 6H); LCMS (APCI+) m/z 410,412 (M + H)+ |
| 148 | 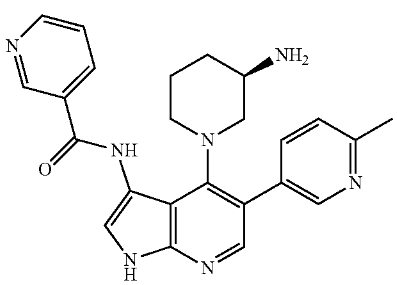 [SMILES: Cc1ccc(-c2cnc3[nH]cc(NC(=O)c4cccnc4)c3c2N2CCC[C@@H](N)C2)cn1] | (R)-N-(4-(3-Aminopiperidin-1-yl)-5-(6-methylpyridin-3-yl)-1H-pyrrolo[2,3-b]pyridin-3-yl)nicotinamide | $^1$H NMR (400 MHz, D$_2$O) δ 9.15 (s, 1H), 8.80 (d, 1H), 8.71 (d, 1H), 8.66 (s, 1H), 8.40 (d, 1H), 7.98 (s, 1H), 7.88 (m, 2H), 7.52 (s, 1H), 3.34 (d, 1H), 3.24 (d, 1H), 2.87 (m, 1H), 2.78 (m, 1H), 2.71 (s, 3H), 2.54 (t, 1H), 1.74 (m, 1H), 1.39 (m, 1H), 1.08 (m, 2H); LCMS (APCI+) m/z 428.2 M + H)+, Retention time = 1.94 minutes (Method 3) |
| 149 | 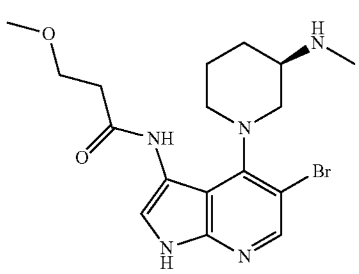 | (R)-N-(5-Bromo-4-{3-(methylamino)piperidin-1-yl}-1H-pyrrolo[2,3-b]pyridin-3-yl)-3-methoxypropanamide | $^1$H NMR (400 MHz, (CD$_3$)$_2$SO) δ □ 11.81 (s, 1H), 9.34 (brs, 1H), 9.13-9.05 (m, 2H), 8.23 (s, 1H), 7.56 (br s, 1H), 3.65 (t, 2H), 3.54-3.46 (m, 2H), 3.33-3.29 (m, 2H), 3.27 (s, 3H), 3.09-3.04 (m, 1H), 2.65-2.60 (m, 2H), 2.57 (t, 4H), 2.26-2.22 (m, 1H), 1.91-1.82 (m, 1H), 1.74-1.67 (m, 1H), 1.55-1.44 (m, 1H); LCMS (APCI+) m/z 410, 412 (M + H)+ |

TABLE 1-continued

| Ex # | Structure | Name | NMR/LCMS |
|---|---|---|---|
| 150 | 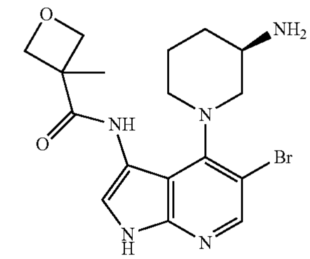 [SMILES: CC1(C(=O)Nc2c[nH]c3ncc(Br)c(N4CCC[C@@H](N)C4)c23)COC1] | (R)-N-(4-(3-Aminopiperidin-1-yl)-5-bromo-1H-pyrrolo[2,3-b]pyridin-3-yl)-3-methyloxetane-3-carboxamide | LCMS (APCI+) m/z 408, 410 (M + H)+ |
| 151 | 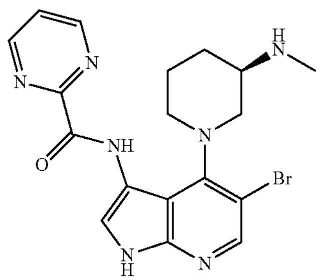 [SMILES: CN[C@@H]1CCCN(c2c(Br)cnc3[nH]cc(NC(=O)c4ncccn4)c23)C1] | (R)-N-(5-Bromo-4-(3-(methylamino)piperidin-1-yl)-1H-pyrrolo[2,3-b]pyridin-3-yl)pyrimidine-2-carboxamide | $^1$H NMR (400 MHz, D$_2$O) δ 8.66 (br s, 2H), 8.07 (s, 1H), 7.57 (s, 1H), 7.43 (s, 1H), 3.56-0.43 (m, 3H), 3.40-3.26 (m, 1H)-2.90-2.77 (m, 1H), 2.57 (s, 3H), 2.28-2.15 (m, 1H), 1.94-1.79 (m, 1H), 1.75-1.60 (m, 1H), 1.50-1.33 (m, 1H); LCMS (APCI+) m/z 430.1, 432.1 (M + H)+, Retention time = 2.11 minutes |
| 152 | 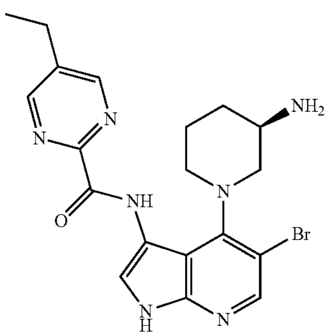 [SMILES: CCc1cnc(C(=O)Nc2c[nH]c3ncc(Br)c(N4CCC[C@@H](N)C4)c23)nc1] | (R)-N-(4-(3-Aminopiperidin-1-yl)-5-bromo-1H-pyrrolo[2,3-b]pyridin-3-yl)-5-ethylpyrimidine-2-carboxamide | $^1$H NMR (400 MHz, D$_2$O) δ 8.63 (s, 2H), 8.25 (s, 1H), 7.90 (s, 1H), 3.65-3.40 (m, 3H), 2.68-2.59 (m, 2H), 1.98-1.95 (m, 1H), 1.89-1.80 (m, 1H), 1.80-1.73 (m, 2H), 1.61-1.50 (m, 1H), 1.22-1.13 (m, 3H); LCMS (APCI+) m/z 444.1 (M)+, Retention time = 2.30 minutes |
| 153 | 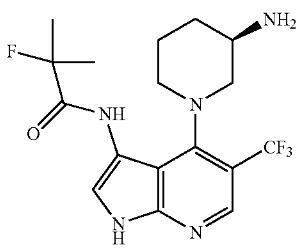 [SMILES: CC(C)(F)C(=O)Nc1c[nH]c2ncc(C(F)(F)F)c(N3CCC[C@@H](N)C3)c12] | (R)-N-(4-(3-Aminopiperidin-1-yl)-5-(trifluoromethyl)-1H-pyrrolo[2,3-b]pyridin-3-yl)-2-fluoro-2-methylpropanamide | $^1$H NMR (400 MHz, D$_2$O) δ 8.56 (s, 1H), 7.94 (s, 1H), 3.45-3.31 (m, 2H), 3.15-2.98 (m, 3H), 2.18-2.10 (m, 1H), 1.94-1.76 (m, 2H), 1.70 (3, 3H), 1.64 (s, 3H), 1.60-1.45 (m, 1H); LCMS (APCI+) m/z 388.1, 389.1 (M + H)+, Retention time = 2.25 minutes |
| 154 | 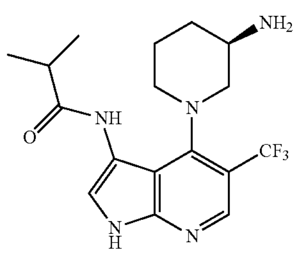 [SMILES: CC(C)C(=O)Nc1c[nH]c2ncc(C(F)(F)F)c(N3CCC[C@@H](N)C3)c12] | (R)-N-(4-(3-Aminopiperidin-1-yl)-5-(trifluoromethyl)-1H-pyrrolo[2,3-b]pyridin-3-yl)isobutyramide | $^1$H NMR (400 MHz, (CD$_3$)$_2$SO) δ 12.24 (br s, 1H), 9.25 (s, 1H), 8.48 (s, 1H), 8.29 (br s, 2H), 7.61 (d, 1H), 6.20-5.76 (m, 2H), 3.05-2.80 (m, 3H), 2.15-2.05 (m, 1H), 1.85-1.74 (m, 1H), 1.73-1.58 (m, 1H), 1.57-1.43 (m, 1H), 1.16 (dd, 6H); LCMS (APCI+) m/z 370.1, 371.1 (M + H)+, Retention time = 2.02 minutes |

TABLE 1-continued

| Ex # | Structure | Name | NMR/LCMS |
|---|---|---|---|
| 155 | 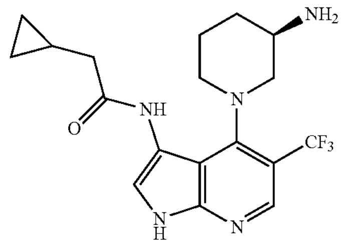 [SMILES: N[C@@H]1CCCN(c2c(C(F)(F)F)cnc3[nH]cc(NC(=O)CC4CC4)c23)C1] | (R)-N-(4-(3-Aminopiperidin-1-yl)-5-(trifluoromethyl)-1H-pyrrolo[2,3-b]pyridin-3-yl)-2-cyclopropylacetamide | $^1$H NMR (400 MHz, (CD$_3$)$_2$SO) δ 12.06 (br s, 1H), 9.07 (s, 1H), 8.25 (s, 1H), 8.13 (br s, 2H), 7.36 (d, 1H), 3.05-3.00 (m, 3H), 2.86-2.75 (m, 1H), 2.73-2.65 (m, 1H), 2.26-2.10 (m, 2H), 1.95-1.85 (m, 1H), 1.62-1.50 (m, 1H), 1.48-1.35 (m, 1H), 1.34-1.20 (m, 1H), 0.94-0.84 (m, 1H), 0.34-0.25 (m, 2H), 0.05-0.0 l(m, 2H); LCMS (APCI+) m/z 382.1 (M + H)+, Retention time = 2.13 minutes |
| 156 | 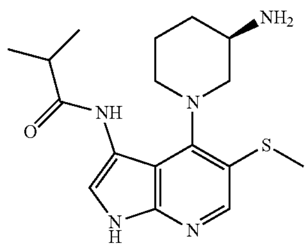 [SMILES: CSc1cnc2[nH]cc(NC(=O)C(C)C)c2c1N1CCC[C@@H](N)C1] | (R)-N-(4-(3-Aminopiperidin-1-yl)-5-(methylthio)-1H-pyrrolo[2,3-b]pyridin-3-yl)isobutyramide | $^1$H NMR (400MHz, D$_2$O) δ 8.10 (s, 1H), 7.27 (s, 1H), 3.93 (d, 1H), 3.67 (m, 1H), 3.43 (d, 1H), 3.16 (m, 2H), 2.66 (m, 1H), 2.34 (s, 3H), 2.10 (m, 1H), 1.83 (m, 1H), 1.60 (m, 2H), 1.10 (m, 6H); LCMS (APCI+) m/z 348.1 (M + H)+, Retention time = 1.99 minutes (Method 3) |
| 157 | 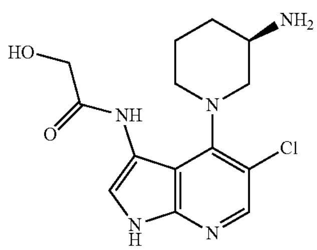 [SMILES: N[C@@H]1CCCN(c2c(Cl)cnc3[nH]cc(NC(=O)CO)c23)C1] | (R)-N-(4-(3-Aminopiperidin-1-yl)-5-chloro-1H-pyrrolo[2,3-b]pyridin-3-yl)-2-hydroxyacetamide | $^1$H NMR (400 MHz, D$_2$O) δ 8.14 (s, 1H), 7.41 (s, 1H), 4.18 (s, 2H), 3.81-.377 (m, 1H), 3.53-3.49 (m, 1H), 3.41-3.38 (m, 1H), 3.25-3.15 (m, 3H), 3.19 (s, 3H), 2.11-2.08 (m, 1H), 1.77-1.68 (m, 2H) 1.56-1.52 (m, 1H); LCMS (APCI+) m/z 324 (M + H)+ |
| 158 | 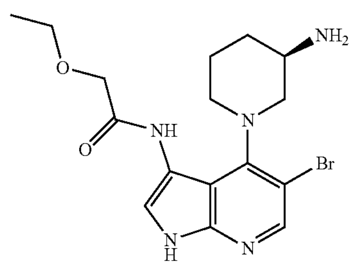 | (R)-N-(4-(3-Aminopiperidin-1-yl)-5-bromo-1H-pyrrolo[2,3-b]pyridin-3-yl)-2-ethoxyacetamide | $^1$H NMR (400 MHz, (CD$_3$)$_2$SO) δ 11.80 (d, 1H), 9.66 (s, 1H), 8.36 (br s, 3H), 8.26 (s, 1H), 7.94 (d, 1H), 4.12 (d, 2H), 3.74-3.66 (m, 2H), 3.63-3.58 (m, 1H), 3.53-3.46 (m, 1H), 3.43-3.36 (m, 1H), 3.33-3.26 (m, 1H), 3.02-2.96 (m, 1H), 2.20-2.13 (m, 1H), 1.91-1.85 (m, 2H), 1.56-1.45 (m, 1H), 1.25 (t, 3H); LCMS (APCI+) m/z 396, 398 (M + H)+ |
| 159 | 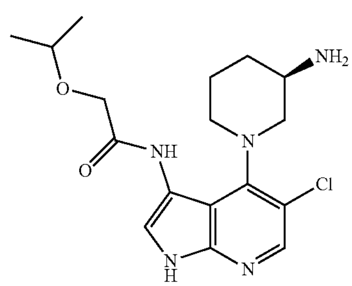 [SMILES: CC(C)OCC(=O)Nc1c[nH]c2ncc(Cl)c(N3CCC[C@@H](N)C3)c12] | (R)-N-(4-(3-Aminopiperidin-1-yl)-5-chloro-1H-pyrrolo[2,3-b]pyridin-3-yl)-2-isopropoxyacetamide | $^1$H NMR (400 MHz, (CD$_3$)$_2$SO) δ 11.81 (d, 1H), 9.38 (s, 1H), 8.34 (br s, 3H), 8.16 (s, 1H), 7.95 (br s, 1H), 4.12 (s, 2H), 3.81 (m, 1H), 3.52-3.46 (m, 1H), 3.39-3.33 (m, 3H), 3.08-3.03 (m, 1H), 2.18-2.11 (m, 1H), 1.92-1.83 (m, 2H), 1.57-1.48 (m, 1H), 1.23 (dd, 6H); LCMS (APCI+) m/z 366.1 (M + H)+ |
| 160 | 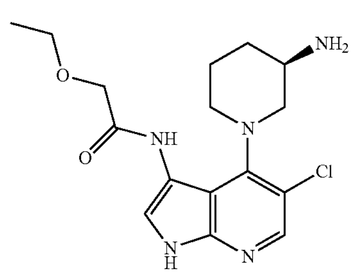 [SMILES: CCOCC(=O)Nc1c[nH]c2ncc(Cl)c(N3CCC[C@@H](N)C3)c12] | (R)-N-(4-(3-Aminopiperidin-1-yl)-5-chloro-1H-pyrrolo[2,3-b]pyridin-3-yl)-2-ethoxyacetamide | $^1$H NMR (400 MHz, (CD$_3$)$_2$SO) δ 11.79 (d, 1H), 9.65 (s, 1H), 8.35 (br s, 3H), 8.17 (s, 1H), 7.95 (d, 1H), 4.16-4.07 (m, 2H), 3.75-3.67 (m, 2H), 3.53-3.47 (m, 1H), 3.40-3.32 (m, 3H), 3.05-3.01 (m, 1H), 2.19-2.13 (m, 1H), 1.93-1.83 (m, 2H), 1.57-1.45 (m, 1H), 1.25 (t, 3H); LCMS (APCI+) m/z 352.1(M + H)+ |

TABLE 1-continued

| Ex # | Structure | Name | NMR/LCMS |
|---|---|---|---|
| 161 | 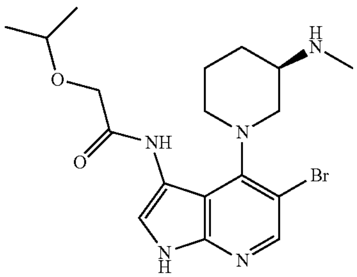 [SMILES: CN[C@@H]1CCCN(c2c(Br)cnc3[nH]cc(NC(=O)COC(C)C)c23)C1] | (R)-N-(5-Bromo-4-(3-(methylamino)piperidin-1-yl)-1H-pyrrolo[2,3-b]pyridin-3-yl)-2-isopropoxyacetamide | $^1$H NMR (400 MHz, (CD$_3$)$_2$SO) δ 11.81 (s, 1H), 9.33 (br s, 1H), 8.93-8.83 (m, 1H), 8.61 (br s, 1H), 8.26 (s, 1H), 7.97-7.92 (m, 1H), 4.17-4.08 (m, 2H), 3.83-3.77 (m, 1H), 3.63-3.40 (m, 3H), 3.33-3.23 (m, 1H), 3.08-2.98 (m, 1H), 2.61 (t, 3H), 2.28-2.20 (m, 1H), 1.95-1.84 (m, 2H), 1.52-1.41 (m, 1H), 1.23 (dd, 6H); LCMS (APCI+) m/z 424.1, 426.1 (M + H)+ |
| 162 | 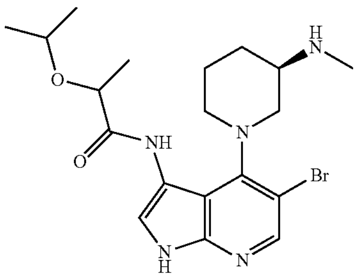 [SMILES: CN[C@@H]1CCCN(c2c(Br)cnc3[nH]cc(NC(=O)C(C)OC(C)C)c23)C1] | N-(5-Bromo-4-((R)-3-(methylamino)piperidin-1-yl)-1H-pyrrolo[2,3-b]pyridin-3-yl)-2-isopropoxypropanamide | $^1$H NMR (400 MHz, (CD$_3$)$_2$SO) δ 11.80 (s, 1H), 9.36-9.31 (m, 1H), 9.13 (br s, 1H), 8.26 (s, 1H), 7.93 (br s, 1H), 4.73-4.57 (m, 1H), 4.15-4.11 (m, 1H), 3.85-3.78 (m, 1H), 3.55-3.46 (m, 1H), 3.387-3.19 (m, 2H), 3.09-3.01 (m, 1H), 2.59-2.54 (m, 3H), 2.31-2.23 (m, 1H), 2.01-1.84 (m, 2H), 1.55-1.46 (m, 1H), 1.37 (dd, 3H), 1.20 (dd, 6H); LCMS (APCI+) m/z 440.2 (M + H)+ |
| 163 | 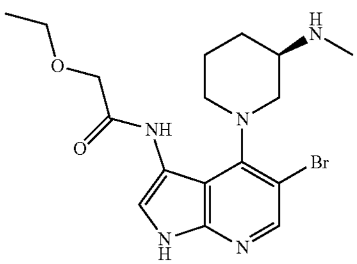 [SMILES: CCOCC(=O)Nc1c[nH]c2ncc(Br)c(N3CCC[C@@H](NC)C3)c12] | (R)-N-(5-Bromo-4-(3-(methylamino)piperidm-1-yl)-1H-pyrrolo[2,3-b]pyridin-3-yl)-2-ethoxyacetamide | $^1$H NMR (400 MHz, (CD$_3$)$_2$SO) δ 11.79 (s, 1H), 9.62 (s, 1H), 9.33 (br s, 1H),9.16-9.06 (m, 1H), 8.26 (s, 1H), 7.94 (s, 1H), 4.12 (s, 2H), 3.74-3.66 (m, 2H), 3.64-3.58 (m, 1H), 3.54-3.43 (m, 2H), 3.32-3.22 (m, 1H), 3.05-2.97 (m, 1H), 2.59-2.54 (m, 3H), 2.33-2.26 (m, 1H), 1.94-1.85 (m, 2H), 1.57-1.45 (m, 1H), 1.24 (t, 3H); LCMS (APCI+) m/z 410.1, 412.1 (M + H)+ |
| 164 | 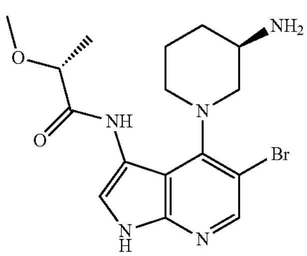 [SMILES: CO[C@H](C)C(=O)Nc1c[nH]c2ncc(Br)c(N3CCC[C@@H](N)C3)c12] | (R)-N-(4-((R)-3-Aminopiperidin-1-yl)-5-bromo-1H-pyrrolo[2,3-b]pyridin-3-yl)-2-methoxypropanamide | $^1$H NMR (400 MHz, D$_2$O) δ 8.18 (s, 1H), 7.51 (s, 1H), 4.00 (q, 1H), 3.53 (m, 2H), 3.38 (s, 3H), 3.35 (m, 1H), 3.24 (m, 1H), 3.01 (m, 1H), 2.08 (m, 1H), 1.83-1.64 (m, 2H), 1.53 (m, 1H), 1.35 (d, 3H); LCMS (APCI+) m/z 398.0 (M + H)+, Retention time = 2.26 minutes (Method 3) |
| 165 | 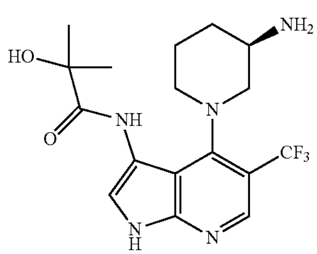 [SMILES: CC(C)(O)C(=O)Nc1c[nH]c2ncc(C(F)(F)F)c(N3CCC[C@@H](N)C3)c12] | (R)-N-(4-(3-Aminopiperidin-1-yl)-5-(trifluoromethyl)-1H-pyrrolo[2,3-b]pyridin-3-yl)-2-hydroxy-2-methylpropanamide | $^1$H NMR (400 MHz, (CD$_3$)$_2$SO) δ 12.04 (br s, 1H), 8.52 (s, 1H), 8.29 (br s, 2H), 8.11 (d, 1H), 3.81-3.49 (m, 1H), 3.42-3.31 (m, 1H), 3.16-3.0 (m, 3H), 2.19-2.08 (m, 2H), 1.85-1.75 (m, 1H), 1.59-1.47 (m, 1H), 1.45-1.38 (m, 7H); LCMS (APCI+) m/z 386.1, 387.1 (M + H)+, Retention time = 2.14 minutes |

TABLE 1-continued

| Ex # | Structure | Name | NMR/LCMS |
|---|---|---|---|
| 166 | 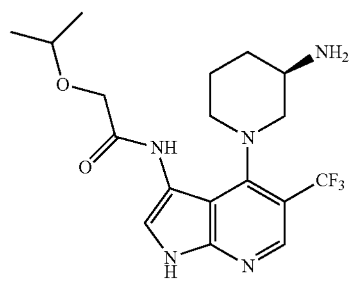 [SMILES: CC(C)OCC(=O)Nc1c[nH]c2ncc(C(F)(F)F)c(N3CCC[C@@H](N)C3)c12] | (R)-N-(4-(3-Aminopiperidin-1-yl)-5-(trifluoromethyl)-1H-pyrrolo[2,3-b]pyridin-3-yl)-2-isopropoxyacetamide | $^1$H NMR (400 MHz, (CD$_3$)$_2$SO) δ 12.19 (br s, 1H), 9.13 (s, 1H), 8.51 (s, 1H), 8.25 (br s, 2H), 7.89 (s, 1H), 4.25-4.10 (m, 2H), 3.84-3.75 (m, 1H), 3.44-3.26 (m, 2H), 3.13-2.96 (m, 3H), 2.18-2.10 (m, 1H), 1.90-1.76 (m, 2H), 1.58-1.40 (m, 1H), 1.23 (d, 3H), 1.21 (d, 3H); LCMS (APCI+) m/z 400.1 (M + H)+, Retention time = 2.32 minutes |
| 167 | 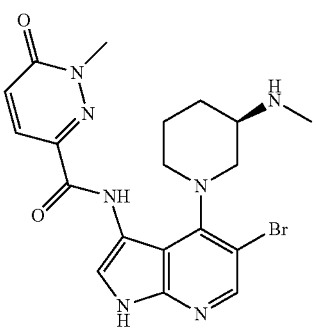 [SMILES: CN[C@@H]1CCCN(c2c(Br)cnc3[nH]cc(NC(=O)c4ccc(=O)n(C)n4)c23)C1] | (R)-N-(5-Bromo-4-(3-(methylamino)piperidin-1-yl)-1H-pyrrolo[2,3-b]pyridin-3-yl)-1-methyl-6-oxo-1,6-dihydropyridazine-3-carboxamide | $^1$H NMR (400 MHz, D$_2$O) δ 8.22 (s, 1H), 7.86 (d, 1H), 7.51 (s, 1H), 7.00 (d, 1H), 3.74 (s, 3H), 3.72 (m, 1H), 3.51 (s, 3H), 3.27 (m, 3H), 2.24 (m, 1H), 2.10 (m, 1H), 1.70 (m, 2H), 1.41 (m, 1H). LCMS (APCI+) m/z 460(M + H)+ |
| 168 | 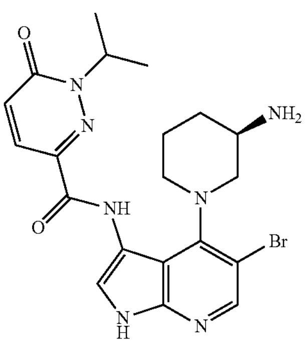 [SMILES: CC(C)n1nc(C(=O)Nc2c[nH]c3ncc(Br)c(N4CCC[C@@H](N)C4)c23)ccc1=O] | (R)-N-(4-(3-Aminopiperidin-1-yl)-5-bromo-1H-pyrrolo[2,3-b]pyridin-3-yl)-1-isopropyl-6-oxo-1,6-dihydropyridazine-3-carboxamide | $^1$H NMR (400 MHz, D$_2$O) δ 8.27 (s, 1H), 7.90 (d, 1H), 7.39 (s, 1H), 7.05 (d, 1H), 5.15 (m, 1H), 3.70 (m, 1H), 3.41 (m, 1H), 3.31 (m, 1H), 3.14-3.24 (m, 2H), 1.90 (m, 1H), 1.70 (m, 1H), 1.55 (m, 1H), 1.37 (m, 1H), 1.32 (d, 6H); LCMS (APCI+) m/z 474(M + H)+ |
| 169A | 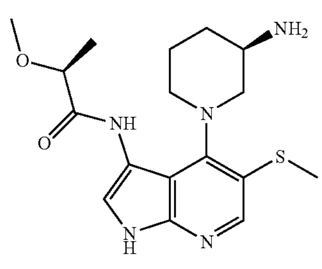 | (S)-N-(4-((R)3-Aminopiperidin-1-yl)-5-(methylthio)-1H-pyrrolo[2,3-b]pyridin-3-yl)-2-methoxypropanamide | $^1$H NMR (400 MHz, D$_2$O) δ 8.12 (s, 1H), 7.40 (s, 1H), 4.04 (q, 1H), 3.83 (d, 1H), 3.64 (m, 1H), 3.37 (s, 3H), 3.35 (m, 1H), 3.22 (m, 2H), 2.35 (s, 3H), 2.11 (m, 1H), 1.82 (m, 1H), 1.72-1.50 (m, 2H), 1.34 (d, 3H); LCMS (APCI+) m/z 398.0 (M + H)+, Retention time = 2.08 minutes (Method 3) |
| 169B | 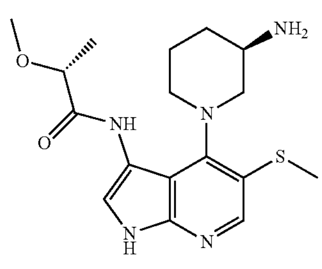 | (R)-N-(4-((R)-3-Aminopiperidin-1-yl)-5-(methylthio)-1H-pyrrolo[2,3-b]pyridin-3-yl)-2-methoxypropanamide | $^1$H NMR (400 MHz, D$_2$O) δ 8.13 (s, 1H), 7.38 (s, 1H), 4.01 (q, 1H), 3.92 (d, 1H), 3.68 (m, 1H), 3.39 (m, 4H), 3.21 (m, 1H), 2.35 (s, 3H), 2.10 (m, 1H), 1.83 (m, 1H), 1.70-1.50 (m, 2H), 1.37 (d, 3H); LCMS (APCI+) m/z 364.1 (M + H)+, Retention time = 2.26 minutes (Method 3) |

| Ex # | Structure | Name | NMR/LCMS |
|---|---|---|---|
| 170 | 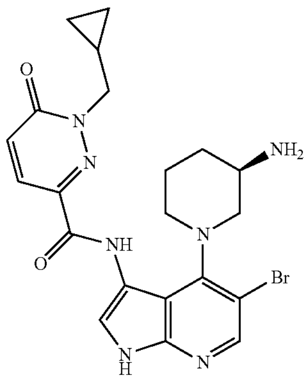 [SMILES: N[C@@H]1CCCN(c2c(Br)cnc3[nH]cc(NC(=O)c4ccc(=O)n(CC5CC5)n4)c23)C1] | (R)-N-(4-(3-Aminopiperidin-1-yl)-5-bromo-1H-pyrrolo[2,3-b]pyridin-3-yl)-1-(cyclopropylmethyl)-6-oxo-1,6-dihydropyridazine-3-carboxamide | ¹H NMR (400 MHz, D₂O) δ 7.94 (s, 1H), 7.62 (d, 1H), 7.18 (s, 1H), 6.75 (d, 1H), 3.80 (m, 1H), 3.63 (m, 1H), 3.34 (m, 1H), 3.14 (m, 1H), 2.93 (m, 3H), 1.68 (m, 1H), 1.42 (m, 1H), 1.34 (m, 1H), 1.11 (m, 1H), 0.94 (m, 1H), 0.14 (m, 2H), 0.01 (m, 2H); LCMS (APCI+) m/z 486(M + H)+ |
| 171 | 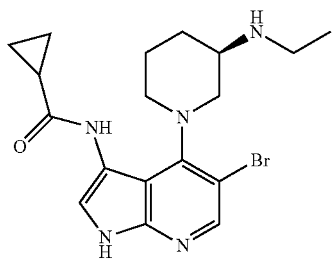 [SMILES: CCN[C@@H]1CCCN(c2c(Br)cnc3[nH]cc(NC(=O)C4CC4)c23)C1] | (R)-N-(5-Bromo-4-(3-(ethylamino)piperidin-1-yl)-1H-pyrrolo[2,3-b]pyridin-3-yl)cyclopropanecarboxamide | ¹H NMR (400 MHz, D₂O) δ 8.25 (s, 1H), 7.27 (s, 1H), 3.88-3.81 (m, 1H), 3.54-3.45 (m, 1H), 3.42-3.34 (m, 1H), 3.24-3.14 (m, 2H), 3.04-2.98 (m, 2H), 2.21-2.14 (m, 1H), 1.81-1.67 (m, 3H), 1.59-1.48 (m, 1H), 1.14 (t, 3H), 0.91-0.82 (m, 4H); LCMS (APCI+) m/z 406.1, 408 (M + H)+ |
| 172 | 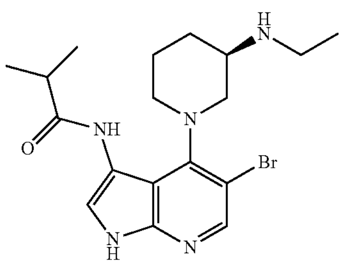 [SMILES: CCN[C@@H]1CCCN(c2c(Br)cnc3[nH]cc(NC(=O)C(C)C)c23)C1] | (R)-N-(5-Bromo-4-(3-(ethylamino)piperidin-1-yl)-1H-pyrrolo[2,3-b]pyridin-3-yl)isobutyramide | ¹H NMR (400 MHz, D₂O) δ 8.25 (s, 1H), 7.28 (s, 1H), 3.91-3.84 (m, 1H), 3.57-3.51 (m, 1H), 3.39-3.32 (m, 1H), 3.20-3.12 (m, 2H), 3.02 (q, 2H), 2.69-2.62 (m, 1H), 2.20-2.12 (m, 1H), 1.82-1.77 (m, 1H), 1.70-1.46 (m, 2H), 1.16-1.09 (m, 9H); LCMS (APCI+) m/z 408.1, 410.1 (M + H)+ |
| 173 | 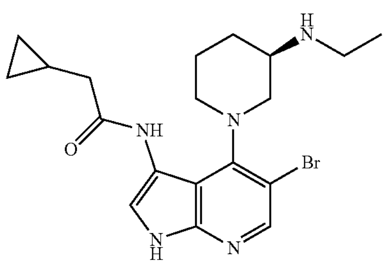 [SMILES: CCN[C@@H]1CCCN(c2c(Br)cnc3[nH]cc(NC(=O)CC4CC4)c23)C1] | (R)-N-(5-Bromo-4-(3-(ethylamino)piperidin-1-yl)-1H-pyrrolo[2,3-b]pyridin-3-yl)-2-cyclopropylacetamide | ¹H NMR (400 MHz, D₂O) δ 11.82 (s, 1H), 9.25 (s, 1H), 9.06 (br s, 2H), 8.24 (s, 1H), 7.55 (br s, 1H), 3.57-3.45 (m, 2H), 3.35-3.25 (m, 2H), 3.12-3.05 (m, 1H), 3.03-2.97 (m, 2H), 2.33 (d, 2H), 2.29-2.24 (m, 1H), 1.90-1.81 (m, 1H), 1.71-1.61 (m, 1H), 1.58-1.46 (m, 1H), 1.22 (t, 3H), 1.13-1.06 (m, 1H), 0.57-0.50 (m, 2H), 0.25-0.21 (m, 2H); LCMS (APCI+) m/z 420.1, 422 (M + H)+ |
| 174 | 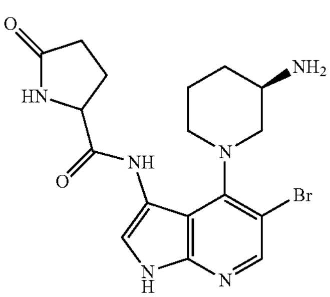 [SMILES: N[C@@H]1CCCN(c2c(Br)cnc3[nH]cc(NC(=O)C4CCC(=O)N4)c23)C1] | N-(4-((R)-3-Aminopiperidin-1-yl)-5-bromo-1H-pyrrolo[2,3-b]pyridin-3-yl)-5-oxopyrrolidine-2-carboxamide | ¹H NMR (400 MHz, D₂O) δ 8.24 (dd, 1H), 7.39 (dd, 1H), 4.49-4.41 (m, 1H), 3.82-3.70 (m, 1H), 3.63-3.52 (m, 1H), 3.34-3.24 (m, 2H), 3.23-3.11 (m, 2H), 2.62-2.50 (m, 1H), 2.41-2.34 (m, 2H), 2.17-2.04 (m, 2H), 1.85-1.76 (m, 1H) 1.70-1.48 (m, 2H); LCMS (APCI+) m/z 421 (M + H)+, Retention time = 2.38 minutes |

TABLE 1-continued

| Ex # | Structure | Name | NMR/LCMS |
|---|---|---|---|
| 175 | 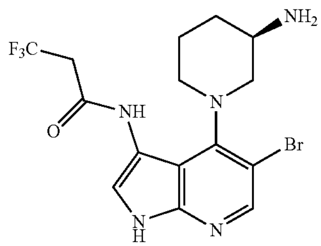 | (R)-N-(4-(3-Aminopiperidin-1-yl)-5-bromo-1H-pyrrolo[2,3-b]pyridin-3-yl)-3,3,3-trifluoropropanamide | $^1$H NMR (400 MHz, (CD$_3$)$_2$SO) δ 11.82 (s, 1H), 8.69 (s, 1H), 8.31 (brs, 2H), 8.21 (s, 1H), 7.39 (s, 1H), 4.06 (br s, 2H), 3.65-3.00 (m, 5H), 2.19-2.10 (m, 1H), 1.90-1.29 (m, 3H); LCMS (APCI+) m/z 420 (M)+, Retention time = 2.47 minutes |
| 176 | 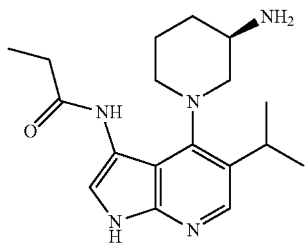 [SMILES: CCC(=O)Nc1c[nH]c2ncc(C(C)C)c(N3CCC[C@@H](N)C3)c12] | (R)-N-(4-(3-Aminopiperidin-1-yl)-5-isopropyl-1H-pyrrolo[2,3-b]pyridin-3-yl)propionamide | $^1$H NMR (400 MHz, D$_2$O) δ 8.08 (s, 1H), 7.33 (s, 1H), 3.51 (m, 1H), 3.36 (m, 1H), 3.32 (m, 2H), 3.08 (m, 2H), 2.42 (q, 2H), 2.11 (m, 1H), 1.82-1.63 (m, 2H), 1.51 (m, 1H), 1.16 (dd, 6H), 1.09 (t, 3H); LCMS (APCI+) m/z 330.1 (M + H)+, Retention time = 2.25 minutes (Method 3) |
| 177 | 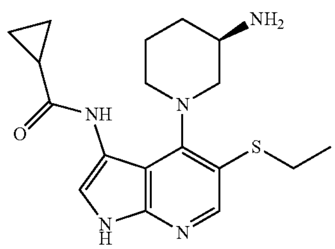 [SMILES: CCSc1cnc2[nH]cc(NC(=O)C3CC3)c2c1N1CCC[C@@H](N)C1] | (R)-N-(4-(3-Aminopiperidin-1-yl)-5-(ethylthio)-1H-pyrrolo[2,3-b]pyridin-3-yl)cyclopropanecarboxamide | $^1$H NMR (400 MHz, D$_2$O) δ 8.17 (s, 1H), 7.26 (s, 1H), 3.89 (d, 1H), 3.64 (m, 1H), 3.47 (m, 1H), 3.20 (m, 2H), 2.74 (q, 2H), 2.12 (m, 1H), 1.84-1.64 (m, 3H), 1.57 (m, 1H), 1.04 (t, 3H), 0.93-0.80 (m, 4H); LCMS (APCI+) m/z 360.0 (M + H)+, Retention time = 2.21 minutes (Method 3) |
| 178 | 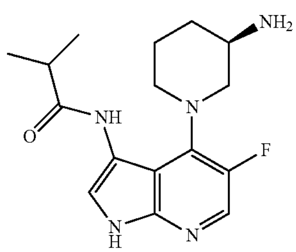 [SMILES: CC(C)C(=O)Nc1c[nH]c2ncc(F)c(N3CCC[C@@H](N)C3)c12] | (R)-N-(4-(3-Aminopiperidin-1-yl)-5-fluoro-1H-pyrrolo[2,3-b]pyridin-3-yl)isobutyramide | $^1$H NMR(400 MHz, D$_2$O) δ 8.08 (d, 1H), 7.28 (s, 1H), 3.90-3.83 (m, 1H), 3.59-3.52 (m, 1H), 3.48-3.39 (m, 1H), 3.36-3.20 (m, 2H), 2.68-2.60 (m, 1H), 2.11-1.99 (m, 1H), 1.80-1.68 (m, 1H), 1.67-1.55 (m, 1H), 1.11-1.06 (m, 6H); LCMS (APCI+) m/z 320.1, 321.1 (M + H)+, Retention time = 2.11 minutes |
| 179 | 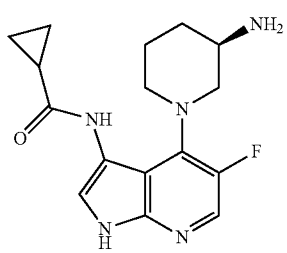 [SMILES: N[C@@H]1CCCN(c2c(F)cnc3[nH]cc(NC(=O)C4CC4)c23)C1] | (R)-N-(4-(3-Aminopiperidin-1-yl)-5-fluoro-1H-pyrrolo[2,3-b]pyridin-3-yl)cyclopropanecarboxamide | $^1$H NMR (400 MHz, D$_2$O) δ 8.07 (d, 1H), 7.27 (s, 1H), 3.80-3.78 (m, 1H), 3.58-3.50 (m, 1H), 3.46-3.37 (m, 1H), 3.36-3.20 (m, 2H), 2.12-2.03 (m, 1H), 1.83-1.54 (m, 4H), 0.92-0.80 (m, 4H); LCMS (APCI+) m/z 318 (M + H)+, Retention time = 1.99 minutes |
| 180 | 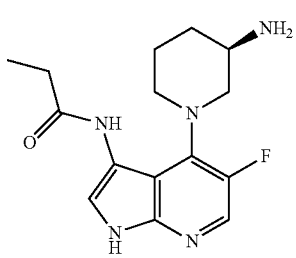 [SMILES: CCC(=O)Nc1c[nH]c2ncc(F)c(N3CCC[C@@H](N)C3)c12] | (R)-N-(4-(3-Aminopiperidin-1-yl)-5-fluoro-1H-pyrrolo[2,3-b]pyridin-3-yl)propionamide | $^1$H NMR (400 MHz, D$_2$O) δ 8.07 (d, 1H), 7.27 (s, 1H), 3.88-3.79 (m, 1H), 3.57-3.48 (m, 1H), 3.47-3.39 (m, 1H), 3.36-3.27 (m, 2H), 3.27-3.18 (m, 1H), 2.43-2.35 (m, 2H), 2.12-2.01 (m, 1H), 1.81-1.68 (m, 1H), 1.68-1.54 (m, 2H), 1.10-1.03 (m, 3H); LCMS (APCI+) m/z 306, 307.1 (M + H)+, Retention time = 1.95 minutes |

TABLE 1-continued

| Ex # | Structure | Name | NMR/LCMS |
|---|---|---|---|
| 181 | 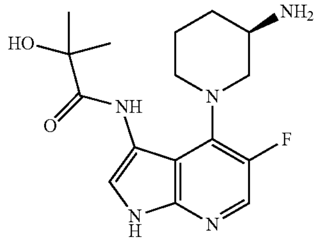 | (R)-N-(4-(3-Aminopiperidin-1-yl)-5-fluoro-1H-pyrrolo[2,3-b]pyridin-3-yl)-2-hydroxy-2-methylpropanamide | $^1$H NMR (400 MHz, D$_2$O) δ 8.07 (d, 1H), 7.44 (s, 1H), 3.80-3.73 (m, 1H), 3.52-3.39 (m, 2H), 3.33-3.17 (m, 2H), 2.12-2.02 (m, 1H), 1.81-1.50 (m, 3H), 1.37 (m, 6H); LCMS (APCI+) m/z 366.1 (M + H)+, Retention time = 2.06 minutes |
| 182 | 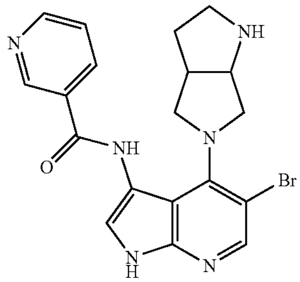 [SMILES: O=C(Nc1c[nH]c2ncc(Br)c(N3CC4CCNC4C3)c12)c1cccnc1] | N-(5-Bromo-4-(hexahydropyrrolo[3,4-b]pyrrol-5(1H)-yl)-1H-pyrrolo[2,3-b]pyridin-3-yl)nicotinamide | $^1$H NMR (400 MHz, D$_2$O) δ 9.15 (s, 1H), 8.84-8.83 (m, 1H), 8.78-8.75 (m, 1H0, 8.24 (s, 1H), 8.00-7.96 (m, 1H), 7.43 (s, 1H), 4.15-4.11 (m, 1H), 3.97-3.92 (m, 1H), 3.73-3.69(m, 1H), 3.65-3.61 (m, 1H), 3.54-3.50 (m, 1H), 3.27-3.23 (m, 2H), 2.90-2.87 (m, 1H) 1.96-1.86 (m, 2H); LCMS (APCI+) m/z 427, 429 (M + H)+ |
| 183A | 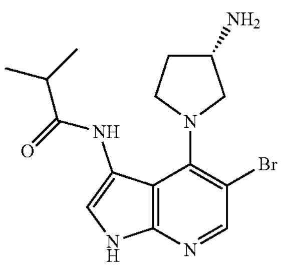 [SMILES: CC(C)C(=O)Nc1c[nH]c2ncc(Br)c(N3CC[C@H](N)C3)c12] | (S)-N-(4-(3-Aminopyrrolidin-1-yl)-5-bromo-1H-pyrrolo[2,3-b]pyridin-3-yl)isobutyramide | $^1$H NMR (400 MHz, D$_2$O) δ 8.15 (s, 1H), 7.25 (s, 1H), 4.06-4.01 (m, 1H), 3.96-3.93 (m, 1H), 3.87-3.84 (m, 1H), 3.82-3.76 (m, 1H), 3.72-3.67 (m, 1H), 2.62-2.58 (m, 1H), 2.38-2.32 (m, 1H), 2.02-2.00 (m, 1H), 1.08-1.06 (d, 6H); LCMS (APCI+) m/z 366, 368 (M + H)+ |
| 183B | 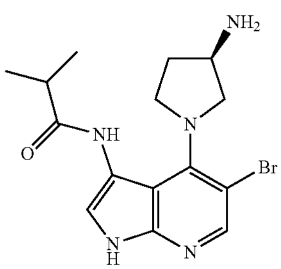 [SMILES: CC(C)C(=O)Nc1c[nH]c2ncc(Br)c(N3CC[C@@H](N)C3)c12] | (R)-N-(4-(3-Aminopyrrolidin-1-yl)-5-bromo-1H-pyrrolo[2,3-b]pyridin-3-yl)isobutyramide | $^1$H NMR (400 MHz, D$_2$O) δ 8.16 (s, 1H), 7.27 (s, 1H), 4.00-3.93 (m, 2H), 3.84-3.73 (m, 2H), 3.69-3.60 (m, 1H), 2.63-2.56 (m, 1H), 2.83-2.33 (m, 1H), 2.04-2.01 (m, 1H), 1.08-1.06 (d, 6H); LCMS (APCI+) m/z 366, 368 (M + H)+ |
| 184 | 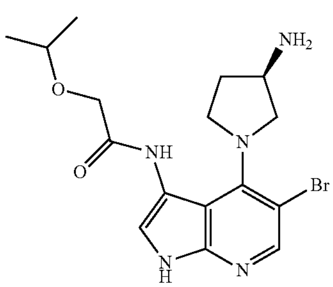 [SMILES: CC(C)OCC(=O)Nc1c[nH]c2ncc(Br)c(N3CC[C@@H](N)C3)c12] | (R)-N-(4-(3-aminopyrrolidin-1-yl)-5-bromo-1H-pyrrolo[2,3-b]pyridin-3-yl)-2-isopropoxyacetamide | $^1$H NMR (400 MHz, D$_2$O) δ 8.17 (s, 1H), 7.32 (s, 1H), 4.10 (s, 2H), 3.97-3.95 (m, 2H), 3.81-3.62 (m, 4H), 2.37-2.35 (m, 1H), 2.10-2.00 (m, 1H), 1.11-1.10 (d, 6H); LCMS (APCI+) m/z 396, 398 (M + H)+ |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from Formula I:

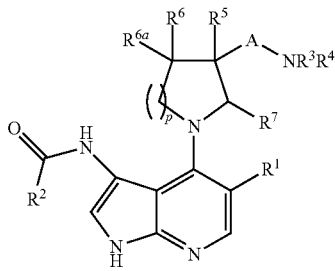

I or a stereoisomer, tautomer, or pharmaceutically acceptable salt thereof, wherein:
A is selected from a direct bond or $CR^aR^b$;
$R^1$ is selected from hydrogen, halogen, CN, $C_1$-$C_6$ alkyl, $C_1$-$C_6$ alkenyl, —O($C_1$-$C_6$ alkyl), —S($C_1$-$C_6$ alkyl), $C_3$-$C_6$ cycloalkyl, a 4 to 6 membered heterocyclic, phenyl, and a 5 or 6 membered heteroaryl, wherein the alkyls, alkenyl, cycloalkyl, heterocyclic, phenyl or heteroaryl are optionally substituted with one or more groups selected from halogen, CN, $CF_3$, $C_1$-$C_3$ alkyl, —O($C_1$-$C_3$ alkyl), and $NR^cR^d$;
$R^2$ is a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, or an 8 to 10 membered bicyclic heteroaryl, wherein the cycloalkyl, phenyl, heterocyclics, heteroaryls and aryl are optionally substituted with one or more groups selected from the group consisting of OH, CN, halogen, oxo (except not on phenyl, aryl or heteroaryl), $CF_3$, cyclopropyl, cyclopropylmethyl, —$SO_2R^i$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from the group consisting of OH, CN, halogen, $CF_3$, $C_1$-$C_3$ alkyl, —O($C_1$-$C_3$ alkyl), and $NR^gR^h$;
$R^3$ and $R^4$ are independently selected from hydrogen or $C_1$-$C_4$ alkyl optionally substituted with OH, F, —O($C_1$-$C_3$ alkyl) or $C_3$-$C_6$ cycloalkyl, or
$R^3$ and $R^4$ together with the atoms to which they are attached form a 5 or 6 membered ring;
$R^5$ is selected from hydrogen and $CH_3$, or
A is $CR^aR^b$, $R^a$ and $R^b$ are hydrogen, and $R^3$ and $R^5$ together with the atoms to which they are attached form a 5 or 6 membered ring;
$R^6$ is selected from hydrogen, F, OH, —$OCH_3$, $C_1$-$C_3$ alkyl and cyclopropyl, or
A is a direct bond, $R^{6a}$ is hydrogen and $R^3$ and $R^6$ together with the atoms to which they are attached form a 5 or 6 membered ring;
$R^{6a}$ is selected from hydrogen, F, OH, and $CH_3$;
$R^7$ is hydrogen, or
A is $CR^aR^b$ and $R^3$ and $R^7$ together with the atoms to which they are attached form a 5 or 6 membered ring;
$R^a$ is hydrogen, or $R^4$ and $R^b$ are absent and $R^3$ and $R^a$ together with the atoms to which they are attached form an aromatic 5 or 6 membered ring;
$R^b$ is hydrogen or absent;
$R^c$ and $R^d$ are independently selected hydrogen and $C_1$-$C_3$ alkyl, or
$R^c$ and $R^d$ together with the atom to which they are attached form a 5 or 6 membered ring;
$R^e$ and $R^f$ are independently selected hydrogen and $C_1$-$C_3$ alkyl;
$R^g$ and $R^h$ are independently selected from hydrogen and $C_1$-$C_3$ alkyl;
$R^i$ is $C_1$-$C_3$ alkyl; and
p is 1.
2. The compound of claim 1, wherein $R^1$ is selected from halogen, $C_3$-$C_6$ cycloalkyl and $C_1$-$C_6$ alkyl, wherein the alkyl is optionally substituted with one or more F groups.
3. The compound of claim 2, wherein $R^1$ is selected from Br, Cl, F, cyclopropyl and $CF_3$.
4. The compound of claim 2, wherein $R^1$ is selected from hydrogen, Br, Cl, F, CN, $CF_3$, methyl, ethyl, isopropyl, prop-1-en-1-yl, —$OCH_2CH_3$, —$OCH_2CH_2OCH_3$, —$SCH_3$, —$SCH_2CH_3$, —$SCH(CH_3)_2$, cyclopropyl, phenyl and 6-methylpyridin-3-yl.
5. The compound of claim 1, wherein $R^2$ is selected from $C_1$-$C_6$ alkyl, a saturated or partially unsaturated $C_3$-$C_6$ cycloalkyl, phenyl, a saturated or partially unsaturated 5 or 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyl, cycloalkyl, phenyl, heterocyclic, heteroaryl and aryl are optionally substituted with one or more groups selected from OH, CN, halogen, oxo (except not on phenyl, aryl or heteroaryl), $CF_3$, $C_1$-$C_6$ alkyl, —O($C_1$-$C_6$ alkyl), —S($C_1$-$C_6$ alkyl), and $NR^eR^f$.
6. The compound of claim 1, wherein $R^2$ is selected from isopropyl, tert-butyl, isobutyl, cyclopropylmethyl, —CH($CH_2CH_3$)$_2$, —$CH_2OCH_3$, —CH($CH_3$)$OCH_3$, —$CH_2CH_2OCH_3$, —C(cyclopropyl)$CF_3$, cyclopropyl, cyclobutyl, cyclopentyl, phenyl, 3-methylphenyl, 4-fluorophenyl, 3-methoxyphenyl, 3-fluorophenyl, 3-chloro-4-fluorophenyl, 3-fluoro-4-methoxyphenyl, 3-trifluoromethylphenyl, 2-fluoro-5-methylphenyl, tetrahydrofuran-2-yl, tetrahydrofuran-3-yl, 1-methyl-6-oxo-1,6-dihydropyridin-3-yl, 1-methyl-6-oxo-1,6-dihydropyridazin-3-yl, morpholin-2-yl, pyrazol-4-yl, 1-methyl-1H-pyrazol-3-yl, 2-methyloxazol-4-yl, 5-methylisoxazol-3-yl, 2-methylthiazol-4-yl, pyridin-2-yl, pyridin-3-yl, 6-methoxy-pyridin-2-yl, 3-methylpyridin-2-yl, 5-chloro-pyridin-2-yl, 5-methylpyridin-2-yl, 2-methylpyridin-3-yl, 5-methylpyridin-3-yl, 5-chloropyridin-3-yl, 6-methylpyridin-3-yl, pyrimidin-2-yl, pyrazin-2-yl, 5-methylpyrazin-2-yl and quinoxalin-2-yl.
7. The compound of claim 1, wherein $R^2$ is selected from methyl, ethyl, propyl, isopropyl, tert-butyl, isobutyl, cyclopropylmethyl, —$CH_2CF_3$, —CH($CH_2CH_3$)$_2$, —$CH_2OH$, —$CH_2OCH_3$, —$CH_2OCH_2CH_3$, —CH($CH_3$)$OCH_3$, —$CH_2CH_2OCH_3$, —CH($CH_3$)OH, —C($CH_3$)$_2$OH, —$CH_2CN$, —$CH_2CH_2F$, —C($CH_3$)$_2$F, —CH($CH_3$)$CH_2F$, —$CH_2OCH(CH_3)_2$, —CH($CH_3$)$OCH(CH_3)_2$, —$CH_2SO_2CH_3$, —CH($CH_3$)phenyl, —$CH_2$(phenyl), —$OCH_2CH_3$, —NH($CH_2CH_3$), cyclopropyl, cyclobutyl, cyclopentyl, 1-(trifluoromethyl)cyclopropyl, 1-(methoxy)cyclopropyl, 2,2-difluorocyclopropyl, 1-methylcyclopropyl, 2-phenylcyclopropyl, 2,2-dimethylcyclopropyl, phenyl, 3-methylphenyl, 4-fluorophenyl, 3-methoxyphenyl, 3-fluorophenyl, 3-chloro-4-fluorophenyl, 3-fluoro-4-methoxyphenyl, 3-trifluoromethylphenyl, 2-fluoro-5-methylphenyl, 3-methyloxetan-3-yl, azetidin-1-yl, tetrahydrofuran-2-yl, tetrahydrofuran-3-yl, 1-methyl-6-oxo-1,6-dihydropyridin-3-yl, 1-methyl-6-oxo-1,6-dihydropyridazin-3-yl, 1-isopropyl-6- oxo-1,6-dihydropyridazin-3-yl, 1-(cyclopropylmethyl)-6-oxo-1,6-dihydropyridazin-3-yl, morpholin-2-yl, pyrrolidin-1-yl, 5-oxopyrrolidin-2-yl, pyrazol-4-yl, 1-methyl-1H-pyrazol-3-yl, 1-methyl-1H-pyrazol-4-yl, 2-methyloxazol-4-yl, 5-methylisoxazol-3-yl, 2-methylthiazol-4-yl, pyridin-2-yl, pyridin-3-yl, 6-methoxy-pyridin-2-yl, 3-methylpyridin-2-yl, 5-chloro-pyridin-2-yl, 5-trifluoromethylpyridin-2-yl, 2-methylpyridin-3-yl, 5-methylpyridin-3-yl, 5-chloropyridin-3-yl, 6-methylpyridin-3-yl, pyrimidin-2-yl, 5-ethylpyrimidin-2-yl, pyrazin-2-yl, 5-methylpyrazin-2-yl, and quinoxalin-2-yl.

8. The compound of claim 1, wherein A is a direct bond.

9. The compound as claimed in claim 1, wherein A is $CR^aR^b$.

10. The compound of claim 1, wherein $R^3$ is selected from hydrogen or $C_1$-$C_4$ alkyl optionally substituted with OH, F or $C_3$-$C_6$ cycloalkyl.

11. The compound of claim 1, wherein $R^3$ is selected from hydrogen, methyl, isopropyl, isobutyl, $CH_2CH_2OH$ and cyclopropylmethyl.

12. The compound of claim 1, wherein $R^3$ is selected from hydrogen, methyl, ethyl, isopropyl, isobutyl, $CH_2CH_2OH$, $CH_2CH_2OCH_3$, $CH_2CH_2F$ and cyclopropylmethyl.

13. The compound as claimed of claim 1, wherein $R^4$ is selected from hydrogen or $C_1$-$C_4$ alkyl optionally substituted with OH, F or $C_3$-$C_6$ cycloalkyl.

14. The compound of claim 1, wherein A is $CR^aR^b$, $R^a$ and $R^b$ are hydrogen, and $R^3$ and $R^5$ together with the atoms to which they are attached form a 5 or 6 membered ring.

15. The compound of claim 1, wherein A is a direct bond, $R^{6a}$ is hydrogen and $R^3$ and $R^6$ together with the atoms to which they are attached form a 5 or 6 membered ring.

16. The compound of claim 1, wherein $R^7$ is hydrogen.

17. The compound of claim 1 that is:

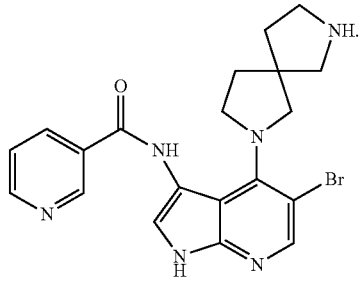 [SMILES: O=C(Nc1c[nH]c2ncc(Br)c(N3CCC4(CCNC4)C3)c12)c1cccnc1]

18. The compound of claim 1 that is:

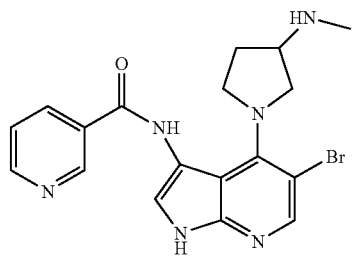

19. The compound of claim 1 that is:

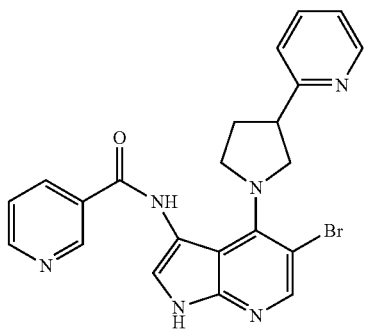

20. The compound of claim 1 that is:

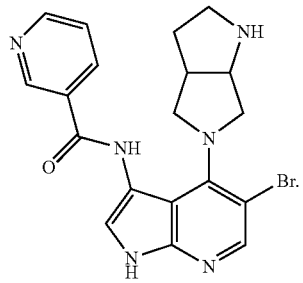 [SMILES: O=C(Nc1c[nH]c2ncc(Br)c(N3CC4CCNC4C3)c12)c1cccnc1]

* * * * *